United States Patent [19]

Psiorz et al.

[11] Patent Number: 5,175,157
[45] Date of Patent: Dec. 29, 1992

[54] CYCLIC AMINE DERIVATIVES, PHARMACEUTICAL COMPOSITIONS CONTAINING THESE COMPOUNDS AND METHODS FOR PREPARING THEM

[75] Inventors: Manfred Psiorz, Biberach; Joachim Heider, Warthausen; Andreas Bomhard, Dusseldorf; Manfred Reiffen; Norbert Hauel, both of Biberach; Klaus Noll, Warthausen; Berthold Narr, Biberach, all of Fed. Rep. of Germany; Christian Lillie; Walter Kobinger, both of Vienna, Austria; Jurgen Dammgen, Sulmingen, Fed. Rep. of Germany

[73] Assignee: Boehringer Ingelheim GmbH, Biberach an der Riss, Fed. Rep. of Germany

[21] Appl. No.: 725,855

[22] Filed: Jul. 3, 1991

Related U.S. Application Data

[63] Continuation-in-part of Ser. No. 552,352, Jul. 12, 1990, abandoned, and a continuation-in-part of Ser. No. 638,001, Jan. 4, 1991, abandoned, which is a continuation of Ser. No. 426,922, Oct. 24, 1989, abandoned, which is a continuation of Ser. No. 197,064, May 20, 1988, abandoned, said Ser. No. 552,352, is a continuation of Ser. No. 438,279, Nov. 16, 1989, abandoned, which is a continuation of Ser. No. 259,228, Oct. 17, 1988, abandoned, which is a continuation of Ser. No. 170,185, Mar. 18, 1988, abandoned, which is a continuation of Ser. No. 934,277, Nov. 24, 1986, abandoned.

[30] Foreign Application Priority Data

Nov. 27, 1985 [DE] Fed. Rep. of Germany ....... 3541811
May 25, 1987 [DE] Fed. Rep. of Germany ....... 3717561

[51] Int. Cl.$^5$ ................ A61K 31/55; C07D 223/16
[52] U.S. Cl. .................................. 514/213; 514/215; 514/217; 540/495; 540/521; 540/524; 540/585; 540/593; 540/594
[58] Field of Search ........... 514/213, 215, 217; 540/495, 521, 524, 586, 593, 594

[56] References Cited

U.S. PATENT DOCUMENTS

| | | | |
|---|---|---|---|
| 4,137,318 | 1/1979 | Eberlein et al. | 424/258 |
| 4,490,369 | 12/1984 | Reiffen et al. | 424/244 |
| 4,616,011 | 10/1986 | Reiffen et al. | 514/213 |
| 4,871,735 | 10/1989 | Heider et al. | 514/221 |

FOREIGN PATENT DOCUMENTS

| | | | |
|---|---|---|---|
| 0161599 | 11/1985 | European Pat. Off. | 514/244 |
| 645632 | 10/1984 | Switzerland | 424/258 |

Primary Examiner—Robert T. Bond
Attorney, Agent, or Firm—David E. Frankhouser; Alan R. Stempel; Mary-Ellen M. Timbers

[57] ABSTRACT

Disclosed are new cyclic amine derivatives of the formula I

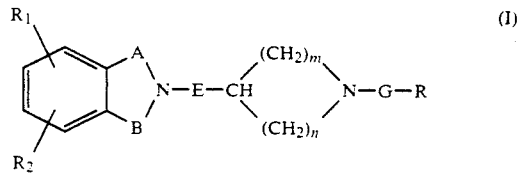

wherein the substituents are defined in the specification. These compounds are useful as for treating sinus tachycardia.

15 Claims, No Drawings

CYCLIC AMINE DERIVATIVES, PHARMACEUTICAL COMPOSITIONS CONTAINING THESE COMPOUNDS AND METHODS FOR PREPARING THEM

This application is a continuation-in-part of application Ser. No. 552,352, filed Jul. 12, 1990, now abandoned, which is a continuation of application Ser. No. 438,279, filed Nov. 16, 1989, now abandoned, which is a continuation of application Ser. No. 259,228, filed Oct. 17, 1989, now abandoned, which is a continuation of application Ser. No. 170,185, filed Mar. 18, 1988, now abandoned, which is a continuation of application Ser. No. 934,277, filed Nov. 24, 1986, now abandoned. This application is also a continuation-in-part of application Ser. No. 638,001, filed Jan. 4, 1991, now abandoned which is a continuation of application Ser. No. 426,922, filed Oct. 24, 1989, now abandoned, which is a continuation of application Ser. No. 197, 064, filed May 20, 1988, now abandoned.

U.S. Pat. No. 4,137,318 describes, inter alia the compound of the formula

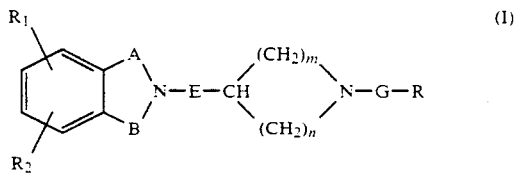

and the physiologically acceptable acid addition salts thereof which have valuable pharmacological properties, namely a mild hypotensive activity and, more particularly a selective heart rate-reducing activity.

Surprisingly, it has now been found that the new cyclic amine derivatives of the formula I

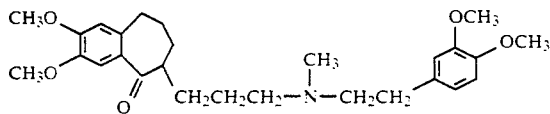

the enantiomers, diastereomers and acid addition salts thereof, particularly their physiologically acceptable acid addition salts with inorganic or organic acids, have even more valuable pharmacological properties, namely a long lasting heart rate reducing activity and the effect of reducing the $O_2$ requirements of the heart.

This invention thus relates to the new cyclic amine derivatives of the formula I above, the enantiomers, the diastereomers, n-oxides and the acid addition salts thereof, particularly to the pharmaceutical use of the physiologically acceptable acid addition salts with inorganic or organic acids, processes for preparing them and pharmaceutical compositions containing these compounds.

In formula I above $R_1$ is hydrogen, halogen, trifluoromethyl, nitro, amino, alkylamino, dialkylamino, alkyl, hydroxy, alkoxy or phenylalkoxy, wherein each alkyl moiety contains 1 to 3 carbon atoms;

$R_2$ is hydrogen, halogen, hydroxy, alkoxy, phenylalkoxy or alkyl, wherein each alkyl moiety may contain 1 to 3 carbon atoms; or, $R_1$ and $R_2$ together form an alkylenedioxy group of 1 or 2 carbon atoms;

E is a straight chain alkylene group having 1 to 3 carbon atoms optionally substituted by an alkyl group having 1 to 3 carbon atoms; and, A, B, G, m, n, and R are defined as set forth in options (i) or (ii) which appear below.

Option (i)

A is a —$CH_2$—$CH_2$—, —CH=CH—, —$\underline{C}H_2$—CO or —NH—CO— group; and,

B is a —$CH_2$—$CH_2$—, —$\underline{C}H_2CO$ or —$\underline{C}H_2CS$— group; or, A is a —CO—CO— or —$\underline{C}HOH$—CO— group; and B is a —$CH_2$—$CH_2$— group;

in which the atoms indicated by underlining are attached to the phenyl nucleus;

G is a straight-chain alkylene group of 1 to 4 carbon atoms which is optionally substituted by an alkyl group of 1 to 3 carbon atoms, or G is the group —G'—G"—, wherein G' is attached to the nitrogen atom and is a straight-chain alkylene group of 2 to 4 carbon atoms which is optionally substituted by an alkyl group of 1 to 3 carbon atoms and G" is attached to the group R and is an oxa, thia, imino, methylimino, sulphinyl or sulfonyl group;

m is 1, 2, 3, 4 or 5;

n is 0, 1 or 2, with the proviso that n+m must equal 3, 4 or 5; and,

R is a group of the formula

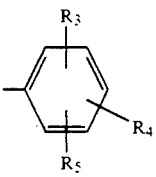

in which $R_3$ is hydrogen, halogen, alkyl or alkoxy of 1 to 3 carbon atoms, hydroxy, nitro, cyano or trifluoromethyl;

$R_4$ is hydrogen, alkoxy, alkylsulfonyloxy of 1 to 3 carbon atoms, amino, alkylamino or dialkylamino of 1 to 3 carbon atoms, or alkanoylamino of 2 or 3 carbon atoms; or, $R_3$ and $R_4$ together form an alkylenedioxy group of 1 or 2 carbon atoms; and, $R_5$ is hydrogen, halogen, hydroxy, or alkyl or alkoxy of 1 to 3 carbon atoms.

Option (ii)

A is a —$CH_2$—, —$CH_2$—$CH_2$— or —CH=CH— group;

B is a —$CH_2$—, —$CH_2$—$CH_2$—, —CO— or —$\underline{C}H_2CO$— group in which the atom indicated by underlining is attached to the phenyl nucleus;

G is a straight-chain alkylene group of 1 to 6 carbon atoms which is optionally substituted by an alkyl group of 1 to 3 carbon atoms, or G is the group —G'—G", wherein G' is attached to the nitrogen atom and is a straight-chain alkylene group of 2 to 5 carbon atoms which is optionally substituted by an alkyl group of 1 to 3 carbon atoms and G" is attached to the group R and is an oxa, thia, sulphinyl or sulfonyl group, or an imino group which is optionally substituted by alkyl of 1 to 3 carbon atoms;

m is 1, 2, 3, 4, 5 or 6;

n is 0, 1, 2 or 3, with the proviso that m+n must equal 3, 4, 5 or 6; and,

R is a ring carbon- or ring nitrogen-attached 5-membered heteroaromatic ring or a ring carbon-attached 6 membered ring each optionally carrying a fused benzene ring, wherein said 5-membered heteroaromatic ring contains one oxygen, sulfur or nitrogen atom, two nitrogen atoms or one nitrogen atom and one oxygen or sulfur atom and said 6-membered heteroaromatic ring contains one or two nitrogen atoms, wherein the carbon structure of the cyclic group optionally is mono- or disubstituted by substituents selected from halogen atoms, alkyl, hydroxy, alkoxy, phenylalkoxy, phenyl, dimethoxyphenyl, nitro, amino, acetylamino, carbamoylamino, N-alkylcarbamoylamino, hydroxymethyl, mercapto, alkylmercapto, alkylsuphinyl, alkylsulphonyl, alkylsulphonyloxy, alkylsulphonylamino, alkoxycarbonylmethoxy, carboxymethoxy and alkoxymethyl groups, or optionally is substituted by a methylenedioxy or ethylenedioxy group, wherein any imino group in the said heteroaromatic ring optionally is substituted by an alkyl, phenylalkyl or phenyl group, wherein in the event the said cyclic ring contains an indolyl group it additionally optionally is substituted by a methylamino, dimethylamino, methoxy, acetoxy, trifluoromethyl, trichloromethyl, carboxy, methoxycarbonyl, ethoxycarbonyl, cyano, cyclohexyl, trimethoxyphenyl, trifluorophenyl, trichlorophenyl, tribromophenyl or dihaloaminophenyl group or by a benzyl, benzyloxy or benzylamino group optionally mono-, di- or trisubstituted in the phenyl ring of the benzyl nucleus by methoxy or methyl groups, or a naphthyl group optionally substituted by an alkylenedioxy group containing 1 or 2 carbon atoms or optionally mono-or disubstituted by substituents selected from halogen atoms, alkyl, hydroxy, alkoxy, alkylsulphonyloxy, nitro, amino and alkanoylamino groups, or a benzyloxy or 4,5,6,7-tetrahydrobenzo[b]thienyl group, or, if B represents a —CH$_2$— or —CO— group, R may also represent a phenyl group optionally substituted by an alkylenedioxy group containing 1 or 2 carbon atoms or by a halogen atom or by an alkyl, hydroxy, alkoxy, phenylalkoxy, nitro, amino, alkanoylamino, alkylsulphonylamino, bis(alkylsuphonyl)amino, alkylsuphonyloxy, trifluoromethyl, trifluoromethoxy or trifluoromethylsulphonyloxy, or disubstituted by substituents selected from halogen atoms, alkyl and alkoxy groups, a trialkoxyphenyl group, a tetraalkylphenyl group or a dihaloaminophenyl group.

In the above definitions, alkyl, alkoxy and alkanoyl moieties contain 1 to 3 carbon atoms except where otherwise stated.

Examples of the definitions given for the groups mentioned hereinbefore include:

for $R_1$: a hydrogen, fluorine, chlorine or bromine atom or a methyl, ethyl, n-propyl, isopropyl, trifluoromethyl, hydroxy, methoxy, ethoxy, n-propoxy, isopropoxy, nitro, amino, methylamino, ethylamino, n-propylamino, isopropylamino, dimethylamino, diethylamino, di-n-propylamino, diisopropylamino, methylethylamino, methyl-n-propylamino, methylisopropylamino, ethyl-n-propylamino, benzyloxy, 1-phenylethoxy, 1-phenyl-propoxy, 2-phenylethoxy or 3-phenylpropoxy group, for $R_2$: a hydrogen, chlorine or bromine atom or a methyl, ethyl, n-propyl, isopropyl, hydroxy, methoxy, ethoxy, n-propoxy, isopropoxy, benzyloxy, 1-phenylethoxy, 2-phenylethoxy, 2-phenylpropoxy or 3-phenylpropoxy group or together with $R_1$ 1 a methylenedioxy or ethylenedioxy group, for $R_3$: a hydrogen, fluorine, chlorine or bromine atom or a methyl, ethyl, n-propyl, isopropyl, hydroxy, methoxy, ethoxy, n-propoxy, isopropoxy, nitro, cyano or trifluoromethyl group, for $R_4$: a hydrogen atom or a methoxy, ethoxy, n-propoxy, isopropoxy, methanesulphonyloxy, ethanesulphonyloxy, n-propanesulphonyloxy, amino, methylamino, ethylamino, n-propylamino, isopropylamino, dimethylamino, diethylamino, di-n-propylamino, diisopropylamino, methylethylamino, methyl-n-propylamino, methyl-isopropylamino, ethyl-n-propylamino, acetylamino or propionylamino group or together with $R_3$ a methylenedioxy or ethylenedioxy group, for $R_5$: a hydrogen, chlorine or bromine atom or a methyl, ethyl, n-propyl, isopropyl, hydroxy, methoxy, ethoxy, n-propoxy or isopropoxy group, for E: a methylene, ethylene, n-propylene, ethylidene, n-propylidene, n-butylidene, 2-methyl-n-propylidene, 1-methylethylene, 1-ethyl-ethylene, 2-methyl-ethylene, 2-ethyl-ethylene, 1-n-propyl-ethylene, 1-methyl-n-propylene, 2-methyl-n-propylene, 3-methyl-n-propylene, 1-ethyl-n-propylene, 2-n-propyl-n-propylene or 3-ethyl-n-propylene group and for G: a methylene, ethylidene, n-propylidene, n-butylidene, 2-methyl-propylidene, ethylene, 1-methyl-ethylene, 2-ethyl-ethylene, 1-propyl-ethylene, 2-methyl-ethylene, 2-ethylethylene, n-propylene, n-butylene, n-pentylene, n-hexylene, 1-methyl-n-propylene, 1-methyl-n-butylene, 1-methyl-n-pentylene, 1-ethyl-n-propylene, 2-ethyl-n-propylene, 1-methyl-n-butylene, ethyleneoxy, n-propyleneoxy, n-butyleneoxy, ethylenethio, n-propylenethio, n-butylenethio, ethylenesulphinyl, ethylenesulphonyl, n-propylenesulphinyl, n-propylenesulphonyl, n-butylenesulphinyl, ethyleneamino, n-propyleneamino, n-butyleneamino, N-methyl-ethyleneamino, N-methyl-n-propyleneamino, N-ethyl-n-propyleneamino, N-isopropyl-n-propyleneamino, or N-methyl-n-butyleneamino group, and for R: a 4-amino-phenyl, 2-fluoro-phenyl, 4-fluoro-phenyl, 2-chloro-phenyl, 4-chloro-phenyl, 2-bromo-phenyl, 4-bromo-phenyl, 3-trifluoromethyl-phenyl, 3-methoxy-4-hydroxy-phenyl, 3-methoxy-4-hydroxyphenyl, 3-methoxy-4-methanesulphonyloxy-phenyl, 3-nitro-4-acetamino-phenyl, 3,4,-dichloro-phenyl, 3,4,5-trimethoxyphenyl, 3,5-dichloro-4-methoxy-phenyl, 4-amino-3,5-dichlorophenyl, 4-amino-3,5-dibromo-phenyl, pyrrol-2-yl, pyrrol-3-yl, N-methyl-pyrrol-2-yl, N-methyl-pyrrol-3-yl, 1,2-dimethyl-pyrrol-3yl, 2,5-dimethyl-pyrrol-3-yl, fur-2-yl, fur-3-yl, 5-methyl-fur-2-yl, 2-methyl-fur-3-yl, 5-nitro-fur-2-yl, 5-methoxymethyl-fur-2-yl, benzo[b]fur-2-yl, benzo[b]fur-3-yl, 7-methylbenzo[b]fur-3-yl, 2-methoxy-benzo[b]fur-3-yl, 3-methoxy-benzo[b]fur-2-yl, 4-methoxy-benzo[b]fur-3-yl, 5-methoxy-benzo[b]fur-3-yl, 6-methoxybenzo[b]fur-3-yl, 7-methoxy-benzo[b]fur-3-yl, 5-methoxy-3-phenylbenzo[b]fur-2-yl, 3-methyl-5-methoxy-benzo[b]fur-2-yl, thien-2-yl, thien-3-yl, 5-methyl-thien-2-yl, 2-methyl-thien-3-yl, 3-methyl-thien-2-yl, 2,5-dimethyl-thien-3-yl, 4,5,6,7-tetrahydrobenzo[b]thien-3-yl, 4,5,6,7-tetrahydro-benzo[b]thien-2-yl, 5-chloro-thien-2-yl, 5-bromo-thien-2-yl, 5-phenyl-thien-2-yl, 2-phenyl-thien-3-yl, benzo[b]thien-2-yl, benzo[b]thien-3-yl, 2,5-dimethyl-benzo[b]thien-3-yl, 5-methyl-benzo[b]thien-3-yl, 6-methyl-benzo[b]thien-3-yl, 5-chloro-benzo[b]thien-2-yl, 5-bromobenzo[b]thien-3-yl, 6-hydroxy-benzo[b]thien-3-yl, 7-hydroxybenzo[b]thien-3-yl, 5-hydroxy-benzo[b]thien-2-yl, 6-hydroxybenzo[b]thien-2-yl, 7-hydroxybenzo[b]thien-2-yl, 6-methanesulphonyloxy-benzo[b]thien-3-yl, 3-methoxy-benzo[b]thien2-yl, 4-methoxybenzo[b]thien-2-yl, 5-methoxy-benzo[b]thien-2-yl, 6-methoxy-benzo[b]thien-2-yl, 7-methoxy-benzo[b]thien-2-yl, 2-methoxy-benzo[b]thien-3-yl, benzo[b]thien-4-yl, benzo[b]thien-5yl, benzo[b]thien-6-yl, benzo[b]thien-7-yl, 4-methoxybenzo[b]thien-3-yl, 5-methoxy-benzo[b]thien-3-yl, 6-methoxybenzo[b]thien-3-yl, 7-methoxy-benzo[b]thien-3-yl, 5,6-dimethoxybenzo[b]thien-3-yl, 5,6-methylenedioxy-benzo[b]thien-3-yl, 6-ethoxy-benzo[b]thien-3-yl, 6-propoxy-benzo[b]thien-3-yl, 6-isopropoxy-benzo[b]thien-3-yl, 6-mercapto-benzo[b]thien-3-yl, 6-methylmercapto-benzo[b]thien-3-yl, 6-methylsulphinylbenzo[b]thien-3-yl, 6-methylsulphonyl-benzo[b]thien-3-yl, 6-methylsulphonyloxy-benzo[b]thien-3-yl, 6-methoxycarbonylmethoxybenzo[b]thien-3-yl, 6-ethoxycarbonylmethoxy-benzo[b]thien-3-yl, 6-carboxymethoxy-benzo[b]thien-3-yl, 6-amino-benzo[b]thien-3-yl, 6-methylamino-benzo[b]thien-3-yl, 6-dimethylamino-benzo[b]thien3-yl, 6-diethylamino-benzo[b]thien-3-yl, 6-acetaminobenzo[b]thien-3-yl, 6-methylsulphonylamino-benzo[b]thien-3-yl, pyrazol-1-yl, pyrazol-3-yl, 3,5-dimethyl-pyrazol-1-yl, 1,5-dimethyl-pyrazol-3-yl, imidazol-1-yl, imidazol-2-yl, imidazol4(5)-yl. 1-methyl-imidazol-4-yl, 1-benzyl-imidazol-4-yl, 5-nitro2-methyl-imidazol-1-yl, 2-(3,4-dimethoxy-phenyl)-imidazol-4(5)yl, benzo[d]imidazol-1-yl, 2-benzyl-benzo[d]imidazol-1-yl, benzo[d]imidazol-2-yl, imidazo[1,2-a]pyrid-3-yl, oxazol-4-yl, oxazol-5-yl, isoxazol-3-yl, 3-methyl-isoxazol-5-yl, 5-methylisoxazol-3-yl, 3,5-dimethyl-isoxazol-4-yl, 4-methyl-thiazol-5-yl, benzo[d]oxazol-2-yl, benzo[d]isoxazol-3-yl, benzo[d]thiazol-2-yl, 5-ethoxy-benzo[d]thiazol-2-yl, benzo[d]isothiazol-3-yl, benzo[d]pyrazol-1-yl, benzo[d]pyrazol-3-yl, pyrid-2-yl, pyrid-3yl, pyrid-4-yl, pyrid-3-yl-N-oxide, 6-methyl-pyrid-2-yl, 4-nitro-pyrid-2-yl, 4-amino-pyrid-2-yl, 4-acetylamino-pyrid-2-yl, 4-carbamoylamino-pyrid-2-yl, 4-N-methyl-carbamoylamino-pyrid-2-yl, 2-chloro-pyrid-3-yl, 2-chloro-pyrid-4-yl, 6-chloro-pyrid-2-yl, 6-hydroxymethyl-pyrid-2-yl, quinol-2-yl, isoquinol-1-yl, 2-methylquinol-4-yl, 7-methyl-quinol-2-yl, 4-chloro-quinol-2-yl, 6,7-dimethoxy-quinol-4-yl, 6,7-dimethoxy-isoquinol-4-yl, 6,7-dimethoxy-isoquinol-4-yl-N-oxide, indol-2-yl, indol-3-yl, 5,7-dibromo-6-cyano-indol-3-yl, 5,7-dichloro-6-aminocarbonyl-indol-3yl, 4,6-dibromo-5-aminocarbonyl-indol-3-yl, 5,7-dibromo-6-methoxy-indol-3-yl, 5,6-dihydroxy-indol-3-yl, 4-dimethylaminoindol-3-yl, 4-methoxy-6-dimethylamino-indol-3-yl, 4-methyl-6-dimethylamino-indol-3-yl, 5-acetoxy-6-dimethylamino-indol-3-yl, 5-acetamido-7-dimethylamino-indol-3-yl, 5-dimethylaminocarbonylindol-3-yl, 5-carboxy-indol-3-yl, 5-acetamido-indol-3-yl, 4-nitro-5-acetamido-indol-3-yl, 5-acetamido-6-nitro-indol-3-yl, 5-nitro-6-acetamido-indol-3-yl, 6-acetamido-7-nitro-indol-3-yl, 4-chloro-5-acetamido-indol-3-yl, 5-acetamido-6-chloro-indol-3-yl, 5-chloro-6-acetamido-indol-3-yl, 6-acetamido-7-chloro-indol-3-yl, 5-dimethylamino-indol-3-yl, 6-dimethylamino-indol-3-yl, 7-dimethylamino-indol-3-yl, 5-dimethylamino-6-chloro-indol-3-yl, 5-chloro-6-dimethylamino-indol-3-yl, 7-benzyl-indol-3-yl, 4-(3,4,5-trimethoxy-benzyl)-indol-3-yl, 5-(3,4,5-trimethoxy-benzyl)-indol-3-yl, 6-(3,4,5-trimethoxy-benzyl)-indol-3-yl, 7-(3,4,5-trimethoxy-benzyl)-indol-3-yl, 4-trifluoromethyl-indol-3-yl, 4-trichloromethyl-indol-3-yl, 4,5-methylenedioxy-indol-3-yl, 4,5-dimethoxy-indol-3-yl, 4,5-dimethyl-indol-3-yl, 5-methyl-6-methoxy-indol-3-yl, 4-methyl-5-methoxy-indol-3-yl, 5-trifluoromethylindol-3-yl, 5-methoxy-7-bromo-indol-3-yl, 5-bromo-7-methoxy-indol-3-yl, 5-bromo-indol-3-yl, 5-chloro-indol-3yl, 5-(3,4,5-trimethoxy-benzyloxy)-indol-3-yl, 6-(3,4,5-trimethoxy-benzyloxy)-indol-3-yl, 5-(3,4,5-trimethoxy-benzylamino)-indol-3-yl, 6-(3,4,5-trimethoxy-benzylamino)-indol-3-yl, 5-(3,5-dichloro-4-amino-benzyloxy)-indol-3-yl, 6-(3,5-dibromo-4-amino-benzyloxy)-indol-3-yl, 5-(3,5-dichloro-4-aminobenzylamino)-indol-3-yl, 6-(3,5-dibromo-4-amino-benzylamino)indol-3-yl, 5-benzyl-indol-3-yl, 4-benzyl-indol-3-yl, 6-benzylindol-3-yl, 5,6,7-trimethoxy-indol-3-yl, 5,6,7-trimethyl-indol-3yl, 5-nitro-indol-3-yl, 4,6-dichloro-5-amino-indol-3-yl, 4,6-dichloro-5-nitro-indol-3-yl, 5,7-dibromo-6-amino-indol-3-yl, 5,7-dibromo-6-nitro-indol-3-yl, 4,6-dichloro-5-methoxy-indol-3-yl, 5,6-dimethoxy-indol-3-yl, 5,7-dimethoxy-indol-3-yl, 6,7-dimethoxy-indol-3-yl, 4,7-dimethoxy-indol-3-yl, 5,6-methylenedioxy-indol-3-yl, 6,7-methylenedioxy-indol-3-yl, 5,6-dimethyl-indol-3-yl, 5,7-dimethyl-indol-3-yl, 6,7-dimethyl-indol-3-yl, 4,7-dimethyl-indol-3-yl, 6-methoxy-7-methyl-indol-3-yl, 4,6-dibromo-5-carboxy-indol-3-yl, 5,7-dichloro-6-carboxy-indol-3yl, 5-ethoxycarbonyl-indol-3-yl, 6-ethoxycarbonyl-indol-3-yl, 4,6-dibromo-5-ethoxycarbonyl-indol-3-yl, 5,7-dichloro-6-ethoxycarbonyl-indol-3-yl, 5-cyano-indol-3-yl, 6-cyano-indol-3yl, 4-cyano-indol-3-yl, 4-hydroxy-indol-3-yl, 7-hydroxy-indol-3yl, 5-phenyl-indol-3-yl, 6-phenyl-indol-3-yl, 5-(3,4,5-tribromophenyl)-indol-3-yl, 6-(3,4,5-trimethoxy-phenyl)-indol-3-yl, 5-(4-trifluoromethyl-phenyl)-indol-3-yl, 6-(3,5-difluoro-4-aminophenyl)-indol-3-yl, 4-phenyl-indol-3-yl, 5-cyclohexyl-indol-3-yl, 5-(2-methoxy-benzyl)-indol-3-yl. 6-(2-methoxy-phenyl)-indol-3-yl, 6-(2,4-dimethyl-benzyl)-indol-3-yl, 5-(2,4-dimethoxy-benzyl)-indol-3-yl, 7-(2-methoxy-benzyloxy)-indol-3-yl, 4-(2,4-dimethylbenzyloxy)-indol-3-yl, 5-(2,4-dimethoxy-benzyloxy)-indol-3-yl, 6-(2-methoxy-benzylamino)-indolyl-3, 5-(2-methoxy-4-methylbenzylamino)-indol-3-yl, 4-(2,4-dimethoxy-benzylamino)-indol-3yl, 5,7-dibromo-6-cyano-indol-2-yl, 5,7-dichloro-6-aminocarbonylindol-2-yl, 4,6-dibromo-5-aminocarbonyl-indol-2-yl, 5,7-dibromo-6-methoxy-indol-2-yl, 5,6-dihydroxy-indol-2-yl, 4-dimethylaminoindol-2-yl, 4-methoxy-6-dimethylamino-indol-2-yl, 4-methyl-6-dimethylamino-indol-2-yl, 5-acetoxy-6-dimethylamino-indol-2-yl, 5-acetamido-7-dimethylamino-indol-2-yl, 5-dimethylamino-carbonylindol-2-yl, 5-carboxy-indol-2-yl, 5-acetamido-indol-2-yl, 4-nitro-5-acetamido-indol-2-yl, 5-acetamido-6-nitro-indol-2-yl, 5-nitro-6-acetamido-indol-2-yl, 6-acetamido-7-nitro-indol-2-yl, 4-chloro-5-acetamido-indol-2-yl, 5-acetamido-6-chloro-indol-2-yl, 5-chloro-6-acetamido-indol-2-yl, 6-acetamido-7-chloro-indol-2-yl, 5-dimethylamino-indol-2-yl, 6-dimethylamino-indol-2-yl, 7-dimethylamino-indol-2-yl, 5-dimethylamino-6-chloro-indol-2-yl, 5-chloro-6-dimethylamino-indol-2-yl, 7-benzyl-indol-2-yl, 4-(3,4,5-trimethoxy-benzyl)-indol-2-yl, 5-(3,4,5-trimethoxy-benzyl)-indol-2-yl, 6-(3,4,5-trimethoxy-benzyl)-indol-2-yl, 7-(3,4,5-trimethoxy-benzyl)-indol-2-yl, 4-trifluoromethyl-indol-2-yl, 4-trichloromethyl-indol-2-yl, 4,5-methylenedioxy-indol-2-yl, 4,5-dimethoxy-indol-2-yl, 4,5-dimethyl-indol-2-yl, 5-methyl-6-methoxy-indol-2-yl, 4-methyl-5-methoxy-indol-2-yl, 5-trifluoromethyl-indol-2-yl, 5-methoxy-7-bromo-indol-2-yl, 5-bromo-7- methoxy-indol-2-yl, 5-bromo-indol-2-yl, 5-chloro-indol-2yl, 5-(3,4,5-trimehhoxy-benzyloxy)-indol-2-yl, 6-(3,4,5-trimethoxy-benzyloxy)-indol-2-yl, 5-(3,4,5-trimethoxy-benzylamino)-indol-2-yl, 6-(3,4,5-trimethoxy-benzylamino)-indol-2-yl, 5-(3,5-dichloro-4-aminobenzyloxy)-indol-2-yl, 6-(3,5-dibromo-4-amino-benzyloxy)-indol-2-yl, 5-(3,5-dichloro-4-amino-benzylamino)-indol-2-yl, 6-(3,5-dibromo-4-amino-benzylamino)-indol-2-yl, 5-benzyl-indol-2-yl, 4-benzyl-indol-2-yl, 6-benzyl-indol-2-yl, 5,6,7-trimethoxy-indol-2-yl, 5,6,7-trimethyl-indol-2yl, 5-nitro-indol-2-yl, 4,6-dichloro-5-amino-indol-2-yl, 4,6-dichloro-5-nitro-indol-2-yl, 5,7-dibromo-6-amino-indol-2-yl, 5,7-dibromo-6-nitro-indol-2-yl, 4,6-dichloro-5-methoxy-indol-2-yl, 5,6-dimethoxy-indol-2-yl, 5,7-dimethoxy-indol-2-yl, 6,7-dimethoxy-indol-2-yl, 4,7-dimethoxy-indol-2-yl, 5,6-methylenedioxy-indol-2-yl, 6,7-methylenedioxy-indol-2-yl, 5,6-dimethyl-indol-2-yl, 5,7-dimethyl-indol-2-yl, 6,7-dimethyl-indol-2-yl, 4,7-dimethyl-indol-2-yl, 6-methoxy-7-methyl-indol-2-yl, 4,6-dibromo-5-carboxy-indol-2-yl, 5,7-dichloro-6-carboxy-indol-2yl, 5-ethoxycarbonyl-indol-2-yl, 6-ethoxycarbonyl-indol-2-yl, 4,6-dibromo-5-ethoxycarbonyl-indol-2-yl, 5,7-dichloro-6-ethoxycarbonyl-indol-2-yl, 5-cyano-indolyl-2, 6-cyano-indol-2-yl, 4-cyano-indol-2-yl, 4-hydroxy-indol-2-yl, 7-hydroxy-indol-2-yl, 5-phenyl-indol-2-yl, 6-phenyl-indol-2-yl, 5-(3,4,5-tribromo-phenyl)-indol-2-yl, 6-(3,4,5-trimethoxy-phenyl)-indol-2-yl, 5-(4-triflurromethyl-phenyl)-indol-2-yl, 6-(3,5-difluoro-4-aminophenyl)-indol-2-yl, 4-phenyl-indol-2-yl, 5-cyclohexyl-indol-2-yl, 5-(2-methoxy-benzyl)-indol-2-yl, 6-(2-methoxy-phenyl)-indol-2-yl, 6-(2,4-dimethyl-benzyl)-indol-2-yl, 5-(2,4-dimethoxy-benzyl)-indol-2-yl, 7-(2-methoxy-benzyloxy)-indol-2-yl, 4-(2,4-dimethyl-benzyloxy)-indol-2-yl, 5-(2,4-dimethoxy-benzyloxy-indol-2-yl, 6-(2-methoxy-benzylamino)-indol-2-yl, 5-(2-methoxy-4-methyl-benzylamino)-indol-2-yl, 4-(2,4-dimethoxy-benzylamino)-indol-2yl, phenyl, 4-methyl-phenyl, 3-methyl-phenyl, 2-methyl-phenyl, 4-ethyl-phenyl, 4-isopropyl-phenyl, 4-cyano-phenyl, 4-trifluoromethyl-phenyl, 2-methoxy-phenyl, 3-methoxy-phenyl, 4-methoxy-phenyl, 2-ethoxy-phenyl, 4-nitro-phenyl, 2-nitro-phenyl, 4-methylamino-phenyl, 4-ethylamino-phenyl, 4-n-propylaminophenyl, 4-dimethylamino-phenyl, 4-diethylamino-phenyl, 4-di-n-propylamino-phenyl, 4-N-ethyl-methylamino-phenyl, 4-formylaminophenyl, 4-acetamido-phenyl, 4-propionyl-amino-phenyl, 3,4-methylenedioxy-phenyl, 3,4-diethylenedioxy-phenyl, 3,4-dimethoxyphenyl, 3,5-dimethoxy-phenyl, 2,6-dimethoxy-phenyl, 2,4-dimethoxy-phenyl, 3,4-diethoxyphenyl, 3,4-dimethyl-phenyl, 3,5-dimethyl-phenyl, 2,6-dimethyl-phenyl, 2,4-dimethyl-phenyl, 3,4-diethyl-phenyl, 2,4-dichloro-phenyl, 2,4-dibromo-phenyl, 3-methyl-4-methoxy-phenyl, 3-methoxy-4-methyl-phenyl, 3-chloro-4-methyl-phenyl, 3-bromo-4-methyl-phenyl, 3-chloro-4-methoxyphenyl, 3-bromo-4-methoxy-phenyl, 3-methyl-4-chloro-phenyl, 3-methyl-4-bromo-phenyl, 3-methoxy-4-chloro-phenyl, 3-methoxy-4-bromo-phenyl, benzyloxy, naphth-1-yl, naphth-2-yl, 2-methyl-naphth-1-yl, 6-methoxy-naphth-2-yl, 7-methoxy-naphth-2-yl, 5-methyl-6-methoxy-naphth-2-yl, 5,6-dimethoxy-naphth-2-yl, 5,6-dichloro-naphth-2-yl, 5,6-dimethoxy-naphth-1-yl, 5,6-dichloro-naphth-1-yl, 6-methoxy-naphth-1-yl, 5-methyl-6-methoxy-naphth-1yl, 6-nitro-naphth-1-yl, 6-nitro-naphth-2-yl, 6-methoxy-5-nitro-naphth-1-yl, 6-methoxy-5-nitro-naphth-2-yl, 6-amino-naphth-2-yl, 4-methoxy-naphth-1-yl, 5,6-diethoxy-naphth-2-yl, 5,6-di-n-propoxy-naphth-2-yl, 6-chloro-naphth-1-yl, 6-chloro-naphth-2-yl, 6-chloro-7-nitro-naphth-2-yl, 6-chloro-7-amino-naphth-2-yl, 6-chloro-7-acetamido-naphth-2-yl, 5,6-methylenedioxy-naphth-2-yl, 5-chloro-6-methoxy-naphth-2-yl, 6-ethyl-naphth-2-yl, 6-methylmercapto-naphth-2-yl or 6-isopropyl-naphth-2-yl group.

Thus, according to the invention, the following compounds are exemplary of those covered by formula I above:

A. Compounds wherein A, B, G, m, n and R are selected from option (i)

3-[(N-(2-(3,4-dimethoxy-phenyl)-ethyl)-piperidin-3-yl)-methyl]-7,8-dimethoxy-1,3,4,5-tetrahydro-2H-3-benzazepin-2-one;

3-[(N-(2-(3,4-dimethoxy-phenyl)-ethyl)-piperidin-3-yl)methyl]-7,8-dimethoxy-1,3-dihydro-2H-3-benzazepin-2-one;

3-[(N-(2-(3,4-dimethoxy-phenyl)-ethyl)-piperidin-3-yl)methyl]-7,8-dimethoxy-2,3,4,5-tetrahydro-1H-3-benzazepine 3-[(N-(2-(3,4-dimethoxy-phenyl)-ethyl)-piperidin-3-yl)methyl]-7,8-dimethoxy-1,3,4,5-tetrahydro-2H-3-benzazepin-2thione;

3-[(N-(2-(3,4-dimethoxy-phenyl)-ethyl)-piperidin-3-yl)methyl]-7,8-dimethoxy-1,3,4,5-tetrahydro-2H-3-benzazepin-1,2dione;

3-[(N-(2-(3,4-dimethoxy-phenyl)-ethyl)-piperidin-3-yl)methyl]-7,8-dimethoxy-1-hydroxy-1,3,4,5-tetrahydro-2H-3-benzazepin-2-one;

3-[(N-(2-(4-amino-phenyl)-ethyl)-piperidin-3-yl)-methyl]-7,8-dimethoxy-1,3,4,5-tetrahydro-2H-3-benzazepin-2-one;

3-[(N-(2-(4-acetamino-phenyl)-ethyl)-piperidin-3 -yl)-methyl]-7,8-dimethoxy-1,3,4,5-tetrahydro-2H-3-benzazepin-2-one;

3-[(N-(3-(4-amino-3,5-dibromo-phenoxy)-propyl)-piperidin-3-yl)-methyl]-7,8-dimethoxy-1,3,4,5-tetrahydro-2H-3-benzazepin-2one;

3-[(N-(2-(3,4-dimethoxy-phenyl)-ethyl)-piperidin-3-yl)methyl]-7,8-methylenedioxy-1,3,4,5-tetrahydro-2H-3-benzazepin-2one;

3-[(N-(3,4-dimethoxy-benzyl)-piperidin-3-yl)-methyl]-7,8-methylenedioxy-1,3,4,5-tetrahydro-2H-3-benzazepin-2-one;

3-[(N-(2-phenylethyl)-piperidin-3-yl)-methyl]-7,8-dimethoxy-1,3,4,5-tetrahydro-2H-3-benzazepin-2-one;

3-[(N-(2-(3-nitro-4-acetamino-phenyl)-ethyl)-piperidin-3-yl)-methyl]-7,8-dimethoxy-1,3,4,5-tetrahydro-2H-3-benzazepin-2one;

3-[(N-(2-(3,4,5-trimethoxy-phenyl)-ethyl)-piperidin-3-yl)methyl]-7,8-dimethoxy-1,3,4,5-tetrahydro-2H-3-benzazepin-2-one;

3-[(N-(3-(4-methoxy-phenyl)-propyl)-piperidin-3-yl)-methyl]-7,8-dimethoxy-1,3,4,5-tetrahydro-2H-3-benzazepin-2-one;

3-[(N-(2-(4-methoxy-phenyl)-ethyl)-piperidin-3-yl)-methyl]-7,8-dimethoxy-1,3,4,5-tetrahydro-2H-3-benzazepin-2-one;

3-[(n-(2-(4-nitro-phenyl)-ethyl)-piperidin-3-yl)-methyl]-7,8-dimethoxy-1,3,4,5-tetrahydro-2H-3-benzazepin-2-one;

3-[(N-(2-(3-methyl-phenyl)-ethyl)-piperidin-3-yl)-methyl]-7,8-dimethoxy-1,3,4,5-tetrahydro-2H-3-benzazepin-2-one;

3-[(N-(2-(3-methoxy-phenyl)-ethyl)-piperidin-3-yl)-methyl]-7,8-dimethoxy-1,3,4,5-tetrahydro-2H-3-benzazepin-2-one;

3-[(N-(2-(4-methyl-phenyl)-ethyl)-piperidin-3-yl)-methyl]-7,8-dimethoxy-1,3,4,5-tetrahydro-2H-3-benzazepin-2-one;

3-[(N-(3-(4-bromo-phenyl)-propyl)-piperidin-3-yl)-methyl]-7,8-dimethoxy-1,3,4,5-tetrahydro-2H-3-benzazepin-2-one;

3-[(N-(2-(3,4-dimethoxy-phenyl)-ethyl)-piperidin-3-yl)methyl]-7,8-dimethoxy-1,3-dihydro-2H-3-benzazepin-2-one;

3-[(N-(2-(3,4-dimethoxy-phenyl)-ethyl)-piperidin-2-yl)ethyl-2]-7,8-dimethoxy-1,3,4,5-tetrahydro-2H-3-benzazepin-2-one;

3-[(N-(2-(3,4-dimethoxy-phenyl)-ethyl)-hexahydro-azepin-2-yl)-ethyl-2]-7,8-dimethoxy-1,3,4,5-tetrahydro-2H-3-benzazepin-2one;

3-[(N-(3-(4-amino-3,5-dibromo-phenoxy)-propyl)-hexahydro-azepin-3-yl)-methyl]-7,8-dimethoxy-1,3,4,5-tetrahydro-2H-3-benzazepin-2-one;

3-[(N-(2-(3,4-dimethoxy-phenyl)-ethyl)-hexahydro-azepin-2-yl)-ethyl-2]-7,8-dimethoxy-1,3-dihydro-2H-3-benzazepin-2-one;

3-[(N-(2-(3,4-methylenedioxy-phenyl)-ethyl)-piperidin-3-yl)methyl]-7,8-methylenedioxy-1,3,4,5-tetrahydro-2H-3-benzazepin-2one;

3-[(N-(3,4-dichloro-benzyl)-piperidin-3-yl)-methyl]-7,8-methylenedioxy-1,3,4,5-tetrahydro-2H-3-benzazepin-2-one;

3-[(N-(2-(3,4-dimethoxy-phenyl)-ethyl)-pyrrolidin-3-yl)methyl]-7,8-dimethoxy-1,3-dihydro-2H-3-benzazepin-2-one;

3-[(N-(2-(3,4-dimethoxy-phenyl)-ethyl)-pyrrolidin-3-yl)methyl]-7,8-dimethoxy-1,3,4,5-tetrahydro-2H-3-benzazepin-2-one;

3-[(N-(3-(3-methoxy-phenoxy)-propyl)-piperidin-3-yl)methyl]-7,8-methylenedioxy-1,3,4,5-tetrahydro-2H-3-benzazepin-2-one;

3-[(N-(3-(3-methyl-phenoxy)-propyl)-piperidin-3-yl)-methyl]-7,8-methylenedioxy-1,3,4,5-tetrahydro-2H-3-benzazepin-2-one;

3-[(N-(2-(4-amino-3,5-dichloro-phenyl)-ethyl)-piperidine-3-yl)-methyl]-7,8-dimethoxy-1,3,4,5-tetrahydro-2H-3-benzazepin-2-one;

3-[(N-(3,4-methylenedioxy-phenoxy)-propyl)-piperidin-3-yl)methyl]-7,8-methylenedioxy-1,3,4,5-tetrahydro-2H-3-benzazepin-2-one;

3-[(N-(4-(4-methoxy-phenyl)-butyl)-piperidin-3-yl)-methyl]-7,8-methylenedioxy-1,3,4,5-tetrahydro-2H-3-benzazepin-2-one;

3-[(N-(2-(4-methoxy-phenyl)-ethyl)-piperidin-3-yl)-methyl]-7,8-methylenedioxy-1,3,4,5-tetrahydro-2H-3-benzazepin-2-one;

3-[(N-(2-(phenoxy)-ethyl)-piperidin-3-yl)-methyl]-7,8-methylenedioxy-1,3,4,5-tetrahydro-2H-3-benzazepin-2-one;

3-[(N-(2-(4-methoxy-phenyl)-ethyl)-piperidin-2-yl)-ethyl-2]-7,8-methylenedioxy-1,3,4,5-tetrahydro-2H-3-benzazepin-2-one;

3-[(N-(4-methoxy-phenyl)-methyl)-piperidin-2-yl)-ethyl-2]7,8-methylenedioxy-1,3,4,5-tetrahydro-2H-3-benzazepin-2-one;

3-[(N-(3,4-dimethoxy-phenyl)-methyl)-piperidin-2-yl)-ethyl-2]-7,8-methylenedioxy-1,3,4,5-tetrahydro-2H-3-benzazepin-2-one;

3-[(N-(2-(4-nitro-phenyl)-ethyl)-piperidin-2-yl)-ethyl-2]-7,8-methylenedioxy-1,3,4,5-tetrahydro-2H-3-benzazepin-2-one;

3-[(N-(2-(3-trifluoromethylphenyl)-ethyl)-piperidin-3-yl)methyl]-7,8-dimethoxy-1,3,4,5-tetrahydro-2H-3-benzazepin-2-one;

3-[(N-(3-(3,5-dimethoxy-phenoxy)-propyl)-piperidin-2-yl)ethyl]-7,8-methylenedioxy-1,3,4,5-tetrahydro-2H-3-benzazepin-2-one;

3-[(N-(2-(3-methoxy-4-methanesulphonyloxy-phenyl)-ethyl)piperidin-3-yl)-methyl]-7,8-dimethoxy-1,3,4,5-tetrahydro-2H-3-benzazepin-2-one;

3-[(N-(2-(4-benzyloxy-3-methoxy-phenyl)-ethyl)-piperidin-3-yl)-methyl]-7,8-dimethoxy-1,3,4,5-tetrahydro-2H-3-benzazepin-2-one;

3-[N-(2-(2-fluorophenyl)-ethyl)-piperidin-3-yl)-methyl]-7,8-dimethoxy-1,3,4,5-tetrahydro-2H-3-benzazepin-2-one;

3-[N-(2-(4-fluorophenyl)-ethyl)-piperidin-3-yl)-methyl]-7,8-dimethoxy-1,3,4,5-tetrahydro-2H-3-benzazepin-2-one;

3-[(N-(2-(3,4-dimethoxy-phenyl)-ethyl)-hexahydro-azepin-2-yl)-ethyl-2]-1,3,4,5-tetrahydro-2H-3-benzazepin-2-one;

3-[(N-(2-(4-amino-phenyl)-ethyl)-piperidin-2-yl)-ethyl-2]-7,8-dimethoxy-1,3,4,5-tetrahydro-2H-3-benzazepin-2-one;

3-[(N-(3-(4-amino-3,5-dibromo-phenoxy)-propyl)-piperidin-2-yl)-ethyl-2]-7,8-dimethoxy-1,3,4,5-tetrahydro-2H-3-benzazepin-2-one;

3-[(N-(3,4-dimethoxy-benzyl)-piperidin-2-yl)-ethyl-2]-7,8 -dimethoxy-1,3,4,5-tetrahydro-2H-3-benzazepin-2-one;

3-[(N-(2-phenylethyl)-piperidin-2-yl)-ethyl-2]-7,8-dimethoxy-1,3,4,5-tetrahydro-2H-3-benzazepin-2-one;

3-[(N-(2-(3,4,5-trimethoxy-phenyl)-ethyl)-piperidin-2-yl)-ethyl-2]-7,8-dimethoxy-1,3,4,5-tetrahydro-2H-3-benzazepin-2-one;

3-[(N-(3-(4-methoxy-phenyl)-propyl)-piperidin-2-yl)-ethyl-2]-7,8-dimethoxy-1,3,4,5-tetrahydro-2H-3-benzazepin-2-one;

3-[(N-(2-(4-methoxy-phenyl)-ethyl)-piperidin-2-yl)-ethyl-2]-7,8-dimethoxy-1,3,4,5-tetrahydro-2H-3-benzazepin-2-one;

3-[(N-(2-(4-nitro-phenyl)-ethyl)-piperidin-2-yl)-ethyl-2]-7,8-dimethoxy-1,3,4,5-tetrahydro-2H-3-benzazepin-2-one;

3-[N-(2-(3-methyl-phenyl)-ethyl)-piperidin-2-yl)-ethyl-2]-7,8-dimethoxy-1,3,4,5-tetrahydro-2H-3-benzazepin-2-one;

3-[(N-(2-(3-methoxy-phenyl)-ethyl)-piperidin-2-yl)-ethyl-2]-7,8-dimethoxy-1,3,4,5-tetrahydro-2H-3-benzazepin-2-one;

3-[(N-(2-(4-methyl-phenyl)-ethyl)-piperidin-2-yl)-ethyl-2]-7,8-dimethoxy-1,3,4,5-tetrahydro-2H-3-benzazepin-2-one;

3-[(N-(3-(4-bromo-phenyl)-propyl)-piperidin-2-yl)-ethyl-2]-7,8-dimethoxy-1,3,4,5-tetrahydro-2H-3-benzazepin-2-one;

3-[(N-(2-(3,4-dimethoxy-phenyl)-ethyl)-piperidin-2-yl)-ethyl-2]-7,8-dimethoxy-1,3,4,5-tetrahydro-2H-3-benzazepin-2-one;

3-[(N-(2-(3,4-dimethoxy-phenyl)-ethyl)-piperidin-3-yl)methyl]-7-methoxy-1,3,4,5-tetrahydro-2H-3-benzazepin-2-one;

3-[(N-(2-(3,4-dimethoxy-phenyl)-ethyl)-piperidin-3-yl)methyl]-7-trifluoromethyl-1,3,4,5-tetrahydro-2H-3-benzazepin-2-one;

3-[(N-(2-(3,4-dimethoxy-phenyl)-ethyl)-piperidin-3-yl)methyl]-7-methylamino-1,3,4,5-tetrahydro-2H-3-benzazepin-2-one;

3-[(N-(2-(3,4-dimethoxy-phenyl)-ethyl)-piperidin-3-yl)methyl]-7-dimethylamino-1,3,4,5-tetrahydro-2H-3-benzazepin-2-one;

3-[(N-(2-(3,4-dimethoxy-phenyl)-ethyl)-piperidin-3-yl)methyl]-7,8-dichloro-1,3,4,5-tetrahydro-2H-3-benzazepin-2-one;

3-[(N-(2-(3,4-dimethoxy-phenyl)-ethyl)-piperidin-3-yl)methyl]-7-methylamino-8-methoxy-1,3,4,5-tetrahydro-2H-3-benzazepin-2-one;

3-[(N-(2-(3,4-dimethoxy-phenyl)-ethyl)-piperidin-3-yl)methyl]-7-bromo-8-methoxy-1,3,4,5-tetrahydro-2H-3-benzazepin-2one;

3-[(N-(2-(3,4-dimethoxy-phenyl)-ethyl)-piperidin-3-yl)methyl]-7-chloro-8-methoxy-1,3,4,5-tetrahydro-2H-3-benzazepin-2one;

3-[(N-(2-(3,4-dimethoxy-phenyl)-ethyl)-piperidin-3-yl)methyl]-7-hydroxy-8-methoxy-1,3,4,5-tetrahydro-2H-3-benzazepin-2one;

3-[(N-(2-phenylethyl)-piperidin-3-yl)-methyl]-7-methoxy-1,3,4,5-tetrahydro-2H-3-benzazepin-2-one;

3-[(N-(2-phenylethyl)-piperidin-3-yl)-methyl]-7-trifluoromethyl-1,3,4,5-tetrahydro-2H-3-benzazepin-2-one;

3-[(N-(2-phenylethyl)-piperidin-3-yl)-methyl]-7-methylamino-1,3,4,5-tetrahydro-2H-3-benzazepin-2-one;

3-[(N-(2-phenylethyl)-piperidin-3-yl)-methyl]-7-dimethylamino-1,3,4,5-tetrahydro-2H-3-benzazepin-2-one;

3-[(N-(2-phenylethyl)-piperidin-3-yl)-methyl]-7,8-dichloro-1,3,4,5-tetrahydro-2H-3-benzazepin-2-one;

3-[(N-(2-phenylethyl)-piperidin-3-yl)-methyl]-7-methylamino-8-methoxy-1,3,4,5-tetrahydro-2H-3-benzazepin-2-one;

3-[(N-(2-phenylethyl)-piperidin-3-yl)-methyl]-7-bromo-8-methoxy-1,3,4,5-tetrahydro-2H-3-benzazepin-2-one;

3-[(N-(2-phenylethyl)-piperidin-3-yl)-methyl]-7-chloro-8-methoxy-1,3,4,5-tetrahydro-2H-3-benzazepin-2-one;

3-[(N-(2-phenylethyl)-piperidin-3-yl)-methyl]-7-hydroxy-8-methoxy-1,3,4,5-tetrahydro-2H-3-benzazepin-2-one;

3-[(N-(3-(3,4-dimethoxy-phenyl)-propyl)-piperidin-3-yl)methyl]-7,8-dimethoxy-1,3,4,5-tetrahydro-2H-1,3-benzodiazepin-2one;

3-[(N-(2-(3,4-dimethoxy-phenyl)-ethyl)-piperidin-3-yl)methyl]-7,8-dimethoxy-1,3,4,5-tetrahydro-2H-1,3-benzodiazepin-2one;

3-[(N-(2-(3,4-methylenedioxy-phenyl)-ethyl)-piperidin-3-yl)methyl]-7,8-dimethoxy-1,3,4,5-tetrahydro-2H-1,3-benzodiazepin-2one;

3-[(N-(2-(3-methoxy-phenyl)-ethyl)-piperidin-3-yl)-methyl]-7,8-dimethoxy-1,3,4,5-tetrahydro-2H-1,3-benzodiazepin-2-one;

3-[(N-(2-(4-methoxy-phenyl)-ethyl)-piperidin-3-yl)-methyl]-7,8-dimethoxy-1,3,4,5-tetrahydro-2H-1,3-benzodiazepin-2-one;

3-[(N-(2-(2-methoxy-phenyl)-ethyl)-piperidin-3-yl)-methyl]-7,8-dimethoxy-1,3,4,5-tetrahydro-2H-1,3-benzodiazepin-2-one;

3-[(N-(2-(N-(3,4-dimethoxy-phenyl)-methylamino)-ethyl))-piperidin-3-yl)-methyl]-7,8-dimethoxy-1,3,4,5-tetrahydro-2H-1,3-benzodiazepin-2-one;

3-[(N-(3-(3,4-dimethoxy-phenylthio)-propyl)-piperidin-3-yl)methyl]-7,8-dimethoxy-1,3,4,5-tetrahydro-2H-3-benzazepin-2-one;

3-[(N-(2-phenylthioethyl)-piperidin-3-yl)-methyl]-7,8-dimethoxy-1,3,4,5-tetrahydro-2H-3-benzazepin-2-one;

3-[(N-(2-phenylaminoethyl)-piperidin-3-yl)-methyl]-7,8-dimethoxy-1,3,4,5-tetrahydro-2H-3-benzazepin-2-one;

3-[(N-(2-phenoxyethyl)-piperidin-3-yl)-methyl]-7,8-dimethoxy-1,3,4,5-tetrahydro-2H-3-benzazepin-2-one;

3-[(N-(2-(3,5-dichloro-4-methoxy-phenoxy)-ethyl)-piperidin-3-yl)-methyl]-7,8-dimethoxy-1,3,4,5-tetrahydro-2H-3-benzazepin-2one;

3-[(N-(2-(3,4-dimethoxy-phenylamino)-ethyl)-piperidin-3-yl)methyl]-7,8-dimethoxy-1,3,4,5-tetrahydro-2H-3-benzazepin-2-one;

3-[(N-(3-(3,4-dimethoxy-phenylsulphinyl)-propyl)-piperidin-3-yl)-methyl]-7,8-dimethoxy-1,3,4,5-tetrahydro-2H-3-benzazepin-2-one;

3-[(N-(3-(3,4-dimethoxy-phenylsulphonyl)-propyl)-piperidin-3-yl)-methyl]-7,8-dimethoxy-1,3,4,5-tetrahydro-2H-3-benzazepin-2one;

3-[(N-(3-(4-dimethylamino-phenoxy)-propyl)-piperidin-3-yl)methyl]-7,8-dimethoxy-1,3,4,5-tetrahydro-2H-3-benzazepin-2-one;

3-[(N-(2-(4-amino-3,5-dibromo-phenylsulphonyl)-ethyl)-piperidin-3-yl)-methyl]-7,8-dimethoxy-1,3,4,5-tetrahydro-2H-3-benzazepin-2-one;

3-[(N-(2-(4-amino-3,5-dibromo-phenylsulphinyl)-ethyl)-piperidin-3-yl)-methyl]-7,8-dimethoxy-1,3,4,5-tetrahydro-2H-3-benzazepin-2-one;

3-[(N-(2-(4-amino-3,5-dibromo-phenylthio)-ethyl)-piperidin-3-yl)-methyl]-7,8-dimethoxy-1,3,4,5-tetrahydro-2H-3-benzazepin-2one;

3-[(N-(2-(3,4-dichloro-phenoxy)-ethyl)-piperidin-3-yl)methyl]-7,8-dimethoxy-1,3,4,5-tetrahydro-2H-3-benzazepin-2-one;

3-[(N-(2-(3,4-dimethoxy-phenoxy)-ethyl)-piperidin-3-yl)methyl]-7,8-dimethoxy-1,3,4,5-tetrahydro-2H-3-benzazepin-2-one;

3-[(N-(3-(N-phenyl-N-methyl-amino)-propyl)-piperidin-3-yl)methyl]-7,8-dimethoxy-1,3,4,5-tetrahydro-2H-3-benzazepin-2-one;

3-[(N-(2-(4-methoxy-phenoxy)-ethyl)-piperidin-3-yl)-methyl-7,8-dimethoxy-1,3,4,5-tetrahydro-2H-3-benzazepin-2-one;

3-[N-(2-(3,4-methylenedioxy-phenoxy)-ethyl)-piperidin-3-yl)methyl]-7,8-dimethoxy-1,3,4,5-tetrahydro-2H-3-benzazepin-2-one;

3-[(N-(3-(4-amino-3,5-dichloro-phenylamino)-propyl)-piperidin-3-yl)-methyl]-7,8-dimethoxy-1,3,4,5-tetrahydro-2H-3-benzazepin-2-one;

3-[(N-(2-(4-hydroxy-3-methoxy-phenyl)-ethyl)-piperidin-3-yl)-methyl]-7,8-dimethoxy-1,3,4,5-tetrahydro-2H-3-benzazepin-2one;

3-[(N-(2-(3,4-dimethoxy-phenyl)-ethyl)-pyrrolidin-3-yl)methyl]-7,8-dimethoxy-1,3,4,5-tetrahydro-2H-3-benzazepin-2-one;

3-[(N-(2-(3,4-dimethoxy-phenyl)-ethyl)-pyrrolidin-2-yl)-ethyl-2]-7,8-dimethoxy-1,3,4,5-tetrahydro-2H-3-benzazepin-2-one;

3-[(N-(3-(4-amino-3,5-dibromo-phenoxy)-propyl-pyrrolidin-3-yl)-methyl]-7,8-dimethoxy-1,3,4,5-tetrahydro-2H-3-benzazepin-2one;

3-[(N-(3-(4-methoxy-phenyl)-propyl)-pyrrolidin-3-yl)methyl]-7,8-dimethoxy-1,3,4,5-tetrahydro-2H-3-benzazepin-2-one;

3-[(N-(2-(4-methoxy-phenyl)-ethyl)-pyrrolidin-3-yl)-methyl]-7,8-dimethoxy-1,3,4,5-tetrahydro-2H-3-benzazepin-2-one;

3- (N-(2-(3-methyl-phenyl)-ethyl)-pyrrolidin-3-yl)-methyl]-7,8-dimethoxy-1,3,4,5-tetrahydro-2H-3-benzazepin-2-one;

3-[(N-(2-(3-methoxy-phenyl)-ethyl)-pyrrolidin-3-yl)-methyl]-7,8-dimethoxy-1,3,4,5-tetrahydro-2H-3-benzazepin-2-one;

3-[(N-(2-(4-nitro-phenyl)-ethyl)-pyrrolidin-3-yl)-methyl]-7,8-dimethoxy-1,3,4,5-tetrahydro-2H-3-benzazepin-2-one;

3-[(N-(3-(4-bromo-phenyl)-propyl)-pyrrolidin-3-yl)-methyl]-7,8-dimethoxy-1,3,4,5-tetrahydro-2H-3-benzazepin-2-one;

3-[(N-(3-(4-bromo-phenyl)-propyl)-hexahydro-azepin-3-yl)-methyl]-7,8-dimethoxy-1,3,4,5-tetrahydro-2H-3-benzazepin-2-one;

3-[(N-(2-(4-nitro-phenyl)-ethyl)-hexahydro-azepin-3-yl)-methyl]-7,8-dimethoxy-1,3,4,5-tetrahydro-2H-3-benzazepin-2-one;

3-[(N-(2-(4-nitro-phenyl)-ethyl)-hexahydro-azepin-3-yl)-methyl]-7,8-dimethoxy-1,3,4,5-tetrahydro-2H-3-benzazepin-2-one;

3-[(N-(2-(4-nitro-phenyl)-ethyl)-hexahydro-azepin-3-yl)-methyl]-7,8-dimethoxy-1,3,4,5-tetrahydro-2H-3-benzazepin-2-one;

3-[(N-(2-phenylethyl)-hexahydro-azepin-3-yl)-methyl]-7,8-dimethoxy-1,3,4,5-tetrahydro-2H-3-benzezepin-2-one;

3-[(N-(2-phenylethyl)-hexahydro-azepin-2-yl)-ethyl-2]-7,8-dimethoxy-1,3,4,5-tetrahydro-2H-3-benzazepin-2-one;

3-[(N-(2-(3-methyl-phenyl)-ethyl)-hexahydro-azepin-2-yl)-ethyl]-7,8-methylenedioxy-1,3,4,5-tetrahydro-2H-3-benzazepin-2-one; and, 3-[(N-(2-(4-fluoro-phenyl)-ethyl)-hexahydro-azepin-2-yl)-ethyl-2]-7,8-methylenedioxy-1,3,4,5-tetrahydro-2H-3-benzazepin-2-one.

B. Compounds wherein A, B, G, m, n and R are selected from option (ii)

2-[(N-(2-naphth-2yl)-ethyl)-hexahydro-azepin-3-yl)-methyl]-6,7-dimethoxy-1,2,3,4-tetrahydro-isoquinoline;

2-[(N-(2-(naphth-2-yl)-ethyl)-azacyclooct-3-yl)-methyl]-6,7-dimethoxy-1,2,3,4-tetrahydro-isoquinoline;

2-[(N-(2-(naphth-1-yl)-ethyl)-hexahydro-azepin-3-yl)-methyl]-6,7-dimethoxy-1-oxo-1,2,3,4-tetrahydro-isoquinoline;

2-[(N-(2-(naphth-1-yl)-ethyl)-azacyclooct-3-yl)-methyl]-6,7-dimethoxy-1-oxo-1,2,3,4-tetrahydro-isoquinoline;

2-[(N-(2-methyl-haphth-1-yl)-methyl)-pyrrolidin-3-yl)-methyl]-6,7-dimethoxy-1-oxo-1,2,3,4-tetrahydro-isoquinoline;

2-[3-(N-(2-methyl-naphth-1-yl)-methyl)-piperidin-3-yl)-propyl]-6,7-dimethoxy-1-oxo-1,2,3,4-tetrahydro-isoquinoline;

2-[(N-(2-(5-methyl-6-methoxy-naphth-2-yl)-ethyl)-pyrrolidin-3-yl)-methyl]-6,7-dimethoxy-1,2,3,4-tetrahydro-isoquinoline;

2-[(N-(2-(5-methyl-6-methoxy-naphth-2-yl)-ethyl)-azacyclooct-3-yl)-methyl]-6,7-dimethoxy-1-oxo-1,2,3,4-tetrahydro-isoquinoline;

2-[(N-(2-(6-methoxy-naphth-2-yl)-ethyl)-hexahydro-azepin-3-yl)-methyl]-6,7-dimethoxy-1-oxo-1,2,3,4-tetrahydro-isoquinoline;

2-[(N-(2-(6-methoxy-naphth-2-yl)-ethyl)-azacyclooct-3-yl)-methyl]-6,7-dimethoxy-1-oxo-1,2,3,4-tetrahydro-isoquinoline;

2-[3-(N-(2-(6-methoxy-naphth-2-yl)-ethyl)-pyrid-3-yl)-propyl]-6,7-dimethoxy-1-oxo-1,2,3,4-tetrahydro-isoquinoline;

2-[(N-(4-(naphthyl-2-oxy)-butyl)-azacyclooct-3-yl)-methyl]-6,7-dimethoxy-1,2,3,4-tetrahydro-isoquinoline;

2-[2-(N-(4-(naphthyl-2-oxy)-butyl)-piperidin-2-yl)-ethyl]-6,7-dimethoxy-1-oxo-1,2,3,4-tetrahydro-isoquinoline;

2-[(N-(3-(naphthyl-2-oxy)-propyl)-azacyclooct-3-yl)-methyl]-6,7-dimethoxy-1-oxo-1,2,3,4-tetrahydro-isoquinoline;

2-[(N-(3-(naphth-2-yl)-propyl)-piperidin-3-yl)-methyl]-6,7-dimethoxy-1,2,3,4-tetrahydro-isoquinoline;

2-[(N-(3-(naphth-2-yl)-propyl)-azacyclooct-3-yl)-methyl]-6,7-dimethoxy-1-oxo-1,2,3,4-tetrahydro isoquinoline;

2-[(N-(2-(naphth-2-yl)-ethyl)-piperidin-3-yl)-methyl]-6,7-methylenedioxy-1,2,3,4-tetrahydro-isoquinoline;

2-[(N-(2-(naphth-2-yl)-ethyl)-azacyclooct-3-yl)-methyl]-6,7-methylenedioxy-1,2,3,4-tetrahydro-isoquinoline;

2-[(N-(2-methyl-naphth-1-yl)-methyl)-pyrrolidin-3-yl)methyl]-6,7-methylenedioxy-1-oxo-1,2,3,4-tetrahydro-isoquinoline;

2-[(N-(2-methyl-naphth-1-yl)-methyl)-piperidin-3-yl)methyl]-6,7-methylenedioxy-1,2,3,4-tetrahydro-isoquinoline;

2-[(N-(2-methyl-naphth-1-yl)-methyl)-azacyclooct-3-yl)methyl]-6,7-methylenedioxy-1-oxo-1,2,3,4-tetrahydro-isoquinoline;

2-[(N-(2-(5-methyl-6-methoxy-naphth-2-yl)-ethyl)-azacyclooct-3-yl)-methyl]-6,7-methylenedioxy-1-oxo-1,2,3,4-tetrahydro-isoquinoline;

2-[2-(N-(2-(5-methyl-6-methoxy-naphth-2-yl)-ethyl)-piperidin-3-yl)-methyl]-6,7-methylenedioxy-1-oxo-1,2,3,4-tetrahydro-isoquinoline;

2-[(N-(2-(6-methoxy-naphth-2-yl)-ethyl)-piperidin-3-yl)methyl]-6,7-methylenedioxy-1-oxo-1,2,3,4-tetrahydro-isoquinoline;

2-[(N-(4-(naphthyl-2-oxy)-butyl)-pyrrolidin-3 -yl)-methyl]-6,7-methylenedioxy-1-oxo-1,2,3,4-tetrahydro-isoquinoline;

2-[(N-(4-(naphthyl-2-oxy)-butyl)-piperidin-3-yl)-methyl]-6,7-methylenedioxy-1-oxo-1,2,3,4-tetrahydro-isoquinoline;

2-[(N-(4-(naphthyl-2-oxy)-butyl)-hexahydro-azepin-3-yl)methyl]-6,7-methylenedioxy-1,2,3,4-tetrahydro-isoquinoline;

2-[(N-(2-(naphth-2-yl)-ethyl)-pyrrolidin-3-yl)-methyl]-6,7-dimethyl-1-oxo-1,2,3,4-tetrahydro-isoquinoline;

2-[(N-(2-(naphth-2-yl)-ethyl)-piperidin-3-yl)-methyl]-6,7-dimethyl-1,2,3,4-tetrahydro-isoquinoline;

2-[(N-(2-(naphth-2-yl)-ethyl)-azacyclooct-3-yl)-methyl]-6,7-dimethyl-1-oxo-1,2,3,4-tetrahydro-isoquinoline;

2-[(N-(2-(naphth-2-yl)-ethyl)-azacyclooct-3-yl)-methyl]-6,7-dimethyl-1,2,3,4-tetrahydro-isoquinoline;

2-[(N-(2-(naphth-1-yl)-ethyl)-pyrrolidin-3-yl)-methyl]-6,7-dimethyl-1,2,3,4-tetrahydro-isoquinoline;

2-[(N-(2-(naphth-1-yl)-ethyl)-hexahydro-azepin-3-yl)methyl]-6,7-dimethyl-1,2,3,4-tetrahydro-isoquinoline;
2-[3-(N-(2-(naphth-1-yl)-ethyl)-piperidin-3-yl)-propyl]-6,7-dimethyl-1-oxo-1,2,3,4-tetrahydro-isoquinoline;
2-[(N-(2-methyl-naphth-1-yl)-methyl)-piperidin-3-yl)methyl]-6,7-dimethyl-1-oxo-1,2,3,4-tetrahydro-isoquinoline;
2-[(N-(2-methyl-naphth-1-yl)-methyl)-piperidin-3-yl)methyl]-6,7-dimethyl-1,2,3,4-tetrahydro-isoquinoline;
2-[(N-(2-methyl-naphth-1-yl)-methyl)-azacyclooct-3-yl)methyl]-6,7-dimethyl-1-oxo-1,2,3,4-tetrahydro-isoquinoline;
2-[2-(N-(2-methyl-naphth-1-yl)-methyl)-piperidin-2-yl)ethyl]-6,7-dimethyl-1-oxo-1,2,3,4-tetrahydro-isoquinoline;
2-[(N-(2-(5-methyl-6-methoxy-naphth-2-yl)-ethyl)-piperidin-3-yl)-methyl]-6,7-dimethyl-1-oxo-1,2,3,4-tetrahydro-isoquinoline;
2-[(N-(2-(5-methyl-6-methoxy-naphth-2-yl)-ethyl)-hexahydro-azepin-3-yl)-methyl]-6,7-dimethyl-1-oxo-1,2,3,4-tetrahydroisoquinoline;
2-[(N-(2-(5-methyl-6-methoxy-naphth-2-yl)-ethyl)-azacyclooct-3-yl)-methyl]-6,7-dimethyl-1-oxo-1,2,3,4-tetrahydroisoquinoline;
2-[(N-(2-(5-methyl-6-methoxy-naphth-2-yl)-ethyl)-azacyclooct-3-yl)-methyl]-6,7-dimethyl-1,2,3,4-tetrahydroisoquinoline;
2-[(N-(2-(6-methoxy-naphth-2-yl)-ethyl)-pyrrolidin-3-yl)methyl]-6,7-dimethyl-1,2,3,4-tetrahydro-isoquinoline;
2-[(N-(2-(6-methoxy-naphth-2-yl)-ethyl)-piperidin-3-yl)methyl]-6,7-dimethyl-1,2,3,4-tetrahydro-isoquinoline;
2-[(N-(2-(6-methoxy-naphth-2-yl)-ethyl)-hexahydro-azepin-3-yl)-methyl]-1,2,3,4-tetrahydro-isoquinoline;
2-[2-(N-(2-(6-methoxy-naphth-2-yl)-ethyl)-piperidin-2-yl)ethyl]-6,7-dimethyl-1-oxo-1,2,3,4-tetrahydro-isoquinoline;
2-[(N-(4-(naphthyl-2-oxy)-butyl)-piperidin-3-yl)methyl]-6,7-dimethyl-1-oxo-1,2,3,4-tetrahydro-isoquinoline;
2-[(N-(4-(naphthyl-2-oxy)-butyl)-hexahydro-azepin-3-yl)methyl]-6,7-dimethyl-1-oxo-1,2,3,4-tetrahydro-isoquinoline;
2-[(N-(4-(naphthyl-2-oxy)-butyl)-azacyclooct-3-yl)-methyl]-6,7-dimethyl-1,2,3,4-tetrahydro-isoquinoline;
2-[(N-(3-(6-methoxy-naphthyl-2-oxy)-propyl)-hexahydro-azepin-3-yl)-methyl]-6,7-dimethyl-1-oxo-1,2,3,4-tetrahydroisoquinoline;
2-[(N-(3-(6-methoxy-naphthyl-2-oxy)-propyl)-azacyclooct-3-yl)-methyl]-6,7-dimethyl-1-oxo-1,2,3,4-tetrahydro-isoquinoline;
2-[(N-(3-(5,6-dimethoxy-naphthyl-2-oxy)-propyl)-azacyclooct-3-yl)-methyl]-6,7-dimethyl-1-oxo-1,2,3,4-tetrahydro-isoquinoline;
2-[(N-(3-(naphthyl)-propyl)-azacyclooct-3-yl)-methyl]-6,7-dimethyl-1-oxo-1,2,3,4-tetrahydro-isoquinoline;
3-[(N-(3-(pyrid-3-yl)-propyl)-pyrrolidin-3-yl)-methyl]-7,8-methylenedioxy-2-oxo-1,3,4,5-tetrahydro-2H-3-benzazepine,
3-[(N-(1-(pyrid-3-yl)-methyl)-pyrrolidin-3-yl)-methyl]-7,8-methylenedioxy-1,3,4,5-tetrahydro-2H-3-benzazepine,
3-[(N-(3-(pyrid-4-yl)-propyl)-pyrrolidin-3-yl)-methyl]-7,8-dimethyl-1,3,4,5-tetrahydro-2H-3-benzazepine, 2-[(N-(1-(pyrid-3-yl)-methyl)-pyrrolidin-3-yl)-methyl]-6,7-dimethyl-1-oxo-1,2,3,4-tetrahydro-isoquinoline;
2-[(N-(3-(pyrid-3-yl)-propyl)-pyrrolidin-3-yl)-methyl]-5,6-methylenedioxy-1-oxo-1,3-dihydro-isoindole;
2-[(N-(3-(pyrid-4-yl)-propyl)-pyrrolidin-3-yl)-methyl]-5,6-methylenedioxy-1,3-dihydro-isoindole;
2-[(N-(2-(6-methyl-pyrid-2-yl)-ethyl)-pyrrolidin-3-yl)methyl]-5,6-methylenedioxy-1-oxo-1,3-dihydro-isoindole;
2-[(N-(2-(6-methyl-pyrid-2-yl)-ethyl)-pyrrolidin-3-yl)methyl]-5,6-methylenedioxy-1,3-dihydro-isoindole;
2-[(N-(1-(pyrid-3-yl)-methyl)-pyrrolidin-3-yl)-methyl]-5,6-dimethyl-1,3-dihydro-isoindole;
3-[(N-(3-(pyrid-3-yl)-propyl)-pyrrolidin-3-yl)-methyl]-7,8-dimethoxy-1,3,4,5-tetrahydro-2H-3-benzazepine,
2-[(N-(3-(pyrid-4-yl)-propyl)-pyrrolidin-3-yl)-methyl]-5,6-dimethoxy-1,3-dihydro-isoindole;
2-[(N-(1-(pyrid-3-yl)-methyl)-pyrrolidin-3-yl)-methyl]-5,6-dimethoxy-1,3-dihydro-isoindole;
2-[(N-(1-(pyrid-3-yl)-methyl)-pyrrolidin-3-yl)-methyl]-5,6-dimethoxy-1-oxo-1,3-dihydro-isoindole;
2-[(N-(2-(6-methyl-pyrid-2-yl)-ethyl)-pyrrolidin-3-yl)methyl]-6,7-dimethoxy-1,2,3,4-tetrahydro-isoquinoline;
2-[(N-(2-(6-methyl-pyrid-2-yl)-ethyl)-pyrrolidin-3-yl)methyl]-5,6-dimethoxy-1,3-dihydro-isoindole;
2-[(N-(2-(6-methyl-pyrid-2-yl)-ethyl)-pyrrolidin-3-yl)methyl]-6,7-dimethoxy-1-oxo-1,2,3,4-tetrahydro-isoquinoline;
2-[(N-(2-(6-methyl-pyrid-2-yl)-ethyl)-pyrrolidin-3-yl)methyl]-5,6-dimethoxy-1-oxo-1,3-dihydro-isoindole;
2-[2-(N-(3-(pyrid-4-yl)-propyl)-piperidin-2-yl)-ethyl]-6,7-dimethoxy-1,2,3,4-tetrahydro-isoquinoline;
2-[2-(N-(3-(pyrid-4-yl)-propyl)-piperidin-2-yl)-ethyl]-6,7-dimethoxy-1-oxo-1,2,3,4-tetrahydro-isoquinoline;
3-[(N-(2-(6,7-dimethoxy-isoquinol-4-yl)-ethyl)-piperidin-2-yl)-methyl]-7,8-dimethyl-2-oxo-1,3,4,5-tetrahydro-2H-3benzazepine,
2-[(N-(1-(pyrid-4-yl)-methyl)-piperidin-3-yl)-methyl]-6,7-dimethyl-1,2,3,4-tetrahydro-isoquinoline;
2-[(N-(2-(6,7-dimethoxy-isoquinol-4-yl)-ethyl)-piperidin-3-yl)-methyl]-5,6-methylenedioxy-1-oxo-1,3-dihydro-isoindole;
2-[2-(N-(3-(pyrid-4-yl)-propyl)-piperidin-2-yl)-ethyl]-5,6-methylenedioxy-1,3-dihydro-isoindole;
2-[(N-(3-(pyrid-3-yl)-propyl)-hexahydro-azepin-3-yl)methyl]-6,7-dimethyl-1-oxo-1,2,3,4-tetrahydro-isoquinoline;
2-[(N-(3-(pyrid-3-yl)-propyl)-hexahydro-azepin-3-yl)methyl]-6,7-dimethyl-1,2,3,4-tetrahydro-isoquinoline;
2-[(N-(2-(6-methyl-pyrid-2-yl)-ethyl)-hexahydro-azepin-3-yl)-methyl]-5,6-dimethoxy-1,3-dihydro-isoindole;
2-[(N-(2-(6-methyl-pyrid-2-yl)-ethyl)-hexahydro-azepin-3-yl)-methyl]-5,6-dimethoxy-1-oxo-1,3-dihydro-isoindole;
3-[(N-(3-(5-hydroxy-indol-3-yl)-propyl)-pyrrolidin-3-yl)methyl]-7,8-dimethyl-2-oxo-1,3,4,5-tetrahydro-2H-3-benzazepine,
2-[(N-(3-(5-hydroxy-indol-3-yl)-propyl)-pyrrolidin-3-yl)-methyl]-6,7-methylenedioxy-1,2,3,4-tetrahydro-isoquinoline;
3-[(N-(3-(5-methoxy-indol-3-yl)-propyl)-pyrrolidin-3-yl)methyl]-7,8-dimethyl-1,3,4,5-tetrahydro-2H-3-benzazepine, 2-[(N-(3-(5-methoxy-indol-3-yl)-propyl)-pyrrolidin-3-yl)methyl]-5,6-methylenedioxy-1,3-dihydro-isoindole;

2-[(N-(3-(5-benzyloxy-indol-3-yl)-propyl)-pyrrolidin-3-yl)methyl]-6,7-methylenedioxy-1-oxo-1,2,3,4-tetrahydro-isoquinoline;

2-[(N-(3-(5-benzyloxy-indol-3-yl)-propyl)-pyrrolidin-3-yl)methyl]-5,6-methylenedioxy-1-oxo-1,3-dihydro-isoindole;

3-[(N-(3-(N-methyl-indol-3-yl)-propyl)-pyrrolidin-3-yl)methyl]-7,8-methylenedioxy-1,3,4,5-tetrahydro-2H-3-benzazepine, 2-[(N-(3-(N-methyl-indol-3-yl)-propyl)-pyrrolidin-3-yl)-methyl]-6,7-dimethyl-1,2,3,4-tetrahydro-isoquinoline;

2-[(N-(3-(indol-3-yl)-propyl)-pyrrolidin-3-yl)-methyl]-5,6-dimethyl-1,3-dihydro-isoindole;

3-[(N-(3-(indol-3-yl)-propyl)-pyrrolidin-3-yl)-methyl]-7,8-dimethoxy-2-oxo-1,3,4,5-tetrahydro-2H-3-benzazepine.

2-[(N-(3-(5-hydroxy-indol-3-yl)-propyl)-pyrrolidin-3-yl)methyl]-5,6-dimethyl-1-oxo-1,3-dihydro-isoindole;

2-[(N-(3-(5-hydroxy-indol-3-yl)-propyl)-pyrrolidin-3-yl)methyl]-6,7-dimethoxy-1-oxo-1,2,3,4-tetrahydro-isoquinoline;

3-[(N-(3-(5-methoxy-indol-3-yl)-propyl)-pyrrolidin-3-yl)methyl]-7,8-dimethoxy-1,3,4,5-tetrahydro-2H-3-benzazepine, 2-[(N-(3-(5-methoxy-indol-3-yl)-propyl)-pyrrolidin-3-yl)methyl]-5,6-dimethoxy-1-oxo-1,3-dihydro-isoindole;

2-[(N-(3-(5-benzyloxy-indol-3-yl)-propyl)-pyrrolidin-3-yl)methyl]-6,7-dimethoxy-1,2,3,4-tetrahydro-isoindole;

2-[(N-(3-(5-benzyloxy-indol-3-yl)-propyl)-pyrrolidin-3-yl)methyl]-6,7-dimethoxy-1-oxo-1,2,3,4-tetrahydro-isoquinoline;

2-[(N-(3-(N-methyl-indol-3-yl)-propyl)-pyrrolidin-3-yl)methyl]-5,6-dimethyl-1-oxo-1,3-dihydro-isoindole;

2-[(N-(3-(N-methyl-indol-3-yl)-propyl)-pyrrolidin-3-yl)methyl]-5,6-dimethoxy-1,3-dihydro-isoindole;

2-[(N-(2-(3,4-dimethoxy-phenyl)-ethyl)-hexahydro-azepin-3-yl)-methyl]-6,7-methylenedioxy-1-oxo-1,2,3,4-tetrahydro-isoquinoline;

2-[(N-(3-(3,4-methylenedioxy-phenoxy)-propyl)-hexahydro-azepin-3-yl)-methyl]-6,7-methylenedioxy-1-oxo-1,2,3,4-tetrahydro-isoquinoline;

2-[(N-(2-(4-trifluoromethoxy-phenyl)-ethyl)-piperidin-3-yl)methyl]-5,6-dimethoxy-1-oxo-1,3-dihydro-isoindole;

2-[(N-(2-(4-trifluoromethyl-phenyl)-ethyl)-piperidin-3-yl)methyl]-5,6-dimethoxy-1-oxo-1,3-dihydro-isoindole;

2-[(N-(2-(3,4-dichloro-phenyl)-ethyl)-piperidin-3-yl)methyl]-5,6-dimethoxy-1-oxo-1,3-dihydro-isoindole;

2-[(N-(2-(3,4,5-trimethoxy-phenyl)-ethyl)-piperidin-3-yl)methyl]-5,6-dimethoxy-1-oxo-1,3-dihydro-isoindole;

2-[(N-(2-(4-methoxy-phenyl)-ethyl)-piperidin-3-yl)-methyl]-5,6-dimethoxy-1-oxo-1,3-dihydro-isoindole;

2-[(N-(2-(3-methyl-phenyl)-ethyl)-piperidin-3-yl)-methyl]-5,6-dimethoxy-1-oxo-1,3-dihydro-isoindole;

2-[(N-(2-(3,4-dimethyl-phenyl)-ethyl)-piperidin-3-yl)methyl]-5,6-dimethoxy-1-oxo-1,3-dihydro-isoindole;

2-[(N-(2-(2,3,4,5-tetramethyl-phenyl)-ethyl)-piperidin-3-yl)-methyl]-5,6-dimethoxy-1-oxo-1,3-dihydro-isoindole;

2-[(N-(2-(4-benzyloxy-phenyl)-ethyl)-piperidin-3-yl)methyl]-5,6-dimethoxy-1-oxo-1,3-dihydro-isoindole;

2-[(N-(2-(4-hydroxy-phenyl)-ethyl)-piperidin-3-yl)-methyl]-5,6-dimethoxy-1-oxo-1,3-dihydro-isoindole;

2-[(N-(2-(4-methanesulphonyloxy-phenyl)-ethyl)-piperidin-3-yl)-methyl]-5,6-dimethoxy-1-oxo-1,3-dihydro-isoindole;

2-[(N-(2-(4-trifluoromethanesulphonyloxy-phenyl)-ethyl)-piperidin-3-yl)-methyl]-5,6-dimethoxy-1-oxo-1,3-dihydroisoindole;

2-[(N-(2-(4-methanesulphonylamino-phenyl)-ethyl)-piperidin-3-yl)-methyl]-5,6-dimethoxy-1-oxo-1,3-dihydro-isoindole;

2-[(N-(2-(4-dimethanesulphonylamino-phenyl)-ethyl)-piperidin-3-yl)-methyl]-5,6-dimethoxy-1-oxo-1,3-dihydroisoindole;

2-[(N-(3-(4-bromo-phenyl)-propyl)-piperidin-3-yl)-methyl]-5,6-dimethoxy-1-oxo-1,3-dihydro-isoindole;

2-[(N-(3-(4-methoxy-phenyl)-propyl)-piperidin-3-yl)methyl]-5,6-dimethoxy-1-oxo-1,3-dihydro-isoindole;

2-[(N-(3-(3-methoxy-phenyl)-propyl)-piperidin-3-yl)methyl]-5,6-dimethoxy-1-oxo-1,3-dihydro-isoindole;

2-[(N-(3-(3,4-dimethoxy-phenyl)-propyl)-piperidin-3-yl)methyl]-5,6-dimethoxy-1-oxo-1,3-dihydro-isoindole;

2-[(N-(4-(4-methoxy-phenyl)-butyl)-piperidin-3-yl)-methyl]-5,6-dimethoxy-1-oxo-1,3-dihydro-isoindole;

2-[(N-(3-(4-amino-3,5-dibromo-phenoxy)-propyl)-piperidin-3-yl)-methyl]-5,6-dimethoxy-1-oxo-1,3-dihydro-isoindole;

3-[(N-(2-(2,5-dimethyl-thien-3-yl)-ethyl)-piperidin-3-yl)methyl]-7,8-dimethoxy-2-oxo-1,3,4,5-tetrahydro-2H-3-benzazepine;

3-[(N-(2-(5-methoxy-benzo[b]thienyl-3)-ethyl)-piperidin-3-yl)-methyl]-7,8-dimethoxy-2-oxo-1,3,4,5-tetrahydro-2H-3benzazepine;

3-[(N-(2-(6-methoxy-benzo[b]thienyl-3)-ethyl)-piperidin-3-yl)-methyl]-7,8-dimethoxy-2-oxo-1,3,4,5-tetrahydro-2H-3benzazepine;

3-[(N-(2-(6-bromo-benzo[b]thienyl-3)-ethyl)-piperidin-3-yl)methyl]-7,B-dimethoxy-2-oxo-1,3,4,5-tetrahydro-2H-3-benzazepine;

3-[(N-(2-(benzo[b]thienyl-2)-ethyl)-piperidin-3-yl)-methyl]-7,8-dimethoxy-2-oxo-1,3,4,5-tetrahydro-2H-3-benzazepine;

3-[(N-(2-(benzo[b]furyl-3)-ethyl)-piperidin-3-yl)-methyl]-7,8-dimethoxy-2-oxo-1,3,4,5-tetrahydro-2H-3-benzazepine;

3-[(N-(2-(2,5-dimethyl-thien-3-yl)-ethyl)-piperidin-3-yl)methyl]-7,8-dimethyl-2-oxo-1,3,4,5-tetrahydro-2H-3-benzazepine;

3-[(N-(2-(5-methoxy-benzo[b]thienyl-3)-ethyl)-piperidiny-3-yl)-methyl]-7,8-dimethyl-2-oxo-1,3,4,5-tetrahydro-2H-3benzazepine;

3-[(N-(2-(6-methoxy-benzo[b]thienyl-3)-ethyl)-piperidin-3-yl)-methyl]-7,8-dimethyl-2-oxo-1,3,4,5-tetrahydro-2H-3-benzazepine;

3-[(N-(2-(6-bromo-benzo[b]thienyl-3)-ethyl)-piperidin-3-yl)methyl]-7,8-dimethyl-2-oxo-1,3,4,5-tetrahydro-2H-3-benzazepine;

3-[(N-(2-(benzo[b]thienyl-2)-ethyl)-piperidin-3-yl)-methyl]-7,8-dimethyl-2-oxo-1,3,4,5-tetrahydro-2H-3-benzazepine;

3-[(N-(2-(benzo[b]furyl-3)-ethyl)-piperidin-3-yl)-methyl]-7,8-dimethyl-2-oxo-1,3,4,5-tetrahydro-2H-3-benzazepine;

3-[(N-(2-(2,5-dimethyl-thien-3-yl)-ethyl)-piperidin-3-yl)methyl]-7,8-methylenedioxy-2-oxo-1,3,4,5-tetrahydro-2H-3benzazepine;

3-[(N-(2-(5-methoxy-benzo[b]thienyl-3)-ethll)-piperidin-3-yl)-methyl]-7,8-methylenedioxy-2-oxo-1,3,4,5-tetrahydro-2H-3benzazepine;

3-[(N-(2-(6-methoxy-benzo[b]thienyl-3)-ethyl)-piperidin-3-yl)-methyl]-7,8-methylenedioxy-2-oxo-1,3,4,5-tetrahydro-2H-3benzazepine;

3-[(N-(2-(6-bromo-benzo[b]thienyl-3)ethyl)-piperidin-3-yl)methyl]-7,8-methylenedioxy-2-oxo-1,3,4,5-tetrahydro-2H-3benzazepine;

3-[(N-(2-(benzo[b]thienyl-2)-ethyl)-piperidin-3-yl)-methyl-7,8-methylenedioxy-2-oxo-1,3,4,5-tetrahydro-2H-3-benzazepine;

3-[(N-(2-(benzo[b]furyl-3)-ethyl)-piperidin-3-yl)-methyl]-7,8-methylenedioxy-2-oxo-1,3,4,5-tetrahydro-2H-3-benzazepine;

3-[(N-(3-(2,5-dimethyl-thien-3-yl)-propyl)-piperidin-3-yl)methyl]-7,8-dimethoxy-2-oxo-1,3,4,5-tetrahydro-2H-3-benzazepine;

3-[(N-(3-(5-methoxy-benzo[b]thienyl-3)-propyl)-piperidin-3-yl)-methyl]-7,8-dimethoxy-2-oxo-1,3,4,5-tetrahydro-2H-3benzazepine;

3-[(N-(3-(6-methoxy-benzo[b]thienyl-3)-propyl)-piperidin-3-yl)-methyl]-7,8-dimethoxy-2-oxo-1,3,4,5-tetrahydro-2H-3benzazepine;

3-[(N-(3-(6-bromo-benzo[b]thienyl-3)-propyl)-piperidin-3-yl)methyl]-7,8-dimethoxy-2-oxo-1,3,4,5-tetrahydro-2H-3-benzazepine;

3-[(N-(3-(benzo[b]thienyl-2)-propyl)-piperidin-3-yl)methyl]-7,8-dimethoxy-2-oxo-1,3,4,5-tetrahydro-2H-3-benzazepine;

3-[(N-(3-(benzo[b]furyl-3)-propyl)-piperidin-3-yl)-methyl]-7,8-dimethoxy-2-oxo-1,3,4,5-tetrahydro-2H-3-benzazepine;

3-[(N-(3-(2,5-dimethyl-thien-3-yl)-propyl)-piperidin-3-yl)methyl]-7,8-dimethyl-2-oxo-1,3,4,5-tetrahydro-2H-3-benzazepine;

3-[(N-(3-(6-methoxy-benzo[b]thienyl-3)-propyl)-piperidin-3-yl)-methyl]-7,8-dimethyl-2-oxo-1,3,4,5-tetrahydro-2H-3-benzazepine;

3-[(N-(3-(benzo[b]thienyl-2)-propyl)-piperidin-3-yl)methyl]-7,8-dimethyl-2-oxo-1,3,4,5-tetrahydro-2H-3-benzazepine;

3-[(N-(3-(benzo[b]furyl-3)-propyl)-piperidin-3-yl)-methyl]-7,8-dimethyl-2-oxo-1,3,4,5-tetrahydro-2H-3-benzazepine;

3-[(N-(3-(2,5-dimethyl-thien-3-yl)-propyl)-piperidin-3-yl)methyl]-7,8-methylenedioxy-2-oxo-1,3,4,5-tetrahydro-2H-3-benzazepine;

3-[(N-(3-(6-methoxy-benzo[b]thienyl-3)-propyl)-piperidin-3-yl)-methyl]-7,8-methylenedioxy-2-oxo-1,3,4,5-tetrahydro-2H-3-benzazepine;

3-[(N-(3-(benzo[b]thienyl-2)-propyl)-piperidin-3-yl)methyl]-7,8-methylenedioxy-2-oxo-1,3,4,5-tetrahydro-2H-3benzazepine;

3-[(N-(3-(benzo[b]furyl-3)-propyl)-piperidin-3-yl)-methyl]-7,8-methylenedioxy-2-oxo-1,3,4,5-tetrahydro-2H-3-benzazepine;

3-[(N-(2-(thien-2-yl)-ethyl)-piperidin-3-yl)-methyl]-7,8-dimethyl-2-oxo-1,3,4,5-tetrahydro-2H-3-benzazepine;

3-[(N-(2-(benzo[b]thienyl-3)-ethyl)-piperidin-3-yl)-methyl]-7,8-dimethyl-2-oxo-1,3,4,5-tetrahydro-2H-3-benzazepine;

3-[(N-(2-(benzo[b]furyl-2)-ethyl)-piperidin-3-yl)-methyl]-7,8-dimethyl-2 oxo-1,3,4,5-tetrahydro-2H-3-benzazepine;

3-[(N-(2-(thien-2-yl)-ethyl)-piperidin-3-yl)-methyl]-7,8-methylenedioxy-2-oxo-1,3,4,5-tetrahydro-2H-3-benzazepine;

3-[(N-(2-(benzo[b]thienyl-3)-ethyl)-piperidin-3-yl)-methyl]-7,8-methylenedioxy-2-oxo-1,3,4,5-tetrahydro-2H-3-benzazepine;

3-[(N-(2-(benzo[b]furyl-2)-ethyl)-piperidin-3-yl)-methyl]-7,8-methylenedioxy-2-oxo-1,3,4,5-tetrahydro-2H-3-benzazepine;

3-[(N-(2-(thien-2-yl)-ethyl)-hexahydro-azepin-3-yl)methyl]-7,8-dimethyl-2-oxo-1,3,4,5-tetrahydro-2H-3-benzazepine;

3-[(N-(2-(benzo[b]thienyl-3)-ethyl)-hexahydro-azepin-3-yl)methyl]-7,8-dimethyl-2-oxo-1,3,4,5-tetrahydro-2H-3-benzazepine;

3-(N-(2-(benzo[b]furyl-2)-ethyl)-hexahydro-azepin-3-yl-methyl]-7,8-dimethyl-2-oxo-1,3,4,5-tetrahydro-2H-3-benzazepine;

3-[(N-(2-(thien-2-yl)-ethyl)-hexahydro-azepin-3-yl)-methyl]-7,8-methylenedioxy-2-oxo-1,3,4,5-tetrahydro-2H-3-benzazepine;

3-[(N-(2-(benzo[b]thienyl-3)-ethyl)-hexahydro-azepin-3-yl)methyl]-7,8-methylenedioxy-2-oxo-1,3,4,5-tetrahydro-2H-3-benzazepine;

3-[(N-(2-(benzo[b]furyl-2)-ethyl)-hexahydro-azepin-3-yl)methyl]-7,8-methylenedioxy-2-oxo-1,3,4,5-tetrahydro-2H-3-benzazepine;

3-[(N-(2-(thien-2-yl)-ethyl)-pyrrolidin-3-yl)-methyl]-7,8-dimethyl-2-oxo-1,3,4,5-tetrahydro-2H-3-benzazepine;

3-[(N-(2-(benzo[b]thienyl-3)-ethyl)-pyrrolidin-3-yl)methyl]-7,8-dimethyl-2-oxo-1,3,4,5-tetrahydro-2H-3-benzazepine;

3-[(N-(2-(benzo[b]furyl-2)-ethyl)-pyrrolidin-3-yl)-methyl]-7,8-dimethyl-2-oxo-1,3,4,5-tetrahydro-2H-3-benzazepine;

3-[(N-(2-(thien-2-yl)-ethyl)-pyrrolidin-3-yl)-methyl]-7,8-methylenedioxy-2-oxo-1,3,4,5-tetrahydro-2H-3-benzazepine;

3-[(N-(2-(benzo[b]thienyl-3)-ethyl)-pyrrolidin-3-yl)methyl]-7,8-methylenedioxy-2-oxo-1,3,4,5-tetrahydro-2H-3benzazepine;

3-[(N-(2-(benzo[b]furyl-2)-ethyl)-pyrrolidin-3-yl)-methyl]-7,8-methylenedioxy-2-oxo-1,3,4,5-tetrahydro-2H-3-benzazepine;

3-[(N-(2-(thien-2-yl)-ethyl)-pyrrolidin-3-yl)-methyl]-7,8-dimethoxy-2-oxo-1,3,4,5-tetrahydro-2H-3-benzazepine;

3-[(N-(2-(benzo[b]thienyl-3)-ethyl)-pyrrolidin-3-yl)methyl]-7,8-dimethoxy-2-oxo-1,3,4,5-tetrahydro-2H-3-benzazepine;

3-[(N-(2-(benzo[b]furyl-2)-ethyl)-pyrrolidin-3-yl)-methyl]-7,8-dimethoxy-2-oxo-1,3,4,5-tetrahydro-2H-3-benzazepine;

3-[(N-(2-(thien-2-yl)-ethyl)-hexahydro-azepin-3-yl)-methyl]-7,8-dimethoxy-2-oxo-1,3,4,5-tetrahydro-2H-3-benzazepine;

3-[(N-(2-(benzo[b]thienyl-3)-ethyl)-hexahydro-azepin-3-yl)methyl]-7,8-dimethoxy-2-oxo-1,3,4,5-tetrahydro-2H-3-benzazepine;

3-[N-(2-(benzo[b]furyl-2)-ethyl)-hexahydro-azepin-3-yl)methyl]-7,8-dimethoxy-2-oxo-1,3,4,5-tetrahydro-2H-3-benzazepine;

7,8-dimethyl-2-oxo-1,3,4,5-tetrahydro-2H-3-benzazepine;

3-[(N-(4-(benzo[b]thienyl-3)-butyl)-piperidin-3-yl)-methyl]-7,8-dimethyl-2-oxo-1,3,4,5-tetrahydro-2H-3-benzazepine;

3-[(N-(4-(benzo[b]furyl-2)-butyl)-piperidin-3-yl)-methyl]-7,8-dimethyl-2-oxo-1,3,4,5-tetrahydro-2H-3-benzazepine;

3-[(N-(5-(thien-2-yl)-pentyl)-piperidin-3-yl)-methyl]-7,8-dimethyl-2-oxo-1,3,4,5-tetrahydro-2H-3-benzazepine;

3-[(N-(5-(benzo[b]thienyl-3)-pentyl)-piperidin-3-yl)methyl]-7,8-dimethyl-2-oxo-1,3,4,5-tetrahydro-2H-3-benzazepine;

3-[(N-(5-(benzo[b]furyl-2)-pentyl)-piperidin-3-yl)-methyl]-7,8-dimethyl-2-oxo-1,3,4,5-tetrahydro-2H-3-benzazepine;

3-[(N-(4-(thien-2-yl)-butyl)-piperidin-3-yl)-methyl]-7,8-methylenedioxy-2-oxo-1,3,4,5-tetrahydro-2H-3-benzazepine;

3-[(N-(4-(benzo[b]thienyl-3)-butyl)-piperidin-3-yl)methyl]-7,8-methylenedioxy-2-oxo-1,3,4,5-tetrahydro-2H-3benzazepine;

3-[(N-(4-(benzo[b]furyl-2)-butyl)-piperidin-3-yl)-methyl]-7,8-methylenedioxy-2-oxo-1,3,4,5-tetrahydro-2H-3-benzazepine;

3-[(N-(5-(thienyl-2)-pentyl)-piperidin-3-yl)-methyl]-7,8-methylenedioxy-2-oxo-1,3,4,5-tetrahydro-2H-3-benzazepine;

3-[(N-(5-(benzo[b]thienyl-3)-pentyl)-piperidin-3-yl)methyl]-7,8-methylenedioxy-2-oxo-1,3,4,5-tetrahydro-2H-3benzazepine;

3-[(N-(5-(benzo[b]furyl-2)-pentyl)-piperidin-3-yl)-methyl]-7,8-methylenedioxy-2-oxo-1,3,4,5-tetrahydro-2H-3-benzazepine;

3-[(N-(4-(benzo[b]thienyl-3)-butyl)-piperidin-3-yl)-methyl]-7,8-dimethoxy-2-oxo-1,3,4,5-tetrahydro-2H-3-benzazepine;

3-[(N-(4-(benzo[b]furyl-2)-butyl)-piperidin-3-yl)-methyl]-7,8-dimethoxy-2-oxo-1,3,4,5-tetrahydro-2H-3-benzazepine;

3-[(N-(5-(benzo[b]thienyl-3)-pentyl)-piperidin-3-yl)methyl]-7,8-dimethoxy-2-oxo-1,3,4,5-tetrahydro-2H-3-benzazepine;

3-[(N-(5-(benzo[b]furyl-2)-pentyl)-piperidinyl-3)-methyl]-7,8-dimethoxy-2-oxo-1,3,4,5-tetrahydro-2H-3-benzazepine.

Further exemplary compounds of formula I would be the enantiomers, diastereomers, N-oxides and acid addition salts, more particularly, for pharmaceutical use, the physiologically acceptable acid addition salts of the above listed compounds.

However, when A, B, G, m, n and R are selected from option (i), the preferred compounds of general formula I above are those wherein:

A, B, m and n are defined as above but m+n equals the number 3, 4 or 5,

E represents a methylene or ethylene group,

G represents an n-alkylene group with 1 to 4 carbon atoms, or G is the group G'—G", wherein G' is attached to the nitrogen atom and is an ethylene or n-propylene group and G" is attached to the group R and is an oxa, thia, imino, methylimino, sulphinyl or sulphonyl group, $R_1$ represents a hydrogen, fluorine, chlorine or bromine atom, or a hydroxy, methoxy, trifluoromethyl, methylamino or dimethylamino group, $R_2$ represents a hydrogen, chlorine or bromine atom or a methoxy group or $R_1$ and $R_2$ together represent a methylenedioxy group, $R_3$ represents a hydrogen, fluorine, chlorine or bromine atom or a methyl, hydroxy, methoxy or nitro group, $R_4$ represents a hydrogen atom or a methoxy, methane-sulphonyloxy, amino or acetylamino group, or $R_3$ and $R_4$ together represent a methylenedioxy group, and $R_5$ represents a hydrogen, chlorine or bromine atom or a methoxy group.

When A, B, G, m, n and R are selected from option (i), particularly preferred compounds of general formula I are those wherein:

m and n are defined as above but m+n equals the number 3, 4 or 5,

A represents a —CH₂CH₂— or —CH=CH— group and B represents a methylene or carbonyl group, or A represents a —CO—CO— group and B represents a methylene group, E represents a methylene or ethylene group, G represents an n-alkylene group of 2 to 4 carbon atoms, or G is the group —G'—G"—, wherein G' is attached to the nitrogen atom and is an ethylene or n-propylene group and G" is attached to the group R and is an oxa group, $R_1$ represents a hydrogen atom or a methoxy group, $R_2$ represents a hydrogen atom or a methoxy group, or $R_1$ and $R_2$ together represent a methylenedioxy group, $R_3$ represents a hydrogen atom or a methyl, hydroxy or methoxy group, $R_4$ represents a hydrogen atom or a methoxy group, or $R_3$ and $R_4$ together represent a methylenedioxy group, and $R_5$ represents a hydrogen atom.

When A, B, G, m, n and R are selected from option (ii), preferred compounds of general formula I above are those wherein:

A, B, m and n are defined as above,

E represents a straight-chain alkylene group with 1 to 3 carbon atoms,

G represents a straight-chain alkylene group of 1 to 6 carbon atoms or G is the group —G'—G"—, wherein G' is attached to the nitrogen atom and is a straight-chain alkylene group of 3 to 5 carbon atoms and G" is attached to the group R and is an oxa, thia, imino, methylimino, sulphinyl or sulfonyl group, $R_1$ represents a methyl or methoxy group, $R_2$ represents a methyl or methoxy group or $R_1$ and $R_2$ together represent a methylenedioxy group, and R represents an optionally methyl-substituted furyl, thienyl, pyridyl, benzo[b]furyl or benzo[b]thienyl group, a benzo[b]thienyl group substituted by a halogen atom or by a methoxy or methanesulphonyloxy group, an indolyl or N-methylindolyl group optionally substituted by a hydroxy, methoxy or benzyloxy group, a dimethyl-thienyl or dimethoxy-isoquinolyl group, a naphthyl group optionally mono-or disubstituted by methyl or methoxy groups, whilst (the substituents may be identical or different), or, if B represents a —CH₂— or CO group, a phenyl group optionally substituted by a methylenedioxy group, a phenyl group mono-or di-substituted by a chlorine or bromine atom or methyl or methoxy groups, whilst the substituents may be identical or different, a phenyl group substituted by a hydroxy, benzyloxy, methanesulphonyloxy, trifluoromethanesulphonyloxy, trifluoromethyl, trifluoromethoxy, nitro, amino, acetamido, methanesulphonylamino or bis(methanesulphonyl)amino group, or a trimethoxy-phenyl, tetramethylphenyl or dihaloaminophenyl group, and, in particular, the compounds of general formula

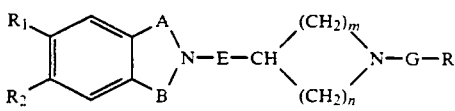

(Ia)

wherein $R_1$, $R_2$, R, A, B, E, G, m and n are defined as hereinbefore.

When A, B, G, m, n and R are selected from option (ii), particularly preferred compounds of general formula Ia above are those wherein:

A represents a $-CH_2CH_2-$ group,

B represents a $-CH_2-$, $-CH_2-CH_2-$, $-CO-$ or $-\underline{C}H_2CO-$ group, wherein the carbon atom designated by underlining is linked to the phenyl nucleus, E represents a methylene or ethylene group, G represents a straight chain alkylene group of 2 to 4 carbon atoms, or G is the group $-G'-G''-$ wherein G' is attached to the nitrogen atom and is a straight cahin alkylene groupf of 2 or 3 carbon atoms and G'' is attached to the group R and is an oxa group, $R_1$ represents a methoxy group, $R_2$ represents a methoxy group or $R_1$ and $R_2$ together represent a methylenedioxy group, m represents the number 2, 3 or 4, n represents the number 1 and R represents a naphth-2-yl, 6-methoxy-naphth-2-yl, 5-methyl-6-methoxy-naphth-2-yl, thien-2-yl, benzo[b]furyl-2 or benzo[b]thienyl-3 group or, if B represents a $-CH_2-$ or $-CO-$ group, a 4-methoxyphenyl or 3,4-dimethoxyphenyl group.

When A, B, G, m, n and R are selected from option (ii) the following are particularly preferred compounds:

3-[(N-(2-(naphth-2-yl)-ethyl)-piperidin-3-yl)-methyl]-7,8-dimethoxy-2-oxo-1,3,4,5-tetrahydro-2H-3-benzazepine, 3-[(N-(2-(5-methyl-6-methoxy-naphth-2-yl)-ethyl)-piperidin-3-yl)-methyl]-7,8-dimethoxy-2-oxo-1,3,4,5-tetrahydro-2H-3benzazepine, 3-[2-(N-(2-(6-methoxy-naphth-2-yl)-ethyl)-piperid-2-yl)ethyl]-7,8-dimethoxy-2-oxo-1,3,4,5-tetrahydro-2H-3-benzazepine, 2-[(N-(2-(6-methoxy-naphth-2-yl)-ethyl)-hexahydro-azepin-3-yl)-methyl]-6,7-methylenedioxy-1-oxo-1,2,3,4-tetrahydroisoquinoline, 2-[(N-(2-(naphth-2-yl)-ethyl)-hexahydro-azepin-3-yl)methyl]-6,7-methylenedioxy-1-oxo-1,2,3,4-tetrahydro-isoquinoline, 2-[(N-(2-(3,4-dimethoxy-phenyl)-ethyl)-piperidin-3 -yl)-methyl]-6,7-dimethyl-1,2,3,4-tetrahydro-isoquinoline, 2-[(N-(2-(3,4-dimethoxy-phenyl)-ethyl)-piperidin-3-yl)methyl]-6,7-dimethyl-1-oxo-1,2,3,4-tetrahydro-isoquinoline, 2-[(N-(3-(4-methoxy-phenoxy)-propyl)-piperidin-3-yl)methyl]-6,7-dimethyl-1-oxo-1,2,3,4-tetrahydro-isoquinoline, 3-[(N-(4-(thien-2-yl)-butyl)-piperidin-3-yl)-methyl]-7,8-dimethoxy-2-oxo-1,3,4,5-tetrahydro-2H-3-benzazepine, 3-[(N-(2-(benzo[b]furyl-2)-ethyl)-piperidin-3-yl)-methyl]-7,8-dimethoxy-2-oxo-1,3,4,5-tetrahydro-2H-3-benzazepine, 3-[(N-(2-(benzo[b]thienyl-3)-ethyl)-piperidin-3-yl)-methyl]-7,8-dimethoxy-2-oxo-1,3,4,5-tetrahydro-2H-3-benzazepine, 2-[(N-(3-(6-methoxy-naphthyl-oxy)-propyl)-pyrrolidin-3-yl)methyl]-6,7-dimethoxy-1-oxo-1,2,3,4-tetrahydro-isoquinoline, 2-[(N-(2-(6-methoxy-naphth-2-yl)-ethyl)-hexahydro-azepin-3-yl)-methyl]-6,7-methylenedioxy-1-oxo-1,2,3,4-tetrahydroisoquinoline, 3-[(N-(2-(4-methoxy-phenyl)-ethyl)-hexahydro-azepin-3-yl)methyl]-7,8-dimethoxy-2-oxo-1,3,4,5-tetrahydro-2H-3-benzazepine, and 3-[(N-(2-(3,4-dimethoxy-phenyl)-ethyl)-hexahydro-azepin-3-yl)-methyl]-7,8-methylenedioxy-2-oxo-1,3,4,5-tetrahydro-2H-3benzazepine, but particularly the following compounds:

3-[(N-(2-(naphth-2-yl)-ethyl)-piperidin-3-yl)-methyl]-7,8-dimethoxy-2-oxo-1,3,4,5-tetrahydro-2H-3-benzazepine, 2-[(N-(3-(4-methoxy-phenoxy)-propyl)-piperidin-3-yl)methyl]-6,7-dimethyl-1-oxo-1,2,3,4-tetrahydro-isoquinoline, 3-[(N-(4-(thienyl-2)-butyl)-piperidin-3-yl)-methyl]-7,8-dimethoxy-2-oxo-1,3,4,5-tetrahydro-2H-3-benzazepine, 2-[(N-(3-(6-methoxy-naphthyl-2-oxy)-propyl)-pyrrolidin-3-yl)-methyl]-6,7-dimethoxy-1-oxo-1,2,3,4-tetrahydro-isoquinoline, 2-[(N-(2-(6-methoxy-naphth-2-yl)-ethyl)-hexahydro-azepin-3-yl)-methyl]-6,7-methylenedioxy-1-oxo-1,2,3,4-tetrahydroisoquinoline, 3-[(N-(2-(4-methoxy-phenyl)-ethyl)-hexahydro-azepin-3-yl)methyl]-7,8-dimethoxy-2-oxo-1,3,4,5-tetrahydro-2H-3-benzazepine, and 3-[(N-(2-(3,4-dimethoxy-phenyl)-ethyl)-hexahydro-azepin-3-yl)-methyl]-7,8-methylenedioxy-2-oxo-1,3,4,5-tetrahydro-2H-3benzazepine.

According to the invention, the new compounds of general formula I can be obtained by the following processes:

I. Synthetic methods for compounds wherein A, B, G, m, n and R are selected from option (i)

a) reacting a compound of general formula

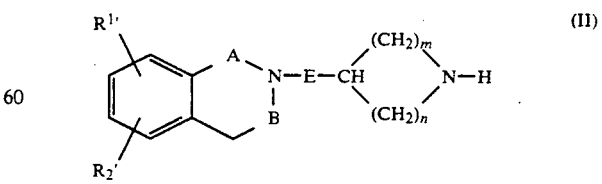

(II)

wherein A, B, E, m and n are as hereinbefore defined, $R_1'$ represents a hydroxy, amino or alkylamino group protected by a protecting group or has the meanings given for $R_1$ hereinbefore, and $R_2'$ represents a hydroxy group protected by a protecting group or has the meanings given for $R_2$ hereinbefore, with a compound of general formula

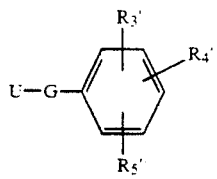

wherein $R_3'$, $R_4'$ and $R_5'$ have the meanings given for $R_3$, $R_4$ and $R_5$ hereinbefore, but the hydroxy, amino or alkylamino groups contained in the groups $R_3$ to $R_5$ may be protected by a protecting group, and U represents a nucleophilic leaving group such as a halogen atom or a sulphonyloxy group, e.g. a chlorine, bromine or iodine atom, a methanesulphonyloxy, p-toluenesulphonyloxy or ethoxysulphonyloxy group, with optional subsequent splitting off of any protecting group used.

The protecting group used for a hydroxy group may be, for example, a trimethylsilyl, acetyl, benzoyl, benzyl or tetrahydropyranyl group and the protecting group used for an amino or alkylamino group may be an acetyl, benzoyl, ethoxycarbonyl or benzyl group.

The reaction is conveniently carried out in a solvent or mixture of solvents such as acetone, diethylether, methylformamide, dimethylformamide, dimethylsulfoxide, benzene, chlorobenzene, tetrahydrofuran, benzene/tetra-hydrofuran, dioxan or in an excess of the compounds of general formulae II and/or III used and optionally in the presence of an acid binding agent, e.g. an alkoxide such as potassium tert.butoxide, an alkali metal hydroxide such as sodium or potassium hydroxide, an alkali metal carbonate such as potassium carbonate, an alkali metal amide such as sodium amide, an alkali metal hydride such as sodium hydride, a tertiary organic base such as triethylamine or pyridine, whilst the latter may simultaneously also serve as solvent, or a reaction accelerator such as potassium iodide depending on the reactivity of the nucleophilically exchangeable group, conveniently at temperatures of between 0° and 150° C., preferably at temperatures of between 50° and 120° C., e.g. at the boiling temperature of the solvent used.

However the reaction may also be carried out without a solvent. It is, however, particularly advantageous to perform the reaction in the presence of a tertiary organic base or an excess of the amine of general formula III used.

The optional subsequent splitting off of a protecting group used is preferably carried out by hydrolysis in an aqueous solvent, e.g. in water, isopropanol/water, tetrahydrofuran/water or dioxan/water, in the presence of an acid such as hydrochloric or sulphuric acid or in the presence of an alkali metal base such as sodium hydroxide or potassium hydroxide at temperatures of between 0° and 100° C., preferably at the boiling temperature of the reaction mixture. However, a benzyl group is preferably split off by hydrogenolysis, e.g. with hydrogen in the presence of a catalyst such as palladium/charcoal in a solvent such as methanol, ethanol, ethyl acetate or glacial acetic acid, optionally with the addition of an acid such as hydrochloric acid at temperatures of between 0° and 50° C., but preferably at ambient temperature, under a hydrogen pressure of from 1 to 7 bar, preferably from 3 to 5 bar.

b) In order to prepare compounds of general formula I wherein G has the meanings given for G hereinbefore, with the exception of the groups containing a sulphenyl, sulphinyl or sulphonyl group, A represents a —CH$_2$—CH$_2$— group, B represents a methylene or carbonyl group and m+n represent the number 4:

hydrogenating a compound of general formula

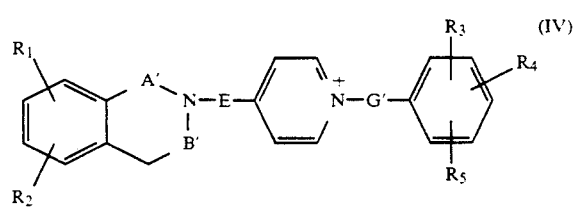

wherein $R_1$ to $R_5$ and E are as hereinbefore defined, G' has the meanings given for G hereinbefore with the exception of the radicals containing a sulphur atom or a sulphinyl or sulphonyl group, A' represents a —CH=CH— or —CH$_2$CH$_2$— group and B' represents a methylene or carbonyl group.

The hydrogenation is carried out in a solvent or mixture of solvents such as methanol, ethanol, ethyl acetate or glacial acetic acid with catalytically activated hydrogen, e.g. with hydrogen in the presence of platinum or palladium/charcoal, optionally in the presence of a base such as an alkoxide, e.g. sodium methoxide, under a hydrogen pressure of from 1 to 7 bar, preferably from 3 to 5 bar, and at temperatures of between 0° and 75° C. but preferably at temperatures of between 20 and 50° C.

In the reaction, any benzyloxy group present may be converted into the corresponding hydroxy group.

c) In order to prepare compounds of general formula I wherein B represents a carbonyl or methylene group:
reacting a compound of general formula

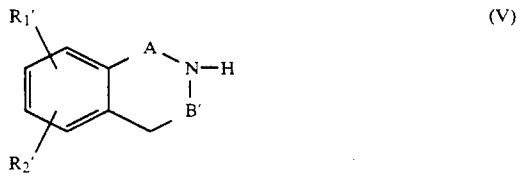

wherein A is as hereinbefore defined, $R_1'$ represents a hydroxy, amino or alkylamino group protected by a protecting group or has the meanings given for $R_1$ hereinbefore, $R_2'$ represents a hydroxy group protected by a protecting group or has the meanings given for $R_2$ hereinbefore, and B' represents a carbonyl or methylene group, with a compound of general formula

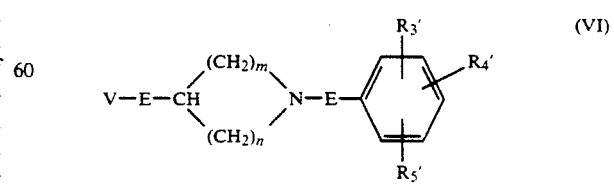

wherein E, G, m and n are as hereinbefore defined, $R_3'$, $R_4'$ and $R_5'$ have the meanings given for $R_3$, $R_4$ and $R_5$ hereinbefore, but the hydroxy, amino or alkylamino groups contained in the groups R₃ to R₅ may be protected by a protecting group, and V represents a nucleophilically exchangeable group such as a halogen atom or a sulphonyloxy group, e.g. a chlorine, bromine or iodine atom, a methane-sulphonyloxy, p-toluenesulphonyloxy or ethoxysulphonyloxy group, with optional subsequent splitting off of any protecting groups used.

Suitable protecting groups for a hydroxy group include, for example, trimethylsilyl, acetyl, benzoyl, benzyl or tetrahydropyranyl groups and suitable protecting groups for an amino or alkylamino group include acetyl, benzoyl, ethoxycarbonyl or benzyl groups.

The reaction is conveniently carried out in a solvent or mixture of solvents such as methylformamide, dimethylformamide, dimethylsulphoxide, benzene, chlorobenzene, tetrahydrofuran, benzene/tetrahydrofuran or dioxan in the presence of an acid binding agent, e.g. an alkoxide such as potassium tert.butoxide, an alkali metal hydroxide such as sodium or potassium hydroxide, an alkali metal carbonate such as potassium carbonate, an alkali metal amide such as sodium amide or an alkali metal hydride such as sodium hydride, conveniently at temperatures of between 0° and 150° C., preferably at temperatures of between 0° and 50° C.

The optional subsequent splitting off of any protecting group used is preferably carried out hydrolytically in an aqueous solvent, e.g. in water, isopropanol/water, tetrahydrofuran/water or dioxan/water, in the presence of an acid such as hydrochloric or sulphuric acid or in the presence of an alkal metal base such as sodium hydroxide or potassium hydroxide at temperatures between 0° and 100° C., preferably at the boiling temperature of the reaction mixture. However, a benzyl group is preferably split off by hydrogenolysis, e.g. with hydrogen in the presence of a catalyst such as palladium/charcoal in a solvent such as methanol, ethanol, ethyl acetate or glacial acetic acid, optionally with the addition of an acid such as hydrochloric acid at temperatures of between 0° and 50° C., but preferably at ambient temperature, under a hydrogen pressure of from 1 to 7 bar, preferably from 3 to 5 bar.

In the reaction, any benzyloxy group present may be converted into the corresponding hydroxy group.

d) In order to prepare compounds of general formula I wherein A represents a —CH₂—CH₂— or —CH=CH— group and B represents a thiocarbonyl group:
reacting a compound of general formula

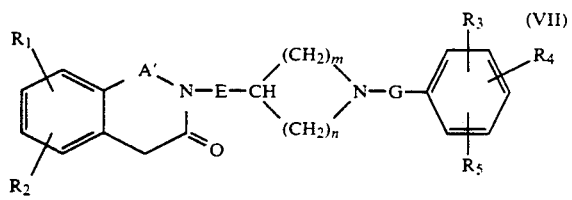

wherein R₁ to R₅, E G m and n are as hereinbefore defined and A' represents a —CH₂—CH₂— or —CH=CH— group, with a sulphurising agent.

The reaction is carried out with a sulphurising agent such as phosphorus pentasulphide or 2,4-bis(4-methoxyphenyl)-1,3-dithia-2,4-diphosphetan-2,4-disulfide conveniently in a solvent such as toluene or xylene at temperatures of between 50° and 50° C., e.g. at the boiling temperature of the reaction mixture.

e) In order to prepare compounds of general formula I wherein A represents a —CHOH—CO— group and B represents a methylene group:
reduction of a compound of general formula

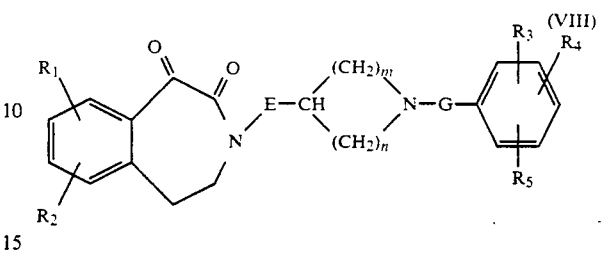

wherein R₁ to R₅, E, G, m and n are as hereinbefore defined.

The reaction is carried out in the presence of a suitable reducing agent such as a metal hydride, e.g. sodium borohydride, in a suitable solvent such as water/methanol or methanol/ether at temperatures of between 0° and 80° C., but preferably at temperatures of between 15° and 40° C.

f) In order to prepare compounds of general formula I wherein A represents a —CH₂—CH₂— or —CH=CH— group and B represents a methylene group:
reduction of a compound of general formula

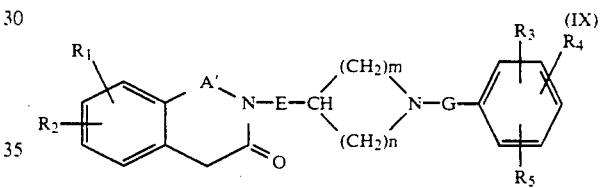

wherein R₁ to R₅, E, G, m and n are as hereinbefore defined and A' represents a —CH₂—CH₂— or —CH=CH— group.

The reduction is preferably carried out with a metal hydride such as lithium aluminium hydride or diborane or with a complex of borane and a thioether, e.g. with a borane-dimethylsulfide complex, in a suitable solvent such as diethyl ether or tetrahydrofuran at temperatures between 0° and 50° C., but preferably at temperatures of between 10° and 25° C.

g) In order to prepare compounds of general formula I wherein A represents a —COCO— group:
oxidation of a compound of general formula

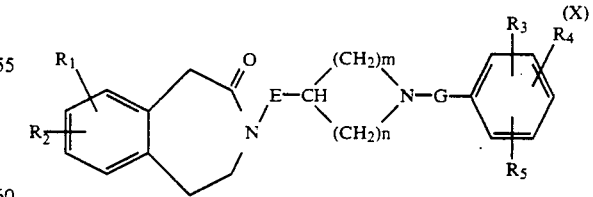

wherein R₁ to R₅, E, G, m and n are as hereinbefore defined.

The Oxidation is preferably carried out with an oxidizing agent such as potassium permanganate, selenium dioxide or sodium dichromate in a suitable solvent or mixture of solvents such as water, water/dioxan, glacial acetic acid, water/glacial acetic acid or acetic anhydride at temperatures of between 0° and 100° C., preferably at temperatures of between 20° and 80° C.

h) In order to prepare compounds of general formula I wherein G has the meanings given for G hereinbefore, with the exception of the radicals containing a sulphur atom or a sulphinyl or sulphonyl group, A represents a —CH$_2$—CH$_2$— group and B represents a methylene or carbonyl group:

hydrogenation of a compound of general formula

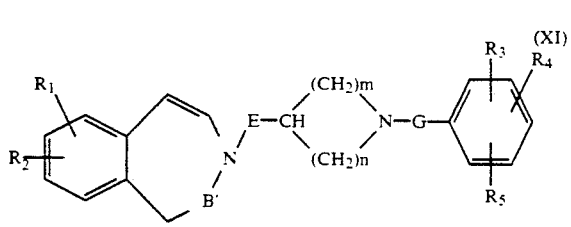

wherein R$_1$ to R$_5$, E, m and n are as hereinbefore defined, G' has the meanings given for G hereinbefore, with the exception of the radicals containing a sulphur atom or a sulphinyl or sulphonyl group and B' represents a methylene or carbonyl group. The hydrogenation is carried out in a solvent or mixture of solvents such as methanol, ethanol, ethyl acetate or glacial acetic acid with catalytically activated hydrogen, e.g. with hydrogen in the presence of platinum or palladium/charcoal, under a hydrogen pressure of from 1 to 7 bar, but preferably from 3 to 5 bar, and at temperatures of between 0° and 75° C., preferably at temperatures of between 20° and 50° C.

If a compound of general formula XI contains a benzyloxy group, this is converted during reduction into the corresponding hydroxy group.

If, according to the invention, a compound of formula I wherein R$_1$ and/or R$_3$ represents a nitro group is obtained, this can be Converted by reduction into a corresponding amino compound of general formula I.

If a compound of general formula I is obtained wherein R$_4$ represents a hydroxy or amino group, this may be converted by acylation into a corresponding alkanesulphonyloxy or alkanoylamino compound of general formula I.

The subsequent reduction of the nitro compound is preferably carried out in a solvent such as water, water-/ethanol, methanol, glacial acetic acid, ethyl acetate or dimethylformamide, conveniently with hydrogen in the presence of a hydrogenation catalyst such as Raney nickel, platinum or palladium/ charcoal, with metals such as iron, tin or zinc in the presence of an acid, with salts such as iron(II)sulphate, tin(II) chloride or sodium dithionite or with hydrazine in the presence of Raney nickel at temperatures of between 0° and 50° C., but preferably at ambient temperature.

The subsequent acylation is conveniently carried out in a solvent such as methylene chloride, chloroform, carbon tetrachloride, ether, tetrahydrofuran, dioxan, benzene, toluene, acetonitrile or dimethylformamide, preferably with a reactive derivative of the acid, for example with methanesulphonic acid chloride, ethanesulphonic acid chloride, n-propanesulphonic acid chloride, acetyl chloride, acetic anhydride or propionic anhydride, and optionally in the presence of an inorganic base such as sodium carbonate or a tertiary organic base such as triethylamine or pyridine, which may simultaneously serve as solvent, at temperatures of between −25° C. and 100° C., but preferably at temperatures of between −10° C. and the boiling temperature of the solvent used.

Since they have at least one chiral centre, the compounds of general formula I obtained can be resolved by conventional methods into their diastereomers, for example by column chromatography, and into their enantiomers, for example by column chromatography on a chiral phase or by crystallisation with optically active acids, e.g. with D- or L-monomethyl tartaric acid, D- or L-diacetyl tartaric acid, D- or L-tartaric acid, D-or L-lactic acid or D- or L-camphoric acid.

The compounds of general formula I obtained may also be converted into the acid addition salts thereof, particularly for pharmaceutical use into the physiologically acceptable acid addition salts thereof with inorganic or organic acids.

The compounds of general formulae II to XI used as starting materials are known from the literature in some cases or may be obtained using methods known per se.

Thus, for example, a starting compound of general formula II is obtained by reacting a corresponding benzazepine with a corresponding halogen compound and optionally by subsequently reacting with a corresponding amine. The corresponding benzazepine of general formula V unsubstituted in the 3-position which is required for this is obtained by cyclising a corresponding compound, e.g. by cyclising a compound of general formula

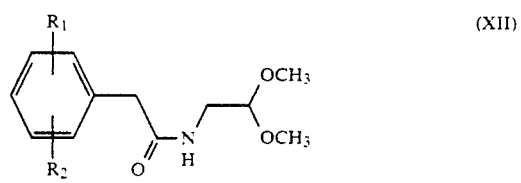

or a compound of general formula

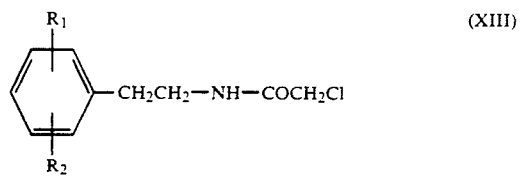

optionally followed by catalytic hydrogenation and/or reduction of the carbonyl group, for example with sodium borohydride/glacial acetic acid (see EP-A1-0,007,070, EP-A1-0,065,229 and EP-A1-0,109,639) and/or oxidation, e.g. with selenium dioxide.

A compound of general formulae IV and VII to XI used as starting material is preferably obtained by reacting a corresponding halogen compound with a corresponding amine, optionally followed by quaternization and/or the splitting off of protecting groups used to protect hydroxy and/or amino groups.

2 Synthetic methods for compounds wherein A, B, G, m, n and R are selected from option (ii)

a) Reacting a compound of general formula

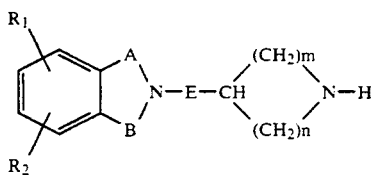

wherein $R_1$, $R_2$, A, B, E, m and n are as hereinbefore defined, with a compound of general formula $$Z_1—G—R \quad \text{(IIIb)}$$

wherein R and G are as hereinbefore defined and $Z_1$ represents a nucleophilic leaving group such as a halogen atom or a sulphonyloxy group, e.g. a chlorine, bromine or iodine atom, a methanesulphonyloxy, p-toluenesulphonyloxy or ethoxysulphonyloxy group, or a hydroxy group, or $Z_1$ together with a hydrogen atom of the adjacent methylene group represents an oxygen atom.

If $Z_1$ represents a nucleophilic leaving group, the reaction is conveniently carried out in a solvent or mixture of solvents such as acetone, diethylether, methylformamide, dimethylformamide, dimethylsulfoxide, benzene, chlorobenzene, tetrahydrofuran, benzene/tetrahydrofuran, dioxan or in an excess of the compounds of general formulae IIb and/or IIIb used and optionally in the presence of an acid binding agent, e.g. an alkoxide such as potassium tert.butoxide, an alkali metal hydroxide such as sodium or potassium hydroxide, an alkali metal carbonate such as potassium carbonate, an alkali metal amide such as sodium amide, an alkali metal hydride such as sodium hydride, a tertiary organic base such as triethylamine or pyridine, whilst the latter may simultaneously also serve as solvent, or a reaction accelerator such as potassium iodide depending on the reactivity of the nucleophilically exchangeable group, conveniently at temperatures of between 0° and 150° C., preferably at temperatures of between 50° and 120° C., e.g. at the boiling temperature of the solvent used. However, the reaction may also be carried out without a solvent advantageous to perform the reaction in the presence of a tertiary organic base or an excess of the amine of general formula IIb used.

If $Z_1$ represents a hydroxy group, the reaction is preferably carried out in a suitable solvent such as methanol, ethanol, tetrahydrofuran, dioxan, ethyl acetate or glacial acetic acid with hydrogen in the presence of a hydrogenation catalyst such as platinum, palladium/charcoal or Raney nickel under a hydrogen pressure of from 2 to 10 bar, preferably 5 bar, and at temperatures of between 20° and 120° C. preferably at temperatures between 50° and 100° C.

If $Z_1$ together with a hydrogen atom of the adjacent methylene group represents an oxygen atom, the reaction is preferably carried out in a suitable solvent such as methanol, ethanol, tetrahydrofuran, dioxan, ethyl acetate or glacial acetic acid with hydrogen in the presence of a hydrogenation catalyst such as platinum, palladium/charcoal or Raney nickel under a hydrogen pressure of from 2 to 10 bar, preferably 5 bar, and at temperatures of between 20° and 120° C. preferably at temperatures of between 50° and 100° C., or in the presence of a suitable complex metal hydride such as sodium cyanoborohydride in a suitable solvent such as methanol, ethanol, tetrahydrofuran, dioxan or acetonitrile at temperatures of between 0° and 50° C., but preferably at ambient temperature.

b) Reacting a compound of general formula

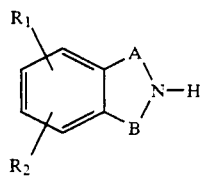

wherein $R_1$, $R_2$, A and B are as hereinbefore defined, with a compound of general formula

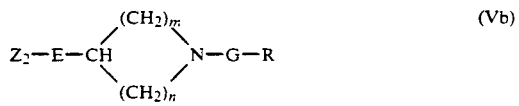

wherein R, E, G, m and n are defined as hereinbefore and $Z_2$ represents a nucleophilic leaving group such as a halogen atom or a sulphonyloxy group, e.g. a chlorine, bromine or iodine atom or a methanesulphonyloxy, p-toluenesulphonyloxy or ethoxysulphonyloxy group.

The reaction is preferably carried out in a solvent or mixture of solvents such as methylformamide, dimethylformamide, dimethylsulphoxide, benzene, chlorobenzene, tetrahydrofuran, benzene/tetrahydrofuran or dioxan in the presence of an acid-binding agent, e.g. an alkoxide such as potassium tert.butoxide, an alkali metal hydroxide such as sodium or potassium hydroxide, an alkali metal carbonate such as potassium carbonate an alkali metal amide such as sodium amide or an alkali metal hydride such as sodium hydride, conveniently at temperatures of between 0° and 150° C., preferably at temperatures of between 0° and 50° C.

c) In order to prepare compounds of general formula I wherein B represents a —CH$_2$— or —CH$_2$CH$_2$— group: reduction of a compound of general formula

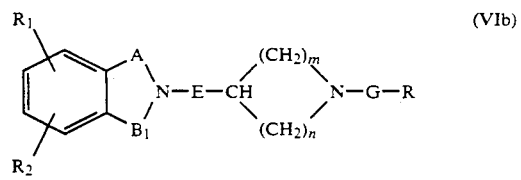

wherein,

R, $R_1$, $R_2$, A, E, G, m and n are defined as hereinbefore; A is a —CH$_2$—, —CO—, —CH$_2$CH$_2$— or —CH=CH— group; and, B$_1$ represents a —CO— or —CH$_2$CO— group, with the carbon atom designated by underlining being linked to the phenyl nucleus.

The reduction is preferably carried out with a metal hydride such as lithium aluminium hydride or diborane or a complex of borane and a thioether, e.g. with borane-dimethylsulphide complex, in a suitable solvent such as diethylether or tetrahydrofuran at temperatures of between 0° and 80° C., but preferably at temperatures between 10° and 45° C.

d) In order to prepare compounds of general formula I wherein A represents a —CH$_2$— group and B represents a —CO— or —CH₂CO— group: reduction of a compound of general formula

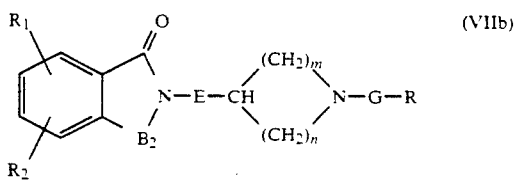
(VIIb)

wherein R, R₁, R₂, E, G, m and n are defined as hereinbefore and B₂ represents a —CO— or —CH₂CO— group, with the carbon atom designated by underlining being linked to the phenyl nucleus, with nascent hydrogen.

The reduction is carried out in a suitable solvent such as glacial acetic acid, glacial acetic acid/water or glacial acetic acid/ethanol with nascent hydrogen, e.g. in the presence of zinc/glacial acetic acid, tin/hydrochloric acid or tin dichloride/hydrochloric acid at temperatures between 20° and 150° C., but preferably at the boiling temperature of the reaction mixture, e.g. at temperatures between 80° and 100° C.

e) In order to prepare compounds of general formula I wherein G has the meanings given for G hereinbefore, with the exception of the groups containing a sulphur atom, a sulphinyl or sulphonyl group, and A represents the —CH₂—CH₂— group and B represents a —CH₂—, —CO— or —CH₂CO— group:

hydrogenation of a compound of general formula

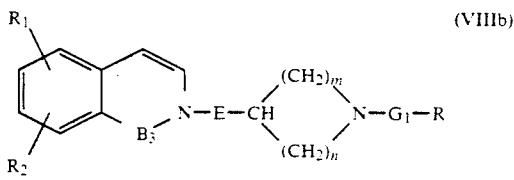
(VIIIb)

wherein R, R₁, R₂, B, E, m and n are defined as hereinbefore, G₁ has the meanings given for G hereinbefore with the exception of the groups containing a sulphur atom or a sulphinyl or sulphonyl group and B₃ represents a —CH₂—, —CO— or —CH₂CO— group.

The hydrogenation is carried out in a solvent or mixture of solvents such as methanol, ethanol, ethyl acetate or glacial acetic acid with catalytically activated hydrogen, e.g. with hydrogen in the presence of platinum or palladium/charcoal, under a hydrogen pressure of from 1 to 7 bar, but preferably from 3 to 5 bar, and at temperatures of between 0° and 75° C., but preferably at temperatures between 20° and 50° C.

In the reaction described above, any reactive groups present such as hydroxy, amino, alkylamino or imino groups may be protected during the reaction by means of conventional protecting groups which are cleaved again after the reaction.

For example, a suitable protecting group for a hydroxy group is a trimethylsilyl, acetyl, benzoyl, benzyl or tetrahydropyranyl group and a suitable protecting group for an amino, alkylamino or imino group is an acetyl, benzoyl, ethoxycarbonyl or benzyl group.

The optional subsequent cleaving of a protecting group is preferably carried out hydrolytically in an aqueous solvent, e.g. in water, isopropanol/water, tetrahydrofuran/water or dioxan/water, in the presence of an acid such as hydrochloric or sulphuric acid or in the presence of an alkali metal base such as sodium hydroxide or potassium hydroxide at temperatures between 0° and 100° C., preferably at the boiling temperature of the reaction mixture. However, a benzyl group is preferably split off by hydrogenolysis, e.g. with hydrogen in the presence of a catalyst such as palladium/charcoal in a solvent such as methanol, ethanol, ethyl acetate or glacial acetic acid, optionally with the addition of an acid such as hydrochloric acid at temperatures between 0° and 50° C., but preferably at ambient temperature, under a hydrogen pressure of from 1 to 7 bar, preferably from 3 to 5 bar.

If, according to the invention, a compound of general formula I wherein R contains a nitro group is obtained, this can be converted by reduction into a corresponding amino compound of general formula I, or if a compound of general formula I is obtained wherein R contains an amino group, this may be converted by acylation into a corresponding alkanoylamino compound of general formula I.

The subsequent reduction of the nitro compound is preferably carried out in a solvent such as water, water/ethanol, methanol, glacial acetic acid, ethyl acetate or dimethylformamide, conveniently with hydrogen in the presence of a hydrogenation catalyst such as Raney nickel, platinum or palladium/char-coal, with metals such as iron, tin or zinc in the presence of an acid, with salts such as iron(II)-sulphate, tin(II) chloride or sodium dithionite or with hydrazine in the presence of Raney nickel at temperatures of between 0° and 50° C., but preferably at ambient temperature.

The subsequent acylation is conveniently carried out in a solvent such as methylene chloride, chloroform, carbon tetrachloride, ether, tetrahydrofuran, dioxan, benzene, toluene, acetonitrile or dimethylformamide, preferably with a reactive derivative of the acid, for example with acetyl chloride, acetic anhydride or propionic anhydride, and optionally in the presence of an inorganic base such as sodium carbonate or a tertiary organic base such as triethylamine or pyridine, which may simultaneously serve as solvent, at temperatures of between −25° C. and 100° C., but preferably at temperatures of between −10° C. and the boiling temperature of the solvent used.

Since they have at least one chiral centre, the compounds of general formula I obtained can be resolved by conventional methods into their diastereomers, for example by column chromatography, and into their enantiomers, for example by column chromatography on a chiral phase or by crystallisation with optically active acids, e.g. with D- or L-monomethyl tartaric acid, D- or L-diacetyl tartaric acid, D- or L-tartaric acid, D-or L-lactic acid or D- or L-camphoric acid.

The compounds of general formula I obtained may also be converted into the acid addition salts thereof, particularly for pharmaceutical use into the physiologically acceptable acid addition salts thereof with inorganic or organic acids.

Suitable acids include, for example, hydrochloric, hydrobromic, sulphuric, phosphoric, acetic, lactic, citric, tartaric, succinic, maleic and fumaric acids.

The compounds of general formulae IIb to VIIIb used as starting materials are known from the literature in some cases or may be obtained using methods known per se.

Thus, for example, a starting compound of general formula IIb is obtained by alkylation of a corresponding imino compound of general formula IVb with a cyclic amine protected at the N atom by a conventional protecting group, said cyclic amine being substituted in the carbon structure by an alkyl group which is in turn substituted in the terminal position by a nucleophilic leaving group, and subsequently cleaving the protecting group used. The cyclic amine required for this is obtained by converting a corresponding cyclic amine substituted by a hydroxyalkyl group into a suitable halogen or sulphonic acid ester thereof and the imino compound of general formula IVb required for this is obtained by cyclising a corresponding compound, e.g. by cyclising a compound of general formula or of general formula

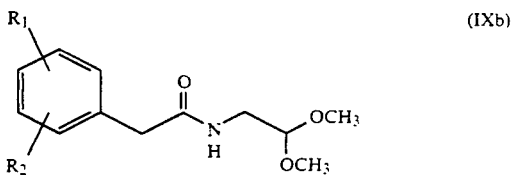

(IXb)

or of general formula

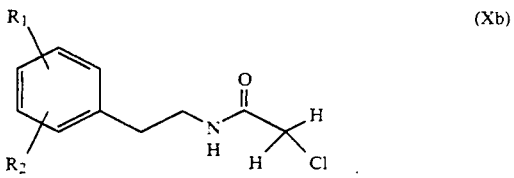

(Xb)

optionally followed by catalytic hydrogenation and/or reduction of the carbonyl group, for example with sodium borohydride/glacial acetic acid (see EP-A1 0,007,070, EP-A1 0,065,229 and EP-A1 0,109,639).

A compound of general formula Vb used as starting material is obtained by N-alkylation of a corresponding cyclic amine, substituted in the carbon structure by a hydroxyalkyl group, with a corresponding compound or with a corresponding 1,ω-dihaloalkane and subsequent reaction with a corresponding HO, SH or HN compound and if necessary subsequent oxidation, a hydroxyalkyl compound thus obtained then being converted into its reactive halogen or sulphonic acid esters.

A compound of general formulae VIb, VIIb or VIIIb used as starting material is preferably obtained by reacting a corresponding halogen compound with a corresponding amine, optionally followed by the splitting off of protecting side-effects on the central nervous system.

PHARMACOLOGICAL PROPERTIES OF COMPOUNDS OF FORMULA I

As already mentioned hereinbefore, the new compounds of general formula I and the physiologically acceptable acid addition salts thereof with inorganic or organic acids have valuable pharmacological properties, particularly a hypotensive effect and an especially long-lasting lowering effect on heart rate and the effect of reducing the $O_2$ requirement of the heart, with only minor side-effects on the central nervous system.

In order to demonstrate the pharmacological properties of the compounds of formula I, exemplary compounds listed below were tested using the experimental protocol described below.

A. Compounds of Formula I wherein A, B, G, m, n and R are selected from option (i)

A = 3-[(N-(2-(3,4-dimethoxy-phenyl)-ethyl)-piperidin-3-yl) methyl]-7,8-dimethoxy-1,3,4,5-tetrahydro- 2H-3-benzazepin-2-one, B = 3-[(N-(2-(3-methyl-phenyl)-ethyl)-piperidin-3- yl)-methyl]-7,8-dimethoxy-1,3,4, 5-tetrahydro-2H- 3-benzazepin-2-one, C = 3-[(N-(3-(4-methoxy-phenyl)-propyl)-piperidin-3-yl)methyl]-7,8-dimethoxy-1,3,4, 5-tetrahydro-2H-3-benzazepin-2-one, and D = 3-[(N-(2-(3,4-dimethoxy-phenyl)-ethyl)-piperidin-2-yl)ethyl-2]-7,8-dimethoxy-1,2,3,4, 5-tetrahydro-2H-3-benzazepin-2-one.

B. Compounds of Formula I wherein A, B, G, m, n, and R are selected from option (ii)

E = 3-[(N-(2-(naphth-2-yl)-ethyl)-piperidin-3-yl)- methyl]-7,8-dimethoxy-2-oxo-1,3,4, 5-tetrahydro- F = 3-[(N-(2-(5-methyl-6-methoxy-naphth-2-yl)-ethyl)-piperidin-3-yl)-methyl]-7, 8-dimethoxy-2-oxo- 1,3,4,5-tetrahydro-2H-3-benzazepine- hydrochloride, G = 3-[2-(N-(2-(6-methoxy-naphth-2-yl)-ethyl)-piperidin-2-yl)ethyl]-7, 8-dimethoxy-2-oxo- 1,3,4,5-tetrahydro-2H-3-benzazepinehydrochloride, H = 2-[(N-(2-(6-methoxy-naphth-2-yl)-ethyl)- hexahydroazepin-3-yl)-methyl]-6, 7-methylenedioxy- 1-oxo-1,2,3,4-tetrahydro isoquinoline hydrochloride, I = 2-[(N-(2-(naphth-2-yl)-ethyl)-hexahydro-azepin-3-yl)methyl]-6,7-methylenedioxy-1-oxo-1,2, 3,4- tetrahydro isoquinoline-hydrobromide.

J = 2-[N-(2-(3,4-dimethoxy-phenyl)-ethyl)-piperidin-3yl)-methyl]-6,7-dimethyl-1,2,3, 4-tetrahydro-isoquinolinedihydrochloride, K = 2-[(N-(2-(3,4-dimethoxy-phenyl)-ethyl)-piperidin-3-yl)methyl]-6,7-dimethyl-1-oxo-1,2,3, 4-tetrahydro-isoquinolinehydrochloride, L = 2-[(N-(3-(4-methoxy-phenoxy)-propyl)-piperidin-3-yl)methyl]-6,7-dimethyl-1-oxo-1,2,3, 4- tetrahydro-isoquinolinehydrochloride, M = 3-[(N-(4-(thienyl-2)-butyl)-piperidin-2-yl)- methyl]-7,8-dimethoxy-2-oxo-1,3,4, 5-tetrahydro- 2H-3-benzazepinehydrochloride, N = 3-[(N-(2-(benzo[b]furyl-2-)-ethyl)-piperidin-3- yl)-methyl]-7,8-dimethoxy-2-oxo-1,3,4, 5- tetrahydro-2H-3-benzazepinehydrochloride, and O = 3-[(N-(2-(benzo[b]thienyl-3-)-ethyl)-piperidin-3-yl)methyl]-7,8-dimethoxy-2-oxo-1,3,4, 5- tetrahydro-2H-3-benzazepinehydrochloride.

Effect on heart rate in rats:

The activity of the test substances on the heart rate was investigated, for each dosage, on 2 rats with an average weight of 250–300 g. The rats were anaesthetized with pentobarbital (50 mg/kg i.p. and 20 mg/kg s.c.). The test substances were injected in aqueous solution into the jugular vein (0.1 ml/100 g).

The blood pressure was measured using a cannula inserted in a carotid artery and the heart rate was recorded from an ECG (second or third derivation) derived with needle electrodes. The heart rate of the animals in the control period was between 350 and 400 beats per minute (b/min).

The following Tables contain the values found:

Lowering of Heart Rate
Measured 20 minutes after administration

-continued

| Substance | Dosage [mg/kg] | of substance [b/min] |
|---|---|---|
| A | 5.0 | −208 |
| B | 5.0 | −148 |
| C | 5.0 | −135 |
| D | 5.0 | −125 |

| Substance | Dosage [mg/kg] | Lowering of Heart Rate in b/m after | | Lowering of blood Pressure in mmHg after | |
|---|---|---|---|---|---|
| | | 5 min. | 20 min. | 5 min | 20 min. |
| E | 5.0 | −128 | −259 | −46 | −32 |
| F | 5.0 | −188 | −218 | −22 | −15 |
| G | 5.0 | −236 | −194 | −40 | −31 |
| H | 5.0 | −173 | −123 | −21 | −16 |
| I | 5.0 | −169 | −150 | −30 | −16 |
| J | 5.0 | −150 | −120 | −49 | −27 |
| K | 5.0 | −207 | −101 | −57 | −8 |
| L | 5.0 | −190 | −180 | −57 | −33 |
| M | 5.0 | −320 | −253 | −65 | −32 |
| N | 2.5 | −138 | −156 | −36 | — |
| O | 2.5 | −110 | −163 | −40 | −24 |

When administered in therapeutic doses the compounds prepared according to the invention show no toxic side effects of any kind. Thus, when administered intravenously to mice, even in a high dosage of 20 mg/kg, substances A, D, E and O showed no toxic side effects apart from a slight sedation.

In view of their pharmacological properties, the compounds prepared according to the invention are suitable for the treatment of sinus tachycardia of various origins and for the prevention and treatment of ischaemic heart dizease.

The dosage required to achieve this effect is conveniently from 0.01 to 0.2 mg/kg of body weight, preferably from 0.03 to 0.15 mg/kg of body weight, once or twice a day. The compounds of general formula I and the physiologically acceptable acid addition salts thereof with inorganic or organic acids produced according to the invention may be incorporated, optionally together with other active substances, with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, carboxymethylcellulose or fatty substances such as hard fat or suitable mixtures thereof, to produce conventional galenic preparations such as tablets, coated tablets, capsules, powders, suspensions, drops, ampoules, syrups or suppositories.

The following examples are intended to illustrate the invention:

A. Examples for compounds of Formula I wherein A, B, G, m, n and R are selected from option (i)

EXAMPLE A

N-Benzyl-3-(hydroxyethyl)-piperidine

A mixture of 40.3 g (0.35 mol) of 3-(hydroxymethyl)-piperidine, 97.4 ml (0.70 mol) of triethylamine and 40.3 ml (0.35 mol) of benzyl chloride is heated to 95° C. within 30 minutes and left at this temperature for 2 hours. After cooling the reaction mixture is dissolved in a mixture of 2 molar sodium hydroxide solution and ethyl acetate. The organic phase is washed with water, separated off, dried over magnesium sulphate and concentrated by evaporation in vacuo. Yield: 57.2 g (79.6% of theory), Rf value: 0.45 (aluminium oxide neutral, eluant: 3% ethanol in methylene chloride).

EXAMPLE B

N-Benzyl-3-(bromomethyl)-piperidine 55.1 g (0.268 mol) of N-benzyl-3-(hydroxymethyl)-piperidine are added to 400 ml of 48% hydrobromic acid with vigorous stirring and the mixture is refluxed for 1 hour. Then hydrogen bromide is introduced to saturation point (about 1 hour), the mixture is refluxed for another hour and left to stand overnight. It is then neutralized with solid potassium carbonate whilst cooling with ice and then extracted with methylene chloride. The organic phase is dried over magnesium sulphate and concentrated by evaporation in vacuo. Yield: 52.0 g (72.2% of theory), Rf value: 0.85 (aluminium oxide neutral, eluant: methylene chloride).

EXAMPLE C

3-[(N-Benzyl-piperidin-3-yl)-methyl]-7,8-dimethoxy-1,3-dihydro-2H-3-benzazepin-2-one 17.54 g (0.08 mol) of 7,8-dimethoxy-1,3-dihydro-2H-3-benzazepin-2-one are suspended in 150 ml of dimethylsulphoxide and 8.98 g (0.08 mol) of potassium tert-.butoxide are added with stirring. After 45 minutes, 21.45 g (0.08 mol) of N-benzyl-3-(bromomethyl)-piperidine dissolved in 50 ml of dimethylsulphoxide are added dropwize to the resulting solution with stirring. After 2 hours the mixture is poured onto ice water. The aqueous phase is extracted three times, each time with 150 ml of ethyl acetate. The combined organic phases are washed with water, dried over magnesium sulphate, concentrated by evaporation in vacuo and purified over 800 g of aluminium oxide (neutral, activity II-III) with methylene chloride and then with increasing amounts of ethanol (up to 3%). Yield: 14.3 g (44% of theory), Rf value: 0.35 (aluminium oxide neutral, eluant: 1% ethanol in methylene chloride).

EXAMPLE D

3-[(Piperidin-3-yl)-methyl]-7,8-dimethoxy-1,3,4,5-tetrahydro-2H-3-benzazepin-2-one 14.3 g (0.0352 mol) of 3-[(N-benzyl-piperidin-3-yl)-methyl]7,8-dimethoxy-1,3-dihydro-2H-3-benzazepin-2-one are hydrogenated in 120 ml of glacial acetic acid in the presence of 1.5 g of 10% palladium/charcoal for 4 hours at 50° C. under 5 bar of hydrogen. The catalyst is then removed by suction filtering, the glacial acetic acid is distilled off in vacuo and, after the addition of water, the residue is neutralized with potassium carbonate. The greasy precipitate is extracted with methylene chloride, the organic phase is dried over magnesium sulphate and concentrated by evaporation in vacuo. Yield: 9.3 g (83% of theory), Melting point: 152°–156° C.

EXAMPLE E

3-[(Pyridin-3-yl)-methyl]-7,8-dimethoxyl-1,3-dihydro-2H-3-benzazepin-2-one 2.2 g (0.01 mol) of 7,8-dimethoxy-1,3-dihydro-2H-3-benzazepin-2-one are suspended in 10 ml of dimethylsulphoxide and 1.12 g (0.01 mol) of potassium tert.butoxide are added with stirring. After 60 minutes, 1.3 g (0.01 mol) of 3picolylchloride dissolved in 10 ml of dimethylsulphoxide are added dropwize to the resulting solution with stirring. After 1 hour it is poured onto ice water. The aqueous phase is extracted twice with ethyl acetate. The combined organic phases are washed with water, dried over magnesium sulphate, concentrated by evaporation in vacuo and purified over 200 g of aluminium oxide (neutral, activity II-III) with methylene chloride and then with increasing quantities of methanol (up to 0.8%). Yield: 1.4 g (45.2% of theory), Melting point: 144°–146° C.

EXAMPLE F

3-[(N-(2-(3,4-Dimethoxy-phenyl)-ethyl)-pyridinium-3-yl)-methyl]7,8-dimethoxy-1,3-dihydro-2H-3-benzazepin-2-one bromide A mixture of 1.1 g (0.0035 mol) of 3-[(pyridin-3-yl)methyl]-7,8-dimethoxy-1,3-dihydro-2H-3-benzazepin-2-one and 2-(3,4-dimethoxyphenyl)-ethyl bromide is heated to 110° C. for 6 hours. After cooling, the reaction mixture is dissolved in a little methanol/ methylene chloride and added dropwize to 200 ml of diethylether, with vigorous stirring. The precipitate obtained is suction filtered and dried. Yield: 1.6 g (80% of theory), Melting point: 147°–150° C.

EXAMPLE G

N-[2-(3,4-Dimethoxy-phenyl)-ethyl]-3-(hydroxymethyl)piperidine

A mixture of 2.30 g (0.02 mol) of 3-(hydroxymethyl)-piperidine, 5.5 ml (0.04 mol) of triethylamine and 4.90 g (0.02 mol) of 2-(3,4-dimethoxy-phenyl)-ethyl bromide is refluxed for 2 hours. After cooling, the reaction mixture is dissolved in a mixture of 2 molar sodium hydroxide solution and methylene chloride. The organic phase is washed with water, separated off, dried over magnesium sulphate, evaporated down in vacuo and purified over 300 g of aluminium oxide (neutral, activity II-III) with methylene chloride and then with increasing amounts of ethanol (up to 2%). Yield: 4.4 g (78.7% of theory), Melting point: 87.5°–89° C.

EXAMPLE H

N-[2-(3,4-Dimethoxy-phenyl)-ethyl]-3-(bromomethyl)-piperidine 4.4 g (0.0157 mol) of N-[2-(3,4-dimethoxy-phenyl)-ethyl]-3(hydroxymethyl)-piperidine are dissolved in 70 ml of carbon tetrachloride and cooled to 0° C. Then 1.63 ml (0.0173 mol) of phosphorus tribromide is added, whereupon a bulky precipitate is immediately formed. The mixture is stirred for 15 hours at ambient temperature, water is added and the mixture is neutralized with 2 molar sodium hydroxide solution. The organic phase is separated off, washed with water, dried over magnesium sulphate, concentrated by evaporation in vacuo and purified over 310 g of aluminium oxide (neutral, activity II-III) with methylene chloride and then with increasing amounts of ethanol (up to 5%). Yield: 2.0 g (37.2% of theory), Rf value: 0.5 (aluminium oxide neutral, eluant: 2% ethanol in methylene chloride).

EXAMPLE I

N-Benzyl-caprolactam 33.9 g (0.3 mol) of caprolactam are dissolved in 200 ml of absolute dimethylsulphoxide and 100 ml of absolute tetramethyl urea and 14.4 g (0.33 mol) of 55% sodium hydride/oil dispersion is added in batches. The resulting jelly-like precipitate is stirred for 2 hours at ambient temperature. Then 38 g=34.4 ml (0.3 mol) of benzyl chloride are added dropwize, the mixture is stirred for 2 hours at ambient temperature and then poured onto ice water. The aqueous phase is extracted twice with ethyl acetate. The organic phases are combined, washed four times with water, dried over magnesium sulphate and concentrated by evaporation in vacuo. The residue remaining is distilled in vacuo. Yield: 49.9 g (81.8% of theory), Bp 0.27 mm Hg: 110°–114° C.

EXAMPLE K

1-Benzyl-caprolactam-3-carboxylic acid 180 ml of 1.6 molar butyl lithium solution in n-hexane are added at −60° C. to 33.9 g=47.1 ml (0.33 mol) of diisopropylamine in 450 ml of absolute ether, with stirring and under nitrogen. Then, whilst cooling is continued, 48.8 g (0.24 mol) of N-benzylcaprolactam dissolved in 150 ml of absolute ether are added dropwize thereto. After the mixture has been stirred for 10 minutes the cooling bath is taken away and carbon dioxide is bubbled in for 15 minutes. The reaction mixture is poured onto ice, the ethereal phase is separated off and extracted twice with 2 molar sodium hydroxide solution. The aqueous/alcoholic phases are combined, extracted with ether, acidified with concentrated hydrochloric acid and extracted twice with methylene chloride. The combined methylene chloride phases are dried over magnesium sulphate and the solvent is distilled off in vacuo. Yield: 15.7 g (26.5% of theory), IR spectrum (methylene chloride): 1735 and 1600 cm$^{-1}$ (CO).

EXAMPLE L

1-Benzyl-3-hydroxymethyl-hexahydro-azepine 14.8 g (0.06 mol) of 1-benzyl-caprolactam-3-carboxylic acid dissolved in 300 ml of absolute tetrahydrofuran are added dropwize to 6.84 g (0.18 mol) of lithium aluminium hydride in 300 ml of absolute tetrahydrofuran. The mixture is then refluxed for 6 hours, then 6.8 ml of water, 6.8 ml of 2-molar sodium hydroxide solution and 21 ml of water are added, whilst cooling with ice water. The precipitate is removed by suction filtering, washed with tetrahydrofuran and the filtrate is concentrated by evaporation in vacuo. The residue s purified by column chromatography over aluminium oxide N (activity II, eluant: methylene chloride). Yield: 8.4 g (63.8% of theory), IR spectrum (methylene chloride): 3620 cm$^{-1}$ (OH).

EXAMPLE M

1-Benzyl-3-bromomethyl-hexahydro-azepine 8.3 g (0.038 mol) of 1-benzyl-3-hydroxymethyl-hexahydroazepine are dissolved in 200 ml of carbon tetrachloride and 16 ml of phosphorus tribromide are added. The mixture is stirred for 6 hours at ambient temperature, water is then added whilst the mixture is cooled with ice and it is made slightly alkaline with 2-molar sodium hydroxide solution. The aqueous solution is separated off and extracted twice with methylene chloride. The organic phases are combined, dried over magnesium sulphate and concentrated by evaporation in vacuo. Yield: 8.9 g (82% of theory).

EXAMPLE N

3[(N-Benzyl-hexahydro-azepin-3-yl)-methyl]-7,8-dimethoxy1,3-dihydro-2H-3-benzazepin-2-one 2.3 g (0.02 mol) of potassium tert.butoxide are added to a solution of 4.4 g (0.02 mol) of 7,8-dimethoxy-1,3-dihydro-2H-3-benzazepin-2-one in 100ml of absolute dimethylsulphoxide. After stirring for 30 minutes at ambient temperature, 5.6 g (0.020 mol) of 1-benzyl-3-bromomethyl-hexahydro-azepine are added and the resulting mixture is stirred for 2 hours at ambient temperature. The reaction mixture is dissolved in ethyl acetate and extracted several times with water. The organic phase is dried over magnesium sulphate and evaporated down in vacuo. The residue is purified by column chromatography over aluminium oxide N (activity II, eluant: methylene chloride, methylene chloride+0.3% ethanol). Yield: 4.2 g (50% of theory), IR spectrum (methylene chloride): 1655 cm−1 (CO).

EXAMPLE O 3-(Hexahydro-azepin-3-yl)-methyl]-7,8-dimethoxy-1,3,4,5tetrahydro-2H-3-benzazepin-2-one 4.2 g (0.01 mol) of 3-[(N-benzyl-hexahydro-azepin-3-yl)methyl]-7,8-dimethoxy-1,3-dihydro-2H- 3-benzazepin-2-one are hydrogenated in 100 ml of glacial acetic acid in the presence of 0.5 g of 10% palladium/charcoal for 14 hours at 50 psi and at 50C. The catalyst is removed by suction filtering and the glacial acetic acid is distilled off in vacuo. The residue is taken up in water, made alkaline with 2-molar sodium hydroxide solution and extracted several times with methylene chloride. The organic extract is dried over magnesium sulphate and concentrated by evaporation in vacuo. Purification by column chromatography is carried out over aluminium oxide N (activity II<eluant: methylene chloride+1% ethanol). Yield: 2.6 g (78.2% of theory), IR spectrum (methylene chloride): 1650 cm−1 (CO).

EXAMPLE P

7-Carbethoxymethyl-caprolactam

At 0° C. 9.2 g=9 ml (0.05 mol) of ethyl cyclohexanone-2acetate are added dropwize to 50 ml of concentrated sulphuric acid. Then 3.25 g (0.05 mol) of sodium azide are added in batches. After stirring for 10 hours at 0° C. the reaction mixture is poured onto ice water and neutralized with concentrated ammonia with further cooling. After the solution has been saturated with sodium chloride it is extracted several times with n-butanol to which 10% methylene chloride is added. The extract is evaporated down in vacuo and the residue is separated by column chromatography over aluminium oxide N (activity II, eluant: methylene chloride+0.5% ethanol). Yield: 5.7 g (56.6% of theory), Melting point: 108°-109° C.

EXAMPLE Q 2-(2-Hydroxyethyl)-hexahydro-azepine-hydrochloride 5.6 g (0.028 mol) of 7-carbethoxymethyl-caprolactam dissolved in 50 ml of absolute dioxan are added dropwize to 2.6 g (0.06 mol) of lithium aluminium hydride in 100 ml of absolute dioxan, with stirring and refluxing. The mixture is refluxed for 18 hours and then whilst it is cooled with ice water, 2.3 ml of water, 2.3 ml of 15% sodium hydroxide solution and 6.9 ml of water are added. The precipitate is removed by suction filtering and washed with ether. The filtrate is concentrated by evaporation in vacuo, the residue is dissolved ether and precipitated with ethereal hydrochloric acid. Yield: 3 g (59.6% of theory), Melting point: 75° C.

EXAMPLE R

N-[2-(3,4-Dimethoxy-phenyl)-ethyl]-2-(2-hydroxyethyl)-hexahydro-azepine 2.9 g (0.016 mol) of 2-(2-hydroxyethyl)-hexahydro-azepinehydrochloride are liberated with concentrated sodium hydroxide solution, taken up in methylene chloride and, after drying, evaporated down over magnesium sulphate. The residue is refluxed for 2 hours with 3.9 g (0.016 mol) of 2-(3,4-dimethoxy-phenyl)ethylbromide in 10 ml of triethylamine. After cooling, the reaction mixture is combined with 2 molar sodium hydroxide solution/methylene chloride. The alkaline phase is separated off and extracted twice with methylene chloride and the combined organic phases are dried over magnesium sulphate. The solvent is distilled off in vacuo and the residue is purified by column chromatography over aluminium oxide N (activity II, eluant: methylene chloride). Yield: 3.7 g (75.2% of theory).

EXAMPLE S 2-(2-Bromoethyl)-1-[2-(3,4-dimethoxy-phenyl)-ethyl]-hexahydro-azepine 4 ml of phosphorus tribromide are added dropwize to 2.9 g (9.4 mmol) of N-[2-(3,4-dimethoxy-phenyl)-ethyl]-2-(2-hydroxyethyl)-hexahydro-azepine in 100 ml of carbon tetrachloride, whilst cooling with ice, and the mixture is stirred for 15 hours at ambient temperature. Then water is added, whilst cooling with ice water is continued, and the mixture is made slightly alkaline with 2 molar sodium hydroxide solution. The aqueous/alkaline solution is separated off and extracted twice with methylene chloride. The combined organic solutions are dried over magnesium sulphate and concentrated by evaporation in vacuo. Yield: 3.6 g (100% of theory).

EXAMPLE T 3-(Pyridin-3-yl)-methyl]-7,8-dimethoxy-1,3-dihydro-2H-3benzazepin-2-one a)(Pyridin-3-yl)-methylamino-N-acetaldehyde-dimethyl acetal 5.36 g (0.050 mol) of pyridine-3-aldehyde and 5.26 g (0.050 mol) of aminoacetaldehyde-dimethylacetal are hydrogenated in 80 ml of ethanol in the presence of 0 8 g of 10% palladium/activated charcoal for 2 hours at 20° C. under 5 bar. The catalyst is then removed by suction filtering and the ethanol is distilled off in vacuo. Yield: 9.4 g (96% of theory), Rf value: 0.25 (aluminium oxide, eluant: 2% ethanol in methylene chloride).

b)3,4-Dimethoxy-phenylacetic acid-N-(acetaldehyde-dimethylacetal)-N-[(pyridin-3-yl)-methyl])-amide 7.85 g (0.040 mol) of (pyridin-3-yl)-methylamino-N-acetaldehyde-dimethylacetal and 4.4 g (0.044 mol) of triethylamine are dissolved in 50 ml of methylene chloride. Whilst cooling with ice, 8.58 g (0.040 mol) of 3,4-dimethoxyphenylacetic acid chloride are added dropwize to this mixture and the resulting mixture is stirred for 1 hour at 20° C. It is then extracted 3 times with water and the organic phase is dried over magnesium sulphate and then concentrated by evaporation. Yield: 12.6 g (84% of theory) Rf value: 0.5 (on silica gel, eluant: 5% ethanol in methylene chloride).

c) 3-[(Pyridin-3-yl)-methyl]-7,8-dimethoxy-1,3-dihydro-2H- 3-benzazepin-2-one 3.74 g (0.010 mol) of 3,4-dimethoxy-phenylacetic acid-N(acetaldehyde-dimethylacetal)-N-[(pyridin-3-yl)-methyl ]-amide are dissolved in 10 ml of concentrated hydrochloric acid and 10 ml of glacial acetic acid and stirred for 60 hours at 20° C. The mixture is then poured onto ice water, neutralized with 25% sodium hydroxide solution and extracted twice with methylene chloride. The organic phase is dried over magnesium sulphate, filtered off and concentrated by rotation. Yield: 1.85 g (60% of theory), Melting point: 144°–146° C. (from acetone).

EXAMPLE U

N-[2-(3,4-Dimethoxy-phenyl)-ethyl]-3-tosyloxymethyl-pyrrolidine a) N-Benzyl-2-pyrrolidone 14.4 g (0.33 mol) of 50% sodium hydride dispersion in oil are added in batches to 25.5 g (0.3 mol) of 2-pyrrolidone in 300 ml of absolute dimethylsulphoxide. The mixture is then stirred for 5 hours at 40° to 50° C. and at 25°–30° C. 56.4 g = 39.2 ml (0.33 mol) of benzyl bromide are added dropwize. After stirring for 10 hours at ambient temperature the reaction mixture is dissolved in 500 ml of ethyl acetate and extracted several times with water. The organic phase is separated off, dried over magnesium sulphate and the solvent is eliminated in vacuo. The residue obtained is purified over 900 g of aluminium oxide (neutral, activity II) with methylene chloride and 0.1% ethanol. Yield: 35.6 g (67.7% of theory), Rf value: 0.77 (aluminium oxide, neutral, eluant: 5% ethanol in methylene chloride).

b) N-Benzyl-2-pyrrolidone-3-carboxylic acid

At −60° C., 150 ml of 1.6 molar butyl lithium solution in n-hexane are added to 28.3 g = 39.3 ml (0.28 mol) of diisopropylamine in 400 ml of absolute ether, with stirring and under nitrogen. 35.1 g (0.2 mol) of N-benzyl-2-pyrrolidone dissolved in 150 ml of absolute ether are added dropwize thereto at −60° C. The cooling bath is taken away and dry carbon dioxide is introduced for 15 minutes. After stirring for 10 minutes the mixture is poured onto ice, the organic phase is separated off and extracted twice with 2 molar sodium hydroxide solution. The combined aqueous phases are extracted once with ether and then acidified with concentrated hydrochloric acid, with cooling. The aqueous phase is extracted twice with methylene chloride and, after the organic phase has been dried over magnesium sulphate, it is concentrated by evaporation in vacuo. Yield: 35 g (79.8% of theory), Rf value: 0.42 (silica gel, eluant: 5% ethanol in methylene chloride).

c) N-Benzyl-3-hydroxymethyl-pyrrolidine 35 g (0.16 mol) of N-benzyl-2-pyrrolidone-3-carboxylic acid dissolved in 250 ml of absolute tetrahydrofuran is added dropwize, with stirring, to 12.2 g (0.32 mol) of lithium aluminium hydride in 350 ml of absolute tetrahydrofuran. After refluxing for 6 hours, 18.2 ml of water, 12.2 ml of 15% sodium hydroxide solution and 36.6 ml of water are added, whilst cooling with ice water. The precipitate formed is suction filtered and washed with tetrahydrofuran. The combined filtrates are concentrated by evaporation in vacuo and the residue obtained is purified over 900 g of aluminium oxide (neutral, activity II) with methylene chloride and then with increasing amounts of ethanol (up to 2%). Yield: 16 g (52.3% of theory), Rf value: 0.42 (aluminium oxide, neutral, eluant: 5% ethanol in methylene chloride).

d) 3-Hydroxymethyl-pyrrolidine 14 g (0.073 mol) of N-Benzyl-3-hydroxymethyl-pyrrolidine are hydrogenated for 7 hours at 50° C. and at 5 bar in 300 ml of methanol and in the presence of 1.5 g of 20% palladium hydroxide/activated charcoal. The catalyst is then removed by suction filtering and the filtrate is concentrated by evaporation in vacuo. Yield: 7.3 g (99% of theory), Mass spectrum: molecular peak 101.

e) N-[2-(3,4-Dimethoxy-phenyl)-ethyl]-3-hydroxymethylpyrrolidine 3 g (0.03 mol) of 3-hydroxymethyl-pyrrolidine and 7.5 g of 2-(3,4-dimethoxy-phenyl)-ethylbromide are heated in 20 ml of triethylamine for 7 hours at 100° C. The excess triethylamine is then distilled off in vacuo and the residue obtained is dissolved in methylene chloride and 6 molar sodium hydroxide solution. The organic phase is separated off, dried over magnesium sulphate and concentrated by evaporation in vacuo. The residue obtained is then purified over 400 g of aluminum oxide (neutral, activity II) with methylene chloride and with increasing amounts of ethanol (up to 1%). Yield: 5.4 g (67.8% of theory), Rf value: 0.41 (aluminium oxide, neutral, eluant: 5% ethanol in methylene chloride).

f) N-[2-(3,4-Dimethoxy-phenyl)-ethyl]-3-tosyloxymethylpyrrolidine 1.3 g (0.005 mol) of N-[2-(3,4-dimethoxy-phenyl)-ethyl]-3-hydroxymethyl-pyrrolidine are dissolved in 10 ml of pyridine, 1.05 g (0 0055 mol) of p-toluenesulphonic acid chloride are added and the mixture is stirred for 6 hours at ambient temperature. The excess pyridine is then distilled off in vacuo, the residue obtained is dissolved in methylene chloride and the organic phase is extracted with ice water. After the organic phase has been dried over magnesium sulphate it is concentrated by evaporation in vacuo. Yield: 1.4 g (66.7% of theory), Rf value: 0.40 (aluminium oxide, neutral, eluant: 2% ethanol in methylene chloride).

EXAMPLE 1

3-[(N-(2-(3,4-Dimethoxy-phenyl)-ethyl)-piperidin-3-yl)methyl]-7,8-dimethoxy-1,3,4, 5-tetrahydro-2H-3-benzazepin-2-one-hydrochloride A mixture of 6.37 g (0.020 mol) of 3-[(piperidin-3-yl)methyl]-7,8-dimethoxy-1,3,4, 5-tetrahydro-2H-3-benzazepin-2-one, 5.6 ml (0.040 mol) of triethylamine and 4.90 g (0.020 mol) of 2-(3,4-dimethoxy-phenyl)-ethyl bromide is refluxed for 2 hours. The initial suspension changes into a clear solution and after about 30 minutes begins to precipitate in a jelly-like form. After cooling, the reaction mixture is dissolved in a mixture of 2 molar sodium hydroxide solution and methylene chloride. The organic phase is separated off, washed with water, dried over magnesium sulphate, evaporated down in vacuo and purified over 800 g of aluminium oxide (neutral, activity II-III) with methylene chloride and then with increasing quantities of ethanol (up to 2%). The hydrochloride is precipitated from a solution in acetone with methanolic hydrochloric acid.

Yield: 6.2 g (59.7% of theory),
Melting point: 218°–219° C.

| | | | |
|---|---|---|---|
| Calculated: | C 64.79 | H 7.57 | N 5.40 |

| | | | |
|---|---|---|---|
| -continued | | | |
| Found: | 64.88 | 7.55 | 5.21 |

EXAMPLE 2

3-[(N-(2-(3,4-Dimethoxy-phenyl)-ethyl)-piperidin-3-yl)methyl]-7,8-dimethoxy-1,3,4,5-tetrahydro-2H-3-benzazepin-2-one hydrobromide 3.7 g (0.0067 mol) of 3-[(N-(2-(3,4-dimethoxy-phenyl-)ethyl)-pyridinium-3-yl)-methyl]7, 8-dimethoxy-1,3-dihydro-2H-3-benzazepin-2-one-bromide are hydrogenated in 70 ml of methanol in the presence of 0.7 g of platinum dioxide for 3 hours at ambient temperature and under 5 bar. The catalyst is removed by suction filtering, the methanol is distilled off in vacuo and the residue is dissolved in a little methanol and mixed with acetone. The precipitate is suction filtered and dried.

Yield: 2.7 g (71.4% of theory),
Melting point: 225°–227° C.

| Calculated: | C 59.68 | H 6.98 | N 4.97 |
|---|---|---|---|
| Found: | 59.45 | 7.10 | 5.00 |

EXAMPLE 3

3-[N-(2-(3,4-Dimethoxy-phenyl)-ethyl)-piperidin-3-yl)methyl]-7,8-dimethoxy-1,2-dihydro-2H-3-benzazepin-2-one-hydrochloride 1.01 g (0.005 mol) of 7,8-dimethoxy-1,3-dihydro-2H-3-benzazepin-2-one are suspended in 10 ml of dimethylsulphoxide and 0.56 g (0.005 mol) of potassium tert-.butoxide are added with stirring. After 45 minutes, 1.7 g (0.005 mol) of N-[2-(3,4dimethoxy-phenyl)-ethyl ]-3-(bromomethyl)-piperidine dissolved in 5 ml of dimethylsulphoxide are added dropwize to the resulting solution with stirring. After 40 minutes it is poured onto ice water. The aqueous phase is extracted three times with ethyl acetate. The combined organic phases are washed with water, dried over magnesium sulphate, concentrated by evaporation in vacuo and purified over 200 g of aluminium oxide (neutral, activity II-III) with methylene chloride and then with increasing amounts of ethanol (up to 0.5%). The hydrochloride is precipitated from a solution in acetone using methanolic hydrochloric acid.

Yield: 0.62 g (23.9% of theory),
Melting point: 117°–121° C.

| Calculated: | C 65.04 | H 7.21 | N 5.42 |
|---|---|---|---|
| Found: | 64.86 | 7.18 | 5.35 |

EXAMPLE 4

3-[(N-(2-(3,4-Dimethoxy-phenyl)-ethyl)-piperidin-3-yl)methyl]-7,8-dimethoxy-2,3,4,5-tetrahydro-1H-3-benzazeoinedihydrochloride A solution of 0.96 g (0.002 mol) of 3-[(N-(2-(3,4-dimethoxyphenyl)-ethyl)-piperidin-3-yl))-methyl]7,8-dimethoxy-1,3,4,5-tetrahydro-2H-3-benzazepin-2-one in 20 ml of tetrahydrofuran is added dropwize, under a nitrogen atmosphere, to a solution of 0.24 ml (0.002 mol) of boron trifluoride etherate and 0.3 ml (0.003 mol) of borane dimethylsulphide complex (10 molar solution in toluene) and the resulting mixture is then refluxed for 3 hours. After the reaction mixture has cooled, methanol is added dropwize thereto. Then 2 ml of methanolic hydrochloric acid are added and the mixture is refluxed for 2 hours. The methanol and tetrahydrofuran are distilled off and the residue is mixed with water and then neutralized with 2 molar sodium hydroxide solution. The greasy precipitate is extracted with methylene chloride. The organic phase is dried over magnesium sulphate, concentrated by evaporation in vacuo and purified over 50 g of aluminium oxide (neutral, activity II-III) with methylene chloride and then with increasing amounts of ethanol (up to 0.5%). The dihydrochloride is precipitated from a solution in acetone using methanolic hydrochloric acid.

Yield: 0.28 g (27.7% of theory),
Melting point: 238°–240° C.

| Calculated: | C 62.09 | H 7.81 | N 5.17 |
|---|---|---|---|
| Found: | 61.88 | 7.84 | 5.42 |

EXAMPLE 5

3-[(N-(2-(3,4-Dimethoxy-phenyl)-ethyl)-piperidin-3-yl)methyl]-7,8-dimethoxy-1,3,4,5-tetrahydro-2H-3-benzazepin-2thione-hydrochloride 1.4 g (0.0029 mol) of 3-[(N-(2-(3,4-dimethoxy-phenyl-)ethyl)-piperidin-3-yl)-methyl]-7, 8-dimethoxy-1,3,4,5-tetrahydro2H-3-benzazepin-2-one and 0.41 g (0.0018 mol) of phosphorus pentasulphide are heated to 100° C. in 20 ml of pyridine for 3 hours. After concentration in vacuo the residue obtained is purified over 120 g of aluminium oxide (neutral, activity II-III) with ethyl acetate/cyclohexane (80/20). The hydrochloride is precipitated from a solution in acetone with methanolic hydrochloric acid.

Yield: 0.47 g (30.3% of theory),
Melting point: 206°–207° C.

| Calculated: | C 62.84 | H 7.35 | N 5.24 | S 5.99 |
|---|---|---|---|---|
| Found: | 62.54 | 7.43 | 5.35 | 6.15 |

EXAMPLE 6

3-[(N-(2-(3,4-Dimethoxy-phenyl)-ethyl)-piperidin-3-yl)methyl]-7,8-dimethoxy-1,3,4,5-tetrahydro-2H-3-benzazepin-1,2-dione 3.8 g (0.0079 mol) of 3-[(N-(2-(3,4-dimethoxyphenyl)-ethyl)-piperidin-3-yl)-methyl]-7, 8-dimethoxy-1,3,4,5-tetrahydro2H-3-benzazepin-2-one are added at 70° C. to a suspension of 1.4 g (0.0128 mol) of selenium dioxide and 0.8 g of kieselguhr in dioxan/water and refluxed for 16 hours. After cooling, the mixture is diluted with a little ethanol and suction filtered The filtrate is evaporated down in vacuo and purified over 310 g of aluminium oxide (neutral, activity II-III) with methylene chloride and increasing amounts of ethanol (up to 1%).

Yield: 2.15 g (54.8% of theory),
Melting point: 130°–132° C.

| Calculated: | C 67.72 | H 7.31 | N 5.64 |
|---|---|---|---|
| Found: | 67.53 | 7.14 | 5.65 |

EXAMPLE 7

3-[(N-(2-(3,4-Dimethoxy-phenyl)-ethyl)-piperidin-3-yl)methyl]-7,8-dimethoxy-1-hydroxy-1,3,4,5-tetrahydro-2H-3-benzazepin-2-one-hydrochloride 0.70 g (0.0014 mol) of 3-[(N-(2-(3,4-dimethoxy-phenyl)ethyl)-piperidin-3-yl)-methyl]-7, 8-dimethoxy-1,3,4,5-tetrahydro2H-3-benzazepin-1,2-dione are dissolved in a mixture of methanol and water (95:5), 0.060 g (0.0016 mol) of sodium borohydride are added and the mixture is stirred for 20 minutes at ambient temperature. Then it is acidified with 2 molar hydrochloric acid, neutralized with ammonia and extracted with methylene chloride. The organic phase is dried over magnesium sulphate, concentrated by evaporation in vacuo and the residue obtained is purified over 100 g of aluminium oxide (neutral, activity II-III) with methylene chloride and then with increasing amounts of ethanol (up to 15%). The hydrochloride is precipitated from a solution in acetone using methanolic hydrochloric acid.

Yield: 0.47 g (62.3% of theory),
Melting point: 118°–124° C.

| Calculated: | C 62.85 | H 7.35 | N 5.24 |
|---|---|---|---|
| Found: | 62.60 | 7.39 | 5.30 |

EXAMPLE 8

3-[(N-(2-(4-Amino-phenyl)-ethyl)-piperidin-3-yl)-methyl7,8-dimethoxy-1,3,4,5-tetrahydro-2H-3-benzazepin-2-one-dihydrochloride 1.7 g (0.0036 mol) of 3-[(N-(2-(4-nitro-phenyl)-ethyl)-piperidin-3-yl)-methyl]-7, 8-dimethoxy-1,3,4,5-tetrahydro-2H-3-benzazepin-2-one are hydrogenated in 40 ml of methanol in the presence of 0.3 g of 10% palladium/charcoal for 2 hours at ambient temperature and under 5 bar of hydrogen. Then the catalyst is removed by suction filtering and the methanol is distilled off in vacuo. The hydrochloride is precipitated from a solution of the residue in acetone using methanolic hydrochloric acid.

Yield: 1.1 g (59.8% of theory),
Melting point: 236°–240° C.

| Calculated: | C 61.17 | H 7.31 | N 8.23 |
|---|---|---|---|
| Found: | 60.85 | 7.63 | 8.12 |

EXAMPLE 9

3-[(N-(2-(4-Acetamino-phenyl)-ethyl)-piperidin-3-yl)methyl]-7,8-dimethoxy-1,3,4,5-tetrahydro-2H-3-benzazepin-2-one-hydrochloride 0.88 g (0.002 mol) of 3-[(N-(2-(4-amino-phenyl)-ethyl)-piperidin-3-yl)-methyl]-7, 8-dimethoxy-1,3,4,5-tetrahydro-2H-3-benzazepin-2-one and 0.3 ml (0.0022 mol) of triethylamine are dissolved in 10 ml of methylene chloride and 0.16 ml (0.0022 mol) of acetyl chloride are added dropwize with stirring. After 30 minutes water is added. The aqueous phase is extracted three times with methylene chloride. The organic phase is dried over magnesium sulphate and evaporated down in vacuo. The hydrochloride is precipitated from a solution of the residue in acetone using methanolic hydrochloric acid.

Yield: 0.61 g (59.1% of theory),
Melting point: 187°–192° C.

| Calculated: | C 65.16 | H 7.42 | N 8.14 |
|---|---|---|---|
| Found | 64.95 | 7.45 | 7.94 |

EXAMPLE 10

3-[(N-(3-(4-Amino-3,5-dibromo-phenoxy)-propyl)-piperidin-3yl)-methyl]-7,8dimethoxy-1,3,4,5-tetrahydro-2H-3-benzazepin-2one-hydrochloride Prepared from 3-[(piperidin-3-yl)-methyl]-7,8-dimethoxy-1,3,4,5-tetrahydro-2H-3-benzazepin-2-one and 3-(4-amino-3,5dibromo-phenoxy)-propyl chloride analogously to Example 1.

Yield: 20 4% of theory,
Melting point: 95° C. (decomp.).

| Calculated: | C 49.00 | H 5.48 | N 6.35 | Br 24.15 |
|---|---|---|---|---|
| Found: | 49.12 | 5.80 | 5.83 | 24.00 |

EXAMPLE 11

3-[(N-(2-(3,4-Dimethoxy-phenyl)-ethyl)-piperidin-3-yl)methyl]-7,8-methylenedioxy-1,3,4,5-tetrahydro-2H-3-benzazepin-2-one-hydrochloride Prepared from 3-[(piperidin-3-yl)-methyl]-7,8-methylene-dioxy-1,3,4,5-tetrahydro-2H-3-benzazepin-2-one and 2-(3,4-dimethoxyphenyl)-ethylbromide analogously to Example 1.

Yield: 31.7% of theory,
Melting point: 142°–143° C.

| Calculated: | C 64.47 | H 7.01 | N 5.57 |
|---|---|---|---|
| Found: | 64.36 | 7.17 | 5.42 |

EXAMPLE 12

3-[(N-(3,4-Dimethoxy-benzyl)-piperidin-3-yl)-methyl]-7,8-methylenedioxy-1,3,4,5-tetrahydro-2H-3-benzazepin-2-one-hydrochloride Prepared from 3-[(piperidin-3-yl)-methyl]-7,8-methylene-dioxy-1,3,4,5-tetrahydro-2H-3-benzazepin-2-one and 3,4-dimethoxybenzyl chloride analogously to Example 1.

Yield: 30.7% of theory,
Melting point: 135° C. (decomp.).

| Calculated: | C 63.68 | H 6.80 | N 5.73 |
|---|---|---|---|
| Found | 63.45 | 7.02 | 5.41 |

EXAMPLE 13

3-[(N-(2-Phenylethyl)-piperidin-3-yl)-methyl]-7,8-dimethoxy1,3,4,5-tetrahydro-2H-3-benzazepin-2-one-hydrochloride Prepared from 3-[(piperidin-3-yl)-methyl]-7,8-dimethoxy-1,3,4,5-tetrahydro-2H-3-benzazepin-2-one and 2-phenylethylbromide analogously to Example 1.

Yield: 43.5% of theory,
Melting point: 241°–243° C.

| Calculated: | C 68.03 | H 7.69 | N 6.10 |
|---|---|---|---|

EXAMPLE 14

3-[(N-(2-(3-Nitro-4-acetamino-phenyl)-ethyl)-piperidin-3-yl)-methyl -7,8-dimethoxy-1,3,4,5-tetrahydro-2H-3-benzazepin-2-one-hydrochloride Prepared from 3-[(piperidin-3-yl)-methyl]-7,8-dimethoxy-1,3,4,5-tetrahydro-2H-3-benzazepin-2-one and 2-(3-nitro-4-acetamino-phenyl)-ethyl bromide analogously to Example 1.
Yield: 22.3% of theory,
Melting point: 173° C. (decomp.).

| | | | |
|---|---|---|---|
| Calculated: | C 59.94 | H 6.65 | N 9.99 |
| Found: | 59.92 | 6.77 | 9.98 |

EXAMPLE 15

3-[(N-(2-(3,4,5-Trimethoxy-phenyl)-ethyl)-piperidin-3-yl)methyl]-7,8-dimethoxy-1,3,4,5-tetrahydro-2H-3-benzazepin-2-one-hydrochloride Prepared from 3-[(piperidin-3-yl)-methyl]-7,8-dimethoxy-1,3,4,5-tetrahydro-2H-3-benzazepin-2-one and 2-(3,4,5-trimethoxyphenyl)-ethyl bromide analogously to Example 1.
Yield: 22.6% of theory,
Melting point: 135°–137° C.

| | | | |
|---|---|---|---|
| Calculated: | C 63.53 | H 7.53 | N 5.10 |
| Found | 63.50 | 7.82 | 5.09 |

EXAMPLE 16

3-[(N-(3-(4-Methoxy-phenyl)-propyl)-piperidin-3-yl)-methyl-7,8-dimethoxy-1,3,4,5-tetrahydro-2H-3-benzazepin-2-one-hydrochloride Prepared from 3-[(piperidin-3-yl)-methyl]-7,8-dimethoxy1,3,4,5-tetrahydro-2H-3-benzazepin-2-one and 3-(4-methoxyphenyl)propyl bromide analogously to Example 1.
Yield: 29.4% of theory.
Melting point: 215°–218° C.

| | | | |
|---|---|---|---|
| Calculated: | C 66.85 | H 7.81 | N 5.57 |
| Found: | 66.67 | 7.65 | 5.53 |

EXAMPLE 17

3-[(N-(2-(3,4-Dimethoxy-phenyl)-ethyl)-piperidin-3-yl)methyl]-7,8-dimethoxy-2,3-dihydro-1H-benzaepine A suspension of 0.06 g (0.0016 mol) of lithium aluminium hydride in 20 ml of absolute tetrahydrofuran is mixed with 0.31 g (0.00065 mol) of 3-[(N-(2-(3,4-dimethoxy-phenyl)-ethyl)piperidin-3-yl)-methyl]-7,8-dimethoxy-1, 3-dihydro-2H-3-benzazepin-2-one and then stirred for 1 hour at ambient temperature. 10% ammonium chloride solution is added, whilst cooling with ice water, and the precipitate formed is suction filtered. The filtrate is concentrated by evaporation in vacuo and the residue is purified over 30 g of aluminium oxide (neutral, activity II-III) with methylene chloride.

Yield: 0.05 g (16.5% of theory), Rf value: 0.5 (aluminium oxide, eluant: 2% ethanol in methylene chloride)

| | | | |
|---|---|---|---|
| Calculated: | C 72.07 | H 8.21 | N 6.00 |
| Found | 71.90 | 8.39 | 5.89 |

EXAMPLE 18

3-[(N-(2-(4-Methoxy-phenyl)-ethyl)-piperidin-3-yl)-methyl]-7,8-dimethoxy-1,3,4,5-tetrahydro-2H-3-benzazepin-2-one-hydrochloride Prepared from 3-[(piperidin-3-yl)-methyl]-7,8-dimethoxy-3,4,5-tetrahydro-2H-3-benzazepin-2-one and 2-(4-methoxyphenyl)-ethylbromide analogously to Example 1.
Yield: 19.8% of theory,
Melting point: 227°–230° C.

| | | | |
|---|---|---|---|
| Calculated: | C 66.31 | H 7.63 | N 5.73 |
| Found: | 66.46 | 7.57 | 5.73 |

EXAMPLE 19

3-[(N-(2-(4-Nitro-phenyl)-ethyl)-piperidin-3-yl)-methyl]-7,8-dimethoxy-1,3,4,5-tetrahydro-2H-3-benzazepin-2-one-hydrochloride Prepared from 3-[(piperidin-3-yl)-methyl]-7,8-dimethoxy-1,3,4,5-tetrahydro-2H-3-benzazepin-2-one and 2-(4-nitro-phenyl)ethylbromide analogously to Example 1.
Yield: 66.8% of theory,
Melting point: 239°–245° C.

| | | | |
|---|---|---|---|
| Calculated: | C 61.91 | H 6.80 | N 8.34 |
| Found: | 62.25 | 6.66 | 8.23 |

EXAMPLE 20

3-[(N-(2-(3-Methyl-phenyl)-ethyl)-piperidin-3-yl)-methyl]-7,8-dimethoxy-1,3,4,5-tetrahydro-2H-3-benzazepin-2-one-hydrochloride Prepared from 3-[(piperidin-3-yl)-methyl]-7,8-dimethoxy-1,3,4 5-tetrahydro-2H-3-benzazepin-2-one and 2-(3-methyl-phenyl)ethylbromide analogously to Example 1.
38.1% of theory,
Melting point: 234°–237° C.

| | | | |
|---|---|---|---|
| Calculated: | C 68.55 | H 7.88 | N 5.92 |
| Found: | 68.68 | 7.87 | 6.14 |

EXAMPLE 21

3-[(N-(2-(3-Methoxy-phenyl)-ethyl)-piperidin-3-yl)-methyl]-7,8-dimethoxy-1,3,4,5-tetrahydro-2H-3-benzazepin-2-one-hydrochloride Prepared from 3-[(piperidin-3-yl)-methyl]-7,8-dimethoxy-1,3,4,5tetrahydro-2H-3-benzazepin-2-one and 2-(3-methoxyphenyl)-ethylbromide analogously to Example 1.
Yield: 23.7% of theory,
Melting point: 199°–202° C.

| Calculated: | C 66.31 | H 7.63 | N 5.73 |
| Found: | 66.61 | 7.59 | 5.91 |

EXAMPLE 22

3-[(N-(2-(4-Methyl-phenyl)-ethyl)-piperidin-3-yl)-methyl]-7,8dimethoxy-1,3,4,5-tetrahydro-2H-3-benzazepin-2-one-hydrochloride Prepared from 3-[(piperidin-3-yl)-methyl]-7,8-dimethoxy-1,3,4,5-tetrahydro-2H-3-benzazepin-2-one and 2-(4-methyl-phenyl)ethylbromide analogously to Example 1.

Yield: 34.7% of theory,
Melting point: 233°–236° C.

| Calculated: | C 68.55 | H 7.88 | N 5.92 |
| Found: | 68.30 | 7.89 | 5.84 |

EXAMPLE 23

3-[(N-(3-(4-Bromo-phenyl)-propyl)-piperidin-3-yl)-methyl]7,8dimethoxy-1,3,4,5-tetrahydro-2H-3-benzazepin-2-one-hydrochloride Prepared from 3-[(piperidin-3-yl)-methyl]-7,8-dimethoxy-1,3,4,5-tetrahydro-2H-3-benzazepin-2-one and 3-(4-bromophenyl)propyl bromide analogously to Example 1.

Yield: 34.8% of theory,
Melting point: 100°–104° C.

| Calculated: | C 58.75 | H 6.57 | N 5.08 | Br 14.48 |
| Found: | 58.40 | 6.66 | 4.79 | 14.21 |

EXAMPLE 24

3-[(N-(2-(3,4-Dimethoxy-phenyl)-ethyl)-piperidin-3-yl)methyl]-7,8-methylenedioxy-1,3-dihydro-2H-3-benzazepin-2-one-hydrochloride Prepared from 7,8-methylenedioxy-1,3-dihydro-2H-3-benzazepin2-one and N-[2-(3,4-dimethoxy-phenyl)-ethyl]-3-bromomethyl)-piperidine analogously to Example 3.

Yield: 8.6% of theory,
Melting point: 199°–201° C.

| Calculated: | C 64.73 | H 6.64 | N 5.59 |
| Found: | 64.77 | 6.55 | 5.57 |

EXAMPLE 25

3-[(N-(2-(3,4-Dimethoxy-phenyl)-ethyl)-piperidin-2-yl)ethyl-2]7,8-dimethoxy-1,3,4,5-tetrahydro-2H-3-benzazepin-2-one-hydrochloride Prepared from 3-[(piperidin-2-yl)-ethyl-2]-7,8-dimethoxy-1,3,4,5-tetrahydro-2H-3-benzazepin-2-one and 2-(3,4-dimethoxyphenyl)-ethylbromide analogously to Example 1.

Yield: 23.8% of theory,
Melting point: 113°–115° C.

| Calculated: | C 65.33 | H 7.75 | N 5.26 |

-continued

| Found: | 65.11 | 7.67 | 5.04 |

EXAMPLE 26

3-[(N-(2-(3,4-Dimethoxy-phenyl)-ethyl)-hexahydro-azepin-3-yl)-methyl]-7,8-dimethoxy-1,3,4,5-tetrahydro-2H-3-benzazepin-2-one-hydrochloride 660 mg (2 mmol) of 3-[(hexahydro-azepin-3-yl)-methyl]-7,8-dimethoxy-1,3,4,5-tetrahydro-2H-3-benzazepin-2-one and 540 mg (2.2 mmol) of 2-(3,4-dimethoxyphenyl)-ethylbromide are refluxed for 1 hour in 3 ml of triethylamine. The reaction mixture is cooled and taken up in methylene chloride and 2-molar sodium hydroxide solution. The alkaline phase is separated off and extracted twice with methylene chloride. The combined organic phases are dried over magnesium sulphate and evaporated down in vacuo. Purification is carried out by column chromatography over 100 g of aluminium oxide (activity II, eluant: methylene chloride+0.3% ethanol). The fractions obtained are concentrated by evaporation in vacuo, the residue is dissolved in acetone and the hydrochloride is precipitated using ethereal hydrochloric acid.

Yield: 600 mg (56.3% of theory),
Melting point: 164°–15° C.

| Calculated: | C 65.33 | H 7.75 | N 5.25 |
| Found: | 65.12 | 7.59 | 5.22 |

EXAMPLE 27

3-[(N-(3-(4-Amino-3,5-dibromo-phenoxy)-propyl)-hexahydro-azepin-3-yl)-methyl]-7,8-dimethoxy-1,3,4,5-tetrahydro-2H-3-benzazepin-2-one-dihydrochloride Prepared from 1.2 g (3.6 mmol) of 3-[(hexahydro-azepin-3-yl)methyl]-7,8-dimethoxy-1,3,4, 5-tetrahydro-2H-3-benzazepin-2-one and 1.36 g (3.96 mmol) of 3-(4-amino-3,5-dibromo-phenoxy)-propyl chloride in 5 ml triethylamine analogously to Example 26.

Yield: 350 mg (13.7% of theory),
Melting point: 134°–136° C.

| Calculated: | C 47.22 | H 5.52 | Br 22.42 | N 5.36 |
| Found: | 47.40 | 5.86 | 22.22 | 5.49 |

EXAMPLE 28

3-[(N-(2-(3,4-Dimethoxy-phenyl)-ethyl)-hexahydro-azepin-2-yl)-ethyl-2]7,8-dimethoxy-1,3-dihydro-2H-3-benzazepin-2-one Prepared from 3.6 g (9 4 mmol) of 2-(2-bromoethyl)-1-[2(3, 4-dimethoxy-phenyl)-ethyl]-hexahydro-azepine and 2.06 g (9.4 mmol) of 7,8-dimethoxy-1,3-dihydro-2H-3-benzazepin-2-one analogously to Example 3.

Yield: 1.3 g (27.2% of theory), Oil, IR spectrum (methylene chloride): 1655 cm−1 (CO).

| Calculated: | C 70.83 | H 7.93 | N 5.51 |
| Found: | 70.56 | 7.80 | 5.27 |

EXAMPLE 29

3-[(N-(2-(3,4-Dimethoxy-phenyl)-ethyl)-hexahydro-azepin-2-yl)-ethyl-2]-7,8-dimethoxy-1,3,4, 5-tetrahydro-2H-3-benzazepin-2one 1.2 g (2.36 mol) of 3-[N-(2-(3,4-dimethoxy-phenyl)-ethyl)hexahydro-azepin-2-yl)-ethyl-2-7, 8-dimethoxy-1,3-dihydro-2H-3-benzazepin-2-one are hydrogenated in 80 ml of glacial acetic acid for 4 hours at 45° C. and under 5 bar in the presence of 1 g of 10% palladium/activated charcoal (10%). The catalyst is removed by suction filtering, the filtrate is concentrated by evaporation in vacuo, the residue is dissolved in 100 ml of methylene chloride and extracted once with 50 ml of 2N sodium hydroxide solution. The organic phase is dried over magnesium sulphate and evaporated down in vacuo. Purification is carried out by column chromatography over 100 g of aluminium oxide (neutral, eluant: methylene chloride+1% ethanol).

Yield: 200 mg (17% of theory),

| Calculated: | C 70.56 | H 8.29 | N 5.49 |
|---|---|---|---|
| Found: | 70.60 | 8.34 | 5.37 |

IR spectrum (methylene chloride): 1650 cm−1 (CO).

EXAMPLE 30

3-[(N-(2-(3,4-Methylenedioxy-phenyl)-ethyl)-piperidin-3-yl)methyl]-7,8-methylenedioxy-1,3,4, 5-tetrahydro-2H-3-benzazepin-2-one-hydrochloride Prepared from 3-[(piperidin-3-yl)-methyl]-7,8-methylenedioxy-1,3,4,5-tetrahydro-2H-3-benzazepin-2-one and 2-(3,4methylenedioxy-phenyl)-ethylbromide analogously to Example 1.

Yield: 85.7% of theory,
Melting point: 234°-235° C.

| Calculated: | C 66.73 | H 6.03 | N 5.99 |
|---|---|---|---|
| Found: | 66.58 | 6.31 | 5.94 |

EXAMPLE 31

3-[(N-(3,4-dichloro-benzyl)-piperidin-3-yl)-methyl]-7,8methylenedioxy-1,3,4, 5-tetrahydro-2H-3-benzazepin-2-one-hydrochloride Prepared from 3-[(piperidinyl-3-yl)-methyl]-7,8-methylenedioxy-1,3,4,5-tetrahydro-2H-3-benzazepin-2-one and 3,4dichloro-benzyl chloride analogously to Example 1.

Yield: 80% of theory,
Melting point: 240°-242° C.

| Calculated: | C 57.90 | H 5.47 | N 5.63 |
|---|---|---|---|
| Found: | 57.77 | 5.35 | 5.46 |

EXAMPLE 32

3-[(N-(2-(3,4-Dimethoxy-phenyl)-ethyl)-pyrrolidin-3-yl)methyl]-7,8-dimethoxy-1,3-dihydro-2H-3-benzazecin-2-one 0.79 g (3.6 mmol) of 7,8-dimethoxy-1,3-dihydro-2H-3-benzazepin-2-one are suspended in 30 ml of absolute dimethylsulphoxide and 160 ml (3.6 mmol) of 55% sodium hydride dispersion in oil are added. After stirring for 2 hours at ambient temperature and for half an hour at 40° C. 1.3 g (3 mmol) of N-[2-(3,4-dimethoxy-phenyl)-ethyl]-3-tosyloxy-methylpyrrolidine are added and the resulting mixture is heated for 3 hours to 50° to 55° C. After cooling, the reaction mixture is then dissolved in ethyl acetate and extracted several times with water and then twice with 25% acetic acid. The acid extract obtained is made alkaline with 6 molar sodium hydroxide solution and extracted twice with methylene chloride. After the organic phase has been dried the solvent is eliminated in vacuo and the residue obtained is purified over 100 g of aluminium oxide (neutral, activity II) with methylene chloride and then with increasing amounts of ethanol (up to 2%).

Yield: 270 mg (19.3% of theory), IR spectrum (methylene chloride): 1655 cm−1 (CO).

| Calculated: | C 69.50 | H 7.35 | N 6.00 |
|---|---|---|---|
| Found: | 69.37 | 7.38 | 6.12 |

EXAMPLE 33

3-[(N-(2-(3,4-Dimethoxy-phenyl)-ethyl)-pyrrolidin-3-yl)methyl]-7,8-dimethoxy-1,3,4, 5-tetrahydro-2H-3-benzazepin-2-one Prepared from 3-[(N-(2-(3,4-dimethoxy-phenyl)-ethyl)pyrrolidin-3-yl)-methyl]-7,8-dimethoxy-1, 3-dihydro-2H-3-benzazepin-2-one analogously to Example 29.

Yield: 21.7% of theory, IR spectrum (methylene chloride): 1650 cm−1 (CO).

| Calculated: | C 69.29 | H 7.75 | N 5.98 |
|---|---|---|---|
| Found: | 69.20 | 7.84 | 5.92 |

EXAMPLE 34

3-[(N-(3-(3-Methoxy-phenoxy)-propyl)-piperidin-3-yl)methyl]-7,8-methylenedioxy-1,3,4, 5-tetrahydro-2H-3-benzazepin-2-one Prepared from 3-[(piperidin-3-yl)-methyl]-7,8-methylenedioxy-1,3,4,5-tetrahydro-2H-3-benzazepin-2-one and 3-(3-methoxyphenoxy)-propyl chloride analogously to Example 1.

Yield: 42% of theory,
Melting point: 135°-138° C.

| Calculated: | C 64.46 | H 7.01 | N 5.57 |
|---|---|---|---|
| Found: | 64.46 | 7.02 | 5.57 |

EXAMPLE 35

3-[(N-(3-(3-Methyl-phenoxy)-propyl)-piperidin-3-yl)-methyl]-7,8-methylendioxy-1,3,4, 5-tetrahydro-2H-3-benzazepin-2-one-hydrochloride Prepared from 3-[(piperidin-3-yl)-methyl]-7,8-methylenedioxy-1,3,4,5-tetrahydro-2H-3-benzazepin-2-one and 3-(3-methylphenoxy)-propylchloride analogously to Example 1.

Yield: 34% of theory,
Melting point: 122°-124° C.

| Calculated: | C 65.36 | H 7.32 | N 5.65 |

| Found: | 65.01 | 7.61 | 5.64 |
|---|---|---|---|

EXAMPLE 36

3-[(N-(2-(4-Amino-3,5-dichloro-phenyl)-ethyl)-piperidin-3-yl)-methyl]-7,8-dimethoxy-1,3,4,5-tetrahydro-2H-3-benzazepin-2-one-hydrochloride Prepared from 3-[(piperidin-3-yl)-methyl]-7,8-dimethoxy1,3,4,5-tetrahydro-2H-3-benzazepin-2-one and 2-(4-amino-3,5-dichloro-phenyl)-ethylbromide analogously to Example 1.
Yield: 60% of theory,
Melting point: 137°–140° C.

| Calculated: | C 57.03 | H 5.58 | N 6.98 |
|---|---|---|---|
| Found: | 57.27 | 5.82 | 6.59 |

EXAMPLE 37

3-[(N-(3-(3,4-Methylenedioxy-phenoxy)-propyl)-piperidin- 3-yl)-methyl]-7,8-methylenedioxy-1,3,4,5-tetrahydro-2H-3-benzazepin-2-one-hydrochloride Prepared from 3-[(piperidin-3-yl)-methyl]-7,8-methylene-dioxy-1,3,4,5-tetrahydro-2H-3-benzazepin-2-one and 3-(3,4-methylenedioxy-phenoxy)-propyl chloride analogously to Example 1.
Yield: 39.9% of theory,
Melting point: 127°–129° C.

| Calculated: | C 62.92 | H 6.43 | N 5.42 |
|---|---|---|---|
| Found: | 62.98 | 6.41 | 5.05 |

EXAMPLE 38

3-(N-(4-(4-Methoxy-phenyl)-butyl)-piperidin-3-yl)-methyl]-7,8-methylenedioxy-1,3,4,5-tetrahydro-2H-3-benzazepin-2-one-hydrochloride Prepared from 3-[(piperidin-3-yl)-methyl]-7,8-methylenedioxy-1,3,4,5-tetrahydro-2H-3-benzazepin-2-one and 4-(4-methoxyphenyl)-butyl bromide analogously to Example 1.
Yield: 42% of theory,
Melting point: 158°–163° C.

| Calculated: | C 67.12 | H 7.44 | N 5.59 |
|---|---|---|---|
| Found: | 66.98 | 7.27 | 5.51 |

EXAMPLE 39

3-[(N-(2-(4-Methoxy-phenyl)-ethyl)-piperidin-3-yl)-methyl]-7,8-methylenedioxy-1,3,4,5-tetrahydro-2H-3-benzazepin-2-one-hydrochloride Prepared from 3-[(piperidin-3-yl)-methyl]-7,8-methylenedioxy-1,3,4,5-tetrahydro-2H-3-benzazepin-2-one and 2-(4-methoxyphenyl)-ethylchloride in dimethylformamide/potassium carbonate at 120° C. analogously to Example 1.
Yield: 55.6% of theory,
Melting point: 226°–228° C.

| Calculated: | C 66.02 | H 7.03 | N 5.92 |
|---|---|---|---|
| Found: | 66.18 | 7.03 | 5.87 |

EXAMPLE 40

3-[(N-(2-(Phenoxy)-ethyl)-piperidin-3-yl)-methyl]-7,8-methylenedioxy-1,3,4,5-tetrahydro-2H-3-benzazepin-2-one-hydrochloride Prepared from 3-[(piperidin-3-yl)-methyl]-7,8-methylenedioxy-1,3,4,5-tetrahydro-2H-3-benzazepin-2-one and 2-phenoxyethylbromide analogously to Example 1.
Yield: 55.7% of theory,
Melting point: 124°–127° C.

| Calculated: | C 64.16 | H 6.98 | N 6.10 |
|---|---|---|---|
| Found: | 64.42 | 7.02 | 6.14 |

EXAMPLE 41

3-[(N-(2-(4-Methoxy-phenyl)-ethyl)-piperidin-2-yl)-ethyl-2]-7,8-methylenedioxy-1,3,4,5-tetrahydro-2H-3-benzazepin-2-one-hydrochloride Prepared from 3-[(piperidin-2-yl)-ethyl-2]-7,8-methylenedioxy-1,3,4,5-tetrahydro-2H-3-benzazepin-2-one and 2-(4-methoxy-phenyl)-ethylbromide analogously to Example 1.
Yield: 34.6% of theory,
Melting point: 110°–115° C.

| Calculated: | C 66.58 | H 7.24 | N 5.75 |
|---|---|---|---|
| Found: | 66.50 | 7.18 | 5.70 |

EXAMPLE 42

3-[(N-(4-Methoxy-phenyl)-methyl)-piperidin-2-yl)-ethyl-2]-7,8-methylenedioxy-1,3,4,5-tetrahydro-2H-3-benzazepin-2-one-hydrochloride Prepared from 3-[(piperidin-2-yl)-ethyl-2]-7,8-methylenedioxy-1,3,4,5-tetrahydro-2H-3-benzazepin-2-one and 4-methoxy-benzylbromide analogously to Example 1.
Yield: 52% of theory,
Melting point: 148°–152° C.

| Calculated: | C 66.02 | H 7.03 | N 5 92 |
|---|---|---|---|
| Found: | 65.90 | 7.10 | 5.98 |

EXAMPLE 43

3-[(N-(3,4-Dimethoxy-phenyl)-methyl)-piperidin-2-yl)-ethyl2-7,8-methylenedioxy-1,3,4,5-tetrahydro-2H-3-benzazepin-2-one-hydrobromide Prepared from 3-[(piperidin-2-yl)-ethyl-2]-7,8-methylenedioxy-1,3,4,5-tetrahydro-2H-3-benzazepin-2-one and 3,4-dimethoxy-benzylbromide analogously to Example 1.
Yield: 27% of theory,
Melting point: 138°–140° C.

| Calculated: | C 59.23 | H 6.42 | N 5.11 |
|---|---|---|---|
| Found: | 59.40 | 6.49 | 5.23 |

EXAMPLE 44

3-[(N-(2-(4-Nitro-phenyl)-ethyl)-piperidin-2-yl)-ethyl-2]-7,8-methylenedioxy-1,3,4,5-tetrahydro-2H-3-benzazepin-2-one-hydrochloride Prepared from 3-[(piperidin-2-yl)-ethyl-2]-7,8-methylenedioxy-1,3,4,5-tetrahydro-2H-3-benzazepin-2-one and 2-(4-nitro-phenyl)-ethylbromide analogously to Example 1.

Yield: 22% of theory,
Melting point: 130°-132° C.

| Calculated: | C 62.20 | H 6.43 | N 8.37 |
|---|---|---|---|
| Found: | 62.16 | 6.57 | 8.32 |

EXAMPLE 45

3-[(N-(2-(3-Trifluoromethylphenyl)-ethyl)-piperidin-3-yl)methyl]-7,8-dimethoxy-1,3,4,5-tetrahydro-2H-3-benzazepin-2-one-hydrochloride Prepared from 3-[(piperidin-3-yl)-methyl]-7,8-dimethoxy-1,3,4,5-tetrahydro-2H-3-benzazepin-2-one and 2-(3-trifluoromethyl-phenyl)-ethylbromide analogously to Example 1.

Yield: 32% of theory,
Melting point: from 150° C. (decomp.).

| Calculated: | C 61.53 | H 6.50 | N 5.32 |
|---|---|---|---|
| Found: | 61.70 | 6.42 | 5.27 |

Rf value: 0.36 (silica gel, methylene chloride/methanol = 10/1).

EXAMPLE 46

3-[(N-(3-(3,5-Dimethoxy-phenoxy)-propyl)-piperidin-3-yl)-ethyl]-7,8-methylenedioxy-1,3,4,5-tetrahydro-2H-3-benzazepin-2-one-hydrochloride Prepared from 3-[(piperidin-3-yl)-methyl]-7,8-methylenedioxy-1,3,4,5-tetrahydro-2H-3-benzazepin-2-one and 3-(3,5-dimethoxy-phenoxy)-propylchloride analogously to Example 1.

Yield: 46.4% of theory,
Melting point: 102°-107° C.

| Calculated: | C 63.09 | H 7.00 | N 5.25 |
|---|---|---|---|
| Found: | 62.96 | 6.86 | 5.50 |

EXAMPLE 47

3-[(N-(2-Phenyl-ethyl)-piperidin-2-yl)-ethyl-2]-7,8-dimethoxy-1,3,4,5-tetrahydro-2H-3-benzazepin-2-one-hydrochloride Prepared from 3-[(piperidin-2-yl)-ethyl-2]-7,8-dimethoxy-2H-3-benzazepin-2-one and 2-phenyl-ethylbromide analogously to Example 1.

Yield: 37% of theory,
Melting point: 130°-132° C.

| Calculated: | C 68.55 | H 7.88 | N 5.92 |
|---|---|---|---|
| Found: | 68.42 | 7.97 | 5.75 |

EXAMPLE 48

3-[(N-(3-(4-Methoxy-phenyl)-propyl)-piperidin-2-yl)-ethyl-2]-7,8-dimethoxy-1,3,4,5-tetrahydro-2H-3-benzazepin-2-one-hydrochloride Prepared from 3-[(piperidin-2-yl)-ethyl-2]-7,8-dimethoxy-2H-3-benzazepin-2-one and 3-(4-methoxy-phenyl)-propylbromide analogously to Example 1.

Yield: 43% of theory,
Melting point: 109°-112° C.

| Calculated: | C 67.36 | H 7.99 | N 5.42 |
|---|---|---|---|
| Found: | 67.19 | 7.88 | 5.38 |

EXAMPLE 49

3-[(N-(2-(3-Methyl-phenyl)-ethyl)-piperidin-2-yl)-ethyl-2]-7,8-dimethoxy-1,3,4,5-tetrahydro-2H-3-benzazepin-2-one-hydrochloride Prepared from 3-[(piperidin-2-yl)-ethyl-2]-7,8-dimethoxy-2H-3-benzazepin-2-one and 2-(3-methylphenyl)-ethylbromide analogously to Example 1.

Yield: 31% of theory,
Melting point: 124°-126° C.

| Calculated: | C 69.04 | H 8.07 | N 5.75 |
|---|---|---|---|
| Found: | 68.91 | 7.69 | 5.72 |

EXAMPLE 50

3-[(N-(2-(4-Methoxy-phenyl)-ethyl)-piperidin-2-yl)-ethyl-2]-7,8-dimethoxy-1,3,4,5-tetrahydro-2H-3-benzazepin-2-one-hydrochloride Prepared from 3-[(piperidin-2-yl)-ethyl-2]-7,8-dimethoxy-2H-3-benzazepin-2-one and 2-(4-methoxy-phenyl)-ethylbromide analogously to Example 1.

Yield: 48% of theory,
Melting point: 112°-114° C.

| Calculated: | C 66.85 | H 7.81 | N 5.57 |
|---|---|---|---|
| Found: | 66.69 | 7.86 | 5.65 |

EXAMPLE 51

3-[(N-(2-(4-Nitro-phenyl)-ethyl)-piperidin-2-yl)-ethyl-2]-7,8-dimethoxy-1,3,4,5-tetrahydro-2H-3-benzazepin-2-one-hydrochloride Prepared from 3-[(piperidin-2-yl)-ethyl-2]-7,8-dimethoxy-2H-3-benzazepin-2-one and 2-(4-nitrophenyl)-ethylbromide analogously to Example 1.

Yield: 8% of theory,
Melting point: 126°-128° C.

| Calculated: | C 62.59 | H 7.00 | N 8.11 |
|---|---|---|---|
| Found: | 62.56 | 6.91 | 8.16 |

EXAMPLE 52

3-[(N-(2-(4-Methyl-phenyl)-ethyl)-piperidin-2-yl)-ethyl-2]-7,8-dimethoxy-1,3,4,5-tetrahydro-2H-3-benzazepin-2-one-hydrochloride Prepared from 3-[(piperidin-2-yl)-ethyl-2]-7,8-dimethoxy-2H-3-benzazepin-2-one and 2-(4-methylphenyl)-ethyl-bromide analogously to Example 1.
Yield: 23% of theory,
Melting point: 109°–111° C.

| Calculated: | C 69.04 | H 8.07 | N 5.75 |
|---|---|---|---|
| Found: | 68.84 | 7.90 | 6.03 |

EXAMPLE 53

3-[(N-(2-(3-Methoxy-phenyl)-ethyl)-piperidin-2-yl)-ethyl-2]-7,8-dimethoxy-1,3,4,5-tetrahydro-2H-3-benzazepin-2-one-hydrochloride Prepared from 3-[(piperidin-2-yl)-ethyl-2]-7,8-dimethoxy-2H-3-benzazepin-2-one and 2-(3-methoxyphenyl)-ethyl-bromide analogously to Example 1.
Yield: 25% of theory,
Melting point: 125°–127° C.

| Calculated: | C 66.85 | H 7.81 | N 5.57 |
|---|---|---|---|
| Found: | 65.68 | 7.67 | 5.20 |

EXAMPLE 54

3-[(N-(2-(3,4,5-Trimethoxy-phenyl)-ethyl)-piperidin-2-yl)-ethyl-2]-7,8-dimethoxy-1,3,4,5-tetrahydro-2H-3-benzazepin-2-one-hydrochloride Prepared from 3-[(piperidin-2-yl)-ethyl-2]-7,8-dimethoxy-2H-3-benzazepin-2-one and 2-(3,4,5-trimethoxyphenyl)-ethylbromide analogously to Example 1.
Yield: 15% of theory,
Melting point: 138°–140° C.

| Calculated: | C 63.98 | H 7.70 | N 4.97 |
|---|---|---|---|
| Found: | 63.74 | 7.55 | 4.65 |

EXAMPLE 55

3-[(N-(2-(3-Methoxy-4-methanesulphonyloxy-phenyl)-ethyl)-piperidin-3-yl)-methyl]-7,8-dimethoxy-1,3,4,5-tetrahydro-2H-3-benzazepin-2-one-hydrochloride Prepared from 3-[(N-(2-(3-methoxy-4-hydroxyphenyl)-ethyl)-piperidin-3-yl)-methyl]-7,8-dimethoxy-1,3,4,5-tetrahydro-2H-3-benzazepin-2-one-hydrochloride and methanesulphonic acid chloride analogously to Example 9.
Yield: 66% of theory,
Melting point: 202°–204° C.

| Calculated: | C 57.67 | H 6.74 | N 4.80 | S 5.50 |
|---|---|---|---|---|
| Found: | 57.72 | 6.91 | 4.87 | 6.31 |

EXAMPLE 56

3-[(N-(2-(3-Methoxy-4-hydroxy-phenyl)-ethyl)-piperidin-3-yl)-methyl]-7,8-dimethoxy-1,3,4,5-tetrahydro-2H-3-benzazepin-2-one a) 3-[(N-(2-(4-Benzyloxy-3-methoxy-phenyl)-ethyl)-piperidin-3-yl)-methyl]-7,8-dimethoxy-1,3,4,5-tetrahydro-2H-3-benzazepin-2-one Prepared from 3-[(piperidin-3-yl)-methyl]-7,8-dimethoxy-1,3,4,5-tetrahydro-2H-3-benzazepin-2-one and 2-(4-benzyloxy-3-methoxy-phenyl)-ethylbromide analogously to Example 1.
Yield: 56% of theory,
Melting point: 216°–217° C.

| Calculated: | C 68.61 | H 7.28 | N 4.71 |
|---|---|---|---|
| Found: | 68.80 | 7.38 | 4.73 | b) 3-[(N-(2-(3-Methoxy-4-hydroxy-phenyl)-ethyl)-piperidin-3-yl)-methyl]-7,8-dimethoxy-1,3,4,5-tetrahydro-2H-3-benzazepin-2-one Prepared from 3-[(N-(2-(4-benzyloxy-3-methoxyphenyl)-ethyl)-piperidin-3-yl)-methyl]-7,8-dimethoxy-1,3,4,5-tetrahydro-2H-3-benzazepin-2-one in glacial acetic acid analogously to Example 8.
Yield: 77% of theory,
Melting point: 173°–175° C.

| Calculated: | C 69.21 | H 7.74 | N 5.98 |
|---|---|---|---|
| Found: | 69.07 | 7.79 | 6.06 |

EXAMPLE 57

3-[N-(2-(2-Fluorophenyl)-ethyl)-piperidin-3-yl)-methyl]-7,8-dimethoxy-1,3,4,5-tetrahydro-2H-3-benzazepin-2-one-dihydrochloride Prepared from 3-[(piperidin-3-yl)-methyl]-7,8-dimethoxy-1,3,4,5-tetrahydro-2H-3-benzazepin-2-one and 2-(2-fluorophenyl)ethylbromide analogously to Example 1. Yield:

| Calculated: | C 60.82 | H 6.87 | N 5.46 |
|---|---|---|---|
| Found: | 60.88 | 6.73 | 5.60 |

Rf value: 0.33 (silica gel, methylene chloride/methanol = 10/1).

EXAMPLE 58

3-[N-(2-(4-Fluorophenyl)-ethyl)-piperidin-3-yl)-methyl]-7,8-dimethoxy-1,3,4,5-tetrahydro-2H-3-benzazepin-2-one-hydrochloride Prepared from 3-[(piperidin-3-yl)-methyl]-7,8-dimethoxy-1,3,4,5-tetrahydro-2H-3-benzazepin-2-one and 2-(4-fluorophenyl)ethylbromide analogously to Example 1.
Yield: 56% of theory,
Melting point: 245° C. (decomp.).

| Calculated: | C 65.47 | H 7.18 | N 5.87 |
|---|---|---|---|
| Found: | 65.78 | 7.25 | 5.99 |

Rf value: 0.31 (silica gel, methylene chloride/methanol = 10/1).

EXAMPLE 59

(+)-3-[(N-(2-(3,4-Dimethoxy-phenyl)-ethyl)-piperidin-3-(S)-yl)-methyl]-7,8-dimethoxy-1,3,4,5-tetrahydro-2H-3-benzazepin-2-one a) (−)-3-[(N-(2-(3,4-Dimethoxy-phenyl)-ethyl)-piperidin-3-(S)-yl)-methyl]-7,8-dimethoxy-1,3-dihydro-2H-3-benzazepin-2-one 2.19 g (0.01 mol) of 7,8-dimethoxy-1,3-dihydro-2H-3-benzazepin-2-one are suspended in 14 ml of dimethyl acetamide and mixed with 1.57 g (0.014 mol) of potassium tert.butoxide. After stirring for 30 minutes, 2.74 g (0.0077 mol) of (−)-N-[2-(3,4-Dimethoxy-phenyl)-ethyl]-piperidin-3-(S)-yl)-methyl mesylate (prepared by reaction of Ethyl (+)-peperidin-3-carbonate with 3,4-dimethoxyphenylacetic chloride, subsequent reduction with lithum aluminium hydride and esterification of the thus obtained alcohol with methane sulfonic acid chloride, $[\alpha]^{20}_D = -3.91°$ (c=2, methanol)) were added to the mixture. After stirring for 4 hours at 130° C. and cooling, the reaction mixture was poured into ice water and extracted with ethyl acetate. After extraction of the organic phase with 0.5 N hydrochloric acid, the aqueous phase was separated, the pH made alkaline, and again extracted with ethyl acetate. The organic phase was evaporated after drying over magnesium sulfate.

Yield: 2.5 g (67.5% of theory),
$[\alpha]^{20}_D = -33.6°$ (c=1, methanol).

b) (+)-3-[(N-(2-(3,4-Dimethoxy-phenyl)-ethyl)-piperidin-3-(S)-yl)-methyl]-7,8-dimethoxy-1,3,4,5-tetrahydro-2H-3-benzazepin-2-one 2.5 g of (−)-3-[N-(2-(3,4-dimethoxy-phenyl)-ethyl)-piperidin-3-(S)-yl)-methyl]-7,8-dimethoxy-1,3-dihydro-2H-3-benzazepin-2-one were hydrogenated in 30 ml of 0.5 N hydrochloric acid in the presence of palladium/charcoal and at a hydrogen pressure of 50 psi for 5 hours. After filtering off the catalyst the pH of the reaction mixture was made alkaline by addition of concentrated sodium hydroxide solution and extracted with ethyl acetate. After drying the organic phase over magnesium sulfate and evaporation the obtained residue is dissolved in 20 ml of acetone at 50° C. and mixed with 0.7 ml 7 N of methanolic hydrochloric acid. The precipitate was suction filtered after stirring for 90 minutes, washed with acetone and dried.

A further fraction was obtained after evaporation of the filtrate. The thus obtained residue was refluxed in 0.6 ml of methanol and 15 ml of ethyl acetate. The organic phase was decanted, evaporated and mixed with 8 ml of acetone. The precipitated crystals were suction filtered after 5 hours. The thus obtained 1.58 g are mixed with 2 ml of water and 5 ml of ethyl acetate and the pH made alkaline by addition of concentrated sodium hydroxide solution. After extraction with ethyl acetate, the organic phase was separated, dried over magnesium sulfate and evaporated. The obtained residue was dissolved in 10 ml of acetone and mixed with 0.45 ml of 7N of methanolic hydrochloric acid. The precipitate crystals was suction filtered, washed with acetone and dried. After again carrying out the above mentioned purification steps, 1.10 g (41% of theory) of product were obtained, having a melting point of 224°–226° C.

$[\alpha]^{20}_D = +14.5°$ (c=1, water).

EXAMPLE 60

(−)-3-[(N-(2-(3,4-Dimethoxy-phenyl)-ethyl)-piperidin-3-(S)-yl)-methyl]-7,8-dimethoxy-1,3,4,5-tetrahydro-2H-3-benzazepin-2-one The title compound was prepared analogously to Example 1 by hydrogenation from (−)-3-[(N-(2-(3,4-dimethoxy-phenyl)-ethyl)-piperidin-3-(S)-yl)-methyl]-7,8-dimethoxy-1,3-dihydro-2H-3-benzazepin-2-one.

Yield: 50% of Theory,
Melting point: 222°–224° C.

EXAMPLE I

Tablets containing 7.5 mg of 3-(N-(2-(3,4-dimethoxy-phenyl)-ethyl)-piperidin-3-yl)-methyl]-7,8-dimethoxy-1,3,4,5-tetrahydro-2H-3-benzazepin-2-one

| Composition: | |
|---|---|
| 1 tablet contains: | |
| Active substance | 7.5 mg |
| Corn starch | 59.5 mg |
| Lactose | 48.0 mg |
| Polyvinylpyrrolidone | 4.0 mg |
| Magnesium stearate | 1.0 mg |
| | 120.0 mg |

Method of Preparation

The active substance, corn starch, lactose and polyvinylpyrrolidone were mixed together and moistened with water. The moist mixture is pushed through a screen with a mesh size of 1.5 mm and dried at about 45° C. The dry granulate is passed through a 1.0 mm mesh screen and mixed with magnesium stearate. The final mixture is compressed in a tablet press with dies 7 mm in diameter provided with a dividing notch to form tablets. Weight of tablet: 120 mg.

EXAMPLE II

Coated tablets containing 5 mg of 3-[(N-(2-(3,4-dimethoxy-phenyl)-ethyl)-piperidin-3-yl)-methyl]-7,8-dimethoxy-1,3,4,5-tetrahydro-2H-3-benzazeoin-2-one

| 1 tablet core contains: | |
|---|---|
| Active substance | 5.0 mg |
| Corn starch | 41.5 mg |
| Lactose | 30.0 mg |
| Polyvinylpyrrolidone | 3.0 mg |
| Magnesium stearate | 0.5 mg |
| | 80.0 mg |

Method of Preparation

The active substance, corn starch, lactose and polyvinylpyrrolidone are throughly mixed and moistened with water. The moist mass is forced through a 1 mm screen, dried at about 45° C. and then the granulate is passed through the same screen. After magnesium stearate has been added, convex tablet cores with a diameter of 6 mm are compressed in a tablet making machine. The tablet cores thus produced are coated in known manner with a coating consisting essentially of sugar and talc. The finished coated tablets are polished with wax. Weight of coated tablet: 130 mg.

EXAMPLE III

Ampoules containing 5 mg of
3-[(N-(2-(3,4-dimethoxy-phenyl)-ethyl)-piperidin-3-yl)-methyl]-7,8-dimethoxy-1,3,4,5-tetrahydro-2H-3-benzazepin-2-one

| 1 ampoule contains: | |
| --- | --- |
| Active substance | 5.0 mg |
| Sorbitol | 50.0 mg |
| Water for injection. ad. | 2.0 ml |

Method of Preparation

In a suitable mixing vessel the active substance is dissolved in water for injection and the solution is made isotonic with sorbitol.

After being filtered through a diaphragm filter the solution is transferred under a current of $N_2$ into purified and sterilized ampoules and auto-claved for 20 minutes in a jet of steam.

EXAMPLE IV

Suppositories containing 10 mg of
3-[(N-(2-(3,4-dimethoxy-phenyl)-ethyl)-piperidin-3-yl)-methyl]-7,8-dimethoxy-1,3,4,5-tetrahydro-2H-3-benzazepin-2-one

| 1 suppository contains: | |
| --- | --- |
| Active substance | 0.010 g |
| Hard fat (e.g. Witepsol H 19 and W 45) | 1.690 g |
| | 1.700 g |

Method of Preparation

The hard fat is melted. At 38° C. the ground active substance is homogeneously dispersed in the melt. It is cooled to 35° C. and poured into slightly chilled suppository moulds.

EXAMPLE V

Drops solution containing 10 mg of
3-[(N-(2-(3,4-dimethoxy-phenyl)-ethyl)-piperidin-3-yl)-methyl]-7,8-dimethoxy-1,3,4,5-tetrahydro-2H-3-benzazepin-2-one

| 100 ml of solution contain: | |
| --- | --- |
| Active substance | 0.2 g |
| Hydroxyethylcellulose | 0.15 g |
| Tartaric acid | 0.1 g |
| Sorbitol solution with 70% dry matter | 30.0 g |
| Glycerol | 10.0 g |
| Benzoic acid | 0.15 g |
| Dist. water ad | 100 ml |

Method of Preparation

The distilled water is heated to 70° C. The hydroxyethylcellulose, benzoic acid and tartaric acid are dissolved therein with stirring. The mixture is cooled to ambient temperature and the glycerol and sorbitol solution are added with stirring. At ambient temperature the active substance is added and stirred until completely dissolved. The syrup is then evacuated of any air with stirring.

B. Examples for compounds of Formula I wherein A, B, G, m, n and R are selected from option (ii)

EXAMPLE A

2-[(Piperidin-3-yl)-methyl]-6,7-dimethoxy-1-oxo-1,2,3,4-tetrahydro-isoquinoline a) N-Benzyl-3-(hydroxymethyl)-piperidine A mixture of 40.3 g (0.35 mol) of 3-(hydroxymethyl)-piperidine, 97.4 ml (0.70 mol) of triethylamine and 40.3 ml (0.35 mol) of benzyl chloride is heated to 95° C. within 30 minutes and kept at this temperature for 2 hours. The reaction mixture is cooled down and dissolved in a mixture of 2 molar sodium hydroxide solution and ethyl acetate. The organic phase is washed with water, separated off, dried over magnesium sulphate and evaporated down in vacuo.

Yield: 57.2 g (79.6% of theory), Rf value: 0.45 (aluminium oxide, neutral, eluant: 3% ethanolin methylene chloride).

b) N-Benzyl-3-(benzenesulphonyloxymethyl)-piperidine

A mixture of 6.8g (0.033 mol) of N-benzyl-3-(hydroxy-methyl)-piperidine, 6.7 ml (0.052 mol) of benzenesulphonic acid chloride, 50 ml of 20% aqueous sodium hydroxide solution, 100 ml of toluene and 1 spatula tip of tetrabutyl ammonium bromide is stirred for 3 hours at ambient temperature. The mixture is then diluted with 250 ml of ethyl acetate and the organic phase is washed with water. The organic phase is separated off, dried over magnesium sulphate and evaporated to dryness in vacuo. The residue is purified over 200 g of silica gel (0.063–0.2 mm) with methylene chloride and then with increasing amounts of ethanol (up to 5%).

Yield: 9.4 g (92% of theory), Rf value: 0.5 (silica gel, eluant: 5% ethanol in methylene chloride).

c) 2-[(N-Benzyl-piperidin-3-yl)-methyl]-6-7-dimethoxy-1-oxo-1,2,3,4-tetrahydro-isoquinoline 5.2 g (0.025 mol) of 6,7-dimethoxy-1-oxo-1,2,3,4-tetrahydro-isoquinoline are dissolved in 70 ml of dimethylsulphoxide and 3.1 g (0.025 mol) of potassium tert-.butoxide are added with stirring. After half an hour, 9.3 g (0.0275 mol) of N-benzyl-3-(benzenesulphonyloxymethyl)-piperidine in 20 ml of dimethylsulphoxide are added to the resulting potassium salt suspension and the mixture is stirred for 2 hours at 40° C. It is then poured onto ice water and extracted three times, each time with 120 ml of ethyl acetate. The combined organic phases are washed with water, dried over magnesium sulphate and evaporated down in vacuo. The residue obtained is purified over 200 g of silica gel (0.063–0.2 mm) with methylene chloride and then with increasing amounts of ethanol (up to 2%).

Yield: 7.7 g (78.5% of theory), Rf value: 0.5 (silica gel, eluant: 5% ethanol in methylene chloride and 1 drop of ammonia).

d) 2-[(Piperidin-3-yl)-methyl]-6,7-dimethoxy-1-oxo-1,2,3,4-tetrahydro-isoquinoline 9.4 g (0.0238 mol) of 2-[(N-benzyl-piperidin-3-yl)-methyl]-6,7-dimethoxy-1-oxo-1,2,3,4-tetrahydro-isoquinoline are hydrogenated in 200 ml of methanol in the presence of 2 g of 20% palladium hydroxide/charcoal for 3 hours at ambient temperature under 5 bar of hydrogen. The catalyst is then removed by suction filtering and the filtrate is evaporated to dryness in vacuo.

Yield: 7.2 g (99% of theory), Rf value: 0.15 (silica gel, eluant: 10% ethanol in methylene chloride and 1 drop of ammonia).

EXAMPLE B

3-Chloromethyl-N-[3-(naphthyl-2-oxy)-propyl-piperidine a) 3-(Hydroxymethyl)-N-[3-(naphthyl-2-oxy)-propyl]-piperidine A mixture of 11.5 g (0.2 mol) of 3-hydroxymethyl-piperidine and 11 g of 2-(3-chloropropoxy)-naphthalene is heated to 120° C. for 1 hour. The residue is purified over silica gel (0.063-0.2 mm) with ethyl acetate/ethanol/ammonia=90:10:1.

Yield: 11.5 g (76.6% of theory),
Melting point: 99°-101° C.

b) 3-Chloromethyl-N-[3-(naphthyl-2-oxy)-propyl]-piperidine

A solution of 1.5 g (5 mmol) of 3-(hydroxymethyl)-N-[3-(naphthyl-2-oxy)-propyl]-piperidine in 25 ml of chloroform is mixed with 1.5 ml of thionyl chloride and refluxed for 1½ hours. The mixture is evaporated to dryness in vacuo. The residue is taken up in methylene chloride, washed with water, 2 molar sodium hydroxide solution and again with water. After the methylene chloride phase has been dried over magnesium sulphate it is evaporated down in vacuo.

Yield: 1.4 g (87.5% of theory), Rf value: 0.8 (silica gel, eluant: ethyl acetate/ethanol/ammonia=90:40:2).

EXAMPLE C

2-[(Hexahydro-azepin-3-yl)-methyl]-6,7-methylenedioxy-1-oxo-1,2,3,4-tetrahydro-isoqainoline a) N-Benzyl-caprolactam 33.9 g (0.3 mol) of caprolactam are dissolved in 250 ml of dimethylsulphoxide and 37 g (0.33 mol) of potassium tert.butoxide are added with stirring. The reaction temperature rises to 60° C. It is stirred for half an hour at 60° C. and then 35 ml (0.3 mol) of benzyl bromide are added dropwise. After another 2½ hours at 60° C. it is poured onto 1 litre of ice water and extracted three times with ethyl acetate. The organic phases are combined, washed with water, dried over magnesium sulphate and evaporated down in vacuo.

Yield: 60.3 g (99% of theory), Rf value: 0.6 (silica gel, eluant: 5% ethanol in methylene chloride).

b) 1-Benzyl-caprolactam-3-carboxylic acid 180 ml of 2.6 molar butyllithium solution in n-hexane are added at −60° C., with stirring and under nitrogen, to 33.9 g=47.1 ml (0.33 mol) of diisopropyl-amine in 450 ml of absolute ether. Then, while cooling is continued, 48.8 g (0.24 mol) of N-benzylcaprolactam dissolved in 150 ml of absolute ether are added dropwise. After stirring for 10 minutes, the cooling bath is removed and carbon dioxide is piped in for 15 minutes. The reaction mixture is poured onto ice, the ethereal phase is separated off and extracted twice with 2 molar sodium hydroxide solution. The aqueous-alcoholic phases are combined, extracted with ether, acidified with concentrated hydrochloric acid and extracted twice with methylene chloride. The combined methylene chloride phases are dried over magnesium sulphate and the solvent is distilled off in vacuo.

Yield: 15.7 g (26.5% of theory), IR spectrum (methylene chloride): 1735 and 1600 cm$^{-1}$ (CO).

c) 1-Benzyl-3-hydroxymethyl-hexahydro-azepine 14.8 g (0.06 mol) of 1-benzyl-caprolactam-3-carboxylic acid dissolved in 300 ml of absolute tetrahydrofuran are added dropwise to 6.84 g (0.28 mol) of lithium aluminium hydride in 300 ml of absolute tetrahydrofuran. Then the mixture is refluxed for 6 hours, then 6.8 ml of water, 6.8 ml of 2 molar sodium hydroxide solution and 21 ml of water are added whilst cooling with ice water. The precipitate is suction filtered, washed with tetrahydrofuran and the filtrate is evaporated down in vacuo. The residue is purified by column chromatography over aluminium oxide N (activity II, eluant: methylene chloride).

Yield: 8.4 g (63.8% of theory), IR spectrum (methylene chloride): 3620 cm$^{-1}$ (OH).

d) 1-Benzyl-3-)4-toluenesulphonyloxymethyl)-hexahydro-azepine 15 g (0.0684 mol) of 1-benzyl-3-hydroxymethyl-hexahydro-azepine are dissolved in 150 ml of pyridine and 14.3 g (0.075 mol) of p-toluenesulphonic acid chloride are added with stirring and the resulting mixture is stirred for 1 hour at ambient temperature. It is evaporated down in vacuo, taken up in methylene chloride and washed with 2 molar sodium hydroxide solution and water. After drying over magnesium sulphate the organic phase is evaporated down in vacuo.

Yield: 23.3 g (91.3% of theory), Rf value: 0.45 (silica gel, eluant: 5% ethanol in methylene chloride).

e) 2-[(N-Benzyl-hexahydro-azepin-3-yl)-methyl]-6,7-methylenedioxy-1-oxo-1,2,3,4-tetrahydro-isoquinoline 7.4 g (0.0387 mol) of 6,7-methylenedioxy-1-oxo-1,2,3,4-tetrahydro-isoquinoline are dissolved in 100 ml of dimethylsulphoxide, 4.5 g (0.04 mol) of potassium tert.butoxide are added and the mixture is stirred for half an hour at ambient temperature. Then 16.8 g (0.044 mol) of 1-benzyl-3-(4-toluenesulphonyl-oxymethyl)-hexahydro-azepine are added and the mixture is stirred for 3 hours at ambient temperature. The reaction mixture is dissolved in ethyl acetate and extracted twice with water. The organic phase is dried over magnesium sulphate and evaporated down in vacuo. The residue is purified over aluminium oxide N (activity II, eluant: methylene chloride, methylene chloride+2% ethanol).

Yield: 3.0 g (19.6% of theory), Rf value: 0.6 (silica gel, eluant: 5% ethanol in methylene chloride).

f) 2-N(Hexahydro-azepin-3-yl)]methyl]-6,7-methylenedioxy-1-oxo-1,2,3,4-tetrahydro-isoquinoline 6.7 g (0.017 mol) of 2-[(N-benzyl-hexahydro-azepin-3-yl)-methyl]-6,7-methylenedioxy-1,2,3,4-tetrahydro-isoquinoline are hydrogenated in 250 ml of methanol in the presence of 2 g of 20% palladium hydroxide/charcoal for 4 hours at ambient temperature under 5 bar of hydrogen. The catalyst is then removed by suction filtering and the filtrate is evaporated down to dryness in vacuo. The residue is crystallized from acetone.

Yield: 4.9 g (95% of theory), M.p.: 267-°269° C.

EXAMPLE D

3-Chloromethyl-N-[3-(naphthyl-2-oxy)-propyl]-hexahydro-azepine a) 3-Hydroxymethyl-hexahydro-azepine 16.6 g (0.0757 mol) of 1-benzyl-3-hydroxymethyl-hexahydro-azepine are hydrogenated in 500 ml of methanol in the presence of 16.6 g of 20% palladium hydroxide/charcoal for 2 hours at ambient temperature under 5 bar of hydrogen.

The catalyst is then removed by suction filtering and the filtrate is evaporated down in vacuo.

Yield: 8 g (81.8% of theory), Rf value: 0.5 (silica gel, eluant: methylene chloride/ ethanol/ammonia = 5:4:1).

b) 3-Hydroxymethyl-N-[3-)naphthyl-2-oxy)-propyl]-hexahydro-azepine-hydrochloride A mixture of 7.8 g (0.06 mol) of 3-hydroxymethyl-hexahydro-azepine and 6.7 g (0.03 mol) of 2-(3-chloropropoxy)-naphthalene is heated for 1 hour to 120° C.

The reaction mixture is purified over silica gel (0.063–0.2 mm) with ethyl acetate/ethanol/ammonia 90:10:1.

Yield: 2.3 g (24.3% of theory),
Melting point: 127°–129° C.

c) 3-Chloromethyl-N-[3-(naphthyl-2-oxy)-propyl[-hexahydro-azepine 2.4 g (6.86 mmol) of 3-hydroxymethyl-N-[3-(naphthyl-2-oxy)-propyl]-hexahydro-azepine hydrochloride dissolved in 30 ml of chloroform are mixed with 5 ml of thionyl chloride and refluxed for 1 hour. The mixture is evaporated to dryness in vacuo. The residue is dissolved in methylene chloride, and extracted with water, 2 molar sodium hydroxide solution and again with water. The methylene chloride phase is dried over magnesium sulphate and evaporated down in vacuo.

Yield: 1.1 g (48.5% of theory), Rf value: 0.55 (silica gel, eluant: 5% ethanol in methylene chloride).

EXAMPLE E

2-[(Pyrrolidin-3-yl)-methyl]-6,7-dimethoxy-1-oxo-1,2,3,4-tetrahydro-isoquinoline a) N-Benzyl-2-pyrrolidone 14.4 g (0.33 mol) of 50% sodium hydride dispersion in oil is added in batches to 25.5 g (0.3 mol) of 2-pyrrolidone in 300 ml of absolute dimethylsulphoxide. The mixture is then stirred for 5 hours at 40° to 50° C. and, at 25° to 30° C., 56.4 g=39.2 ml (0.33 mol) of benzyl bromide are added dropwise. After stirring for 10 hours at ambient temperature the reaction mixture is dissolved in 500 ml of ethyl acetate and extracted several times with water. The organic phase is separated off, dried over magnesium sulphate and the solvent is eliminated in vacuo. The residue obtained is purified over 900 g of aluminium oxide (neutral, activity II) with methylene chloride and 0.1% ethanol.

Yield: 35.6 g (67.7% of theory), Rf value: 0.77 (aluminium oxide, neutral, eluant: 5% ethanol in methylene chloride).

b) N-Benzyl-2-pyrrolidone-3-carboxylic acid 150 ml of 1.6 molar butyllithium solution in n-hexane are added with stirring and under nitrogen at −60° C. to 28.3 g=39.3 ml (0.28 mol) of diisopropyl-amine in 400 ml of absolute ether. 35.1 g (0.2 mol) of N-benzyl-2-pyrrolidone dissolved in 150 ml of absolute ether are added dropwise thereto at −60° C. The cooling bath is removed and dry carbon dioxide is introduced for 15 minutes. After stirring for 10 minutes, the mixture is poured onto ice, the organic phase is separated off and extracted twice with 2 molar sodium hydroxide solution. The combined aqueous phases are extracted once with ether and then acidified with concentrated hydrochloric acid whilst being cooled. The aqueous phase is extracted twice with methylene chloride and after the organic phase has been dried over magnesium sulphate it is evaporated down in vacuo.

Yield: 35 g (79.8% of theory), Rf value: 0.42 (silica gel, eluant: 5% ethanol in methylene chloride).

c) N-Benzyl-3-hydroxymethyl-pyrrolidine 35 g (0.16 mol) of N-benzyl-2-pyrrolidone-3-carboxylic acid dissolved in 250 ml of absolute tetrahydrofuran are added dropwise, with stirring to 12.2 g (0.32 mol) of lithium aluminium hydride in 350 ml of absolute tetrahydrofuran. After refluxing for 6 hours, 18.2 ml of water, 12.2 ml of 15% aqueous sodium hydroxide solution and 36.6 ml of water are added whilst cooling with ice water.

The precipitate formed is suction filtered and washed with tetrahydrofuran. The combined filtrates are evaporated down in vacuo and the residue obtained is purified over 900 g of aluminium oxide (neutral, activity II) with methylene chloride and then with increasing amounts of ethanol (up to 2%).

Yield: 16 g (52.3% of theory), Rf value: 0.42 (aluminium oxide, neutral, eluant: 5% ethanol in methylene chloride).

d) 3-(Benzenesulphonyloxymethyl)-1-benzyl-pyrrolidine 40 ml of 20% sodium hydroxide solution are added dropwise, for a period of 1 hour, to a mixture of 3.8 g (20 mmol) of N-benzyl-3-hydroxy-pyrrolidine and 3.7 ml (24 mmol) of benzenesulphonic acid chloride. 150 ml of toluene are added, the organic phase is washed with water, dried over magnesium sulphate and evaporated to dryness in vacuo.

Yield: 5.9 g (89.4% of theory), Rf value: 0.4 (silica gel, eluant: 5% ethanol in methylene chloride).

e) 2-[N-(Benzyl-pyrrolidin-3-yl)-methyl]-6,7-dimethoxy-1-oxo-1,2,3,4-tetrahydro-isoquinoline 3.3 g (15.9 mmol) of 6,7-dimethoxy-1-oxo-1,2,3,4-tetrahydro-isoquinoline are dissolved in 50 ml of dimethylsulphoxide and combined with 2 g (17.5 mmol) of potassium tert.butoxide with stirring at ambient temperature. After half an hour, 5.8 g (17.5 mmol) of 3-(benzenesulphonyloxymethyl)-1-benzyl-pyrrolidine in 10 ml of dimethylsulphoxide are added to the resulting potassium salt suspension and the mixture is stirred for 3 hours at 60° C.

It is poured onto ice water and extracted with ethyl acetate. The combined organic phases are washed with water and dried over magnesium sulphate. The organic phase is evaporated down in vacuo and the residue obtained is purified over 350 g of aluminium oxide N (activity II) with methylene chloride and then with increasing quantities of ethanol (up to 1%).

Yield: 3.3 g (54.4% of theory), Rf value: 0.74 (aluminium oxide N, eluant: 5% ethanol in methylene chloride).

f) 2-[(Pyrrolidin-3-yl)-methyl]-6,7-dimethoxy-1-oxo-1,2,3,4-tetrahydro-isoquinoline 3.2 g (8.4 mmol) of 2-[(N-benzyl-pyrrolidyl)-methyl]-6,7-dimethoxy-1-oxo-1,2,3,4-tetrahydro-isoquinoline are dissolved in 250 ml of methanol and hydrogenated in the presence of 1 g of 20% palladium hydroxide/charcoal for 3 hours at ambient temperature under 5 bar of hydrogen. The catalyst is then removed by suction filtering and the filtrate is evaporated to dryness in vacuo. The residue is purified over 150 g of silica gel (0.063–0.2 mm) with methylene chloride/ ethanol/ammonia = 6:1:0.5.

Yield: 0.9 g (37.5% of theory), Rf value: 0.6 (silica gel, eluant: methylene chloride/ ethanol/ammonia = 5:4:1).

EXAMPLE F 3-(p-Toluenesulphonyloxymethyl)-N-[2-(6-methoxy-naphth-2-yl)-ethyl-pyrrolidine a) 3-Hydroxymethyl-pyrrolidine 14 g (0.073 mol) of N-benzyl-3-hydroxymethyl-pyrrolidine are hydrogenated for 7 hours at 50° C. and under 5 bar in 300 ml of methanol and in the presence of 1.5 g of 20% palladium hydroxide/activated charcoal. The catalyst is then removed by suction filtering and the filtrate is evaporated down in vacuo.

Yield: 7.3 g (99% of theory), Mass spectrum: molecular peak 101.

b) 3-Hydroxymethyl-N-[2-(6-methoxy-naphth-2-yl)-ethyl]-pyrrolidine

A mixture of 3.6 g (29.4 mmol) of 3-hydroxymethyl-pyrrolidine and 4.7 g (14.7 mmol) of 2-(2-bromoethyl)-6-methoxy-naphthalene is heated to 120° C. for 2 hours. The reaction mixture is purified over 200 g of silica gel (0.063–0.2 mm) with methylene chloride and then with increasing amounts of ethanol (up to 5%).

Yield: 3.48 g (82.5% of theory),
Melting point: 121°–123° C.

c) 3-(p-Toluenesulphonyloxymethyl)-N-[2-(6-methoxy-naphthalene-2)-ethyl]-pyrrolidine 0.8 g (2.8 mmol) of 3-hydroxymethyl-N-[2-(6-methoxy-naphth-2-yl)-ethyl]-pyrrolidine are dissolved in 10 ml of pyridine and 1.2 g (6.3 mmol) of p-toluenesulphonic acid chloride are added with stirring. After 2 hours at ambient temperature the mixture is evaporated to dryness in vacuo. The residue is dissolved in methylene chloride, washed with 2 molar sodium hydroxide solution and water. The organic phase is then dried over magnesium sulphate and evaporated down in vacuo. The residue is purified over 150 g of silica gel (0.063–0.2 mm) with ethyl acetate and then with increasing amounts of ethanol.

Yield: 0.6 g (48.8% of theory), Rf value: 0.45 (silica gel, eluant: 5% ethanol in methylene chloride).

EXAMPLE G

2-[(Azacyclooctyl-3)-methyl-6,7-dimethoxy-1-oxo-1,2,3,4-tetrahydro-isoquinoline a) Benzloxy-azacyclooctane 25 g (0.196 mol) of 2-azacyclooctanone are dissolved in 150 ml of dimethylsulphoxide and combined, with stirring, with 24.2 g (0.216 mol) of potassium tert.butoxide and stirred for half an hour at 40° C. Then 24 ml (0.2 mol) of benzylbromide are added dropwise over a period of a quarter of an hour, during which time the temperature rises to 80° C.

The mixture is stirred for 2 hours, during which the reaction temperature falls back to ambient temperature. The reaction mixture is poured onto 1 litre of ice water and extracted 4 times, each time with 150 ml of ethyl acetate.

The combined organic phase is washed with water, dried over magnesium sulphate and evaporated down in vacuo.

Yield: 42.7 g (100% of theory), Rf value: 0.55 (silica gel, eluant: 5% ethanol in methylene chloride).

b) 1-Benzyl-azacyclooctane-2-oxo-3-carboxylic acid 147 ml of 1.6 molar butyl lithium solution in n-hexane are added dropwise at-60° C., with stirring and under nitrogen, to 26.7 g=38.4 ml (0.26 mol) of diisopropylamine in 250 ml of absolute ether. Then at −60° C., 42.7 g (0.196 mol) of 1-benzyl-2-oxoazacyclooctane in 100 ml of absolute ether were added dropwise thereto. After 10 minutes, dry carbon dioxide was introduced for 20 minutes. The reaction mixture is poured onto ice, the ethereal phase is separated off and extracted twice with 2 molar sodium hydroxide solution. The combined aqueous phases are extracted once with ether and then acidified with concentrated hydrochloric acid, whilst being cooled. The mixture was extracted 3 times with methylene chloride, and the methylene chloride phase is dried over magnesium sulphate and evaporated down in vacuo. Yield: 25.9 g (50.6% of theory), Rf value: 0.15 (aluminium oxide, eluant: 5% ethanol in methylene chloride).

c) 1-Benzyl-3-hydroxymethyl-azacyclooctane 53.6 g (0.205 mol) of 1-benzyl-2-oxo-azacyclooctane-3-carboxylic acid dissolved in 100 ml of absolute tetrahydrofuran is added dropwise with stirring to 22.7 g (0.6 mol) of lithium aluminium hydride in 800 ml of absolute ether. After refluxing for half an hour, the mixture is combined with 28.4 ml of water, 19 ml of 15% sodium hydroxide solution and 57 ml of water, whilst cooling with ice water. The precipitate formed is suction filtered and washed with tetrahydrofuran. The combined filtrates are evaporated down in vacuo and the residue obtained is purified over 700 g of aluminium oxide (neutral, activity II) with 1% ethanol in methylene chloride.

Yield: 9.3 g (19.6% of theory), Rf value: 0.5 (silica gel, eluant: 5% ethanol in methylene chloride).

d) 1-Benzyl-3-chloromethyl-azacyclooctane 9.3 g (39.8 mol) of 1-benzyl-3-hydroxymethyl-azacyclo-octane are combined in 30 ml of pyridine with 10 ml (79.6 mmol) of benzenesulphonic acid chloride and stirred for 2½ hours at ambient temperature. The reaction mixture is evaporated down in vacuo. The residue remaining is dissolved in 150 ml of methylene chloride, then washed with 2N sodium hydroxide solution and water. The organic phase is dried over magnesium sulphate, evaporated to dryness and purified over 150 g of silica gel (0.063–0.2 mm) with methylene chloride.

Yield: 3.5 g (35% of theory) Rf value: 0.75 (silica gel, eluant: 5% ethanol in methylene chloride).

e) 2-[(N-Benzyl-azacyclooct-3-yl)-methyl]-6,7-dimethoxy-1-oxo-1,2,3,4-tetrahydro-isoquinoline 2.3 g (11.1 mmol) of 6,7-dimethoxy-1-oxo-1,2,3,4-tetrahydro-isoquinoline are dissolved in 40 ml of dimethylsulphoxide and 1.33 g (12.2 mmol) of potassium tert.butoxide are added with stirring. After half an hour, 3.5 g (9.4 mmol) of 1-benzyl-3-chloromethyl-azacyclooctane in 40 ml of dimethylsulphoxide are added to the resulting potassium salt suspension and the mixture is stirred for 2½ hours at 120° C. It is poured onto ice water and extracted 3 times, each time with 50 ml of ethyl acetate. The combined organic phases are washed with water, dried over magnesium sulphate and evaporated down in vacuo. The residue obtained is purified over 150 g of silica gel (0.063–0.2 mm) with 1% ethanol in methylene chloride.

Yield: 1 g (25.1% of theory), Rf value: 0.5 (silica gel, eluant: 2% ethanol in methylene chloride).

f) 2-[(Azacyclooct-3-yl)-methyl]-6,7-dimethoxy-1-oxo-1,2,3,4-tetrahydro-isoquinoline 0.85 g (2 mmol) of 2-[(N-benzyl-azacyclooctyl-3)-methyl]-6,7-dimethoxy-1-oxo-1,2,3,4-tetrahydro-isoquinoline are hydrogenated in 50 ml of methanol in the presence of 0.85 g of 20% palladium hydroxide/char-coal for 4½ hours at ambient temperature under 5 bar of hydrogen. The catalyst is then removed by suction filtering and the filtrate is evaporated to dryness.

Yield: 0.5g (74.6% of theory), Rf value: 0.45 (silica gel, eluant: 25% ethanol in methylene chloride and 1 drop of ammonia).

EXAMPLE H

1-Chloro-3-(4-methoxy-N-methylamino-phenyl)-propane 10 g (0.073 mol) of N-methyl-4-methoxy-aniline are dissolved in 50 ml of dimethylsulphoxide and 9 g (0.08 mol) of potassium tert.butoxide are added with stirring. After half an hour, 10 ml of 1-bromo-3-chloropropane are added and the mixture is stirred for 3 hours at ambient temperature. It is poured onto ice water, extracted with ethyl acetate, the organic phase is washed with water, dried over sodium sulphate and evaporated to dryness. The residue is purified over silica gel (0.063-0.2 mm) with methylene chloride.

Yield: 9.1 g (58.3% of theory), Rf value: 0.55 (silica gel, eluant: methylethyl ketone/xylene = 1:6).

| | | | | |
|---|---|---|---|---|
| Calculated: | C 61.82 | H 7.55 | N 6.55 | Cl 16.59 |
| Found: | 61.71 | 7.88 | 6.69 | 16.24. |

EXAMPLE I

2-[(N-(3-(Pyrid-3-yl)-propyl)-piperidin-3-yl)-methyl[-5,6-methylenedioxy-phthalimide 2.1 g (0.011 mol) of 5,6-methylenedioxy-phthalimide are dissolved in 100 ml of dimethylsulphoxide and 1.25 g (0.012 mol) of potassium tert.butoxide are added with stirring.

The potassium salt is precipitated. It is stirred for a further ½ hour at ambient temperature, a solution of 2.5 g (0.01 mol) of 3-chloromethyl-N-(3-(pyrid-3-yl)-propyl)-piperidine in 20 ml of dimethylsulphoxide is added and the mixture is heated to 120° C. for 8 hours. It is poured onto ice water, extracted three times, each time with 150 ml of ethyl acetate, and after drying over magnesium sulphate, the organic phase is evaporated down in vacuo. The residue is purified over 200 g of silica gel (0.063-0.2 mm) with ethyl acetate/ethanol/ammonia = 80:10:0.5.

Yield: 3 g (74% of theory),

| | | | | |
|---|---|---|---|---|
| Calc. (2 × HCl) | C 55.42 | H 5.86 | N 8.43 | Cl 14.22 |
| Found: | 55.28 | 6.06 | 8.26 | 14.64 |

EXAMPLE K

2-N-(3-Chloropropyl)-piperidin-3-yl-methly]-6,7-dimethoxy-1-oxo-1,2,3,4-tetrahydro-isoquinoline 3 g (0.01 mol) of 2-[(piperidin-3-yl)-methyl]-6,7-dimethoxy-1-oxo-1,2,3,4-tetrahydro-isoquinoline are dissolved in 50 ml of dimethylsulphoxide and 1.3 g (0.011 mol) of potassium tert.butoxide are added with stirring. After half an hour, 3 ml of 1-bromo-3-chloro-propane are added and the mixture is stirred for 1 hour at ambient temperature. It is poured into ice water, extracted with ethyl acetate, and the organic phase is washed with water, dried over sodium sulphate and evaporated to dryness in vacuo.

Yield: 2.7 g (71% of theory), Rf value: 0.65 (silica gel, eluant: ethyl acetate/ethanol/ ammonia = 50:45:5).

EXAMPLE 1

2-[(N-(3-Naphth-2-yl)-propyl)-piperidin-3-yl)-methyl-6,7-dimethoxy-1-oxo-1,2,3,4-tetrahydro-isoquinoline-hydrochloride A mixture of 1 g (3.2 mmol) of 2-(piperidin-3-yl-methyl)-6,7-dimethoxy-1-oxo-1,2,3,4-tetrahydro-isoquinoline, 5 ml of dimethylsulphoxide, 0.5 g (0.36 mmol) of potassium carbonate and 0.75 g (3.66 mmol) of 2-(3-chloropropyl)-naphthalene is heated to 120° C. for 3 hours. The reaction mixture is poured onto ice water and extracted three times, each time with 50 ml of ethyl acetate. The combined organic phases are washed with 2 molar sodium hydroxide solution and water, dried over magnesium sulphate, evaporated down in vacuo and the residue obtained is purified over silica gel (0.063-0.2 mm) with 1% ethanol in methylene chloride. The hydrochloride is precipitated from a solution in acetone with ethereal hydrochloric acid and recrystallized from acetone.

Yield: 0.74 g (44% of theory),
Melting point: 179°-181° C.

| | | | | |
|---|---|---|---|---|
| Calculated: | C 70.77 | H 7.37 | N 5.50 | Cl 6.96 |
| Found: | 70.47 | 7.40 | 5.47 | 7.06. |

EXAMPLE 2

2-[(N-(3-(Naphthyl-2-oxy)-propyl)-piperidin-3-yl)-methyl-6,7-dimethyl-1-oxo-1,2,3,4-tetrahydro-isoquinoline-hydrochloride 1.58 g (9 mmol) of 6,7-dimethyl-1-oxo-1,2,3,4-tetrahydro-isoquinoline are dissolved in 30 ml of dimethylsulphoxide and 1.1 g (9.9 mmol) of potassium tert.butoxide are added with stirring. After 1 hour, a solution of 2.9 g (9.1 mmol) of 3-chloromethyl-N-[3-(naphthyl-2oxy)-propyl]-piperidine in 10 ml of dimethylsulphoxide is added and the reaction mixture is stirred for 16 hours at 80° C. It is then poured onto ice water, extracted 3 times, each time with 50 ml of ethyl acetate, the organic phase is washed with water, dried over magnesium sulphate and, after evaporation, purified on silica gel (0.63-0.2 mm) with ethyl acetate/ethanol/ammonia = 95:5:0.5. The hydrochloride is obtained as a hydrate from a solution in acetone using ethereal hydrochloric acid.

Yield: 2 g (45.1% of theory),
Melting point: 152°-154° C.

| | | | | |
|---|---|---|---|---|
| Calculated: | C 70.50 | H 7.69 | N 5.49 | Cl 6.93 |
| Found: | 70.31 | 7.52 | 5.49 | 7.10 |

EXAMPLE 3

2-[(N-(3-(Naphth-2-yl)-propyl)-piperidin-3-yl)-methyl-6,7-dimethyl-1,2,3,4-tetrahydro-isoquinoline-dihydrochloride 0.8 g (18 mmol) of 2-[(N-(3-(naphth-2-yl)-propyl)-piperidin-3-yl)-methyl]-6,7-dimethyl-1-oxo-1,2,3,4-tetrahydro-isoquinoline are dissolved in 10 ml of absolute tetrahydrofuran and 20 ml of absolute ether, 70 mg (18 mmol) of lithium aluminium hydride are added and the mixture is refluxed for 1 hour. The reaction mixture is decomposed by the addition of 5 ml of saturated aqueous sodium sulphate solution, filtered to remove the sodium sulphate precipitated and washed with tetrahydrofuran. The filtrate is dried over magnesium sulphate and after evaporation, purified over 150 g of silica gel (0.063–0.2 mm) with ethyl acetate/ethanol/ammonia=90:10:0.05. The hydrochloride is precipitated from a solution in acetone with ethereal hydrochloric acid.

Yield: 0.49 g (54.4% of theory),
Melting point: 148°–150° C.

| | | | |
|---|---|---|---|
| Calculated: C 69.61 | H 8.18 | N 5.41 | Cl 13.70 |
| Found: 69.46 | 8.32 | 5.26 | 14.17 |

EXAMPLE 4

2-[(N-(3-(Pyrid-3-yl)-propyl)-piperidin-3-yl)-methyl-5,6-methylenedioxy-1-oxo-1,3-dihydro-isoindole-dihydrochloride 2.4 g (5.9 mmol) of 2-[(N-(3-(pyrid-3-yl)-propyl)-piperidin-3-yl)-methyl]-5,6-methylenedioxy-phthalimide are dissolved in 50 ml of glacial acetic acid and refluxed for 5 hours. At intervals of 1 hour, 1 g batches of zinc powder are added. After the reaction time has ended, the mixture is suction filtered and evaporated with ethanol. The residue is dissolved in methylene chloride, extracted with concentrated ammonia, dried over magnesium sulphate and after evaporation in vacuo purified over 150 g of silica gel (0.063–0.2 mm) ethyl acetate/ethanol/ammonia=90:10:0.2. The hydrochloride is precipitated from a solution in acetone.

Yield: 2.05 g (75% of theory),
Melting point: 165°–167° C.

| | | | |
|---|---|---|---|
| Calculated: C 59.22 | H 6.27 | N 9.00 | Cl 15.20 |
| Found: 59.03 | 6.45 | 8.85 | 15.06 |

EXAMPLE 5

3-[(N-(3-(Pyrid-3-yl)-propyl)-pyrrolidin-3-yl)-methyl-7,8-dimethoxy-2-oxo-1,3,4,5-tetrahydro-2H-3-benzoazepine-dihydrochloride 1.1 g (2.6 mmol) of 3-[(N-(3-(pyrid-3-yl)-propyl)-pyrrolidin-3-yl)-methyl]-7,8-dimethoxy-2-oxo-1,3-dihydro-2H-3-benzoazepine, dissolved in 50 ml of ethanol, are hydrogenated in the presence of 1 g of 10% palladium on activated charcoal at 80° C. and under 5 bar of hydrogen for 2 hours. Then the catalyst is removed by suction filtering and, after being evaporated down in vacuo, the filtrate is purified over 100 g of silica gel (0.063–0.2 mm) with ethyl acetate/ethanol/ammonia=80:40:1. The hydro-chloride is precipitated from a solution in acetone.

Yield: 0.37 g (33% of theory),
Melting point: 96°–98° C.

| | | | |
|---|---|---|---|
| Calculated: C 60.42 | H 7.11 | N 8.46 | Cl 14.28 |
| Found: 60.35 | 7.46 | 8.43 | 14.58 |

EXAMPLE 6

2-[(N-(3-(3,4-Dimethyl-N-ethyl-amino-phenyl)-propyl)-piperidin-3-yl)-methyl]-6,7-dimethoxy-1-oxo-1,2,3,4-tetrahydro-isoquinoline-dihydrochloride A mixture of 1.3 g (0.0034 mol) of 2-[(N-(3-chloro-propyl)-piperidine-3-yl)-methyl]-6,7-dimethoxy-1-oxo-1,2,3,4-tetrahydro-isoquinoline, 15 ml of dimethylsulphoxide, 1.4 g (0.1 mol) of potassium carbonate and 1 g (0.0066 mol) of 3,4-dimethyl-N-ethylaniline is heated to 120° C. for 6 hours. The reaction mixture is poured onto ice water, extracted with ethyl acetate, the organic phase is washed with water, dried over sodium sulphate and evaporated down in vacuo. The residue obtained is purified over silica gel (0.036–0.2 mm) with 5% ethanol in methylene chloride.

Yield: 633 mg (37.7% of theory),
Melting point: 97°–100° C.

| | | | |
|---|---|---|---|
| Calculated: C 61.63 | H 8.10 | N 7.18 | Cl 12.12 |
| Found: 61.52 | 8.15 | 6.92 | 11.82 |

EXAMPLE 7

2-(N-(2-(4-Amino-phenyl)-ethyl)-piperidin-3-yl)-methyl]-5,6-dimethoxy-1-oxo-1,3-dihydro-isoindole-dihydrochloride 2.1 g (4.78 mmol) of 2-[(N-(2-(4-nitro-phenyl)-ethyl)-piperidin-3-yl)-methyl]-5,6-dimethoxy-1-oxo-1,3-dihydro-isoindole are dissolved in 50 ml of glacial acetic acid and 0.4 ml (8.22 mmol) of hydrazine hydrate and 1 spatula tip of Raney nickel are added with stirring. The addition of 0.2 ml of hydrazine and 1 spatula tip of Raney nickel is repeated 3 times at intervals of 1 hour. The catalyst is removed by suction filtering, the residue is washed with methanol, the filtrate is dried with magnesium sulphate, evaporated down in vacuo and the residue obtained is purified over aluminium oxide (neutral, activity II) with methylene chloride and then with increasing quantities of ethanol.

Yield: 1.8 g (91.8% of theory), 1 g is dissolved in acetone and the dihydrochloride is precipitated with ethereal hydrochloric acid.

Yield: 1.02 g (86.4% of theory based on the base),
Melting point: 232°–235° C.

| | | | |
|---|---|---|---|
| Calculated: C 59.72 | H 6.89 | N 8.71 | Cl 14.69 |
| Found: 59.54 | 7.08 | 8.56 | 14.45 |

EXAMPLE 8

2-[(N-(2-(4-Acetamino-phenyl)-ethyl)-piperidin-3-yl)-methyl]-5,6-dimethoxy-1-oxo-1,3-dihydro-isoindole 819 mg (2 mmol) of 2-[(N-(2-(4-amino-phenyl)-ethyl)-piperidin-3-yl)-methyl]-5,6-dimethoxy-1-oxo-1,3-dihydro-isoindole are mixed with 10 ml of methylene chloride and after the addition of 0.3 ml (2.2 mmol) of triethylamine, 0.16 ml (2.2 mmol) of acetyl chloride are added dropwise. The reaction temperature rises to 30° C. The mixture is stirred for half an hour at ambient temperature, extracted twice with water, the organic phase is dried over magnesium sulphate and evaporated down in vacuo. The residue is crystallised from acetone.

Yield: 660 mg (73.2% of theory), M.p.: 195°–196° C.

| | | |
|---|---|---|
| Calculated: C 69.16 | H 7.37 | N 9.31 |
| Found: 69.33 | 7.11 | 9.16 |

EXAMPLE 9

3-[(N-(3-(Furyl-2)-propyl)-piperidin-3-yl)-methyl-7,8-dimethoxy-2-oxo-1,3,4,5-tetrahydro-2H-3-benzazepine-hydrochloride 3.2 g (0.010 mol) of 3-[(piperidin-3-yl)-methyl]-7,8-dimethoxy-2-oxo-1,3,4,5-tetrahydro-2H-3-benzazepine are hydrogenated in 100 ml of absolute ethanol in the presence of 1.3 g (0.010 mol) of 3-(furyl-2)-propanal and 1 g of Raney nickel at 80° C. for 2 days under 5 bar. The catalyst is removed by suction filtering, the filtrate is evaporated down and purified over a silica gel column with methylene chloride/methanol as eluant. The hydrochloride is precipitated with ethereal hydrochloric acid and crystllized from acetone.

Yield: 0.50 g (11% of theory),
Melting point: 204°–206° C.

| | | | | |
|---|---|---|---|---|
| Calculated: | C 64.85 | H 7.62 | N 6.05 | Cl 7.66 |
| Found: | 64.88 | 7.76 | 5.93 | 7.55 |

Rf value: 0.69 (silica gel; methylene chloride/methanol=10:1; ammonia/atmosphere).

EXAMPLE 10

2-[(N-(3-(3-Methylphenoxy)-propyl)-piperidin-3-yl)-methyl]-6,7-dimethoxy-1,2,3,4-tetrahydro-isoquinoline-dihydrochloride Prepared from 2-[(N-(3-(3-methylphenoxy)-propyl)-piperidin-3-yl)-methyl]-6,7-dimethoxy-1-oxo-1,2,3,4-tetrahydro-isoquinoline and lithium aluminium hydride in diethylether and tetrahydrofuran analogously to Example 3.

Yield: 92.9% of theory,
Melting point: 100°–103° C.

| | | | | |
|---|---|---|---|---|
| Calculated: | C 61.23 | H 7.99 | N 5.29 | Cl 13.39 |
| Found: | 61.21 | 8.13 | 5.10 | 13.15 |

EXAMPLE 11

2-[(N-(3-(Naphthyl-2-oxy)-propyl)-pyrrolidin-3-yl)-methyl-6,7-dimethoxy-1-oxo-1,2,3,4-tetrahydro-isoquinoline-hydrochloride Prepared from 6,7-dimethoxy-1-oxo-1,2,3,4-tetrahydro-isoquinoline and 3-chloromethyl-N-[3-(naphthyl-2-oxy)-propyl]-pyrrolidine analogously to Example 2.

Yield: 22% of theory,
Melting point: 78°–80° C.

| | | | | |
|---|---|---|---|---|
| Calc. (× H₂O): | C 65.83 | H 7.04 | N 5.29 | Cl 6.70 |
| Found: | 65.79 | 7.00 | 5.03 | 6.99 |

EXAMPLE 12

2-[(N-(3-(Naphthyl-2-oxy)-propyl)-pyrrolidin-3-yl)-methyl-6,7-methylenedioxy-1-oxo-1,2,3,4-tetrahydro-isoquinoline-hydrochloride Prepared from 6,7-methylenedioxy-1-oxo-1,2,3,4-tetrahydro-isoquinoline and 3-chloromethyl-N-[3-(naphthyl-2-oxy)-propyl]-pyrrolidine analogously to Example 2.

Yield: 53% of theory,
Melting point: 78°–80° C.

| | | | | |
|---|---|---|---|---|
| Calc. (× H₂O): | C 65.56 | H 6.48 | N 5.46 | Cl 6.91 |
| Found: | 65.44 | 6.32 | 5.38 | 7.13 |

EXAMPLE 13

2-(N-(2-(Naphth-2-yl)-ethyl)-pyrrolidin-3-yl)-methyl-6,7-dimethoxy-1,2,3,4-tetrahydro-isoquinoline-hydrochloride Prepared from 2-[(N-(2-(naphth-2-yl)-ethyl)-pyrrolidin-3-yl)-methyl]-6,7-dimethoxy-1-oxo-1,2,3,4-tetrahydro-isoquinoline and lithium aluminium hydride in tetrahydro-furan and ether analogously to Example 3.

Yield: 66.2% of theory,
Melting point: 239°–241° C.

| | | | | |
|---|---|---|---|---|
| Calc. (× H₂O): | C 64.48 | H 7.44 | N 5.37 | Cl 13.91 |
| Found: | 64.30 | 7.34 | 5.52 | 13.69 |

EXAMPLE 14

2-[(N-(2-(Methyl-naphth-1-yl)-methyl)-hexahydro-azepin-3-yl)-methyl]-6,7-dimethoxy-1,2,3,4-tetrahydro-isoquinoline-hydrochloride Prepared from 2-[(N-(2-(methyl-naphth-1-yl)-methyl)-hexahydro-azepin-3-yl)-methyl]-6,7-dimethoxy-1-oxo-1,2,3,4-tetrahydro-isoquinoline and lithium aluminium hydride in tetrahydrofuran and ether analogously to Example 3.

Yield: 73.8% of theory,
Melting point: 182°–184° C.

| | | | | |
|---|---|---|---|---|
| Calc. (× H₂O): | C 65.56 | H 7.70 | N 5.09 | Cl 12.90 |
| Found: | 65.52 | 7.57 | 5.32 | 12.72 |

EXAMPLE 15

2-[(N-(4-(Naphthyl-2-oxy)-butyl)-pyrrolidin-3-yl)-methyl]-6,7-dimethyl-1-oxo-1,2,3,4-tetrahydro-isoquinoline-hydrochloride Prepared from 2-(pyrrolidin-3-yl-methyl)-6,7-dimethyl-1-oxo-1,2,3,4-tetrahydro-isoquinoline and 2-(4-bromo-butyloxy)naphthalene analogously to Example 1.

Yield: 30% of theory,
Melting point: 133°–136° C.

| | | | | |
|---|---|---|---|---|
| Calculated: | C 67.02 | H 6.92 | N 5.21 | Br 14.86 |
| Found: | 67.26 | 7.03 | 5.36 | 14.89 |

EXAMPLE 16

2-[(N-(2-Methyl-naphth-1-yl)-methyl)-pyrrolidin-3-yl)-methyl]-6,7-dimethyl-1-oxo-1,2,3,4-tetrahydro-isoquinoline-hydrochloride Prepared from 2-(pyrrolidin-3-yl-methyl)-6,7-dimethyl-1-oxo-isoquinoline and 1-chloromethyl-2-methyl-naphthalene analogously to Example 1.

Yield: 32.5% of theory,
Melting point: 142°–144° C.

| | | | | |
|---|---|---|---|---|
| Calculated: | C 69.34 | H 7.69 | N 5.77 | Br 7.37 |

-continued

| | Found: | 69.59 | 7.63 | 5.72 | 7.89 |
|---|---|---|---|---|---|

EXAMPLE 17

2-[(N-(2-(5-Methyl-6-methoxy-naphth-2-yl)-ethyl)-pyrrolidin-3-yl)-methyl-6,7-dimethyl-1-oxo-1,2,3,4-tetrahydro-isoquinoline-hydrobromide Prepared from 2-[N-(pyrrolidin-3-yl-methyl)]-6,7-dimethyl-1-oxo-1,2,3,4-tetrahydro-isoquinoline and 2-(2-bromoethyl)-5-methyl-6-methoxy-naphthalene analogously to Example 1.
Yield: 19% of theory,
Melting point: 230°–232° C.

| Calculated: | C 67.02 | H 6.93 | N 5.21 | Br 14.86 |
|---|---|---|---|---|
| Found: | 67.10 | 7.12 | 5.33 | 15.01 |

EXAMPLE 18

2-[(N-(2-(Naphth-2-yl)-ethyl)-pyrrolidin-3-yl)-methyl]-6,7-dimethoxy-1-oxo-1,2,3,4-tetrahydro-isoquinoline-hydrochloride Prepared from 2-(pyrrolidin-3-yl-methyl)-6,7-dimethoxy-1-oxo-1,2,3,4-tetrahydro-isoquinoline and 2-(2-bromoethyl)-naphthalene analogously to Example 1.
Yield: 7.8% of theory,
Melting point: 219°–221° C.

| Calc. (× H₂O): | C 67.39 | H 7.07 | N 5.61 | Cl 7.10 |
|---|---|---|---|---|
| Found: | 67.21 | 7.23 | 5.57 | 7.63 |

EXAMPLE 19

2-[(N-(2-(6-Methoxy-naphth-2-yl)-ethyl)-pyrrolidin-3-yl)-methyl]-6,7-dimethoxy-1-oxo-1,2,3,4-tetrahydro-isoquinoline-hydrochloride Prepared from 2-(pyrrolidin-3-yl-methyl)-6,7-dimethoxy-1-oxo-1,2,3,4-tetrahydro-isoquinoline and 2-(2-bromoethyl)-6-methoxy-naphthalene analogously to Example 1.
Yield: 39.2% of theory.
Melting point: 224°–226° C.

| Calc. (× H₂O): | C 65.84 | H 7.05 | N 5.29 | Cl 7.05 |
|---|---|---|---|---|
| Found: | 66.08 | 7.13 | 5.39 | 6.77 |

EXAMPLE 20

2-[(N-(3-(Naphth-2-yl)-propyl)-piperidin-3-yl)-methyl]-6,7-dimethyl-1-oxo-1,2,3,4-tetrahydro-isoquinoline-hydrochloride Prepared from 6,7-dimethyl-1-oxo-1,2,3,4-tetrahydro-isoquinoline and 3-chloromethyl-N-[3-(naphth-2-yl)-propyl]-piperidine analogously to Example 2.
Yield: 40.4% of theory,
Melting point: 185°–187° C.

| Calculated: | C 75.52 | H 7.82 | N 5.87 | Cl 7.43 |
|---|---|---|---|---|
| Found: | 75.39 | 7.85 | 5.82 | 7.52 |

EXAMPLE 21

2-[(N-(3-(Naphthyl-2-oxy)-propyl)-piperid-2-yl)-ethyl]-6,7-methylenedioxy-1-oxo-1,2,3,4-tetrahydro-isoquinoline-hydrochloride Prepared from 2-(piperid-2-yl)-ethyl-6,7-methylenedioxy-1-oxo-isoquinoline and 2-(3-chloropropoxy)-naphthalene analogously to Example 1.
Yield: 21.2% of theory,
Melting point: 85°–87° C.

| Calc. (× H₂O): | C 66.59 | H 6.89 | N 5.17 | Cl 6.53 |
|---|---|---|---|---|
| Found: | 66.77 | 6.98 | 4.95 | 6.74 |

EXAMPLE 22

2-[(N-(3-(Naphthyl-2-oxy)-propyl)-piperidin-3-yl)-methyl]-6,7-dimethyl-1,2,3,4-tetrahydro-isoquinoline-dihydrochloride Prepared from 2-[(N-(3-(naphthyl-2-oxy)-propyl)-piperidin-3-yl)-methyl]-6,7-dimethyl-1-oxo-1,2,3,4-tetrahydro-isoquinoline and lithium aluminium hydride in tetrahydrofuran/ether analogously to Example 3.
Yield: 53% of theory,
Melting point: 133°–135° C.

| Calc. (× H₂O): | C 68.30 | H 6.87 | N 5.31 | Cl 13.44 |
|---|---|---|---|---|
| Found: | 68.05 | 6.85 | 5.23 | 13.03 |

EXAMPLE 23

2-[(N-(3-(Naphthyl-2-oxy)-propyl)-piperidin-3-yl)-methyl]-6,7-methylenedioxy-1,2,3,4-tetrahydro-isoquinoline-dihydrochloride Prepared from 2-[(N-(3-(naphthyl-2-oxy)-propyl)-piperidin-3-yl)-methyl]-6,7-methylenedioxy-1-oxo-1,2,3,4-tetrahydro-isoquinoline and lithium aluminium hydride in tetrahydrofuran/ether analogously to Example 3.
Yield: 44.7% of theory,
Melting point: 130°–132° C.

| Calc. (× H₂O): | C 63.62 | H 6.62 | N 5.11 | Cl 12.95 |
|---|---|---|---|---|
| Found: | 63.49 | 6.86 | 4.97 | 12.64 |

EXAMPLE 24

2-[(N-((2-Methyl-naphth-1-yl)-methyl)-piperidin-3-yl)-methyl]-6,7-dimethoxy-1,2,3,4-tetrahydro-isoquinoline-dihydrochloride Prepared from 2-[(N-((2-methyl-naphth-1-yl)-methyl)-piperidin-3-yl)-methyl]-6,7-dimethoxy-1-oxo-1,2,3,4-tetrahydro-isoquinoline and lithium aluminium hydride in tetrahydrofuran/ether analogously to Example 3.
Yield: 80.5% of theory,
Melting point: 210°–212° C.

| Calc. (× H₂O): | C 65.05 | H 7.53 | N 5.23 |
|---|---|---|---|
| Found: | 65.23 | 7.78 | 5.03 |

EXAMPLE 25

2-[2-(N-(2-(6-Methoxy-naphth-2-yl)-ethyl)-piperid-2-yl)-ethyl]-6,7-methylenedioxy-1-oxo-1,2,3,4-tetrahydro-isoquinoline-hydrochloride Prepared from 2-[2-(piperid-2-yl)-ethyl]-6,7-methylene-dioxy-1-oxo-1,2,3,4-tetrahydro-isoquinoline and 2-(2-bromo-ethyl)-6-methoxy-naphthalene analogously to Example 1.
Yield: 27.6% of theory,
Melting point: 112°–117° C.

| Calc. (× ½ H₂O): | C 67.74 | H 6.82 | N 5.26 | Cl 6.65 |
|---|---|---|---|---|
| Found: | 67.54 | 6.73 | 5.47 | 6.86 |

EXAMPLE 26

2-[(N-(2-(6-Naphth-1-yl)-ethyl)-piperidin-3-yl)-methyl]-6,7-dimethoxy-1-oxo-1,2,3,4-tetrahydro-isoquinoline-hydrochloride Prepared from 2-[(piperidin-3-yl)-methyl]-6,7-dimethoxy-1-oxo-1,2,3,4-tetrahydro-isoquinoline and 1-(2-benzene-sulphonyloxy-ethyl)-naphthalene analogously to Example 1.
Yield: 26.9% of theory,
Melting point: 220°–225° C.

| Calculated: | C 67.89 | H 7.27 | N 5.46 | Cl 6.91 |
|---|---|---|---|---|
| Found: | 67.75 | 6.92 | 5.56 | 7.00 |

EXAMPLE 27

2-[(N-(2-(Naphth-2-yl)-ethyl)-piperidin-3-yl)-methyl]-6,7-methylenedioxy-1-oxo-1,2,3,4-tetrahydro-isoquinoline-hydrochloride Prepared from 2-[(piperidin-3-yl)-methyl]-6,7-methylenedioxy-1-oxo-1,2,3,4-tetrahydro-isoquinoline and 2-(2-benzene-sulphonyloxy-ethyl)-naphthalene analogously to Example 1.
Yield: 27.9% of theory,
Melting point: 128°–130° C.

| Calc. (× H₂O): | C 67.66 | H 6.69 | N 5.63 | Cl 7.13 |
|---|---|---|---|---|
| Found: | 67.64 | 6.70 | 5.76 | 7.35 |

EXAMPLE 28

2-[(N-(2-(5-Methyl-6-methoxy-naphth-2-yl)-ethyl)-piperidin-3-yl)-methyl]-6,7-methylenedioxy-1-oxo-1,2,3,4-tetrahydro-isoquinoline-hydrochloride Prepared from 2-[(piperidin-3-yl)-methyl]-6,7-methylenedioxy-1-oxo-1,2,3,4-tetrahydro-isoquinoline and 2-(2-bromoethyl)-5-methyl-6-methoxy-naphthalene analogously to Example 1.
Yield: 51.2% of theory,
Melting point: 128°–131° C.

| Calculated: | C 68.88 | H 6.74 | N 5.34 | Cl 6.77 |
|---|---|---|---|---|
| Found: | 68.90 | 6.61 | 5.30 | 7.05 |

EXAMPLE 29

2-[(N-((2-Methyl-naphth-1-yl)-methyl)-piperidin-3-yl)-methyl]-6,7-dimethoxy-1-oxo-1,2,3,4-tetrahydro-isoquinoline-hydrochloride Prepared from 2-[(piperidin-3-yl)-methyl]-6,7-dimethoxy-1-oxo-1,2,3,4-tetrahydro-isoquinoline and 1-chloromethyl-2-methyl-naphthalene analogously to Example 1.
Yield: 57.9% of theory,
Melting point: 212°–214° C.

| Calc. (× 2 H₂O): | C 67.63 | H 7.63 | N 5.44 | Cl 6.88 |
|---|---|---|---|---|
| Found: | 67.46 | 7.56 | 5.54 | 6.67 |

EXAMPLE 30

2-[(N-(4-(Naphthyl-2-oxy)-butyl)-piperidin-3-yl)-methyl]-6,7-dimethoxy-1-oxo-1,2,3,4-tetrahydro-isoquinoline-hydrochloride Prepared from 2-[(piperidin-3-yl)-methyl]-6,7-dimethoxy-1-oxo-1,2,3,4-tetrahydro-isoquinoline and 2-(4-bromo-butoxy)-naphthalene analogously to Example 1.
Yield: 46.3% of theory,
Melting point: 80°–84° C.

| Calc. (× H₂O): | C 66.83 | H 7.41 | N 5.03 | C 16.36 |
|---|---|---|---|---|
| Found: | 66.79 | 7.22 | 4.90 | 6.64 |

EXAMPLE 31

2-[(N-(2-(6-Methoxy-naphth-2-yl)-ethyl)-piperidin-3-yl)-methyl]-6,7-dimethoxy-1-oxo-1,2,3,4-tetrahydro-isoquinoline-hydrochloride Prepared from 2-[(piperidin-3-yl)-methyl]-6,7-dimethoxy-1-oxo-1,2,3,4-tetrahydro-isoquinoline and 2-(2-bromo-ethyl)-6-methoxy-naphthalene analogously to Example 1.
Yield: 22.8% of theory,
Melting point: 80°–85° C.

| Calc.: (× H₂O × HCl × CH3COCH3): | | | | |
|---|---|---|---|---|
| | C 64.01 | H 7.65 | N 4.52 | Cl 5.72 |
| Found: | 64.26 | 7.70 | 4.62 | 5.49 |

EXAMPLE 32

2-[3-(N-(2-(6-Methoxy-naphth-2-yl)-ethyl)-piperid-3-yl)-propyl]-6,7-methylenedioxy-1-oxo-1,2,,3,4-tetrahydro-isoquinoline Prepared from 2-[N-(3-(piperidin-3-yl)-propyl]-6,7-methylenedioxy-1-oxo-1,2,3,4-tetrahydro-isoquinoline and 2-(2-bromo-ethyl)-6-methoxy-naphthalene analogously to Example 1.
Yield: 36.8% of theory,
Melting point: 118°–121° C.

| Calculated: | C 74.37 | H 7.25 | N 5.60 |
|---|---|---|---|
| Found: | 74.60 | 7.43 | 5.65 |

EXAMPLE 33

2-[3-(N-(2-Naphth-1-yl)-ethyl)-piperidin-3-yl)-propyl]-6,7-methylenedioxy-1-oxo-1,2,3,4-tetrahydro-isoquinoline-hydrochloride Prepared from 2-[N-(3-(piperidin-3-yl)-propyl]-6,7-methylenedioxy-1-oxo-1,2,3,4-tetrahydro-isoquinoline and 1-(2-benzenesulphonyloxy-ethyl)-naphthalene analogously to Example 1.
Yield: 20.8% of theory,
Melting point: 195°–197° C.

| | | | | |
|---|---|---|---|---|
| Calculated: | C 71.07 | H 6.95 | N 5.53 | Cl 16.99 |
| Found: | 71.30 | 6.95 | 5.65 | 6.80 |

EXAMPLE 34

2-[2-(N-(2-(5-Methyl-6-methoxy-naphth-2-yl)-ethyl)-piperid-2-yl)-ethyl]-6,7-dimethoxy-1-oxo-1,2,3,4-tetrahydro-isoquinoline-hydrochloride Prepared from 2-[2-(piperid-2-yl)-ethyl]-6,7-dimethoxy-1-oxo-1,2,3,4-tetrahydro-isoquinoline and 2-(2-bromo-ethyl)-5-methyl-6-methoxy-naphthalene analogously to Example 1.
Yield: 33.6% of theory,
Melting point: 95°–100° C.

| | | | | |
|---|---|---|---|---|
| Calc. (× ½ H$_2$O): | C 68.38 | H 7.52 | N 4.98 | Cl 6.30 |
| Found: | 68.14 | 7.43 | 4.92 | 6.77 |

EXAMPLE 35

2-[(N-(3-(Naphthyl-2-oxy)-propyl)-piperidin-3-yl)-methyl]-6,7-dimethylenedioxy-1-oxo-1,2,3,4-tetrahydro-isoquinoline-hydrochloride Prepared from 6,7-methylenedioxy-1-oxo-1,2,3,4-tetrahydro-isoquinoline and 3-chloromethyl-N-[3-(naphthyl-2-oxy)-propyl]-piperidine analogously to Example 2.
Yield: 27.3% of theory,
Melting point: 104°–106° C.

| | | | | |
|---|---|---|---|---|
| Calc. (× H$_2$O): | C 66.09 | H 6.69 | N 5.31 | Cl 6.72 |
| Found: | 66.19 | 6.34 | 5.24 | 7.22 |

EXAMPLE 36

2-(N-(3-(Naphthyl-2-oxy)-propyl)-piperidin-3-yl)-methyl]-6,7-dimethoxy-1-oxo-1,2,3,4-tetrahydro-isoquinoline-hydrochloride Prepared from 6,7-dimethoxy-1-oxo-1,2,3,4-tetrahydro-isoquinoline and 3-chloromethyl-N-[3-(naphthyl-2-oxy)-propyl]-piperidine analogously to Example 2.
Yield: 28.6% of theory,
Melting point: 191°–193° C.

| | | | | |
|---|---|---|---|---|
| Calc. (× H$_2$O): | C 66.34 | H 7.23 | N 5.15 | Cl 6.53 |
| Found: | 66.59 | 7.19 | 5.03 | 6.65 |

EXAMPLE 37

2-[(N-(3-(Naphthyl-2-oxy)-propyl)-hexahydro-azepin-3-yl)-methyl]-6,7-dimethoxy-1-oxo-1,2,3,4-tetrahydro-isoquinoline-hydrochloride Prepared from 2-[(hexahydro-azepin-3-yl)-methyl]-6,7-dimethoxy-1-oxo-isoquinoline and 2-(3-chloropropoxy)-naphthalene analogously to Example 1.
Yield: 16.1% of theory,
Melting point: 86°–88° C.

| | | | | |
|---|---|---|---|---|
| Calc. (× H$_2$O): | C 66.83 | H 7.42 | N 5.03 | Cl 6.36 |
| Found: | 66.90 | 7.40 | 5.26 | 6.87 |

EXAMPLE 38

2-[(N-(3-(Naphthyl-2-oxy)-propyl)-hexaydro-azepin-3-yl)-methyl]-6,7-dimethyl-1-oxo-1,2,3,4-tetrahydro-isoquinoline-hydrochloride Prepared from 6,7-dimethyl-1-oxo-1,2,3,4-tetrahydro-isoquinoline and 3-chloromethyl-N-[3-(naphthyl-2-oxy)-propyl]-hexahydro-azepine analogously to Example 2.
Yield: 22.5% of theory,
Melting point: 191°–193° C.

| | | | | |
|---|---|---|---|---|
| Calculated: | C 73.42 | H 7.75 | N 5.52 | Cl 6.99 |
| Found: | 73.37 | 7.67 | 5.52 | 7.12 |

EXAMPLE 39

2-[(N-(2-(5-Methyl-6-methoxy-naphth-2-yl)-ethyl)-hexahydro-azepin-3-yl)-methyl]-6,7-dimethoxy-1-oxo-1,2,3,4-tetrahydro-isoquinoline-dihydrochloride Prepared from 2-[(N-(2-(5-methyl-6-methoxy-naphth-2-yl)-ethyl)-hexahydro-azepin-3-yl)-methyl]-6,7-dimethoxy-1-oxo-1,2,3,4-tetrahydro-isoquinoline and lithium aluminium hydride in tetrahydrofuran analogously to Example 3.
Yield: 77.6% of theory,
Melting point: 170°–172° C.

| | | | | |
|---|---|---|---|---|
| Calc. (× H$_2$O): | C 64.96 | H 7.49 | N 4.73 | Cl 11.98 |
| Found: | 65.11 | 7.62 | 4.95 | 11.84 |

EXAMPLE 40

2-[(N-(2-(5-Methyl-6-methoxy-naphth-2-yl)-ethyl)-hexahydro-azepin-3-yl)-methyl]-6,7-dimethoxy-1-oxo-1,2,3,4-tetrahydro-isoquinoline Prepared from 2-[(hexahydro-azepin-3-yl)-methyl]-6,7-dimethoxy-1-oxo-1,2,3,4-tetrahydro-isoquinoline and 2-(2-bromoethyl)-5-methyl-6-methoxy-naphthalene analogously to Example 1.
Yield: 43.5% of theory,
Melting point: 125°–127° C.

| | | | | |
|---|---|---|---|---|
| Calculated: | C 74.39 | H 7.80 | N 5.42 | |
| Found: | 74.31 | 7.82 | 5.35 | |

EXAMPLE 41

2-[(N-(2-Methyl-naphth-1-yl)-methyl)-hexahydro-azepin-3-yl)-methyl]-6,7-dimethoxy-1-oxo-1,2,3,4-tetrahydro-isoquinoline-hydrochloride Prepared from 2-[(hexahydro-azepin-3-yl)-methyl]-6,7-dimethoxy-1-oxo-1,2,3,4-tetrahydro-isoquinoline and 1-chloromethyl-2-methylnaphthalene analogously to Example 1.
Yield: 67.5% of theory,
Melting point: 128°–130° C.

| Calc. (x 2 H$_2$O): | C 66.10 | H 7.58 | N 5.13 | Cl 6.50 |
|---|---|---|---|---|
| Found: | 66.24 | 7.44 | 5.23 | 6.85 |

EXAMPLE 42

2-[(N-(4-(Naphthyl-2-oxy)-butyl)-hexahydro-azepin-3-yl)-methyl]-6,7-dimethoxy-1-oxo-1,2,3,4-tetrahydro-isoquinoline-hydrochloride Prepared from 2-[(hexahydro-azepin-3-yl)-methyl]-6,7-dimethoxy-1-oxo-1,2,3,4-tetrahydro-isoquinoline and 2-(4-bromo-butyloxy)-naphthalene analogously to Example 1.
Yield: 26% of theory,
Melting point: 192°–194°C.

| Calculated: | C 69.22 | H 7.80 | N 5.04 | Cl 6.38 |
|---|---|---|---|---|
| Found: | 70.01 | 7.70 | 5.15 | 6.48 |

EXAMPLE 43

2-[(N-(2-(Naphth-1-yl)-ethyl)-hexahydro-azepin-3-yl)-methyl]-6,7-methylenedioxy-1-oxo-1,2,3,4-tetrahydro-isoquinoline-hydrochloride Prepared from 2-[(hexahydro-azepin-3-yl)-methyl]-6,7-methylenedioxy-1-oxo-1,2,3,4-tetrahydro-isoquinoline and 2-(2-benzenesulphonyloxy-ethyl)-naphthalene analogously to Example 1.
Yield: 15.4% of theory,
Melting point: 236°–238° C.

| Calc. (x ½ H$_2$O): | C 69.40 | H 6.82 | N 5.58 | Cl 7.06 |
|---|---|---|---|---|
| Found: | 69.07 | 6.74 | 6.13 | 7.29 |

EXAMPLE 44

2-[(N-(2-(Naphth-2-yl)-ethyl)-hexahydro-azepin-3-yl)-methyl]-6,7-methylenedioxy-1-oxo-1,2,3,4-tetrahydro-isoquinoline-hydrobromide Prepared from 2-[(hexahydro-azepin-3-yl)-methyl]-6,7-methylenedioxy-1-oxo-1,2,3,4-tetrahydro-isoquinoline and 2-(2-bromo-ethyl)-naphthalene analogously to Example 1.
Melting point: 100°–102° C.
Yield: 31.6% of theory,

| Calculated: | C 64.80 | H 6.18 | N 5.21 | Br 14.86 |
|---|---|---|---|---|
| Found: | 65.02 | 6.07 | 5.39 | 14.78 |

EXAMPLE 45

2-[(N-(2-(6-Methoxy-naphth-2-yl)-ethyl)-hexahydro-azepin-3-yl)-methyl]-6,7-methylenedioxy-1-oxo-1,2,3,4-tetrahydro-isoquinoline-hydrochloride Prepared from 2-[(hexahydro-azepin-3-yl)-methyl]-6,7-methylenedioxy-1-oxo-1,2,3,4-tetrahydro-isoquinoline and 2-(2-bromo-ethyl)-6-methoxy-naphthalene analogously to Example 1.
Yield: 34.1% of theory,
Melting point: 147°–149° C.

| Calc. (x H$_2$O): | C 68.62 | H 7.10 | N 5.33 | Cl 6.75 |
|---|---|---|---|---|
| Found: | 68.88 | 6.98 | 5.41 | 6.78 |

EXAMPLE 46

2-[(N-(2-(5-Methyl-6-methoxy-naphth-2-yl)-ethyl)-hexahydro-azepin-3-yl)-methyl]-6,7-methylenedioxy-1-oxo-1,2,3,4-tetrahydro-isoquinoline-hydrochloride Prepared from 2-[(hexahydro-azepin-3-yl)-methyl]-6,7-methylenedioxy-1-oxo-isoquinoline and 2-(2-bromo-ethyl)-5-methyl-6-methoxy-naphthalene analogously to Example 1.
Yield: 36.1% of theory,
Melting point: 112°–114° C.

| Calc. (x H$_2$O): | C 67.07 | H 7.08 | N 5.04 | Cl 6.38 |
|---|---|---|---|---|
| Found: | 67.13 | 7.15 | 4.97 | 6.56 |

EXAMPLE 47

2-[(N-(3-(4-Methoxy-phenoxy)-propyl)-piperidin-3-yl)-methyl]-6,7-dimethoxy-1,2,3,4-tetrahydro-isoquinoline-dihydrochloride Prepared from 2-[(N-(3-(4-methoxy-phenoxy)-propyl)-piperidin-3-yl)-methyl]-6,7-dimethoxy-1-oxo-1,2,3,4-tetrahydro-isoquinoline and lithium aluminium hydride in tetrahydrofuran analogously to Example 3.
Yield: 88.5% of theory,
Melting point: 189°–191° C.

| Calculated: | C 59.44 | H 7.76 | N 5.13 | Cl 12.99 |
|---|---|---|---|---|
| Found: | 59.55 | 7.99 | 5.12 | 12.61 |

EXAMPLE 48

2-[(N-(2-(3,4-Dimethoxy-phenyl)-ethyl)-piperidin-3-yl)-methyl]-6,7-dimethoxy-1,2,3,4-tetrahydro-isoquinoline-dihydrochloride Prepared from 2-[(N-(2-(3,4-dimethoxy-phenyl)-ethyl)-piperidin-3-yl)-methyl]-6,7-dimethoxy-1-oxo-1,2,3,4-tetrahydro-isoquinoline and lithium aluminium hydride in tetrahydrofuran analogously to Example 3.
Yield: 92.8% of theory,
Melting point: 175°–176° C.

| Calculated: | C 60.66 | H 7.35 | N 5.33 | Cl 13.49 |
|---|---|---|---|---|
| Found: | 60.58 | 7.56 | 5.32 | 13.22 |

EXAMPLE 49

2-[(N-(3-(3-Methoxy-phenoxy)-propyl)-piperidin-3-yl)-methyl]-6,7-methylenedioxy-1,2,3,4-tetrahydro-isoquinoline-dihydrochloride Prepared from 2-[(N-(3-(3-methoxy-phenoxy)-propyl)-piperidin-3-yl)-methyl]-6,7-methylenedioxy-1-oxo-1,2,3,4-tetrahydro-isoquinoline and lithium aluminium hydride in tetrahydrofuran analogously to Example 3.

Yield: 96.6% of theory,
Melting point: 178°–181° C.

| | | | | |
|---|---|---|---|---|
| Calculated: | C 59.08 | H 7.62 | N 5.30 | Cl 14.31 |
| Found: | 58.90 | 7.50 | 5.40 | 14.15 |

EXAMPLE 50

2-[(N-(3-(3-Methoxy-phenoxy)-propyl)-piperidin-3-yl)methyl]-6,7-methylenedioxy-1,2,3,4-tetrahydro-isoquinoline-dihydrochloride Prepared from 2-[(N-(3-(3-methoxy-phenoxy)-propyl)-piperidin-3-yl)-methyl]-6,7-methylenedioxy-1-oxo-1,2,3,4-tetrahydro-isoquinoline and lithium aluminium hydride in tetrahydrofuran analogously to Example 3.

Yield: 94.5% of theory,
Melting point: 169°–171° C.

| | | | | |
|---|---|---|---|---|
| Calculated: | C 57.03 | H 7.36 | N 5.11 | Cl 13.86 |
| Found: | 56.91 | 7.26 | 5.15 | 13.68 |

EXAMPLE 51

2-[(N-(2-(3,4-Dimethoxy-phenyl)-ethyl)-piperidin-3-yl)-methyl]-6,7-dimethyl-1,2,3,4-tetrahydro-isoquinoline-dihydrochloride Prepared from 2-[(N-(2-(3,4-dimethoxy-phenyl)-ethyl)-piperidin-3-yl)-methyl]-6,7-dimethyl-1-oxo-1,2,3,4-tetrahydro-isoquinoline and lithium aluminium hydride in tetrahydrofuran analogously to Example 3.

Yield: 91.3% of theory,
Melting point: 140°–142° C.

| | | | | |
|---|---|---|---|---|
| Calculated: | C 62.00 | H 8.34 | N 5.27 | Cl 13.44 |
| Found: | 61.85 | 8.27 | 5.31 | 13.33 |

EXAMPLE 52

2-[(N-(3-(4-Methoxy-phenoxy)-propyl)-piperidin-3-yl)-methyl]-6,7-dimethyl-1,2,3,4-tetrahydro-isoquinoline-dihydrochloride Prepared from 2-[(N-(3-(4-methoxy-phenoxy)-propyl)-piperidin-3-yl)-methyl]-6,7-dimethyl-1-oxo-1,2,3,4-tetrahydro-isoquinoline and lithium aluminium hydride in tetrahydrofuran analogously to Example 3.

Yield: 88.3% of theory,
Melting point: 170°–172° C.

| | | | | |
|---|---|---|---|---|
| Calculated: | C 63.14 | H 8.24 | N 5.65 | Cl 14.31 |
| Found: | 63.09 | 8.33 | 5.82 | 14.02 |

EXAMPLE 53

2-[(N-(2-(3,4-Dimethoxy-phenyl)-ethyl)-piperidin-3-yl)-methyl]-6,7-methylenedioxy-1,2,3,4-tetrahydro-isoquinoline-dihydrochloride Prepared from 2-[(N-(3-(3,4-dimethoxy-phenyl)-ethyl)-piperidin-3-yl)-methyl]-6,7-methylenedioxy-1-oxo-1,2,3,4-tetrahydro-isoquinoline and lithium aluminium hydride in tetrahydrofuran analogously to Example 3.

Yield: 93.3% of theory,
Melting point: 150°–154° C.

| | | | | |
|---|---|---|---|---|
| Calculated: | C 60.01 | H 7.34 | N 5.39 | Cl 13.64 |
| Found: | 59.96 | 7.41 | 5.25 | 13.43 |

EXAMPLE 54

2-[(N-(3-(4-Methoxy-phenoxy)-propyl)-piperidin-3-yl)methyl]-6,7-methylenedioxy-1,2,3,4-tetrahydro-isoquinoline-dihydrochloride Prepared from 2-[(N-(3-(4-methoxy-phenoxy)-propyl)-piperidin-3-yl-3)-methyl]-6,7-dimethoxy-1-oxo-1,2,3,4-tetrahydro-isoquinoline and lithium aluminium hydride in tetrahydrofuran analogously to Example 3.

Yield: 95.3% of theory,
Melting point: 182°–185° C.

| | | | | |
|---|---|---|---|---|
| Calculated: | C 61.05 | H 7.09 | N 5.48 | Cl 13.86 |
| Found: | 61.10 | 6.95 | 5.68 | 13.55 |

EXAMPLE 55

2-[2-(N-(3-(3,4-Methylenedioxy-phenoxy)-propyl)-piperidin-3-yl)-ethyl]-6,7-dimethoxy-1-oxo-1,2,3,4-tetrahydro-isoquinoline-hydrochloride Prepared from 2-[(piperidin-3-yl)-ethyl]-6,7-dimethoxy-1-oxo-1,2,3,4-tetrahydro-isoquinoline and 1-chloro-3-(3,6-methylenedioxy-phenoxy)-propane analogously to Example 1.

Yield 35.5% of theory,
Melting point: 97°–100° C.

| | | | | |
|---|---|---|---|---|
| Calculated: | C 59.09 | H 7.28 | N 4.62 | Cl 6.65 |
| Found: | 58.97 | 7.36 | 4.66 | 6.52 |

EXAMPLE 56

2-[2-(N-(2-(3,4-Dimethoxy-phenyl)-ethyl)-piperidin-3-yl)-ethyl]-6,7-dimethoxy-1-oxo-1,2,3,4-tetrahydro-isoquinoline-hydrochloride Prepared from 2-[(piperidin-3-yl)-ethyl]-6,7-dimethoxy-1-oxo-1,2,3,4-tetrahydro-isoquinoline and 1-bromo-2-(3,4-dimethoxy-phenyl)-ethane analogously to Example 1.

Yield: 35.9% of theory,
Melting point: 103°–105° C.

| | | | | |
|---|---|---|---|---|
| Calculated: | C 62.60 | H 7.79 | N 5.21 | Cl 6.83 |
| Found: | 62.41 | 7.82 | 5.09 | 7.19 |

EXAMPLE 57

2-[3-(N-(2-(3,4-Dimethoxy-phenyl)-ethyl)-piperidin-3-yl)-propyl]-6,7-dimethoxy-1-oxo-1,2,3,4-tetrahydro-isoquinoline-hydrochloride Prepared from 2-[3-(piperidin-3-yl)-propyl]-6,7-dimethoxy-1-oxo-1,2,3,4-tetrahydro-isoquinoline and 1-bromo-2-(3,4-dimethoxy-phenyl)-ethane analogously to Example 1.
Yield: 32.6% of theory,
Melting point: 102°–106° C.

| Calculated: | C 63.20 | H 7.86 | N 5.08 | Cl 6.43 |
| --- | --- | --- | --- | --- |
| Found: | 63.39 | 7.90 | 4.86 | 6.13 |

EXAMPLE 58

2-[3-(N-(3-(3,4-Methylenedioxy-phenoxy)-propyl)-piperidin-3-yl)-propyl]-6,7-dimethoxy-1-oxo-1,2,3,4-tetrahydro-isoquinoline-hydrochloride Prepared from 2-[3-(piperidin-3-yl)-propyl]-6,7-dimethoxy-1-oxo-1,2,3,4-tetrahydro-isoquinoline and 1-chloro-3-(3,4-methylenedioxy-phenoxy)-propane analogously to Example 1.
Yield: 29.7% of theory,
Melting point: 97°–100° C.

| Calculated: | C 61.63 | H 7.31 | N 4.96 | Cl 6.47 |
| --- | --- | --- | --- | --- |
| Found: | 61.94 | 7.46 | 5.16 | 6.48 |

EXAMPLE 59

2-[(N-(3,4-Dimethoxy-benzyl)-piperidin-3-yl]-methyl]-6,7-dimethoxy-1-oxo-1,2,3,4-tetrahydro-isoquinoline-hydrochloride Prepared from 2-(piperidin-3-yl-methyl)-6,7-dimethoxy-1-oxo-1,2,3,4-tetrahydro-isoquinoline and 3,4-dimethoxy-benzylbromide analogously to Example 1.
Yield: 53.3% of theory,
Melting point: 127°–132° C.

| Calculated: | C 63.58 | H 7.18 | N 5.70 | Cl 7.22 |
| --- | --- | --- | --- | --- |
| Found: | 63.30 | 7.22 | 5.52 | 7.14 |

EXAMPLE 60

2-[(N-(3-(4-Methoxy-phenyl)-propyl)-piperidin-3-yl)-methyl]-6,7-dimethoxy-1-oxo-1,2,3,4-tetrahydro-isoquinoline-hydrochloride Prepared from 2-(piperidin-3-yl-methyl)-6,7-dimethoxy-1-oxo-1,2,3,4-tetrahydro-isoquinoline and 1-bromo-3-(4-methoxyphenyl)propane analogously to Example 1.
Yield: 42% of theory,
Melting point: 229°–231° C.

| Calculated: | C 66.31 | H 7.63 | N 5.73 | Cl 7.25 |
| --- | --- | --- | --- | --- |
| Found: | 66.27 | 7.64 | 5.65 | 7.33 |

EXAMPLE 61

2-[2-(N-(3-(3-Methyl-phenoxy)-propyl)-piperid-2-yl)-ethyl]-6,7-dimethoxy-1-oxo-1,2,3,4-tetrahydro-isoquinoline-hydrochloride Prepared from 2-[2-(piperid-2-yl)-ethyl]-6,7-dimethoxy-1-oxo-1,2,3,4-tetrahydro-isoquinoline and 1-chloro-3-(3-methyl-phenoxy)-propane analogously to Example 1.
Yield: 52.4% of theory,
Melting point: 142°–144° C.

| Calculated: | C 66.85 | H 7.81 | N 5.57 | Cl 7.05 |
| --- | --- | --- | --- | --- |
| Found: | 66.73 | 7.68 | 5.53 | 6.94 |

EXAMPLE 62

2-[2-(N-(2-(3,4-Dimethoxy-phenyl)-ethyl)-piperid-2-yl)ethyl]-6,7-dimethoxy-1-oxo-1,2,3,4-tetrahydro-isoquinoline-hydrochloride Prepared from 2-[2-(piperid-2-yl)-ethyl]-6,7-dimethoxy-1-oxo-1,2,3,4-tetrahydro-isoquinoline and 1-bromo-2-(3,4-dimethoxy-phenyl)-ethane analogously to Example 1.
Yield: 47.3% of theory,
Melting point: 150°–155° C.

| Calculated: | C 64.72 | H 7.68 | N 5.39 | Cl 6.82 |
| --- | --- | --- | --- | --- |
| Found: | 64.40 | 7.83 | 5.27 | 6.90 |

EXAMPLE 63

2-[2-(N-(3-Benzyloxy-propyl)-piperid-2-yl)-ethyl]-6,7-dimethoxy-1-oxo-1,2,3,4-tetrahydro-isoquinoline hydrochloride Prepared from 2-[2-(piperid-2-yl)-ethyl]-6,7-dimethoxy-1-oxo-1,2,3,4-tetrahydro-isoquinoline and 1-chloro-3-benzyloxy-propane analogously to Example 1.
Yield: 56.3% of theory,
Melting point: 116°–120° C.

| Calculated: | C 66.85 | H 7.81 | N 5.57 | Cl 7.05 |
| --- | --- | --- | --- | --- |
| Found: | 66.60 | 7.75 | 5.25 | 7.25 |

EXAMPLE 64

2-[2-(N-(4-(4-Methoxy-phenyl)-butyl)-piperid-2-yl)-ethyl]-6,7-dimethoxy-1-oxo-1,2,3,4-tetrahydro-isoquinoline-hydrochloride Prepared from 2-[2-(piperid-2-yl)-ethyl]-6,7-dimethoxy-1-oxo-1,2,3,4-tetrahydro-isoquinoline and 1-bromo-4-(4-methoxy-phenyl)butane analogously to Example 1.
Yield: 42.8% of theory,
Melting point: 107°–112° C.

| Calculated: | C 67.36 | H 7.99 | N 5.42 | Cl 6.86 |
| --- | --- | --- | --- | --- |
| Found: | 67.16 | 8.05 | 5.35 | 7.34 |

EXAMPLE 65

2-[2-(N-(3-(3,5-Dimethoxy-phenoxy)-propyl)-piperid-2-yl)-ethyl]-6,7-dimethoxy-1-oxo-1,2,3,4-tetrahydro-isoquinoline-hydrochloride Prepared from 2-[2-(piperid-2-yl)-ethyl]-6,7-dimethoxy-1-oxo-1,2,3,4-tetrahydro-isoquinoline and 1-chloro-3-(3,5-dimethoxy-phenoxy)-propane analogously to Example 1.
Yield: 56.3% of theory,
Melting point: 127°–132° C.

| Calculated: | C 61.41 | H 7.64 | N 5.10 | Cl 6.46 |
|---|---|---|---|---|
| Found: | 61.56 | 7.65 | 5.28 | 6.89 |

EXAMPLE 66

2-[2-(N-(3-(3,4-Methylenedioxy-phenoxy)-propyl)-piperid-2-yl)-ethyl]-6,7-dimethoxy-1-oxo-1,2,3,4-tetrahydro-isoquinoline-hydrochloride Prepared from 2-[2-(piperid-2-yl)-ethyl]-6,7-dimethoxy-1-oxo-1,2,3,4-tetrahydro-isoquinoline and 1-chloro-3-(3,4-methylenedioxy-phenoxy)-propane analogously to Example 1.
Yield: 49% of theory,
Melting point: 118°–120° C.

| Calculated: | C 63.09 | H 7.00 | N 5.26 | Cl 6.65 |
|---|---|---|---|---|
| Found: | 62.90 | 7.04 | 5.46 | 6.79 |

EXAMPLE 67

2-[(N-(3-(3,5-Dimethoxy-phenoxy)-propyl)-piperidin-3-yl)-methyl]-6,7-dimethoxy-1-oxo-1,2,3,4-tetrahydro-isoquinoline-hydrochloride Prepared from 2-[(piperidin-3-yl)-methyl]-6,7-dimethoxy-1-oxo-1,2,3,4-tetrahydro-isoquinoline and 1-chloro-3-(3,5-dimethoxy-phenoxy)-propane analogously to Example 1.
Yield: 37.5% of theory,
Melting point: 98°–102° C.

| Calculated: | C 62.85 | H 7.35 | N 5.24 | Cl 6.63 |
|---|---|---|---|---|
| Found: | 62.81 | 7.41 | 5.10 | 6.75 |

EXAMPLE 68

2-[(N-(3-(3,4-Methylenedioxy-phenyl)-propyl)-piperidin-3-yl)-methyl]-6,7-dimethoxy-1-oxo-1,2,3,4-tetrahydro-isoquinoline-hydrochloride Prepared from 2-[(piperid-2-yl)-methyl]-6,7-dimethoxy-1-oxo-1,2,3,4-tetrahydro-isoquinoline and 1-chloro-3-(3,4-methylenedioxy-phenyl)-propane analogously to Example 1.
Yield: 50% of theory,
Melting point: 236°–238° C.

| Calculated: | C 64.46 | H 7.01 | N 5.57 | Cl 7.04 |
|---|---|---|---|---|
| Found: | 64.30 | 6.97 | 5.59 | 7.08 |

EXAMPLE 69

2-[(N-(3-(3,4-Methylenedioxy-phenoxy)-propyl)-piperidin-3-yl)-methyl]-6,7-dimethoxy-1-oxo-1,2,3,4-tetrahydro-isoquinoline-hydrochloride Prepared from 2-[(piperid-2-yl)-methyl]-6,7-dimethoxy-1-oxo-1,2,3,4-tetrahydro-isoquinoline and 1-chloro-3-(3,4-methylenedioxy-phenoxy)-propane analogously to Example 1.
Yield: 46.2% of theory,
Melting point: 149°–153° C.

| Calculated: | C 60.38 | H 6.94 | N 5.21 | Cl 6.60 |
|---|---|---|---|---|
| Found: | 60.30 | 6.93 | 5.29 | 6.37 |

EXAMPLE 70

2-[(N-(3-(2,6-Dimethyl-phenoxy)-propyl)-piperidin-3-yl)-methyl]-6,7-dimethoxy-1-oxo-1,2,3,4-tetrahydro-isoquinoline-hydrochloride Prepared from 2-[(piperidin-3-yl)-methyl]-6,7-dimethoxy-1-oxo-1,2,3,4-tetrahydro-isoquinoline and 1-chloro-3-(2,6-dimethylphenoxy)-propane analogously to Example 1.
Yield: 53.3% of theory,
Melting point: 131°–135° C.

| Calculated: | C 66.85 | H 7.81 | H 5.57 | Cl 7.05 |
|---|---|---|---|---|
| Found: | 66.88 | 7.95 | 5.59 | 6.85 |

EXAMPLE 71

2-[(N-(4-(2,4-Dichloro-phenoxy)-butyl)-piperidin-3-yl)-methyl]-6,7-dimethoxy-1-oxo-1,2,3,4-tetrahydro-isoquinoline-hydrochloride Prepared from 2-[(piperidin-3-yl)-methyl]-6,7-dimethyoxy-1-oxo-1,2,3,4-tetrahydro-isoquinoline and 1-chloro-4-(2,4-dichlorophenoxy)-butane analogously to Example 1.
Yield: 54.1% of theory,
Melting point: 125°–128° C.

| Calculated: | C 58.12 | H 6.32 | N 5.02 | Cl 19.06 |
|---|---|---|---|---|
| Found: | 58.21 | 6.38 | 5.08 | 18.85 |

EXAMPLE 72

2-[(N-(2-(3,4-Dimethoxy-phenyl)-ethyl)-piperidin-3-yl)-methyl]-6,7-dimethoxy-1-oxo-1,2,3,4-tetrahydro-isoquinoline-hydrochloride Prepared from 2-[(piperidin-3-yl)-methyl]-6,7-dimethoxy-1-oxo-1,2,3,4-tetrahydro-isoquinoline and 1-bromo-2-(3,4-dimethoxy-phenyl)-ethane analogously to Example 1.
Yield: 57.5% of theory,
Melting point: 118°–121° C.

| Calculated: | C 64.21 | H 7.38 | N 5.55 |
|---|---|---|---|
| Found: | 64.18 | 7.36 | 5.19 |

EXAMPLE 73

2-[(N-(3-(3,4-Dimethoxy-phenoxy)-propyl)-piperid-3-yl)-methyl]-6,7-dimethoxy-1-oxo-1,2,3,4-tetrahydro-isoquinoline-hydrochloride Prepared from 2-[(piperidin-3-yl)-methyl]-6,7-dimethoxy-1-oxo-1,2,3,4-tetrahydro-isoquinoline and 1-chloro-3-(3,4-dimethoxy-phenoxy)-propane analogously to Example 1.
Yield: 62.5% of theory,
Melting point: 112°–115° C.

| Calculated: | C 60.80 | H 7.47 | N 5.24 |
|---|---|---|---|
| Found: | 60.65 | 7.69 | 5.27 |

EXAMPLE 74

2-[(N-(3-(3,4-Dimethoxy-phenoxy)-propyl)-piperidyl-3)-methyl]-6,7-methylenedioxy-1-oxo-1,2,3,4-tetrahydro-isoquinoline-hydrochloride Prepared from 2-[(piperidin-3-yl)-methyl]-6,7-methylenedioxy-1-oxo-1,2,3,4-tetrahydro-isoquinoline and 1-chloro-3-(3,4-dimethoxy-phenoxy)-propane analogously to Example 1.
Yield: 60% of theory,
Melting point: 97°–100° C.

| Calculated: | C 60.38 | H 6.94 | N 5.40 | Cl 6.60 |
|---|---|---|---|---|
| Found: | 60.20 | 6.97 | 5.21 | 6.83 |

EXAMPLE 75

2-[(N-(2-(4-Methoxy-phenyl)-ethyl)-piperidin-3-yl)-methyl]-6,7-methylenedioxy-1-oxo-1,2,3,4-tetrahydro-isoquinoline-hydrochloride Prepared from 2-[(piperidin-3-yl)-methyl]-6,7-methylenedioxy-1-oxo-1,2,3,4-tetrahydro-isoquinoline and 1-chloro-2-(4-methoxy-phenyl)-ethane analogously to Example 1.
Yield: 71.4% of theory,
Melting point: 195°–197° C.

| Calculated: | C 62.94 | H 6.97 | N 5.87 | Cl 7.73 |
|---|---|---|---|---|
| Found: | 62.90 | 6.98 | 5.68 | 8.04 |

EXAMPLE 76

2-[(N-(2-(3,4-Dimethoxy-phenyl)-ethyl)-piperidin-3-yl)-methyl]-6,7-dimethyl-1-oxo-1,2,3,4-tetrahydro-isoquinoline-hydrochloride Prepared from 2-[(piperidin-3-yl)-methyl]-6,7-dimethyl-1-oxo-1,2,3,4-tetrahydro-isoquinoline and 1-bromo-2-(3,4-dimethoxy-phenyl)-ethane analogously to Example 1.
Yield: 41.9% of theory,
Melting point: 132°–134° C.

| Calculated: | C 63.57 | H 8.10 | N 5.49 | Cl 6.95 |
|---|---|---|---|---|
| Found: | 63.70 | 8.26 | 5.45 | 7.13 |

EXAMPLE 77

2-[(N-(3-(4-Methoxy-phenoxy)-propyl)-piperidin-3-yl)-methyl]-6,7-dimethyl-1-oxo-1,2,3,4-tetrahydro-isoquinoline-hydrochloride Prepared from 2-[(piperidin-3-yl)-methyl]-6,7-dimethyl-1-oxo-1,2,3,4-tetrahydro-isoquinoline and 1-chloro-3-(4-methoxy-phenoxy)-propane analogously to Example 1.
Yield: 57.8% of theory,
Melting point: 144°–146° C.

| Calculated: | C 68.55 | H 7.88 | N 5.92 | Cl 7.49 |
|---|---|---|---|---|
| Found: | 68.45 | 7.80 | 6.11 | 7.33 |

EXAMPLE 78

2-[(N-(3-(3-Methoxy-phenoxy)-propyl)-piperidin-3-yl)-methyl]-6,7-methylenedioxy-1-oxo-1,2,3,4-tetrahydro-isoquinoline-hydrochloride Prepared from 2-[(piperidin-3-yl)-methyl]-6,7-methylenedioxy-1-oxo-1,2,3,4-tetrahydro-isoquinoline and 1-chloro-3-(3-methoxy-phenoxy)-propane analogously to Example 1.
Yield: 32.5% of theory,
Melting point: 142°–145° C.

| Calculated: | C 60.58 | H 6.95 | N 5.52 | Cl 6.99 |
|---|---|---|---|---|
| Found: | 60.42 | 6.92 | 5.50 | 7.18 |

EXAMPLE 79

2-[(N-(3-(3-Methyl-phenoxy)-propyl)-piperidin-3-yl)-methyl]-6,7-methylenedioxy-1-oxo-1,2,3,4-tetrahydro-isoquinoline-hydrochloride Prepared from 2-[(piperidin-3-yl)-methyl]-6,7-methylenedioxy-1-oxo-1,2,3,4-tetrahydro-isoquinoline and 3-(3-methyl-phenoxy)-1-chloro-propane analogously to Example 1.
Yield: 31.6% of theory,
Melting point: 178°–180° C.

| Calculated: | C 63.59 | H 6.97 | N 5.70 | Cl 7.22 |
|---|---|---|---|---|
| Found: | 63.59 | 6.92 | 5.86 | 7.50 |

EXAMPLE 80

2-[(N-(3-(4-Methoxy-N-methyl-phenylamino)-propyl)-piperidin-3-yl)-methyl]-6,7-dimethoxy-1-oxo-1,2,3,4-tetrahydro-isoquinoline-dihydrochloride Prepared from 2-[(piperidin-3-yl)-methyl]-6,7-dimethoxy-1-oxo-1,2,3,4-tetrahydro-isoquinoline and 1-chloro-3-(4-methoxy-N-methyl-phenylamino)-propane analogously to Example 1.
Yield: 52.5% of theory,
Melting point: 180°–183° C.

| Calculated: | C 60.64 | H 7.45 | N 7.58 | Cl 12.79 |
|---|---|---|---|---|
| Found: | 60.50 | 7.35 | 7.56 | 12.87 |

EXAMPLE 81

2-[(N-(3-(4-Methoxy-phenoxy)-propyl)-pyrrolidyl-3)-methyl]-6,7-dimethoxy-1-oxo-1,2,3,4-tetrahydro-isoquinoline-hydrochloride Prepared from 6,7-dimethoxy-1-oxo-1,2,3,4-tetrahydro-isoquinoline and N-(3-(4-methoxy-phenoxy)-propyl)-3-benzenesulphonyloxymethyl-pyrrolidine analogously to Example 2.
Yield: 84.4% of theory,
Melting point: 142°–144° C.

| | | | | |
|---|---|---|---|---|
| Calculated: | C 63.60 | H 7.18 | N 5.71 | Cl 7.22 |
| Found: | 63.75 | 7.12 | 5.64 | 7.32 |

EXAMPLE 82

2-[(N-(3-(6-Methoxy-naphthyl-2-oxy)-propyl)-pyrrolidin-3-yl)-6,7-dimethoxy-1-oxo-1,2,3,4-tetrahydro-isoquinoline Prepared from 6,7-dimethoxy-1-oxo-1,2,3,4-tetrahydro-isoquinoline and 3-(p-toluenesulphonyloxymethyl)-N-(6-methoxy-naphthyl-2-oxy)pyrrolidine analogously to Example 2.
Yield: 47% of theory,
Melting point: 142°–144° C.

| | | | |
|---|---|---|---|
| Calculated: | C 71.41 | H 7.19 | N 5.55 |
| Found: | 71.14 | 7.16 | 5.53 |

EXAMPLE 83

2-[(N-(3-(4-Methoxy-phenoxy)-propyl)-pyrrolidin-3-yl)-methyl]-6,7-dimethoxy-1,2,3,4-tetrahydro-isoquinoline-dihydrochloride Prepared from 2-[(N-(3-(4-methoxy-phenoxy)-propyl)-pyrrolidin-3-yl)-methyl]-6,7-dimethoxy-1-oxo-1,2,3,4-tetrahydro-isoquinoline and lithium aluminium hydride in tetrahydrofuran analogously to Example 3.
Yield: 90.9% of theory,
Melting point: 248°–250° C.

| | | | | |
|---|---|---|---|---|
| Calculated: | C 60.81 | H 7.46 | N 5.46 | Cl 13.81 |
| Found: | 60.79 | 7.61 | 5.48 | 13.84 |

EXAMPLE 84

2-[(N-(3-(4-Methoxy-phenoxy)-propyl)-pyrrolidin-3-yl)-methyl]-6,7-dimethyl-1-oxo-1,2,3,4-tetrahydro-isoquinoline-hydrochloride Prepared from 6,7-dimethyl-1-oxo-1,2,3,4-tetrahydro-isoquinoline and N-[3-(4-methoxy-phenoxy)-propyl]-3-benzenesulphonyloxymethyl-pyrrolidine analogously to Example 2.
Yield: 60.6% of theory,
Melting point: 118°–121° C.

| | | | | |
|---|---|---|---|---|
| Calculated: | C 68.03 | H 7.69 | N 6.10 | Cl 7.72 |
| Found: | 67.90 | 7.71 | 6.04 | 7.90 |

EXAMPLE 85

2-[(N-(2-(3,4-Dimethoxy-phenyl)-ethyl)-pyrrolidin-3-yl)-methyl]-6,7-dimethoxy-1-oxo-1,2,3,4-tetrahydro-isoquinoline-hydrochloride Prepared from 6,7-dimethoxy-1-oxo-1,2,3,4-tetrahydro-isoquinoline and N-[2-(3,4-dimethoxy-phenoxy)-ethyl]-3-benzenesulphonyloxymethyl-pyrrolidine analogously to Example 2.
Yield: 56.7% of theory,
Melting point: 116°–118° C.

| | | | | |
|---|---|---|---|---|
| Calculated: | C 63.60 | H 7.19 | N 5.71 | Cl 7.22 |
| Found: | 63.82 | 7.32 | 5.60 | 7.66 |

EXAMPLE 86

2-[(N-(3-(4-Methoxy-phenoxy)-propyl)-pyrrolidin-3-yl)-methyl]-6,7-dimethyl-1,2,3,4-tetrahydro-isocuinoline-dihydrochloride Prepared from 2-[N-(3-(4-methoxy-phenoxy)-propyl)-pyrrolidin-3-yl)-methyl]-6,7-dimethyl-1-oxo-1,2,3,4-tetrahydro-isoquinoline and lithium aluminium hydride in tetrahydrofuran analogously to Example 3.
Yield: 90.9% of theory,
Melting point: 243°–246° C.

| | | | | |
|---|---|---|---|---|
| Calculated: | C 64.85 | H 7.95 | N 5.82 | Cl 14.73 |
| Found: | 64.88 | 7.92 | 5.63 | 14.80 |

EXAMPLE 87

2-[(N-(2-(3,4-Dimethoxy-phenyl)-ethyl)-pyrrolidin-3-yl)-methyl]-6,7-dimethoxy-1,2,3,4-tetrahydro-isoquinoline-dihydrochloride Prepared from 2-[(N-(2-(3,4-dimethoxy-phenyl)-ethyl)-pyrrolidin-3-yl)-methyl]-6,7-dimethoxy-1-oxo-1,2,3,4-tetrahydro-isoquinoline and lithium aluminium hydride in tetrahydrofuran analogously to Example 3.
Yield: 92.9% of theory,
Melting point: 240°–242° C.

| | | | | |
|---|---|---|---|---|
| Calculated: | C 60.81 | H 7.46 | N 5.46 | Cl 13.81 |
| Found: | 60.64 | 7.61 | 5.31 | 13.50 |

EXAMPLE 88

2-[(N-(3-(Pyrid-4-yl)-propyl)-pyrrolidin-3-yl)-methyl]-5,6-dimethyl-1-oxo-1,3-dihydro-isoindole-dihydrochloride-semihydrate Prepared from 2-[(N-(3-pyrid-4-yl)-propyl)-pyrrolidin-3-yl)-methyl]-5,6-dimethyl-phthalimide and zinc/glacial acetic acid analogously to Example 4.
Yield: 65% of theory,
Melting point: 119°–122° C.

| | | | | |
|---|---|---|---|---|
| Calculated: | C 62.02 | H 7.24 | N 9.43 | Cl 15.92 |
| Found: | 62.25 | 7.47 | 9.39 | 15.90 |

EXAMPLE 89

2-[3-(N-(3-(Pyrid-3-yl)-propyl)-piperidin-3-yl)-propyl]-5,6-dimethoxy-1-oxo-1,3-dihydro-isoindole-dihydrochloride-monohydrate Prepared from 2-[3-(N-(3-(pyrid-3-yl)-propyl)-piperidin-3-yl)propyl]-5,6-dimethoxy-phthalimide and zinc/glacial acetic acid analogously to Example 4.

Yield: 72% of theory,
Melting point: 118°–121° C.

| Calculated: | C 59.08 | H 7.43 | N 7.95 | Cl 13.41 |
|---|---|---|---|---|
| Found: | 59.02 | 7.23 | 7.12 | 13.27 |

EXAMPLE 90

2-[(N-(3-(Pyrid-3-yl)-propyl)-piperidin-3-yl)-methyl]-5,6-dimethoxy-1-oxo-1,3-dihydro-isoindole-dihydrochloride-monohydrate Prepared from 2-[(N-(3-(pyrid-3-yl)-propyl)-piperidin-3-yl)-methyl]-5,6-dimethoxy-phthalimide and zinc/glacial acetic acid analogously to Example 4.

Yield: 42% of theory,
Melting point: 91°–96° C.

| Calculated: | C 59.08 | H 7.43 | N 7.95 | Cl 13.41 |
|---|---|---|---|---|
| Found: | 59.02 | 7.23 | 7.12 | 13.27 |

EXAMPLE 91

2-[(N-(2-(6,7-Dimethoxy-isoquinol-4-yl)-ethyl)-piperidin-3-yl)-methyl]-5,6-dimethoxy-1-oxo-1,3-dihydro-isoindole Prepared from 2-[(N-(2-(6,7-dimethoxy-isoquinol-4-yl)-ethyl)-piperidin-3-yl)-methyl]-5,6-dimethoxy-phthalimide and zinc/glacial acetic acid analogously to Example 4.

Yield: 64% of theory,
Melting point: 85°–88° C.

| Calculated: | C 65.39 | H 7.19 | N 7.88 |
|---|---|---|---|
| Found: | 65.16 | 7.27 | 7.53 |

EXAMPLE 92

2-[2-(N-(3-(Pyrid-4-yl)-propyl)-piperid-2-yl)-ethyl]-5,6-dimethyl-1-oxo-1,3-dihydro-isoindole Prepared from 2-[2-(N-(3-(pyrid-4-yl)-propyl)-piperid-2-yl)-ethyl]-5,6-dimethyl-phthalimide and zinc/glacial acetic acid analogously to Example 4.

Yield: 73% of theory,
Melting point: 103°–104° C.

| Calculated: | C 76.68 | H 8.49 | N 10.73 |
|---|---|---|---|
| Found: | 76.57 | 8.54 | 10.60 |

EXAMPLE 93

2-[(N-(3-(Pyrid-4-yl)-propyl)-pyrrolid-3yl)-methyl]-5,6-dimethyl-1,3-dihydro-isoindole-trihydrochloride-semihydrate Prepared from 2-[(N-(3-(pyrid-4-yl)-propyl)-pyrrolidin-3-yl)-methyl]-5,6-dimethyl-1-oxo-1,3-dihydro-isoindole and lithium aluminium hydride in tetrahydrofuran/ether analogously to Example 3.

Yield: 68% of theory,
Melting range: 118°–127° C. (amorphous).

| Calculated: | C 59.03 | H 7.54 | N 8.98 | Cl 22.73 |
|---|---|---|---|---|
| Found: | 58.93 | 7.48 | 8.84 | 22.92 |

EXAMPLE 94

2-[2-(N-(3-(Pyrid-4-yl)-propyl)-piperid-2-yl)-ethyl]-5,6-dimethyl-1,3-dihydro-isoindole Prepared from 2-[2-(N-(3-(pyrid-4-yl)-propyl)-piperid-2-yl)-ethyl]-5,6-dimethyl-1-oxo-1,3-dihydro-isoindole and lithium aluminium hydride in tetrahydrofuran/ether analogously to Example 3.

Yield: 70% of theory,
Melting range: 135°–148° C. (amorphous).

| Calculated: | C 54.59 | H 8.24 | N 7.63 | Cl 19.33 |
|---|---|---|---|---|
| Found: | 54.48 | 8.26 | 7.51 | 19.60 |

EXAMPLE 95

2-[(N-(1-(Pyrid-4-yl)-methyl)-piperidin-3-yl)-methyl]-5,6-dimethoxy-1,3-dihydro-isoindole-trihydrochloride-trihydrate Prepared from 2-[(N-(1-(pyrid-4-yl)-methyl)-piperidin-3-yl)-methyl]-5,6-dimethoxy-phthalimide and lithium aluminium hydride in ether analogously to Example 3.

Yield: 68% of theory,
Melting range: 176°–189° C. (amorphous).

| Calculated: | C 49.76 | H 7.21 | N 7.91 | Cl 20.03 |
|---|---|---|---|---|
| Found: | 49.93 | 7.12 | 8.00 | 20.44 |

EXAMPLE 96

2-[(N-(2-(6,7-Dimethoxy-isoquinol-4-yl)-ethyl)-piperidin-3-yl)-methyl]-5,6-dimethyl-1,3-dihydro-isoindole-dihydrochloride-semihydrate Prepared from 2-[(N-(2-(6,7-dimethoxy-isoquinol-4-yl)-ethyl)-piperidin-3-yl)-methyl]-5,6-dimethyl-1-oxo-1,3-dihydro-isoindole and lithium aluminium hydride in tetrahydrofuran/ether analogously to Example 3.

Yield: 22.7% of theory,
Melting range: 222°–236° C. (amorphous).

| Calculated: | C 62.22 | H 7.20 | N 7.50 | Cl 15.83 |
|---|---|---|---|---|
| Found: | 62.01 | 7.64 | 7.08 | 15.79 |

EXAMPLE 97

2-[(N-(1-(Pyrid-4-yl)-methyl)-piperidin-3-yl)-methyl]-5,6-methylenedioxy-1,3-dihydro-isoindole-trihydrochloride-semihydrate Prepared from 2-[(N-(1-(pyrid-4-yl)-methyl)-piperidin-3-yl)-methyl]-5,6-methylenedioxy-phthalimide and lithium aluminium hydride in tetrahydrofuran/ether analogously to Example 3.

Yield: 55% of theory,
Melting range: 215°–225° C. (amorphous).

| Calculated: | C 53.68 | H 6.22 | N 8.94 | Cl 22.63 |
|---|---|---|---|---|
| Found: | 53.60 | 6.45 | 8.65 | 22.28 |

EXAMPLE 98

2-[(N-(3-(Pyrid-4-yl)-propyl)-pyrrolidin-3-yl)-methyl]-6,7-dimethyl-1,2,3,4-tetrahydro-isoquinoline-trihydrochloride-monohydrate Prepared from 2-[(N-(3-(pyrid-4-yl)-propyl)-pyrrolidin-3-yl)-methyl]-6,7-dimethyl-1-oxo-1,2,3,4-tetrahydro-isoquinoline and lithium aluminium hydride in tetrahydro-furan/ether analogously to Example 3.
Yield: 63% of theory,
Melting point: 254°–256° C.

| Calculated: | C 58.71 | H 7.80 | N 8.56 | Cl 21.66 |
|---|---|---|---|---|
| Found: | 58.53 | 7.72 | 8.25 | 21.53 |

EXAMPLE 99

2-[(N-(1-(Pyrid-4-yl)-methyl)-piperidin-3-yl)-methyl]-6,7-dimethoxy-1,2,3,4-tetrahydro-isoquinoline-trihydro-chloride-dihydrate Prepared from 2-[(N-(1-(pyrid-4-yl)-methyl)-piperidin-3-yl)-methyl]-6,7-dimethoxy-1-oxo-1,2,3,4-tetrahydro-isoquinoline and lithium aluminium hydride in tetrahydro-furan/ether analogously to Example 3.
Yield: 63% of theory,
Melting range: 158°–169° C. (amorphous).

| Calculated: | C 52.42 | H 7.27 | N 7.97 | Cl 20.18 |
|---|---|---|---|---|
| Found: | 52.55 | 7.49 | 7.57 | 20.25 |

EXAMPLE 100

2-[2-(N-(3-(Pyrid-4-yl)-propyl)-piperid-2-yl)-ethyl]-6,7-methylenedioxy-1,2,3,4-tetrahydro-isoquinoline-trihydrochloride-trihydrate Prepared from 2-[2-(N-(3-(pyrid-4-yl)-propyl)-piperid-2-yl)-ethyl]-6,7-methylenedioxy-1-oxo-1,2,3,4-tetrahydro-isoquinoline and lithium aluminium hydride in tetrahydro-furan/ether analogously to Example 3.
Yield: 90% of theory,
Melting range: 108°–119° C. (amorphous).

| Calculated: | C 52.58 | H 7.41 | N 7.36 | Cl 18.62 |
|---|---|---|---|---|
| Found: | 52.56 | 7.25 | 7.38 | 19.49 |

EXAMPLE 101

2-[(N-(3-(Pyrid-3-yl)-propyl)-piperidin-3-yl)-methyl]-6,7-methylenedioxy-1,2,3,4-tetrahydro-isoquinoline-dihydrochloride-monohydrate Prepared from 2-[(N-(3-(pyrid-3-yl)-propyl)-piperidin-3-yl)-methyl]-6,7-methylenedioxy-1-oxo-1,2,3,4-tetrahydro-isoquinoline and lithium aluminium hydride in tetrahydrofuran/ether analogously to Example 3.
Yield: 72% of theory,
Melting range: 126°–138° C. (amorphous).

| Calculated: | C 59.50 | H 7.28 | N 8.67 | Cl 14.64 |
|---|---|---|---|---|
| Found: | 59.57 | 7.29 | 8.49 | 14.51 |

EXAMPLE 102

2-[(N-(3-(Pyrid-3-yl)-propyl)-piperidin-3-yl)-methyl]-6,7-dimethyl-1,2,3,4-tetrahydro-isoquinoline-trihydrochloride Prepared from 2-[(N-(3-(pyrid-3-yl)-propyl)-piperidin-3-yl)-methyl]-6,7-dimethyl-1-oxo-1,2,3,4-tetrahydro-isoquinoline and lithium aluminium hydride in tetrahydro-furan/ether analogously to Example 3.
Yield: 59% of theory,
Melting range: 138°–154° C. (amorphous).

| Calculated: | C 61.66 | H 7.86 | N 8.62 | Cl 21.84 |
|---|---|---|---|---|
| Found: | 61.53 | 8.00 | 8.64 | 21.35 |

EXAMPLE 103

2-[(N-(3-(Pyrid-4-yl)-propyl)-pyrrolidin-3-yl)-methyl]-6,7-dimethyl-1-oxo-1,2,3,4-tetrahydro-isoquinoline-dihydrochloride-monohydrate Prepared from 6,7-dimethyl-1-oxo-1,2,3,4-tetrahydro-isoquinoline and 3-chloromethyl-N-[3-(pyrid-4-yl)-propyl]-pyrrolidine analogously to Example 2.
Yield: 39% of theory,
Melting range: 74°–86° C. (amorphous).

| Calculated: | C 61.53 | H 7.53 | N 8.97 | Cl 15.13 |
|---|---|---|---|---|
| Found: | 61.42 | 7.62 | 8.83 | 15.05 |

EXAMPLE 104

2-[(N-(3-(Pyrid-3-yl)-propyl)-piperidin-3-yl)-methyl]-6,7-dimethoxy-1-oxo-1,2,3,4-tetrahydro-isoquinoline-dihydrochloride-monohydrate Prepared from 6,7-dimethyl-1-oxo-1,2,3,4-tetrahydro-isoquinoline and 3-(benzenesulphonyloxy-methyl-N-[3-(pyrid-3-yl)propyl]piperidine in dimethylsulphoxide with potassium tert.butoxide analogously to Example 2.
Yield: 45% of theory,
Melting range: 140°–148° C. (amorphous).

| Calc. (× 2 HCl × H₂O): | C 58.36 | H 7.25 | N 8.16 | Cl 13.78 |
|---|---|---|---|---|
| Found: | 58.35 | 7.32 | 8.04 | 13.65 |

EXAMPLE 105

2-[3-(N-(3-(Pyrid-4-yl)-propyl)-piperidin-3-yl)-propyl)-6,7-dimethoxy-1-oxo-1,2,3,4-tetrahydro-isoquinoline-dihydrochloride-dihydrate Prepared from 2-[3-(pyrid-3-yl)-propyl]-6,7-dimethoxy-1-oxo-1,2,3,4-tetrahydro-isoquinoline and 4-(3-chloropropyl)-pyridine analogously to Example 1.
Yield: 48% of theory,
Melting range: 85°–96° C. (amorph).

| Calculated: | C 57.84 | H 7.73 | N 7.49 | Cl 12.65 |
|---|---|---|---|---|
| Found: | 57.71 | 7.91 | 7.35 | 13.04 |

EXAMPLE 106

2-[3-(N-(2-(6,7-Dimethoxy-isoquinol-4-yl)-ethyl)-piperidin-3-yl)-propyl]-6,7-dimethoxy-1-oxo-1,2,3,4-tetrahydro-isoquinoline-dihydrochloride-monohydrate Prepared from 2-[3-(pyrid-3-yl)-propyl]-6,7-dimethoxy-1-oxo-1,2,3,4-tetrahydro-isoquinoline and 4-(2-chloroethyl)-6,7-dimethoxy-isoquinoline analogously to Example 1.
Yield: 34% of theory,
Melting range: 162°–171° C. (amorphous).

| Calculated: | C 60.17 | H 7.10 | N 6.57 | Cl 11.10 |
|---|---|---|---|---|
| Found: | 59.85 | 7.00 | 6.86 | 11.04 |

EXAMPLE 107

2-[(N-(3-(Pyrid-3-yl)-propyl)-piperidin-3-yl)-methyl]-6,7-methylenedioxy-1-oxo-1,2,3,4-tetrahydro-isoquinoline-hydrochloride Prepared from 6,7-methylenedioxy-1-oxo-1,2,3,4-tetrahydro-isoquinoline and 3-chloromethyl-N-[3-(pyrid-3-yl)-propyl]-piperidine analogously to Example 2.
Yield: 60% of theory,
Melting range: 194°–196° C. (amorphous).

| Calculated: | C 64.92 | H 6.81 | N 9.46 | Cl 7.98 |
|---|---|---|---|---|
| Found: | 64.91 | 6.95 | 9.67 | 7.80 |

EXAMPLE 108

2-[(N-(1-(Pyrid-4-yl)-methyl)-piperidin-3-yl)-methyl]-6,7-dimethoxy-1-oxo-1,2,3,4-tetrahydro-isoquinoline-dihydrochloride-monohydrate Prepared from 6,7-dimethoxy-1-oxo-1,2,3,4-tetrahydro-isoquinoline in dimethylsulphoxide with potassium tert.butoxide and 3-chloromethyl-N-[1-(pyrid-4-yl)-methyl]-piperidine analogously to Example 2.
Yield: 41% of theory,
Melting range: 142°–158° C. (amorphous).

| Calculated: | C 56.78 | H 6.83 | N 8.63 | Cl 14.58 |
|---|---|---|---|---|
| Found: | 56.45 | 6.59 | 8.66 | 14.62 |

EXAMPLE 109

2-[(N-(2-(6,7-Dimethoxy-isoquinol-4-yl)-ethyl)-piperidin-3-yl)-methyl]-6,7-dimethyl-1-oxo-1,2,3,4-tetrahydro-isoquinoline-dihydrochloride Prepared from 6,7-dimethyl-1-oxo-1,2,3,4-tetrahydro-isoquinoline in dimethylsulphoxide with potassium tert.butoxide and 3-chloromethyl-N-[2-(6,7-dimethoxy-isoquinol-4-yl)-ethyl]-piperidine analogously to Example 2.
Yield: 62% of theory,
Melting range: 148°–162° C. (amorphous).

| Calculated: | C 64.27 | H 7.01 | N 7.49 | Cl 12.65 |
|---|---|---|---|---|
| Found: | 64.11 | 7.20 | 7.59 | 12.89 |

EXAMPLE 110

2-[2-(N-(3-(Pyrid-4-yl)-propyl)-piperid-2-yl)-ethyl]-6,7-methylenedioxy-1-oxo-1,2,3,4-tetrahydro-isoquinoline-dihydrochloride-dihydrate Prepared from 6,7-methylenedioxy-1-oxo-1,2,3,4-tetrahydro-isoquinoline and 2-(2-chloroethyl)-N-[3-(pyrid-4-yl)-propyl]piperidine analogously to Example 2.
Melting range: 115°–128° C. (amorphous).

| Calculated: | C 56.59 | H 7.03 | N 7.92 | Cl 13.37 |
|---|---|---|---|---|
| Found: | 56.61 | 6.90 | 7.84 | 13.41 |

EXAMPLE 111

2-[(N-(3-(Pyrid-3-yl)-propyl)-piperidin-3-yl)-methyl]-6,7-dimethyl-1-oxo-1,2,3,4-tetrahydro-isoquinoline-dihydrochloride-dihydrate Prepared from 6,7-dimethyl-1-oxo-1,2,3,4-tetrahydro-isoquinoline in dimethylsulphoxide with potassium tert.butoxide and 3-chloromethyl-N-[3-(pyrid-3-yl)-propyl]-piperidine analogously to Example 2.
Yield: 62% of theory,
Melting range: 118°–127° C. (amorphous).

| Calculated: | C 60.00 | H 7.85 | N 8.39 | Cl 14.16 |
|---|---|---|---|---|
| Found: | 60.24 | 8.07 | 8.36 | 14.62 |

EXAMPLE 112

2-[(N-(3-(Pyrid-3-yl)-propyl)-pyrrolidin-3-yl)-methyl]-6,7-methylenedioxy-1-oxo-1,2,3,4-tetrahydro-isoquinoline-dihydrochloride Prepared from 6,7-methylenedioxy-1-oxo-1,2,3,4-tetrahydro-isoquinoline and 3-chloromethyl-N-[3-(pyrid-3-yl)-propyl]-pyrrolidine analogously to Example 2.
Yield: 26% of theory,
Melting range: 102°–113° C. (amorphous).

| Calculated: | C 59.22 | H 6.27 | N 9.01 | Cl 15.20 |
|---|---|---|---|---|
| Found: | 59.27 | 6.49 | 8.92 | 14.48 |

EXAMPLE 113

2-[(N-(3-(Pyrid-4-yl)-propyl)-pyrrolidin-3-yl)-methyl]-7,8-methylenedioxy-2-oxo-1,3-dihydro-2H-3-benzazepine-dihydrochloride Prepared from 7,8-methylenedioxy-2-oxo-1,3-dihydro-2H-benzazepine and 3-chloromethyl-N-[3-(pyrid-4-yl)-propyl]pyrrolidine analogously to Example 2.
Yield: 58% of theory,
Melting range: 132°–141° C. (amorphous).

| Calculated: | C 60.25 | H 6.11 | N 8.78 | Cl 14.82 |
|---|---|---|---|---|
| Found: | 60.00 | 6.40 | 8.52 | 14.56 |

EXAMPLE 114

2-[(N-(3-(Pyrid-3-yl)-propyl)-pyrrolidin-3-yl)-methyl]-7,8-dimethoxy-2-oxo-1,3-dihydro-2H-3-benzazepine-dihydrochloride-dihydrate Prepared from 7,8-dimethoxy-2-oxo-1,3-dihydro-2H-benzazepine and 3-chloromethyl-N-[3-(pyrid-3-yl)-propyl]-piperidine analogously to Example 2.
Yield: 67% of theory,
Melting range: 128°–134° C. (amorphous).

| | | | | |
|---|---|---|---|---|
| Calculated: | C 57.34 | H 7.21 | N 7.71 | Cl 13.02 |
| Found: | 57.80 | 7.37 | 7.92 | 13.06 |

EXAMPLE 115

3-[(N-(3-(Pyrid-3-yl)-propyl)-piperidin-3-yl)-methyl]-7,8-dimethyl-2-oxo-1,3-dihydro-2H-3-benzazepine-dihydrochloride-dihydrate Prepared from 7,8-dimethyl-2-oxo-1,3-dihydro-2H-benzazepine and 3-chloromethyl-N-[3-(pyrid-3-yl)-propyl]-piperidine analogously to Example 2.
Yield: 94% of theory,
Melting range: 77°–86° C. (amorphous).

| | | | | |
|---|---|---|---|---|
| Calculated: | C 60.92 | H 7.67 | N 8.19 | Cl 13.83 |
| Found: | 60.75 | 7.60 | 8.37 | 13.72 |

EXAMPLE 116

3-[2-(N-(3-(Pyrid-4-yl)-propyl)-piperid-2-yl)-ethyl]-7,8-dimethyl-2-oxo-1,3-dihydro-2H-3-benzazepine-dihydrochloride Prepared from 7,8-dimethyl-2-oxo-1,3-dihydro-2H-benzazepine and 2-(2-chloroethyl)-N-[3-(pyrid-4-yl)-propyl]-piperidine analogously to Example 2.
Yield: 94% of theory,
Melting range: 118°–130° C. (amorphous).

| | | | | |
|---|---|---|---|---|
| Calculated: | C 66.11 | H 7.60 | N 8.56 | Cl 14.45 |
| Found: | 65.92 | 7.86 | 8.33 | 14.09 |

EXAMPLE 117

3-[(N-(2-(6,7-Dimethoxy-isoquinol-4-yl)-ethyl)-piperidin-3-yl)-methyl]-7,8-dimethoxy-2-oxo-1,3-dihydro-2H-3-benzazepine-monohydrate Prepared from 7,8-dimethoxy-2-oxo-1,3-dihydro-2H-3-benzazepine and 3-chloromethyl-N-[2-(6,7-dimethoxy-isoquinol-4-yl)-ethyl]piperidine analogously to Example 2.
Yield: 69% of theory,
Melting range: 85°–96° C. (amorphous).

| | | | |
|---|---|---|---|
| Calculated: | C 67.73 | H 7.15 | N 7.64 |
| Found: | 67.96 | 7.19 | 7.75 |

EXAMPLE 118

3-[3-(N-(3-(Pyrid-3-yl)-propyl)-piperidin-3-yl)-propyl)-7,8-dimethoxy-2-oxo-1,3-dihydro-2H-3-benzazepine-dihydrochloride-monohydrate Prepared from 7,8-dimethoxy-2-oxo-1,3-dihydro-2H-3-benzazepine and 3-(3-chloropropyl)-N-[3-(pyrid-3-yl)-propyl]-piperidine analogously to Example 2.
Yield: 72% of theory,
Melting range: 94°–106° C. (amorphous).

| | | | | |
|---|---|---|---|---|
| Calculated: | C 60.64 | H 7.45 | N 7.57 | Cl 12.78 |
| Found: | 60.80 | 7.44 | 7.46 | 12.59 | monohydrate

EXAMPLE 119

3-[2-(N-(3-(Pyrid-4-yl)-propyl)-piperid-2-yl)-ethyl]-7,8-methylenedioxy-2-oxo-1,3-dihydro-2H-3-benzazepine-dihydrochloride-dihydrate Prepared from 7,8-methylenedioxy-2-oxo-1,3-dihydro-2H-3-benzazepine and 2-(2-chloroethyl)-N-[3-(pyrid-4-yl)-propyl]-piperidine in dimethylsulphoxide and potassium tert.butoxide analogously to Example 2.
Yield: 67% of theory,
Melting range: 148°–161° C. (amorphous).

| | | | | |
|---|---|---|---|---|
| Calculated: | C 57.56 | H 6.87 | N 7.74 | Cl 13.07 |
| Found: | 57.72 | 7.03 | 7.61 | 13.62 |

EXAMPLE 120

3-[(N-(1-(Pyrid-4-yl)-methyl)-piperidin-3-yl)-methyl]-7,8-dimethyl-2-oxo-1,3-dihydro-2H-3-benzazepine-dihydrochloride-monohydrate Prepared from 7,8-dimethoxy-2-oxo-1,3-dihydro-2H-3-benzazepine and 3-chloromethyl-N-[1-(pyrid-4-yl)-methyl]-piperidine in dimethylsulphoxide and potassium tert.butoxide analogously to Example 2.
Yield: 75% of theory
Melting range: 113°–127° C. (amorphous),

| | | | | |
|---|---|---|---|---|
| Calculated: | C 61.79 | H 7.13 | N 9.01 | Cl 15.20 |
| Found: | 61.55 | 7.32 | 9.04 | 15.11 |

EXAMPLE 121

3-[(N-(3-(Pyrid-4-yl)-propyl)-pyrrolidin-3-yl)-methyl]-7,8-methylenedioxy-2-oxo-1,3,4,5-tetrahydro-2H-3-benzazepine-dihydrochloride-monohydrate Prepared from 3-[(N-(3-(pyrid-4-yl)-propyl)-pyrrolidin-3-yl)-methyl]-7,8-methylenedioxy-2-oxo-1,3-dihydro-2H-3H-benzazepine and 10% palladium/charcoal under a hydrogen pressure of 5 bar at ambient temperature analogously to Example 5.
Yield: 71% of theory,
Melting range: 95°–106° C. (amorphous).

| | | | | |
|---|---|---|---|---|
| Calculated: | C 57.83 | H 6.67 | N 8.43 | Cl 14.22 |
| Found: | 57.67 | 6.82 | 8.27 | 14.05 |

EXAMPLE 122

3-[2-(N-(3-(Pyrid-4-yl)-propyl)-piperid-2-yl)-ethyl]-7,8-dimethyl-2-oxo-1,3,4,5-tetrahydro-2H-3-benzazepine-dihydrochloride-semihydrate Prepared from 3-[2-(N-(3-(pyrid-4-yl)-propyl)-piperid-2-yl)-ethyl]-7,8-dimethyl-2-oxo-1,3-dihydro-2H-3-benzazepine and 10% palladium/charcoal under a hydrogen pressure of 5 bar at 80° C. analogously to Example 5.

Yield: 73% of theory,
Melting point: 236°–238° C.

| Calculated: | C 64.65 | H 8.04 | N 8.37 | Cl 14.14 |
|---|---|---|---|---|
| Found: | 64.91 | 8.02 | 8.25 | 13.92 |

EXAMPLE 123

3-[3-(N-(2-(2-Methyl-pyrid-6-yl)-ethyl)-piperidin-3-yl)-propyl)-7,8-dimethoxy-2-oxo-1,3,4,5-tetrahydro-2H-3-benzazepine-dihydrochloride-monohydrate Prepared from 3-[3-(piperidin-3-yl)-propyl)]-7,8-dimethoxy-2-oxo-1,3,4,5-tetrahydro-2H-3-benzazepine and 2-(benzenesulphonyloxy-ethyl)-6-methyl-pyridine in dimethylsulphoxide with potassium carbonate at 120° C. analogously to Example 1.

Yield: 29% of theory.
Melting range: 105°–113° C. (amorphous).

| Calculated: | C 60.42 | H 7.78 | N 7.55 |
|---|---|---|---|
| Found: | 60.68 | 7.50 | 7.42 |

EXAMPLE 124

3-[(N-(3-(Pyrid-3-yl)-propyl)-piperidin-3-yl)-methyl]-7,8-dimethoxy-2-oxo-1,3,4,5-tetrahydro-2H-3-benzazepine-dihydrochloride Prepared from 3-[(N-(3-(pyrid-3-yl)-propyl)-piperidin-3-yl)-methyl]-7,8-dimethoxy-2-oxo-1,3-dihydro-2H-3-benzazepine by hydrogenation at 5 bar hydrogen pressure in ethanol with 10% palladium charcoal at 70° C. analogously to Example 5.

Yield: 52% of theory,
Melting range: 113°–122° C. (amorphous).

| Calculated: | C 61.17 | H 7.30 | N 8.23 |
|---|---|---|---|
| Found: | 61.31 | 7.50 | 8.28 |

EXAMPLE 125

3-[(N-(2-(6,7-Dimethoxy-isoquinol-4-yl)-ethyl)-piperidin-3-yl)-methyl]-7,8-dimethoxy-2-oxo-1,3,4,5-tetrahydro-2H-3-benzazepine × ½H2O Prepared from 3-[(N-(2-(6,7-dimethoxy-isoquinol-4-yl)-ethyl)-piperidin-3-yl)-methyl]-7,8-dimethoxy-2-oxo-1,3-dihydro-2H-3benzazepine by hydrogenation at 5 bar hydrogen pressure with 10% palladium/charcoal in ethanol at 70° C. analogously to Example 5.

Yield: 50% of theory,
Melting range: 82°–86° C. (amorphous).

| Calculated: | C 66.40 | H 7.55 | N 7.48 |
|---|---|---|---|
| Found: | 66.26 | 7.50 | 7.59 |

EXAMPLE 126

3-[3-(N-(3-(Pyrid-3-yl)-propyl)-piperidin-3-yl)-propyl)-7,8-dimethoxy-2-oxo-1,3,4,5-tetrahydro-2H-3-benzazepine-dihydrochloride-dihydrate Prepared from 3-[3-(N-(3-(pyrid-3-yl)-propyl)-piperidin-3-yl)-propyl]-7,8-dimethoxy-2-oxo-1,3-dihydro-2H-3-benzazepine by hydrogenation at 5 bar hydrogen pressure with 10% palladium/charcoal in ethanol at 70° C. analogously to Example 5.

Yield: 64% of theory,
Melting range: 106°–115° C. (amorphous).

| Calculated: | C 58.53 | H 7.89 | N 7.31 | Cl 12.34 |
|---|---|---|---|---|
| Found: | 58.46 | 7.61 | 7.14 | 12.57 |

EXAMPLE 127

3-[(N-(3-(Pyrid-3-yl)-propyl)-piperidin-3-yl)-methyl]-7,8-methylenedioxy-2-oxo-1,3,4,5-tetrahydro-2H-3-benzazepine-dihydrochloride-monohydrate Prepared from 3-[(N-(3-(pyrid-3-yl)-propyl)-piperidin-3-yl)-methyl]-7,8-methylenedioxy-2-oxo-1,3-dihydro-2H-3-benzazepine at 5 bar hydrogen pressure with 10% palladium/charcoal in ethanol at 80° C. analogously to Example 5.

Yield: 81% of theory,
Melting range: 126°–138° C. (amorphous).

| Calculated: | C 58.58 | H 6.88 | N 8.19 | Cl 13.83 |
|---|---|---|---|---|
| Found: | 58.43 | 7.00 | 7.85 | 13.71 |

EXAMPLE 128

3-[2-(N-(3-(Pyrid-4-yl)-propyl)-piperid-2-yl)-ethyl]-7,8-methylenedioxy-2-oxo-1,3,4,5-tetrahydro-2H-3-benzazepine-dihydrochloride-monohydrate Prepared from 3-[2-(N-(3-(pyrid-4-yl)-propyl)-piperid-2-yl)-ethyl]-7,8-methylenedioxy-2-oxo-1,3-dihydro-2H-3-benzazepine at 5 bar hydrogen pressure with 10% palladium/charcoal in ethanol at 80° C. analogously to Example 5.

Yield: 74% of theory,
Melting range: 132°–146° C. (amorphous).

| Calculated: | C 59.31 | H 7.08 | N 7.98 | Cl 13.46 |
|---|---|---|---|---|
| Found: | 59.18 | 7.41 | 7.80 | 13.25 |

EXAMPLE 129

3-[(N-(3-(Pyrid-3-yl)-propyl)-piperidin-3-yl)-methyl]-7,8-dimethyl-2-oxo-1,3,4,5-tetrahydro-2H-3-benzazepine-dihydrochloride Prepared from 3-[(N-(3-(pyrid-3-yl)-propyl)-piperidin-3-yl)-methyl]-7,8-dimethyl-2-oxo-1,3-dihydro-2H-3-benzazepine and 5 bar hydrogen pressure with 10% palladium/charcoal in ethanol at 80° C. analogously to Example 5.

Yield: 54% of theory,
Melting range: 92°–105° C. (amorphous).

| Calculated: | C 62.90 | H 7.92 | N 8.46 | Cl 14.28 |
|---|---|---|---|---|
| Found: | 63.19 | 7.90 | 8.45 | 14.30 |

EXAMPLE 130

3-[(N-(3-(Pyrid-4-yl)-pyrrolidin-3-yl)-methyl]-7,8-methylenedioxy-1,3,4,5-tetrahydro-2H-3-benzazepine-trihydrochloride-monohydrate Prepared from 3-[(N-(3-(pyrid-4-yl)-propyl)-pyrrolidin-3-yl)-methyl]-7,8-methylenedioxy-2-oxo-1,3,4,5-tetrahydro-2H-3-benzazepine and lithium aluminium hydride in tetrahydrofuran/ether analogously to Example 3.

Yield: 73% of theory,
Melting range: 96°–108° C. (amorphous).

| Calculated: | C 55.53 | H 6.97 | N 8.06 | Cl 20.42 |
|---|---|---|---|---|
| Found: | 55.06 | 7.28 | 7.77 | 20.07 |

EXAMPLE 131

3-[(N-(3-(Pyrid-3-yl)-propyl)-piperidin-3-yl)-methyl]-7,8-dimethoxy-1,3,4,5-tetrahydro-2H-3-benzazepine-dihydrochloride Prepared from 3-[(N-(3-(pyrid-3-yl)-propyl)-piperidin-3-yl)-methyl]-7,8-dimethoxy-2-oxo-1,3,4,5-tetrahydro-2H-3-benzazepine and lithium aluminium hydride in tetrahydrofuran/ether analogously to Example 3.

Yield: 71% of theory,
Melting point: 208°–210° C.

| Calculated: | 62.89 | H 7.91 | N 8.46 | Cl 14.28 |
|---|---|---|---|---|
| Found: | 62.70 | 7.53 | 8.22 | 14.50 |

EXAMPLE 132

3-[2-(N-(3-(Pyrid-4-yl)-propyl)-piperid-2-yl)-ethyl]-7,8-methylenedioxy-1,3,4,5-tetrahydro-2H-3-benzazepine-trihydrochloride Prepared from 3-[2-(N-(3-(pyrid-4-yl)-propyl)-piperid-2-yl)-ethyl]-7,8-methylenedioxy-2-oxo-1,3,4,5-tetrahydro-2H-3-benzazepine and lithium aluminium hydride in tetrahydrofuran/ether analogously to Example 3.

Yield: 63% of theory,
Melting range: 123°–136° C. (amorphous).

| Calculated: | C 58.81 | H 7.21 | N 7.91 | Cl 20.00 |
|---|---|---|---|---|
| Found: | 58.51 | 7.41 | 7.92 | 19.86 |

EXAMPLE 133

3-[(N-(3-(Pyrid-3-yl)-propyl)-piperidin-3-yl)-methyl]-7,8-methylenedioxy-1,3,4,5-tetrahydro-2H-3-benzazepine-trihydrochloride-semihydrate Prepared from 3-[(N-(3-(pyrid-3-yl)-propyl)-piperidin-3-yl)-methyl]-7,8-methylenedioxy-2-oxo-1,3,4,5-tetrahydro-2H-3-benzazepine and lithium aluminium hydride in tetrahydrofuran/ether analogously to Example 3.

Yield: 75% of theory,
Melting range: 126°–138° C. (amorphous).

| Calculated: | C 57.09 | H 7.10 | N 7.99 | Cl 20.22 |
|---|---|---|---|---|
| Found: | 57.05 | 7.32 | 8.05 | 20.37 |

EXAMPLE 134

3-[2-(N-(3-(Pyrid-4-yl)-propyl)-piperid-2-yl)-ethyl]-7,8-dimethyl-1,3,4,5-tetrahydro-2H-3-benzazepine-trihydrochloride Prepared from 3-[2-(N-(3-(pyrid-4-yl)-propyl)-piperid-2-yl)-ethyl]-7,8-dimethyl-2-oxo-1,3,4,5-tetrahydro-2H-3-benzazepine and lithium aluminium hydride in tetrahydrofuran/ether analogously to Example 3.

Yield: 92% of theory,
Melting point: 180°–182° C.

| Calculated: | C 62.96 | H 8.22 | N 8.16 | Cl 20.65 |
|---|---|---|---|---|
| Found: | 63.00 | 8.29 | 8.16 | 20.34 |

EXAMPLE 135

3-[(N-(3-(Pyrid-3-yl)-propyl)-piperidin-3-yl)-methyl]-7,8-dimethyl-1,3,4,5-tetrahydro-2H-3-benzazepine-trihydrochloride Prepared from 3-[(N-(3-(pyrid-3-yl)-propyl)-piperidin-3-yl)-methyl]-7,8-dimethyl-2-oxo-1,3,4,5-tetrahydro-2H-3-benzazepine and lithium aluminium hydride in tetrahydrofuran/ether analogously to Example 3.

Yield: 81% of theory,
Melting range: 184°–196° C. (amorphous).

| Calculated: | C 60.17 | H 8.16 | N 8.10 | Cl 20.49 |
|---|---|---|---|---|
| Found: | 60.28 | 8.25 | 8.00 | 20.39 |

EXAMPLE 136

3-[2-(N-(2-(6-Methoxy-naphth-2-yl)-ethyl)-piperid-2-yl)-ethyl]-7,8-dimethoxy-2-oxo-1,3,4,5-tetrahydro-2H-3-benzazepine-hydrochloride Prepared from 3-[2-(piperid-2-yl)-ethyl]-7,8-dimethoxy-2-oxo-1,3,4,5-tetrahydro-2H-3-benzazepine and 2-(6-methoxy-naphth-2-yl)-ethyl bromide analogously to Example 1.

Yield: 20% of theory,
Melting point: 158°–160° C.

| Calculated: | C 69.48 | H 7.47 | N 5.06 | Cl 6.41 |
|---|---|---|---|---|
| Found: | 69.40 | 7.56 | 5.17 | 6.62 |

EXAMPLE 137

3-[2-(N-(2-(5-Methyl-6-methoxy-naphth-2-yl)-ethyl)-piperid-2-yl)-ethyl]-7,8-dimethoxy-2-oxo-1,3,4,5-tetrahydro-2H-3-benzazepine-hydrochloride Prepared from 3-[2-(piperid-2-yl)-ethyl]-7,8-dimethoxy- 2-oxo-1,3,4,5-tetrahydro-2H-3-benzazepine and 2-(5-methyl-6-methoxy-naphth-2-yl)-ethyl bromide analogously to Example 1.

Yield: 28% of theory,
Melting point: 140°–143° C.

| Calculated: | C 69.88 | H 7.64 | N 4.94 | Cl 6.25 |
|---|---|---|---|---|

EXAMPLE 138

3-[2-(N-(2-(Naphthyl-1-oxy)-ethyl)-piperid-2-yl)-ethyl]-7,8-dimethoxy-2-oxo-1,3,4,5-tetrahydro-2H-3-benzazepine-hydrochloride Prepared from 3-[2-(piperid-2-yl)-ethyl]-7,8-dimethoxy-2-oxo-1,3,4,5-tetrahydro-2H-3-benzazepine and 2-(naphthyl-1-oxy)-ethyl bromide analogously to Example 1.
Yield: 27% of theory,
Melting point: 146°–148° C.

| | | | | |
|---|---|---|---|---|
| Calculated: | C 69.06 | H 7.29 | N 5.20 | Cl 6.58 |
| Found: | 69.00 | 7.07 | 5.31 | 6.68 |

EXAMPLE 139

3-[2-(N-(2-(Naphth-1-yl)-ethyl)-piperid-2-yl)-ethyl]-7,8-dimethoxy-2-oxo-1,3,4,5-tetrahydro-2H-3-benzazepine-hydrochloride Prepared from 3-[2-(piperid-2-yl)-ethyl]-7,8-dimethoxy-2-oxo-1,3,4,5-tetrahydro-2H-3-benzazepine and 2-(naphth-1-yl)-ethyl bromide analogously to Example 1.
Yield: 24% of theory,
Melting point: 148°–150° C.

| | | | | |
|---|---|---|---|---|
| Calculated: | C 71.18 | H 7.51 | N 5.36 | Cl 6.78 |
| Found: | 70.92 | 7.44 | 5.57 | 7.06 |

EXAMPLE 140

3-[2-(N-(4-(Naphthyl-2-oxy)-butyl)-piperid-2-yl)-ethyl]-7,8-dimethoxy-2-oxo-1,3,4,5-tetrahydro-2H-benzazepine-hydrochloride Prepared from 3-[2-(piperid-2-yl)-ethyl]-7,8-dimethoxy-2-oxo-1,3,4,5-tetrahydro-2H-3-benzazepine and 4-(naphthyl-2-oxy)-butyl bromide analogously to Example 1.
Yield: 39% of theory,
Melting point: 112°–114° C.

| | | | | |
|---|---|---|---|---|
| Calculated: | C 69.88 | H 17.64 | N 4.64 | Cl 6.25 |
| Found: | 69.69 | 7.58 | 4.82 | 6.52 |

EXAMPLE 141

3-[2-(N-(2-(Naphth-2-yl)-ethyl)-piperid-2-yl)-ethyl]-7,8-dimethoxy-2-oxo-1,3,4,5-tetrahydro-2H-3-benzazepine-hydrochloride Prepared from 3-[2-(piperid-2-yl)-ethyl]-7,8-dimethoxy-2-oxo-1,3,4,5-tetrahydro-2H-3-benzazepine and 2-(naphth-2-yl)-ethyl bromide analogously to Example 1.
Yield: 41% of theory,
Melting point: 120°–122° C.

| | | | | |
|---|---|---|---|---|
| Calculated: | C 71.18 | H 7.51 | N 5.36 | Cl 6.78 |
| Found: | 71.10 | 7.31 | 5.40 | 7.05 |

EXAMPLE 142

3-[2-(N-((2-Methyl-naphth-1-yl)-methyl)-piperid-2-yl)-ethyl]-7,8-dimethoxy-2-oxo-1,3,4,5-tetrahydro-2H-3-benzazepine-hydrochloride Prepared from 3-[2-(piperid-2-yl)-ethyl]-7,8-dimethoxy-2-oxo-1,3,4,5-tetrahydro-2H-3-benzazepine and 1-chloromethyl-2-methyl-naphthalene analogously to Example 1.
Yield: 24% of theory,
Melting point: 144°–146° C.

| | | | | |
|---|---|---|---|---|
| Calculated: | C 71.18 | H 7.51 | N 5.36 | Cl 6.78 |
| Found: | 70.93 | 7.38 | 5.48 | 6.89 |

EXAMPLE 143

3-[(N-(2-(Naphth-2-yl)-ethyl)-hexahydro-azepin-3-yl)-methyl]-7,8-dimethoxy-2-oxo-1,3,4,5-tetrahydro-2H-3-benzazepine-hydrochloride Prepared from 3-[(hexahydro-azepin-3-yl)-methyl)-7,8-dimethoxy-2-oxo-1,3,4,5-tetrahydro-2H-3-benzazepine and 2-(naphth-2-yl)-ethyl bromide analogously to Example 1.
Yield: 58% of theory,
Melting point: 204°–205° C.

| | | | | |
|---|---|---|---|---|
| Calculated: | C 71.18 | H 7.52 | N 5.36 | Cl 6.78 |
| Found: | 71.41 | 7.51 | 5.35 | 6.50 |

EXAMPLE 144

3-[(N-(2-(Naphth-2-yl)-ethyl)-piperidin-3-yl)-methyl]-7,8-dimethoxy-2-oxo-1,3,4,5-tetrahydro-2H-3-benzazepine-hydrochloride Prepared from 3-[(piperidin-3-yl)-methyl]-7,8-dimethoxy-2-oxo-1,3,4,5-tetrahydro-2H-3-benzazepine and 2-(naphth-2-yl)-ethylbromide analogously to Example 1.
Yield: 35% of theory,
Melting point: 239°–240° C.

| | | | | |
|---|---|---|---|---|
| Calculated: | C 70.78 | H 7.33 | N 5.50 | Cl 6.96 |
| Found: | 70.70 | 7.10 | 5.46 | 7.16 |

EXAMPLE 145

3-[(N-((Naphth-2-yl)-methyl)-piperidin-3-yl)-methyl]-7,8-dimethoxy-2-oxo-1,3,4,5-tetrahydro-2H-3-benzazepine Prepared from 3-[(piperidin-3-yl)-methyl]-7,8-dimethoxy-2-oxo-1,3,4,5-tetrahydro-2H-3-benzazepine and 2-bromomethyl-naphthalene analogously to Example 1.
Yield: 27% of theory,
Melting point: 176°–177° C.

| | | | |
|---|---|---|---|
| Calculated: | C 75.95 | H 7.47 | N 6.11 |
| Found: | 76.11 | 7.28 | 6.10 |

EXAMPLE 146

3-[(N-(4-(Naphthyl-2-oxy)-butyl)-piperidin-3-yl)-methyl]-7,8-dimethoxy-2-oxo-1,3,4,5-tetrahydro-2H-3-benzazepine-hydrochloride Prepared from 3-[(piperidin-3-yl)-methyl]-7,8-dimethoxy-2-oxo-1,3,4,5-tetrahydro-2H-3-benzazepine and 4-(naphthyl-2- oxy)butylbromide analogously to Example 1.

Yield: 24% of theory,
Melting point: 196°-197° C.

| | | | | |
|---|---|---|---|---|
| Calculated: | C 69.48 | H 7.47 | N 5.06 | Cl 6.41 |
| Found: | 69.30 | 7.36 | 4.99 | 6.56 |

EXAMPLE 147

3-[(N-(4-(Naphth-1-yl)-ethyl)-piperidin-3-yl)-methyl]-7,8-dimethoxy-2-oxo-1,3,4,5-tetrahydro-2H-3-benzazepine-hydrochloride Prepared from 3-[(piperidin-3-yl)-methyl]-7,8-dimethoxy-2-oxo-1,3,4,5-tetrahydro-2H-3-benzazepine and 2-(naphth-1-yl)-ethyl bromide analogously to Example 1.

Yield: 18% of theory,
Melting point: 230°-231° C.

| | | | | |
|---|---|---|---|---|
| Calculated: | C 70.78 | H 7.33 | N 5.50 | Cl 6.96 |
| Found: | 70.71 | 7.07 | 5.67 | 6.99 |

EXAMPLE 148

3-[(N-(2-(Naphthyl-1-oxy)-ethyl)-piperidin-3-yl)-methyl]-7,8-dimethoxy-2-oxo-1,3,4,5-tetrahydro-2H-3-benzazepine-hydrochloride Prepared from 3-[(piperidin-3-yl)-methyl]-7,8-dimethoxy-2-oxo-1,3,4,5-tetrahydro-2H-3-benzazepine and 2-(naphthyl-1-oxy)-ethyl bromide analogously to Example 1.

Yield: 40% of theory,
Melting point: 214°-215° C.

| | | | | |
|---|---|---|---|---|
| Calculated: | C 68.62 | H 7.10 | N 5.34 | Cl 6.75 |
| Found: | 68.40 | 7.10 | 5.21 | 6.77 |

EXAMPLE 149

3-[(N-((2-Methyl-naphth-1-yl)-methyl)-piperidin-3-yl)-methyl]-7,8-dimethoxy-2-oxo-1,3,4,5-tetrahydro-2H-3-benzazepine-hydrochloride Prepared from 3-[(piperidin-3-yl)-methyl]-7,8-dimethoxy-2-oxo-1,3,4,5-tetrahydro-2H-3-benzazepine and 1-chloromethyl-2-methylnaphthalene analogously to Example 1.

Yield: 67% of theory,
Melting point: 242°-243° C.

| | | | | |
|---|---|---|---|---|
| Calculated: | C 70.78 | H 7.33 | N 5.50 | Cl 6.96 |
| Found: | 70.50 | 7.22 | 5.34 | 6.89 |

EXAMPLE 150

3-[(N-(2-(6-Methoxy-naphth-2-yl)-ethyl)-piperidin-3-yl)-methyl]-7,8-dimethoxy-2-oxo-1,3,4,5-tetrahydro-2H-3-benzazepine-hydrochloride Prepared from 3-[(piperidin-3-yl)-methyl]-7,8-dimethoxy-2-oxo- 1,3,4,5-tetrahydro-2H-3-benzazepine and 2-(6-methoxy-naphth-2-yl)-ethyl bromide analogously to Example 1.

Yield: 50% of theory,
Melting point: 156°-157° C.

| | | | |
|---|---|---|---|
| Calculated: | C 74.07 | H 7.62 | N 5.57 |
| Found: | 73.90 | 7.55 | 5.64 |

EXAMPLE 151

3-[(N-(2-(5-Methyl-6-methoxy-naphth-2-yl)-ethyl)-piperidin-3-yl)-methyl]-7,8-dimethoxy-2-oxo-1,3,4,5-tetrahydro-2H-3-benzazepine-hydrochloride Prepared from 3-[(piperidin-3-yl)-methyl]-7,8-dimethoxy-2-oxo-1,3,4,5-tetrahydro-2H-3-benzazepine and 2-(5-methyl-6-methoxy-naphthyl)-ethyl bromide analogously to Example 1.

Yield: 53% of theory,
Melting point: 240°-241° C.

| | | | | |
|---|---|---|---|---|
| Calculated: | C 69.48 | H 7.47 | N 5.06 | Cl 6.41 |
| Found: | 69.58 | 7.48 | 5.00 | 6.54 |

EXAMPLE 152

2-[N-(2-(3,4-Dimethoxy-phenyl)-ethyl)-piperidin-3-yl)-methyl]-5,6-dimethoxy-1-oxo-1,3-dihydro-isoindole-hydrochloride Prepared from 2-[(piperidin-3-yl)-methyl]-5,6-dimethoxy-1,3-dihydro-isoindole and 2-(3,4-dimethoxy-phenyl)-ethyl bromide analogously to Example 1.

Yield: 68% of theory,
Melting point: 225°-226° C.

| | | | | |
|---|---|---|---|---|
| Calculated: | C 63.60 | H 7.18 | N 5.20 | Cl 7.22 |
| Found: | 63.61 | 7.30 | 5.70 | 7.44 |

EXAMPLE 153

2-[(N-(2-(6-Methoxy-naphth-2-yl)-ethyl)-piperidin-3-yl)-methyl]-5,6-dimethoxy-1-oxo-1,3-dihydro-isoindole-hydrochloride Prepared from 2-[(piperidin-3-yl)-methyl]-5,6-dimethoxy-1-oxo-1,3-dihydro-isoindole and 2-(6-methoxy-naphth-2-yl)-ethyl bromide analogously to Example 1.

Yield: 75% of theory,
Melting point: 234°-236° C.

| | | | | |
|---|---|---|---|---|
| Calculated: | C 68.16 | H 6.90 | N 5.48 | Cl 6.94 |
| Found: | 68.10 | 7.10 | 5.39 | 7.10 |

EXAMPLE 154

2-[(N-(2-(Naphthyl-1-oxy)-ethyl)-piperidin-3-yl)-methyl]-5,6-dimethoxy-1-oxo-1,3-dihydro-isoindole-hydrochloride Prepared from 2-[(piperidin-3-yl)-methyl]-5,6-dimethoxy-1-oxo-1,3-dihydro-isoindole and 2-(naphthyl-1-oxy)-ethyl bromide analogously to Example 1.
Yield: 60% of theory,
Melting point: 150°–152° C.

| Calculated: | C 67.66 | H 6.69 | N 5.63 | Cl 7.13 |
|---|---|---|---|---|
| Found: | 67.50 | 6.76 | 5.74 | 7.54 |

EXAMPLE 155

2-[(N-(2-(4-Methyl-phenyl)-ethyl)-piperidin-3-yl)-methyl]-5,6-dimethoxy-1-oxo-1,3-dihydro-isoindole Prepared from 2-[(piperidin-3-yl)-methyl]-5,6-dimethoxy-1-oxo-isoindole and 2-(4-methyl-phenyl)-ethyl bromide analogously to Example 1.
Yield: 57% of theory,
Melting point: 134°–136° C.

| Calculated: | C 73.50 | H 7.90 | N 6.86 |
|---|---|---|---|
| Found: | 73.40 | 8.04 | 7.06 |

EXAMPLE 156

2-[(N-(2-(3-Methoxy-phenyl)-ethyl)-piperidin-3-yl)-methyl]-5,6-dimethoxy-1-oxo-1,3-dihydro-isoindole-hydrochloride Prepared from 2-[(piperidin-3-yl)-methyl]-5,6-dimethoxy-1-oxo-isoindole and 2-(3-methoxy-phenyl)-ethyl bromide analogously to Example 1.
Yield: 54% of theory,
Melting point: 226°–228° C.

| Calculated: | C 65.28 | H 7.01 | N 6.09 | Cl 7.71 |
|---|---|---|---|---|
| Found: | 65.30 | 7.37 | 5.91 | 7.61 |

EXAMPLE 157

2-[(N-(2-(5-Methyl-6-methoxy-naphth-2-yl)-ethyl)-piperidin-3-yl)-methyl]-5,6-dimethoxy-1-oxo-1,3-dihydro-isoindole-hydrochloride Prepared from 2-[(piperidin-3-yl)-methyl]-5,6-dimethoxy-1-oxo-1,3-dihydro-isoindole and 2-(5-methyl-6-methoxy-naphth-2-yl)-ethyl bromide analogously to Example 1.
Yield: 38% of theory,
Melting point: 214°–216° C.

| Calculated: | C 68.62 | H 7.10 | N 5.33 | Cl 6.75 |
|---|---|---|---|---|
| Found: | 68.94 | 7.23 | 4.98 | 6.61 |

EXAMPLE 158

2-[(N-(2-(4-Nitro-phenyl)-ethyl)-piperidin-3-yl)-methyl]-5,6-dimethoxy-1-oxo-1,3-dihydro-isoindole-hydrochloride Prepared from 2-[(piperidin-3-yl)-methyl]-5,6-dimethoxy-1-oxo-1,3-dihydro-isoindole and 2-(4-nitrophenyl)-ethyl bromide analogously to Example 1.
Yield: 79% of theory,
Melting point: 215°–218° C.

| Calculated: | C 60.56 | H 6.35 | N 8.83 | Cl 7.45 |
|---|---|---|---|---|
| Found: | 60.41 | 6.26 | 8.84 | 7.62 |

EXAMPLE 159

3-[(N-(2-(Thien-2-yl)-ethyl)-piperidin-3-yl)-methyl]-7,8-dimethoxy-2-oxo-1,3,4,5-tetrahydro-2H-3-benzazepine-hydrochloride Prepared from 3-[(piperidin-3-yl)-methyl]-7,8-dimethoxy-2-oxo-1,3,4,5-tetrahydro-2H-3-benzazepine and 2-(2-bromo-ethyl)thiophene analogously to Example 1.
Yield: 43% of theory,
Melting point: 232°–236° C.

| Calculated: | C 61.99 | H 7.15 | N 6.02 | Cl 7.62 | S 6.89 |
|---|---|---|---|---|---|
| Found: | 61.90 | 7.06 | 5.78 | 7.96 | 6.84 |

EXAMPLE 160

3-[(N-(2-(Thien-3-yl)-ethyl)-piperidin-3-yl)-methyl]-7,8-dimethoxy-2-oxo-1,3,4,5-tetrahydro-2H-3-benzazepine-hydrochloride Prepared from 3-[(piperidin-3-yl)-methyl]-7,8-dimethoxy-2-oxo-1,3,4,5-tetrahydro-2H-3-benzazepine and 3-(2-bromo-ethyl)-thiophene analogously to Example 1.
Yield: 36% of theory,
Melting point: sinters at 75°–80°, melts at 225°–230° C.

| Calculated: | C 61.99 | H 7.15 | N 6.02 | C 17.62 | S 6.89 |
|---|---|---|---|---|---|
| Found: | 62.00 | 7.08 | 5.98 | 8.43 | 6.62 |

EXAMPLE 161

3-[(N-(4-(Thien-2-yl)-butyl)-piperidin-3-yl)-methyl]-7,8-dimethoxy-2-oxo-1,3,4,5-tetrahydro-2H-3-benzazepine-hydrochloride Prepared from 3-[(piperidin-3-yl)-methyl]-7,8-dimethoxy-2-oxo-1,3,4,5-tetrahydro-2H-3-benzazepine and 2-(4-bromo-butyl)thiophene analogously to Example 1.
Yield: 68% of theory,
Melting range: 190°–196° C.

| Calculated: | C 63.33 | H 7.56 | N 5.68 | Cl 7.19 | S 6.50 |
|---|---|---|---|---|---|
| Found: | 63.18 | 7.72 | 5.72 | 7.29 | 6.59 |

EXAMPLE 162

3-[(N-(2-(Benzo[b]fur-2-yl)-ethyl)-piperidin-3-yl)-methyl]-7,8-dimethoxy-2-oxo-1,2,3,4-tetrahydro-2H-3-benzazepine-hydrochloride Prepared from 3-[(piperidin-3-yl)-methyl]-7,8-dimethoxy-2-oxo-1,3,4,5-tetrahydro-2H-3-benzazepine and 2-(2-bromo-ethyl)-benzo[b]furan analogously to Example 1.

Yield: 22% of theory,
Melting point: above 216° C. (decomp.).

| Calculated: | C 67.39 | H 7.07 | N 5.61 |
|---|---|---|---|
| Found: | 67.14 | 7.36 | 5.53 |

EXAMPLE 163

3-[(N-(2-(Benzo[b]thien-3-yl)-ethyl)-piperidin-3-yl)-methyl]-7,8-dimethoxy-2-oxo-1,3,4,5-tetrahydro-2H-3-benzazepine-hydrochloride Prepared from 3-[(piperidin-3-yl)-methyl]-7,8-dimethoxy-2-oxo-1,3,4,5-tetrahydro-2H-3-benzazepine and 3-(2-bromo-ethyl)benzo[b]thiophene analogously to Example 1.

Yield: 73% of theory,
Melting range: 70°–75° C. (decomp.).

| Calculated: | C 65.29 | H 6.85 | N 5.44 |
|---|---|---|---|
| Found: | 65.10 | 6.87 | 5.73 |

EXAMPLE 164

3-[(N-(2-(4-Methoxy-benzo[b]thien-3-yl)-ethyl)-piperidin-3-yl)-methyl]-7,8-dimethoxy-2-oxo-1,3,4,5-tetrahydro-2H-3-benzazepine-hydrochloride Prepared from 3-[(piperidin-3-yl)-methyl]-7,8-dimethoxy-2-oxo-1,3,4,5-tetrahydro-2H-3-benzazepine and 3-(2-chloroethyl)-4-methoxy-benzo[b]thiophene analogously to Example 1.

Yield: 25% of theory,
Melting range: 85°–105° (decomp.).

| Calculated: | C 63.96 | H 6.84 | N 5.14 | Cl 6.50 | S 5.88 |
|---|---|---|---|---|---|
| Found: | 63.95 | 6.85 | 4.99 | 6.53 | 5.75 |

EXAMPLE 165

3-[(N-(2-(6-Methylsulphonyloxy-benzo[b]thien-3-yl)-ethyl)-piperidin-3-yl)-methyl]-7,8-dimethoxy-2-oxo-1,3,4,5-tetrahydro-2H-3-benzazepine-hydrochloride Prepared from 3-[(piperidin-3-yl)-methyl]-7,8-dimethoxy-2-oxo-1,3,4,5-tetrahydro-2H-3-benzazepine and 3-[2-(methylsulphonyloxy)-ethyl]-6-methylsulphonyloxy-benzo[b]thiophene analogously to Example 1.

Yield: 55% of theory,
Melting point: 90° C. (decomp.).

| Calculated: | C 57.18 | H 6.12 | N 4.60 | Cl 5.82 | S 10.53 |
|---|---|---|---|---|---|
| Found: | 57.25 | 6.14 | 4.50 | 5.97 | 10.36 |

EXAMPLE 166

3-[(N-(5-(Thien-2-yl)-pentyl)-piperidin-3-yl)-methyl]-7,8-dimethoxy-2-oxo-1,3,4,5-tetrahydro-2H-3-benzazepine-hydrochloride Prepared from 3-[(piperidin-3-yl)-methyl]-7,8-dimethoxy-2-oxo-1,3,4,5-tetrahydro-2H-3-benzazepine and 2-(5-methylsulphonyloxy-pentyl)-thiophene analogously to Example 1.

Yield: 39% of theory,
Melting point: 177° C.

| Calculated: | C 63.95 | H 7.75 | N 5.52 | Cl 6.99 | S 6.32 |
|---|---|---|---|---|---|
| Found: | 63.70 | 7.92 | 5.40 | 7.24 | 6.62 |

EXAMPLE 167

3-[(N-(2-(Fur-2-yl)-ethyl)-piperidin-3-yl)-methyl]-7,8-dimethoxy-2-oxo-1,3,4,5-tetrahydro-2H-3-benzazepine-hydrochloride Prepared from 3-[(piperidin-3-yl)-methyl]-7,8-dimethoxy-2-oxo-1,3,4,5-tetrahydro-2H-3-benzazepine and 2-(2-methylsulphonyloxy-ethyl)-furan analogously to Example 1.

Yield: 44% of theory,
Melting range: 205°–215° C.

| Calculated: | C 64.20 | H 7.41 | N 6.24 | Cl 7.90 |
|---|---|---|---|---|
| Found: | 64.00 | 7.45 | 6.00 | 7.80 |

EXAMPLE 168

3-[(N-(3-(Fur-2-yl)-propyl)-piperidin-3-yl)-methyl-7,8-dimethoxy-2-oxo-1,3,4,5-tetrahydro-2H-3-benzazepine-hydrochloride Prepared from 3-[(piperidin-3-yl)-methyl]-7,8-dimethoxy-2-oxo-1,3,4,5-tetrahydro-2H-3-benzazepine and 3-(fur-2-yl)propionaldehyde analogously to Example 9.

Yield: 11% of theory,
Melting point: 201°–206° C.

| Calculated: | C 64.85 | H 7.62 | N 6.05 | Cl 7.66 |
|---|---|---|---|---|
| Found: | 64.88 | 7.76 | 5.93 | 7.55 |

EXAMPLE 169

3-[(N-(6-(Thien-2-yl)-hexyl)-piperidin-3-yl)-methyl]-7,8-dimethoxy-2-oxo-1,3,4,5-tetrahydro-2H-3-benzazepine-hydrochloride Prepared from 3-[(piperidin-3-yl)-methyl]-7,8-dimethoxy-2-oxo-1,3,4,5-tetrahydro-2H-3-benzazepine and 2-(6-methylsulphonyloxy-hexyl)-thiophene analogously to Example 1.

Yield: 27% of theory,
Melting point: 160° C.

| Calculated: | C 64.39 | H 8.10 | N 5.40 | Cl 6.79 |
|---|---|---|---|---|
| Found: | 64.55 | 7.90 | 5.23 | 7.00 |

EXAMPLE 170

3-[(N-(3-(Indol-3-yl)-propyl)-piperidin-3-yl)-methyl]-7,8-dimethoxy-2-oxo-1,3,4,5-tetrahydro-2H-3-benzazepine-hydrochloride Prepared from 3-[(piperidin-3-yl)-methyl]-7,8-dimethoxy-2-oxo-1,3,4,5-tetrahydro-2H-3-benzazepine and 3-(3-methylsulphonyloxy-propyl)-indole analogously to Example 1.
Yield: 19% of theory,
Melting point: greater than 80° C. (decomp.).

| | | | |
|---|---|---|---|
| Calculated: | C 60.42 | H 6.30 | N 6.45 |
| Found: | 60.32 | 6.57 | 6.67 |

EXAMPLE 171

3-[(N-(2-(Indol-3-yl)-ethyl)-piperidin-3-yl)-methyl]-7,8-dimethoxy-2-oxo-1,3,4,5-tetrahydro-2H-3-benzazepine-hydrochloride Prepared from 3-[(piperidin-3-yl)-methyl]-7,8-dimethoxy-2-oxo-1,3,4,5-tetrahydro-2H-3-benzazepine and 3-(2-methylsulphonyloxy-ethyl)-indole analogously to Example 1.
Yield: 23% of theory,
Melting point: greater than 80° C. (decomp.).

| | | | |
|---|---|---|---|
| Calculated: | C 65.53 | H 6.42 | N 7.69 |
| Found: | 65.33 | 6.55 | 7.80 |

EXAMPLE 172

2-[(N-(3-(Naphthyl-2-oxy)-propyl)-hexahydro-azepin-3-yl)-methyl]-6,7-methylenedioxy-1-oxo-isoquinoline Prepared from 6,7-methylenedioxy-1-oxo-1,3,4,5-tetrahydro-isoquinoline and 3-chloromethyl-[N-(3-naphthyl-2-oxy)-propyl]-hexahydro-azepine analogously to Example 2.
Yield: 21% of theory,
Melting point: 74°-76° C.

| | | | | |
|---|---|---|---|---|
| Calc. (x 2 H$_2$O): | C 64.45 | H 7.02 | N 5.01 | Cl 6.34 |
| Found: | 64.32 | 7.20 | 5.28 | 6.44 |

EXAMPLE 173

2-[(N-(3-(Naphth-2-yl)-propyl)-pyrrolidin-3-yl)-methyl]-6,7-dimethyl-1-oxo-1,2,3,4-tetrahydro-isoquinoline Prepared from 6,7-dimethyl-1-oxo-1,3,4,5-tetrahydro-isoquinoline and 3-(p-toluenesulphonyloxymethyl)-N-[3-(naphth-2-yl)-propyl]-pyrrolidine analogously to Example 2.
Yield: 20% of theory,
Melting point: 72°-76° C.

| | | | | |
|---|---|---|---|---|
| Calc. (x H$_2$O): | C 72.41 | H 7.75 | N 5.82 | Cl 7.36 |
| Found: | 72.27 | 7.85 | 5.70 | 7.96 |

EXAMPLE 174

2-[(N-(3-(5,6-Dimethoxy-naphthyl-2-oxy)-propyl)-pyrrolidin-3-yl)-methyl]-6,7-dimethoxy-1-oxo-1,2,3,4-tetrahydro-isoquinoline-hydrochloride Prepared from 6,7-dimethoxy-1-oxo-1,3,4,5-tetrahydro-isoquinoline and 3-(p-toluenesulphonyloxymethyl)-N-[3-(5,6-dimethoxy-naphthyl-2-oxy)-propyl]-pyrrolidine analogously to Example 2.
Yield: 9.5% of theory,
Melting point: 60°-63° C.

| | | | | |
|---|---|---|---|---|
| Calc. (x H$_2$O): | C 63.20 | H 7.01 | N 4.75 | Cl 6.02 |
| Found: | 63.40 | 7.04 | 4.49 | 6.38 |

EXAMPLE 175

2-[(N-(3-(5,6-Dimethoxy-naphthyl-2-oxy)-propyl)-hexahydro-azepin-3-yl)-methyl]-6,7-dimethoxy-1-oxo-1,2,3,4-tetrahydro-isoquinoline-hydrochloride Prepared from 6,7-dimethoxy-1-oxo-1,2,3,4-tetrahydro-isoquinoline and 3-(p-toluenesulphonyloxymethyl)-N-[3-(5,6-dimethoxy-naphthyl-2-oxy)-propyl]-hexahydro-azepine analogously to Example 2.
Yield: 63.2% of theory,
Melting point: 199°-201° C.

| | | | | |
|---|---|---|---|---|
| Calculated: | C 66.15 | H 7.23 | N 4.67 | Cl 5.92 |
| Found: | 65.99 | 7.00 | 4.44 | 6.02 |

EXAMPLE 176

2-[(N-(3-(5,6-Dimethoxy-naphthyl-2-oxy)-propyl)-hexahydro-azepin-3-yl)-methyl]-6,7-dimethoxy-1,2,3,4-tetrahydro-isoquinoline-dihydrochloride Prepared from 2-[(N-(3-(5,6-dimethoxy-naphthyl-2-oxy)-propyl)-hexahydro-azepin-3-yl)-methyl]-6,7-dimethoxy-1-oxo-1,2,3,4-tetrahydro-isoquinoline and lithium aluminium hydride in tetrahydrofuran/ether analogously to Example 3.
Yield: 86.3% of theory,
Melting point: 114°-116° C.

| | | | | |
|---|---|---|---|---|
| Calculated: | C 61.97 | H 7.56 | N 4.38 | Cl 11.08 |
| Found: | 62.05 | 7.65 | 4.06 | 10.84 |

EXAMPLE 177

2-[(N-(2-(4-Methoxy-phenyl)-ethyl)-pyrrolidin-3-yl)-methyl]-6,7-methylenedioxy-1,2,3,4-tetrahydro-isoquinoline-dihydrochloride Prepared from 2-[(N-(2-(4-methoxy-phenyl)-ethyl)-pyrrolidin-3-yl)-methyl]-6,7-methylenedioxy-1-oxo-1,2,3,4-tetrahydro-isoquinoline and lithium aluminium hydride/tetrahydrofuran analogously to Example 3.
Yield: 86.7% of theory,
Melting point: 213°-215° C.

| | | | | |
|---|---|---|---|---|
| Calculated: | C 60.49 | H 6.98 | N 5.87 | Cl 14.88 |
| Found: | 60.59 | 6.96 | 5.84 | 14.98 |

EXAMPLE 178

2-[(N-(3-(3,4-Dimethoxy-phenoxy)-propyl)-pyrrolidin-3-yl)-methyl]-6,7-methylenedioxy-1-oxo-1,2,3,4-tetrahydro-isoquinoline-hydrochloride Prepared from 1-oxo-1,2,3,4-tetrahydro-6,7-methylenedioxy-isoquinoline and N-[3-(3,4-dimethoxy-phenoxy)-propyl]-3-benzosulphonyloxymethyl-pyrrolidine analogously to Example 2.
Yield: 57.4% of theory,
Melting point: 108°–110° C.

| Calculated: | C 59.76 | H 6.74 | N 5.35 | Cl 7.02 |
|---|---|---|---|---|
| Found: | 60.07 | 6.87 | 5.23 | 7.61 |

EXAMPLE 179

2-[(N-(2-(4-Methoxy-phenyl)-ethyl)-pyrrolidin-3-yl)-methyl]-6,7-methylenedioxy-1-oxo-1,2,3,4-tetrahydro-isoquinoline-hydrochloride Prepared from 1-oxo-1,2,3,4-tetrahydro-6,7-methylene-dioxy-isoquinoline and N-[2-(4-methoxy-phenyl)-ethyl]-3-benzenesulphonyloxymethyl-pyrrolidine analogously to Example 2.
Yield: 54.7% of theory,
Melting point: 105°–108° C.

| Calculated: | C 62.26 | H 6.74 | N 6.05 | Cl 7.97 |
|---|---|---|---|---|
| Found: | 62.34 | 6.74 | 5.88 | 8.05 |

EXAMPLE 180

3-[(N-(3-(4-Methoxy-N-methyl-phenylamino)-propyl)-piperidin-3-yl)-methyl]-7,8-methylenedioxy-2-oxo-1,3,4,5-tetrahydro-2H-benzazepine-dihydrochloride Prepared from 2-(piperidin-3-yl-methyl)-7,8-methylenedioxy-2-oxo-1,3,4,5-tetrahydro-2H-benzazepine and 1-chloro-3-(4-methoxy-N-methyl-phenylamino)-propane analogously Example 1.
Yield: 24.2% of theory,
Melting point: 219°–221° C.

| Calculated: | C 58.94 | H 7.25 | N 7.61 |
|---|---|---|---|
| Found: | 59.08 | 7.45 | 7.75 |

EXAMPLE 181

3-[(N-(2-(6-Methyl-pyrid-2-yl)-ethyl)-pyrrolidin-3-yl)-methyl]-7,8-dimethyl-1,3,4,5-tetrahydro-2H-3-benzazepine×2.5 HCl×H2O Prepared from 3-[(N-(2-(6-methyl-pyrid-2-yl)-ethyl)-pyrrolidin-3-yl)-methyl]-7,8-dimethyl-2-oxo-1,3,4,5-tetrahydro-2H-3-benzazepine and lithium aluminium hydride in diethylether and tetrahydrofuran analogously to Example 3.
Yield: 50% of theory,
Melting point: 80°–91° C. amorphous.

| Calculated: | C 61.68 | H 8.18 | N 8.63 | Cl 18.21 |
|---|---|---|---|---|
| Found: | 61.55 | 8.36 | 8.44 | 18.10 |

EXAMPLE 182

3-[(N-(2-(6-Methyl-pyrid-2-yl)-ethyl)-pyrrolidin-3-yl)-methyl]-7,8-dimethyl-2-oxo-1,3,4,5-tetrahydro-2H-3-benzazepine-dihydrochloride-semihydrate Prepared from 3-[(N-(2-(6-methyl-pyrid-2-yl)-ethyl)-pyrrolidin-3-yl)-methyl]-7,8-dimethyl-2-oxo-1,3-dihydro-2H-3-benzazepine with 10% palladium/charcoal at 5 bar hydrogen and at 80° C. in ethanol analogously to Example 5.
Yield: 92% of theory,
Melting point: 86°–94° C. amorphous.

| Calculated: | C 63.41 | H 7.66 | N 8.87 | Cl 14.97 |
|---|---|---|---|---|
| Found: | 63.52 | 7.14 | 8.81 | 14.94 |

EXAMPLE 183

2-[(N-(3-(6-Methoxy-naphthyl-2-oxy)-propyl)-pyrrolidin-3-yl)-methyl]-6,7-dimethyl-1-oxo-1,2,3,4-tetrahydro-isoquinoline Prepared from 6,7-dimethoxy-1-oxo-1,2,3,4-tetrahydro-isoquinoline and 3-(p-toluenesulphonyloxymethyl)-N-[3-(6-methoxy-naphthyl-2-oxy)-propyl]-pyrrolidine analogously to Example 2.
Yield: 44.7% of theory,
Melting point: 102°–104° C.

| Calculated: | C 76.24 | H 7.68 | N 5.93 |
|---|---|---|---|
| Found: | 75.90 | 7.62 | 5.94 |

EXAMPLE 184

2-[(N-(3-(6-Methoxy-naphthyl-2-oxy)-propyl)-pyrrolidin-3-yl)-methyl]-6,7-dimethoxy-1,2,3,4-tetrahydro-isoquinoline Prepared from 2-[N-(3-(6-methoxy-naphthyl-2-oxy)-propyl)-pyrrolidin-3-yl)-methyl]-6,7-dimethoxy-1-oxo-1,2,3,4-tetrahydro-isoquinoline and lithium aluminium hydride in tetrahydrofuran and ether analogously to Example 3.
Yield: 68% of theory,
Melting point: 106°–108° C.

| Calculated: | C 73.44 | H 7.82 | N 5.71 |
|---|---|---|---|
| Found: | 73.26 | 7.72 | 5.81 |

EXAMPLE 185

3-[(N-(3-(Indol-3-yl)-propyl)-pyrrolidin-3-yl)-methyl]-7,8-methylenedioxy-2-oxo-1,3,4,5-tetrahydro-2H-3-benzazepine-monohydrate Prepared from 3-[(N-(3-(indol-3-yl)-propyl)-pyrrolidin-3-yl)-methyl]-7,8-methylenedioxy-2-oxo-1,3-dihydro-2H-3-benzazepine with 20% palladium/charcoal at 5 bar hydrogen in ethanol at 80° C. analogously to Example 5.
Yield: 40% of theory,
Melting range: 67°–74° C.

| Calculated: | C 69.95 | H 7.17 | N 9.06 |
|---|---|---|---|
| Found: | 70.00 | 7.03 | 8.97 |

EXAMPLE 186

3-[(N-(2-(6-Methyl-pyrid-2-yl)-ethyl)-methyl]-7,8-dimethyl-2-oxo-1,3-dihydro-2H-3-benzazepine-dihydro-chloride-semihydrate Prepared from 7,8-dimethyl-2-oxo-1,3-dihydro-2H-3-benzazepine and 3-chloromethyl-N-[2-(6-methyl-pyrid-2-yl)-ethyl]-pyrrolidine analogously to Example 2.
Yield: 81% of theory,
Melting point: 86°–98° C. amorphous.

| | | | | |
|---|---|---|---|---|
| Calculated: | C 63.68 | H 7.27 | N 8.91 | Cl 15.04 |
| Found: | 63.39 | 7.43 | 8.87 | 14.93 |

EXAMPLE 187

2-[(N-(3-(3-Methylphenoxy)propyl)-piperidin-3-yl)-methyl]-6,7-dimethoxy-1-oxo-1,2,3,4-tetrahydro-isoquinoline-hydrochloride Prepared from 6,7-dimethoxy-1-oxo-1,2,3,4-tetrahydro-isoquinoline and N-[3-(3-methylphenoxy)-propyl]-3-benzenesulphonyloxymethyl-piperidine analogously to Example 2.
Yield: 75.6% of theory,
Melting point: 106°–109° C. amorphous.

| | | | | |
|---|---|---|---|---|
| Calculated: | C 63.95 | H 7.75 | N 5.52 | Cl 7.25 |
| Found: | 64.66 | 7.91 | 5.48 | 7.28 |

EXAMPLE 188

2-[(N-(2-(5-Methyl-6-methoxy-naphthyl)-pyrrolidin-3-yl)-methyl]-6,7-methylenedioxy-1-oxo-1,2,3,4-tetrahydro-isoquinoline-hydrochloride Prepared from 6,7-methylenedioxy-1-oxo-1,2,3,4-tetrahydro-isoquinoline and 3-(p-toluenesulphonyloxymethyl)-N-[2-(5-methyl-6-methoxy-naphthyl)-ethyl]-pyrrolidine analogously to Example 2.
Yield: 27.1% of theory.
Melting point: 249°–251° C.

| | | | | |
|---|---|---|---|---|
| Calculated: | C 68.43 | H 6.53 | N 5.50 | Cl 6.96 |
| Found: | 68.47 | 6.66 | 5.30 | 7.16 |

EXAMPLE 189

2-[(N-(3-(Naphth-2-yl)-propyl)-pyrrolidin-3-yl)-methyl]-6,7-dimethoxy-1-oxo-isoquinoline-hydrochloride Prepared from 6,7-dimethoxy-1-oxo-1,2,3,4-tetrahydro-isoquinoline and 3-(p-toluenesulphonyloxymethyl)-N-[3-(naphth-2-yl)-propyl]-pyrrolidine analogously to Example 2.
Yield: 20.2% of theory,
Melting point: 84°–86° C.

| | | | | |
|---|---|---|---|---|
| Calculated: | C 67.88 | H 7.26 | N 5.46 | Cl 6.91 |
| Found: | 67.86 | 7.40 | 5.40 | 7.17 |

EXAMPLE 190

2-[(N-(3-(3,4-Dimethoxy-phenoxy)-propyl)-pyrrolidin-3-yl)-methyl]-6,7-dimethoxy-1,2,3,4-tetrahydro-isoquinoline-dihydrochloride Prepared from 2-[(N-[3-(3,4-dimethoxy-phenoxy)-propyl)-pyrrolidin-3-yl)-methyl]-6,7-dimethoxy-1-oxo-1,2,3,4-tetrahydro-isoquinoline and lithium aluminium hydride in diethyl ether and tetrahydrofuran analogously to Example 3.
Yield: 92.3% of theory,
Melting point: 220°–221° C.

| | | | | |
|---|---|---|---|---|
| Calculated: | C 59.20 | H 6.88 | N 5.31 | Cl 13.44 |
| Found: | 59.28 | 6.97 | 5.20 | 13.44 |

EXAMPLE 191

2-[(N-(2-(3,4-Dimethoxy-phenyl)-ethyl)-pyrrolidin-3-yl)-methyl]-6,7-dimethyl-1-oxo-1,2,3,4-tetrahydro-isoquinoline Prepared from 6,7-dimethyl-1-oxo-1,2,3,4-tetrahydro-isoquinoline and N-[2-(3,4-dimethoxy-phenyl)-ethyl]-3-benzenesulphonyloxymethyl-pyrrolidine analogously to Example 2.
Yield: 70% of theory,
Melting point: 168°–170° C.

| | | | |
|---|---|---|---|
| Calculated: | C 73.90 | H 8.11 | N 6.63 |
| Found: | 73.96 | 8.11 | 6.55 |

EXAMPLE 192

2-[(N-(3-(4-Methoxy-phenoxy)-propyl)-piperidin-3-yl)-methyl]-6,7-dimethoxy-1-oxo-1,2,3,4-tetrahydro-isoquinoline-hydrochloride Prepared from 6,7-dimethoxy-1-oxo-1,2,3,4-tetrahydro-isoquinoline and N-[3-(4-methoxy-phenoxy)-propyl]-3-benzenesulphonyloxymethyl-piperidine analogously to Example 2.
Yield: 78.7% of theory.
Melting point: 98°–102° C.

| | | | | |
|---|---|---|---|---|
| Calculated: | C 63.08 | H 7.51 | N 5.35 | Cl 7.02 |
| Found: | 62.87 | 7.69 | 5.16 | 7.28 |

EXAMPLE 193

2-[(N-(3-(3-Methoxy-phenoxy)-propyl)-piperidin-3-yl)-methyl]-6,7-dimethoxy-1-oxo-1,2,3,4-tetrahydro-isoquinoline-hydrochloride Prepared from 6,7-dimethoxy-1-oxo-1,2,3,4-tetrahydro-isoquinoline and N-[3-(3-methoxy-phenoxy)-propyl]-3-benzenesulphonyloxymethyl-piperidine analogously to Example 2.
Yield: 87% of theory,
Melting point: 103°–105° C.

| | | | | |
|---|---|---|---|---|
| Calculated: | C 64.21 | H 7.38 | N 5.55 | Cl 7.02 |
| Found: | 64.00 | 7.55 | 5.37 | 7.12 |

EXAMPLE 194

2-[(N-(3-(3-Methoxy-phenoxy)-propyl)-piperidin-3-yl)-methyl]-6,7-dimethoxy-1,2,3,4-tetrahydro-isoquinoline-dihydrochloride Prepared from 2-[(N-(3-(3-methoxy-phenoxy)-propyl)-piperidin-3-yl)-methyl]-6,7-dimethoxy-1-oxo-1,2,3,4-tetrahydro-isoquinoline and lithium aluminium hydride in diethylether and tetrahydrofuran analogously to Example 3.

Yield: 95.4% of theory,
Melting point: 170°-173° C.

| Calculated: | C 60.43 | H 7.70 | N 5.22 | Cl 13.21 |
|---|---|---|---|---|
| Found: | 60.50 | 7.71 | 4.91 | 12.97 |

EXAMPLE 195

2-[(N-(2-(3,4-Dimethoxy-phenyl)-ethyl)-pyrrolidin-3-yl)-methyl]-6,7-dimethyl-1,2,3,4-tetrahydro-isoquinoline-dihydrochloride Prepared from 2-[(N-(2-(3,4-dimethoxy-phenyl)-ethyl)-pyrrolidin-3-yl)-methyl]-6,7-dimethyl-1-oxo-1,2,3,4-tetrahydro-isoquinoline and lithium aluminium hydride in diethylether and tetrahydrofuran analogously to Example 3.

Yield: 94.1% of theory,
Melting point: 260°-262° C.

| Calculated: | C 64.85 | H 7.96 | N 5.82 | Cl 14.73 |
|---|---|---|---|---|
| Found: | 64.60 | 8.11 | 5.91 | 14.67 |

EXAMPLE 196

2-[(N-(3-(6-Methoxy-naphthyl-2-oxy)-propyl)-azacyclo-oct-3-yl)-methyl]-6,7-dimethoxy-1-oxo-1,2,3,4-tetrahydro-isoquinoline-hydrochloride Prepared from 2-[(azacyclooct-3-yl)-methyl]-6,7-dimethoxy-1-oxo-1,2,3,4-tetrahydro-isoquinoline and 2-(3-chloropropoxy)-6-methoxy-naphthalene analogously to Example 1.

Yield: 24.4% of theory,
Melting point: 176°-178° C.

| Calculated: | C 67.96 | H 7.43 | N 4.80 | Cl 6.08 |
|---|---|---|---|---|
| Found: | 67.74 | 7.29 | 4.71 | 6.23 |

EXAMPLE 197

3-[(N-(3-(Indol-3-yl)-propyl)-pyrrolidin-3-yl)-methyl]-7,8-dimethyl-2-oxo-1,3,4,5-tetrahydro-2H-benzazepine-hydrochloride Prepared from 3-[(pyrrolidin-3-yl)-methyl]-7,8-dimethyl-2-oxo-1,2,3,4-tetrahydro-2H-3-benzazepine and 3-(3-benzenesulphonyloxy-propyl)-indole analogously to Example 1.

Yield: 62% of theory,
Melting point: 106°-108° C.

| Calculated: | C 69.47 | H 7.91 | N 8.68 | Cl 7.32 |
|---|---|---|---|---|
| Found: | 69.57 | 7.80 | 8.67 | 8.51 |

EXAMPLE 198

3-[(N-(3-(6-Methoxy-naphthyl-2-oxy)-propyl)-hexahydro-azepin-3-yl)-methyl]-7,8-dimethoxy-1,2,3,4-tetrahydro-2H-3-benzazepine Prepared from 3-[(N-(3-(6-methoxy-naphthyl-2-oxy)-propyl)-hexahydro-azepin-3-yl)-methyl]-7,8-dimethoxy-1,2,3,4-tetrahydro-2-oxo-2H-3-benzazepine and lithium aluminium hydride in tetrahydrofuran/ether analogously to Example 3.

Yield: 26.8% of theory,
Melting point: 98°-100° C.

| Calc. (× H₂O): | C 71.97 | H 8.42 | N 5.09 |
|---|---|---|---|
| Found: | 72.07 | 8.23 | 5.10 |

EXAMPLE 199

3-[(N-(3-(6-Methoxy-naphthyl-2-oxy)-propyl)-hexahydro-azepin-3-yl)-methyl]-1,2,3,4-tetrahydro-2-oxo-2H-3-benzazepine Prepared from 3-[(hexahydro-azepin-3-yl)-methyl]-1,2,3,4-tetrahydro-2-oxo-2H-3-benzazepine and 2-(3-chloropropoxy)-6-methoxy-naphthalene analogously to Example 1.

Yield: 45% of theory,
Melting point: 109°-111° C.

| Calculated: | C 72.50 | H 7.74 | N 5.12 |
|---|---|---|---|
| Found: | 72.35 | 7.68 | 4.93 |

EXAMPLE 200

2-[(N-(3-(-Methoxy-naphthyl-2-oxy)-propyl)-hexahydro-azepin-3-yl)-methyl]-1,3-dihydro-5,6-dimethoxy-isoindole Prepared from 2-[(N-(3-(6-methoxy-naphthyl-2-oxy)-propyl)-hexahydro-azepin-3-yl)-methyl]-5,6-dimethoxy-phthalimide and lithium aluminium hydride in tetrahydro-furan/ether analogously to Example 3.

Yield: 49.2% of theory,
Melting point: 104°-146° C.

| Calculated: | C 73.78 | H 7.99 | N 5.55 |
|---|---|---|---|
| Found: | 73.63 | 7.99 | 5.39 |

EXAMPLE 201

2-[(N-(3-(6-Methoxy-naphthyl-2-oxy)-propyl)-hexahydro-azepin-3-yl)-methyl]-4,5-dimethoxy-phthalimide Prepared from 2-[(hexahydro-azepin-3-yl)-methyl]-4,5-dimethoxyphthalimide and 3-(3-chloropropoxy)-6-methoxy-naphthalene analogously to Example 1.

Yield: 56.7% of theory,
Melting point: 179°-181° C.

| Calculated: | C 69.91 | H 6.81 | N 5.26 |
|---|---|---|---|
| Found: | 69.79 | 6.73 | 5.09 |

EXAMPLE 202

3-[(N-(3-(6-Methoxy-naphthyl-2-oxy)-propyl)-hexahydro-azepin-3-yl)-methyl]-1,3,4,5-tetrahydro-7,8-methylenedioxy-2H-3-benzazepine Prepared from 3-[(N-(3-(6-methoxy-naphthyl-2-oxy)-propyl)-hexahydro-azepin-3-yl)-methyl]-1,3,4,5-tetrahydro-7,8-methylenedioxy-2-oxo-2H-3-benzazepine and lithium aluminium hydride/tetrahydrofuran/ether analogously to Example 3.
Yield: 25% of theory,
Melting point: 109°–111° C.

| Calculated: | C 74.39 | H 7.80 | N 5.42 |
|---|---|---|---|
| Found: | 74.27 | 7.94 | 5.43 |

EXAMPLE 203

3-[(N-(3-(6-Methoxy-naphthyl-2-oxy)-propyl)-hexahydro-azepin-3-yl)-methyl]-1,3,4,5-tetrahydro-7,8-methylenedioxy-2-oxo-2H-3-benzazepine-hydrochloride Prepared from 3-[(hexahydro-azepin-3-yl)-methyl]-1,3,4,5-tetrahydro-7,8-methylenedioxy-2-oxo-2H-3-benzazepine and 2-(3-chloropropoxy)-6-methoxy-naphthalene analogously to Example 1.
Yield: 68.1% of theory,
Melting range: 104°–108° C.

| Calc. ($\cdot$ 2 H$_2$O): | C 65.46 | H 7.38 | N 4.79 | Cl 6.06 |
|---|---|---|---|---|
| Found: | 65.60 | 7.25 | 5.01 | 6.43 |

EXAMPLE 204

2-[(N-(3-(6-Methoxy-naphthyl-2-oxy)-propyl)-hexahydro-azepin-3-yl)-methyl]-6,7-methylenedioxy-1-oxo-1,3,4,5-tetrahydro-isoquinoline-hydrochloride Prepared from 2-[(hexahydro-azepin-3-yl)-methyl]-6,7-methylenedioxy-1-oxo-1,3,4,5-tetrahydro-isoquinoline and 2-(3-chloro-propoxy)-6-methoxy-naphthalene analogously to Example 1.
Yield: 18.2% of theory,
Melting point: 65°–67° C.

| Calc. ($\cdot$ H$_2$O): | C 65.19 | H 6.88 | N 4.90 | Cl 6.20 |
|---|---|---|---|---|
| Found: | 65.20 | 6.75 | 4.82 | 6.54 |

EXAMPLE 205

2-[(N-(3-(6-Methoxy-naphthyl-2-oxy)-propyl)-piperidin-3-yl)methyl]-6,7-methylenedioxy-1-oxo-1,2,3,4-tetrahydro-isoquinoline Prepared from 6,7-methylenedioxy-1-oxo-1,2,3,4-tetrahydroisoquinoline and 3-(benzenesulphonyloxymethyl)-N-[3-(6-methoxynaphthalene-2-oxy)-propyl]-piperidine analogously to Example 2.
Yield: 5.3% of theory,
Melting point: 144°–146° C.

| Calculated: | C 71.69 | H 6.82 | N 5.57 |
|---|---|---|---|
| Found: | 71.52 | 6.62 | 5.46 |

EXAMPLE 206

2-[(N-(3-(6-Methoxy-naphthyl-2-oxy)-propyl)-hexahydroazepin-3-yl)-methyl]-5,6-dimethyl-1,3-dihydro-1-oxo-isoindole Prepared from 2-[(N-(3-(6-methoxy-naphthyl-2-oxy)-propyl)hexahydro-azepin-3-yl)-methyl]-4,5-dimethyl-phthalimide and zinc/glacial acetic acid analogously to Example 4.
Yield: 18.2% of theory,
Melting point: 232°–234° C.

| Calc. ($\times$ acetone): | C 74.97 | H 8.14 | N 5.14 |
|---|---|---|---|
| Found: | 74.96 | 7.90 | 5.30 |

EXAMPLE 207

2-[(N-(3-(6-Methoxy-naphthyl-2-oxy)-propyl)-hexahydroazepin-3-yl)-methyl]-6,7-dimethyl-1-oxo-1,2,3,4-tetrahydroisoquinoline-hydrochloride Prepared from 2-[(hexahydro-azepin-3-yl)-methyl]-6,7-dimethyl-1-oxo-1,2,3,4-tetrahydro-isoquinoline and 2-(3-chloro-propoxy)-6-methoxy-naphthalene analogously to Example 1.
Yield: 17.3% of theory,
Melting range: 68°–73° C.

| Calc. ($\times$ 2 H$_2$O): | C 67.06 | H 7.93 | N 4.46 | Cl 6.66 |
|---|---|---|---|---|
| Found: | 67.05 | 7.73 | 4.88 | 6.18 |

EXAMPLE 208

2-[(N-(3-(6-Methoxy-naphthyl-2-oxy)-propyl)-piperidin-3-yl)-methyl]-6,7-dimethoxy-1-oxo-1,2,3,4-tetrahydro-isoquinoline Prepared from 6,7-dimethoxy-1-oxo-1,2,3,4-tetrahydro-isoquinoline and 3-(benzenesulphonyloxymethyl)-N-[3-(6-methoxy-naphthyl-2-oxy)-propyl]-piperidine analogously to Example 2.
Yield: 12.9% of theory,
Melting point: 124°–126° C.

| Calculated: | C 71.79 | H 7.38 | N 5.40 |
|---|---|---|---|
| Found: | 71.83 | 7.33 | 5.21 |

EXAMPLE 209

3-[(N-(3-(5,6-Dimethoxy-naphthyl-2-oxy)-propyl)-hexahydroazepin-3-yl)-methyl]-1,3,4,5-tetrahydro-7,8-dimethoxy-2H-3-benzazepine Prepared from 3-[(N-(3-(5,6-dimethoxy-naphthyl-2-oxy)-propyl)hexahydro-azepin-3-yl)-methyl]-1,3,4,5-tetrahydro-7,8-dimethoxy-2-oxo-2H-3-benzazepine and lithium aluminium hydride/tetrahydrofuran/ether analogously to Example 3.
Yield: 29.1% of theory,
Melting point: 94°–96° C.

| Calculated: | C 72.57 | H 8.24 | N 4.98 |
|---|---|---|---|
| Found: | 72.56 | 8.35 | 4.94 |

EXAMPLE 210

2-[(N-(3-(6-Methoxy-naphthyl-2-oxy)-propyl)-hexahydroazepin-3-yl)-methyl]-1,3-dihydro-5,6-dimethoxy-1-oxo-isoindole Prepared from 2-[(N-(3-(6-methoxy-naphthyl-2-oxy)-propyl)hexahydro-azepin-3-yl)-methyl]-5,6-dimethoxyphthalimide and zinc/glacial acetic acid analogously to Example 4.
Yield: 20.5% of theory,
Melting point: 265°–267° C.

| | | | |
|---|---|---|---|
| Calc. (× 2 H$_2$O): | C 67.13 | H 7.63 | N 5.05 |
| Found: | 67.11 | 7.64 | 5.07 |

EXAMPLE 211

3-[(N-(3-(5,6-Dimethoxy-naphthyl-2-oxy)-propyl)-hexahydroazepin-3-yl)-methyl]-1,3,4,5-tetrahydro-7,8-dimethoxy-2-oxo-2H-3-benzazepine Prepared from 3-[(hexahydro-azepin-3-yl)-methyl]-1,3,4,5-tetrahydro-7,8-dimethoxy-2-oxo-2H-3-benzazepine and 2-(3-chloropropoxy)-5,6-dimethoxy-naphthalene analogously to Example 1.
Yield: 52.4% of theory.
Melting point: 129°–131° C.

| | | | |
|---|---|---|---|
| Calculated: | C 70.81 | H 7.69 | N 4.86 |
| Found: | 70.66 | 7.84 | 4.63 |

EXAMPLE 212

2-[(N-(3-(5,6-Dimethoxy-naphthyl-2-oxy)-propyl)-hexahydroazepin-3-yl)-methyl]-5,6-dimethoxy-1,3-dihydro-isoindoledihydrochloride Prepared from 2-[(N-(3-(5,6-dimethoxy-naphthyl-2-oxy)-propyl)hexahydro-azepin-3-y)-methyl]-4,5-dimethoxy-phthalimide and lithium aluminium hydride in tetrahydrofuran/ether analogously to Example 3.
Yield: 48.2% of theory, Melting range: 172°–177° C.

| | | | | |
|---|---|---|---|---|
| Calc. (× H$_2$O): | C 61.43 | H 7.41 | N 4.47 | Cl 11.33 |
| Found: | 61.50 | 7.71 | 4.59 | 11.45 |

EXAMPLE 213

2-[(N-(3-(5,6-Dimethoxy-naphthyl-2-oxy)-propyl)-hexahydroazepin-3-yl)-methyl]-5,6-dimethoxy-1,3-dihydro-1-oxo-isoindolehydrochloride Prepared from 2-[(N-(3-(5,6-dimethoxy-naphthyl-2-oxy)-propyl)hexahydro-azepin-3-yl)-methyl]-4,5-dimethoxy-phthalimide and zinc/glacial acetic acid analogously to Example 4.
Yield: 36.4% of theory,
Melting range: 215°–223° C.

| | | | | |
|---|---|---|---|---|
| Calc. (× H$_2$O): | C 61.87 | H 7.30 | N 4.50 | Cl 5.70 |
| Found: | 62.08 | 7.15 | 4.55 | 5.80 |

EXAMPLE 214

2-[(N-(3-(5,6-Dimethoxy-naphthyl-2-oxy)-propyl)-hexahydroazepin-3-yl)-methyl]-4,5-dimethoxy-phthalimide Prepared from 2-[(hexahydro-azepin-3-yl)-methyl]-4,5-dimethoxyphthalimide and 2-(3-chloropropoxy)-5,6-dimethoxy-naphthalene analogously to Example 1.
Yield: 55.2% of theory,
Melting point: 152°–154° C.

| | | | |
|---|---|---|---|
| Calculated: | C 68.31 | H 6.81 | N 4.98 |
| Found: | 68.10 | 6.91 | 5.03 |

EXAMPLE 215

3-[(N-(3-(5,6-Dimethoxy-naphthyl-2-oxy)-propyl)-hexahydroazepin-3-yl)-methyl]-1,3,4,5-tetrahydro-7,8-dimethyl-2H-3-benzazepine-dihydrochloride Prepared from 3-[(N-(3-(5,6-dimethoxy-naphthyl-2-oxy)-propyl)hexahydro-azepin-3-yl)-methyl]-1,3,4,5-tetrahydro-7,8-dimethyl-2-oxo-2H-3-benzazepine and lithium aluminium hydride/tetrahydrofuran/ether analogously to Example 3.
Yield: 76.9% of theory,
Melting range: 138°–144° C.

| | | | | |
|---|---|---|---|---|
| Calculated: | C 67.64 | H 8.01 | N 4.64 | Cl 11.74 |
| Found: | 67.73 | 8.26 | 4.47 | 11.50 |

EXAMPLE 216

3-[(N-(3-(5,6-Dimethoxy-naphthyl-2-oxy)-propyl)-hexahydroazepin-3-yl)-methyl]-1,3,4,5-tetrahydro-7,8-dimethyl-2-oxo-2H-3-benzazepine-hydrochloride Prepared from 3-[(hexahydro-azepin-3-yl)-methyl]-1,3,4,5-tetrahydro-7,8-dimethyl-2-oxo-2H-3-benzazepine and 2-(3-chloropropoxy)-5,6-dimethoxy-naphthalene analogously to Example 1.
Yield: 47.5% of theory,
Melting range: 90°–96° C.

| | | | | |
|---|---|---|---|---|
| Calc. (× H$_2$O): | C 68.15 | H 7.90 | N 4.67 | Cl 5.91 |
| Found: | 67.93 | 7.94 | 5.05 | 6.09 |

EXAMPLE 217

2-[(N-(3-(5,6-Dimethoxy-naphthyl-2-oxy)-propyl)-piperidin-3-yl)-methyl]-6,7-methylenedioxy-1-oxo-1,2,3,4-tetrahydroisoquinoline-hydrochloride Prepared from 2-[(piperidin-3-yl)-methyl]-6,7-methylenedioxy-1-oxo-1,2,3,4-tetrahydro-isoquinoline and 2-(3-chloropropoxy)-5,6-dimethoxy-naphthalene analogously to Example 1.
Yield: 22.5% of theory,
Melting range: 93°–98° C.

| | | | | |
|---|---|---|---|---|
| Calc. (× H$_2$O): | C 63.42 | H 6.69 | N 4.77 | Cl 6.03 |
| Found: | 63.59 | 6.80 | 4.70 | 6.28 |

EXAMPLE 218

2-[(N-(3-(5,6-Dimethoxy-naphthyl-2-oxy)-propyl)-pyrrolidin-3-yl)-methyl]-6,7-methylenedioxy-1-oxo-1,2,3,4-tetrahydroisoquinoline-hydrochloride Prepared from 2-[(pyrrolidin-3-yl)-methyl]-6,7-methylene-dioxy-1-oxo-1,2,3,4-tetrahydro-isoquinoline and 2-(3-chloropropoxy)-5,6-dimethoxy-naphthalene analogously to Example 1.

Yield: 22.5% of theory,
Melting point: 87°–90° C.

| | | | | |
|---|---|---|---|---|
| Calc. (× H₂O): | C 62.87 | H 6.50 | N 4.88 | Cl 6.18 |
| Found: | 62.72 | 6.38 | 4.93 | 6.30 |

EXAMPLE 219

2-[(N-(3-(5,6-Dimethoxy-naphthyl-2-oxy)-propyl)-piperidin-3-yl)-methyl]-6,7-dimethyl-1-oxo-1,2,3,4-tetrahydro-isoquinolinehydrochloride Prepared from 2-[(piperidin-3-yl)-methyl]-6,7-dimethyl-1-oxo-1,2,3,4-tetrahydro-isoquinoline and 2-(3-chloropropoxy)-5,6-dimethoxy-naphthalene analogously to Example 1.

Yield: 21.3% of theory,
Melting range: 72°–78° C.

| | | | | |
|---|---|---|---|---|
| Calc. (× H₂O): | C 67.30 | H 7.59 | N 4.90 | Cl 6.21 |
| Found: | 67.44 | 7.74 | 5.06 | 6.53 |

EXAMPLE 220

2-(N-(3-(5,6-Dimethoxy-naphthyl-2-oxy)-propyl)-hexahydroazepin-3-yl)-methyl]-6,7-dimethyl-1-oxo-1,2,3,4-tetrahydroisoquinoline-hydrochloride Prepared from 2-[(hexahydro-azepin-3-yl)-methyl]-6,7-dimethyl-1-oxo-1,2,3,4-tetrahydro-isoquinoline and 2-(3-chloropropoxy)-5,6-dimethoxy-naphthalene analogously to Example 1.

Yield: 12% of theory,
Melting range: 84°–90° C.

| | | | | |
|---|---|---|---|---|
| Calc. (× H₂O): | C 67.73 | H 7.73 | N 4.78 | Cl 6.06 |
| Found: | 67.64 | 7.81 | 4.94 | 6.20 |

EXAMPLE 221

2-[(N-(2-(4-Methoxy-phenyl)-ethyl)-hexahydro-azepin-3-yl)methyl]-6,7-methylenedioxy-1-oxo-1,2,3,4-tetrahydro-isoquinolinehydrochloride Prepared from 6,7-methylenedioxy-1-oxo-1,2,3,4-tetrahydroisoquinoline and N-[2-(4-methoxy-phenyl)-ethyl]-3-chloromethylhexahydro-azepine analogously to Example 2.

Yield: 46.7% of theory,
Melting point: 101°–105° C.

| | | | | |
|---|---|---|---|---|
| Calculated: | C 62.44 | H 7.26 | N 5.60 | Cl 7.50 |
| Found: | 62.62 | 7.27 | 5.48 | 7.66 |

EXAMPLE 222

2-[(N-(3-(4-Methoxy-phenoxy)-propyl)-hexahydro-azepin-3-yl)methyl]-6,7-methylenedioxy-1-oxo-1,2,3,4-tetrahydro-isoquinolinehydrochloride Prepared from 6,7-methylenedioxy-1-oxo-1,2,3,4-tetrahydro-2-isoquinoline and N-[3-(4-methoxy-phenoxy)-propyl]-3-chloromethylhexahydro-azepine analogously to Example 2.

Yield: 43.8% of theory,
Melting point: 123°–126° C.

| | | | | |
|---|---|---|---|---|
| Calculated: | C 62.23 | H 7.16 | N 5.37 | Cl 7.05 |
| Found: | 62.42 | 7.34 | 5.30 | 6.94 |

EXAMPLE 223

2-[(N-(3-(4-Methoxy-phenoxy)-propyl)-hexahydro-azepin-3-yl)methyl]-6,7-dimethyl-1-oxo-1,2,3,4-tetrahydro-isoquinolinehydrochloride Prepared from 6,7-dimethyl-1-oxo-1,2,3,4-tetrahydro-2-isoquinoline and N-[3-(4-methoxy-phenoxy)-propyl]-3-chloromethylhexahydro-azepine analogously to Example 2.

Yield: 42% of theory,
Melting point: 172°–173° C.

| | | | | |
|---|---|---|---|---|
| Calculated: | C 69.04 | H 8.07 | N 5.75 | Cl 7.28 |
| Found: | 69.06 | 8.25 | 5.57 | 7.39 |

EXAMPLE 224

2-[(N-(3-(4-Methoxy-phenoxy)-propyl)-hexahydro-azepin-3-yl)methyl]-6,7-dimethoxy-1-oxo-1,2,3,4-tetrahydro-isoquinolinehydrochloride Prepared from 6,7-dimethyl-1-oxo-1,2,3,4-tetrahydro-isoquinoline and N-[3-(4-methoxy-phenoxy)-propyl]-3-chloromethyl-hexahydrobenzazepine analogously to Example 2.

Yield: 63.3% of theory,
Melting range: 115°–120° C.

| | | | | |
|---|---|---|---|---|
| Calculated: | C 62.58 | H 7.67 | N 5.21 | Cl 6.83 |
| Found: | 62.44 | 7.68 | 4.91 | 6.81 |

EXAMPLE 225

2-[(N-(2-(4-Methoxy-phenyl)-ethyl)-hexahydro-azepin-3-yl)methyl]-6,7-dimethoxy-1-oxo-1,2,3,4-tetrahydro-isoquinolinehydrochloride Prepared from 5,6-dimethoxy-1-oxo-1,2,3,4-tetrahydro-isoquinoline and N-[2-(4-methoxy-phenyl)-ethyl]-3-chloromethyl-hexahydroazepine analogously to Example 2.

Yield: 51.6% of theory,
Melting point: 110°–113° C.

| | | | | |
|---|---|---|---|---|
| Calculated: | C 61.75 | H 7.87 | N 5.28 | Cl 7.25 |
| Found: | 61.84 | 8.02 | 5.16 | 7.22 |

EXAMPLE 226

2-[(N-(2-(3,4-Dimethoxy-phenyl)-ethyl)-hexahydro-azepin-3-yl)-methyl]-6,7-dimethoxy-1-oxo-1,2,3,4-tetrahydro-isoquinolinehydrochloride Prepared from 6,7-dimethoxy-1-oxo-1,2,3,4-tetrahydro-isoquinoline and N-[2-(3,4-dimethoxy-phenyl)-ethyl]-3-chloromethyl-hexahydroazepine analogously to Example 2.
Yield: 45.5% of theory,
Melting point: 107°–111° C.

| Calculated: | C 62.61 | H 7.69 | 5.21 | Cl 6.60 |
|---|---|---|---|---|
| Found: | 62.78 | 8.00 | 5.00 | 6.43 |

EXAMPLE 227

2-[(N-2-(3,4-Dimethoxy-phenyl)-ethyl)-hexahydro-azepin-3-yl)-methyl]-6,7-dimethyl-1-oxo-1,2,3,4-tetrahydro-isoquinolinehydrochloride Prepared from 6,7-dimethyl-1-oxo-1,2,3,4-tetrahydro-isoquinoline and N-[2-(3,4-dimethoxy-phenyl)-ethyl]-3-chloromethyl-hexahydroazepine analogously to Example 2.
Yield: 44.8% of theory,
Melting point: 162°–163° C.

| Calculated: | C 66.57 | H 8.18 | N 5.54 | Cl 7.02 |
|---|---|---|---|---|
| Found: | 66.67 | 8.47 | 5.35 | 7.11 |

EXAMPLE 228

3-[(N-(2-(3,4-Dimethoxy-phenyl)-ethyl)-hexahydro-azepin-3-yl)-methyl]-7,8-dimethoxy-2-oxo-1,3,4,5-tetrahydro-2H-3-benzazepine-hydrochloride Prepared from 7,8-dimethoxy-1,3,4,5-tetrahydro-2-oxo-3-benzazepine and N-[2-(3,4-dimethoxy-phenyl)-ethyl]-3-chloromethyl-hexahydro-azepine analogously to Example 2.
Yield: 41.7% of theory,
Melting point: 102°–105° C.

| Calculated: | C 63.19 | H 7.36 | N 5.08 | Cl 6.65 |
|---|---|---|---|---|
| Found: | 63.09 | 7.52 | 4.94 | 6.72 |

EXAMPLE 229

3-[(N-(2-(3,4-Dimethoxy-phenyl)-ethyl)-hexahydro-azepin-3-yl)-methyl]-7,8-methylenedioxy-2-oxo-1,3,4,5-tetrahydro-2H-3-benzazepine-hydrochloride Prepared from 7,8-methylenedioxy-1,3,4,5-tetrahydro-2-oxo-3-benzazepine and N-[2-(3,4-dimethoxyphenyl)-ethyl]-3-chloromethyl-hexahydro-azepine analogously to Example 2.
Yield: 38.7% of theory,
Melting point: 98°–102° C.

| Calculated: | C 61.01 | H 7.69 | N 5.08 | Cl 6.43 |
|---|---|---|---|---|
| Found: | 60.86 | 7.43 | 4.87 | 6.25 |

EXAMPLE 230

3-[(N-(2-(4-Methoxy-phenyl)-ethyl)-hexahydro-azepin-3-yl)methyl]-7,8-dimethoxy-2-oxo-1,3,4,5-tetrahydro-2H-3-benzazepinehydrochloride Prepared from 7,8-dimethoxy-2-oxo-1,3,4,5-tetrahydro-2H-3-benzazepine and N-[2-(4-methoxy-phenyl)-ethyl]-3-chloromethylhexahydro-azepine analogously to Example 2.
Yield: 51.2% of theory,
Melting point: 110°–113° C.

| Calculated: | C 63.43 | H 7.98 | N 5.28 | Cl 7.02 |
|---|---|---|---|---|
| Found: | 63.31 | 7.99 | 4.93 | 7.05 |

EXAMPLE 231

3-[(N-(3-(3,4-Methylenedioxy-phenoxy)-propyl)-hexahydroazepin-3-yl)-methyl]-7,8-methylenedioxy-2-oxo-1,3,4,5-tetrahydro-2H-3-benzazepine-hydrochloride Prepared from 7,8-methylenedioxy-2-oxo-1,3,4,5-tetrahydro-2H-3-benzazepine and N-[3-(3,4-methylenedioxy-phenoxy)-propyl]-3-chloromethyl-hexahydroazepine analogously to Example 2.
Yield: 30.6% of theory,
Melting point: 106°–109° C.

| Calculated: | C 62.27 | H 6.71 | N 5.18 | C 16.68 |
|---|---|---|---|---|
| Found: | 62.36 | 6.70 | 5.00 | 6.46 |

EXAMPLE 232

3-[(N-(3-(3-Methyl-phenoxy)-propyl)-hexahydro-azepin-3-yl)methyl]-7,8-dimethoxy-2-oxo-1,3,4,5-tetrahydro-2H-3-benzazepinehydrochloride Prepared from 7,8-dimethoxy-2-oxo-1,3,4,5-tetrahydro-2H-3-benzazepine and N-[3-(3-methyl-phenoxy)-propyl]-3-chloromethylhexahydro-azepine analogously to Example 2.
Yield: 44.4% of theory,
Melting point: 112°–115° C.

| Calculated: | C 66.20 | H 8.04 | 5.32 | Cl 6.86 |
|---|---|---|---|---|
| Found: | 65.98 | 7.96 | 5.36 | 6.90 |

EXAMPLE 233

3-[(N-(3-(4-Methoxy-phenoxy)-propyl)-hexahydro-azepin-3-yl)methyl]-6,7-methylenedioxy-2-oxo-1,3,4,5-tetrahydro-2H-3-benzazepine-hydrochloride Prepared from 6,7-methylenedioxy-2-oxo-1,3,4,5-tetrahydro-2H-3-benzazepine and N-[3-(4-methoxyphenoxy)-propyl]-3-chloromethylhexahydro-azepine analogously to Example 2.
Yield: 38.7% of theory,
Melting point: 121°–126° C.

| Calculated: | C 62.84 | H 7.34 | N 5.23 | C 16.86 |
|---|---|---|---|---|
| Found: | 63.05 | 7.33 | 5.28 | 7.04 |

EXAMPLE 234

2-[(N-(3-(3-Methyl-phenoxy)-propyl)-hexahydro-azepin-3-yl)methyl]-6,7-methylenedioxy-1-oxo-1,2,3,4-tetrahydro-isoquinolinehydrochloride Prepared from 6,7-methylenedioxy-1-oxo-1,2,3,4-tetrahydroisoquinoline and N-[3-(3-methyl-phenoxy)-propyl]-3-chloromethylhexahydro-azepine analogously to Example 2.

Yield: 46.8% of theory,
Melting point: 159°–161° C.

| | | | | |
|---|---|---|---|---|
| Calculated: | C 65.37 | H 7.31 | N 5.64 | Cl 7.28 |
| Found: | 65.44 | 7.40 | 5.39 | 7.23 |

EXAMPLE 235

2-[(N-(3-(3-Methyl-phenoxy)-propyl)-hexahydro-azepin-3-yl)methyl]-6,7-dimethoxy-1-oxo-1,2,3,4-tetrahydro-isoquinolinehydrochloride Prepared from 6,7-dimethoxy-1-oxo-1,2,3,4-tetrahydro-isoquinoline and N-[3-(3-methoxy-phenoxy)-propyl]-3-chloromethyl-hexahydroazepine analogously to Example 2.

Yield: 55.2% of theory,
Melting point: 107°–111° C.

| | | | | |
|---|---|---|---|---|
| Calculated: | C 65.67 | H 7.87 | N 5.47 | Cl 7.05 |
| Found: | 65.47 | 8.00 | 5.50 | 6.97 |

EXAMPLE 236

2[-(N-(3-(3,4-Methylenedioxy-phenoxy)-propyl)-hexahydroazepin-3-yl)-methyl]-6,7-dimethyl-1-oxo-1,2,3,4-tetrahydroisoquinoline-hydrochloride Prepared from 6,7-dimethyl-1-oxo-1,2,3,4-tetrahydro-isoquinoline and N-[2-(3,4-methylenedioxy-phenoxy)-propyl]-3-chloromethylhexahydro-azepine analogously to Example 2.

Yield: 40.6% of theory,
Melting point: 123°–126° C.

| | | | | |
|---|---|---|---|---|
| Calculated: | C 64.78 | H 7.57 | N 5.39 | C 16.83 |
| Found: | 64.88 | 7.59 | 5.29 | 7.18 |

EXAMPLE 237

2-[(N-(3-(3,4-Dimethoxy-phenoxy)-propyl)-hexahydroazepin-3-yl)-methyl]-6,7-dimethoxy-1-oxo-1,2,3,4-tetrahydro-isoquinolinehydrochloride Prepared from 6,7-dimethoxy-1-oxo-1,2,3,4-tetrahydro-isoquinoline and N-[3-(3,4-dimethoxy-phenoxy)-propyl]-3-chloromethylhexahydro-azepine analogously to Example 2.

Yield: 30.6% of theory,
Melting point: 101°–105° C.

| | | | | |
|---|---|---|---|---|
| Calculated: | C 62.61 | H 7.59 | N 5.01 | Cl 6.46 |
| Found: | 62.56 | 7.76 | 4.94 | 6.39 |

EXAMPLE 238

2-[(N-(2-(3,4-Dimethoxy-phenyl)-ethyl)-hexahydro-azepin-3-yl)-methyl]-5,6-dimethoxy-1-oxo-1,3-dihydro-isoindolehydrochloride Prepared from 2-[(N-(2-(3,4-dimethoxy-phenyl)-ethyl)-hexahydroazepin-3-yl)-methyl]-5,6-dimethoxy-phthalimide and zinc/glacial acetic acid analogously to Example 4.

Yield: 41.8% of theory,
Melting point: 150°–151° C.

| | | | | |
|---|---|---|---|---|
| Calculated: | C 61.99 | H 7.57 | N 5.35 | Cl 6.57 |
| Found: | 61.89 | 7.48 | 5.17 | 6.52 |

EXAMPLE 239

2-[(N-(2-(3-Methyl-phenoxy)-propyl)-hexahydro-azepin-3-yl)methyl]-5,6-dimethoxy-1-oxo-1,3-dihydro-isoindole-hydrochloride Prepared from 2-[(N-(3-(3-methyl-phenoxy)-propyl)-hexahydroazepin-3-yl)-methyl]-5,6-dimethoxy-phthalimide and zinc/glacial acetic acid analogously to Example 4.

Yield: 88.9% of theory,
Melting point: 95°–100° C.

| | | | | |
|---|---|---|---|---|
| Calculated: | C 63.95 | H 7.75 | N 5.52 | Cl 7.25 |
| Found: | 64.09 | 7.64 | 5.35 | 7.37 |

EXAMPLE 240

2-[(N-(3-(4-Methoxy-phenoxy)-propyl)-hexahydro-azepin-3-yl)methyl]-5,6-dimethoxy-1-oxo-1,3-dihydro-isoindole-hydrochloride Prepared from 2-[(N-(3-(4-methoxy-phenoxy)-propyl)-hexahydroazepin-3-yl)-methyl]-5,6-dimethoxy-phthalimide and zinc/glacial acetic acid analogously to Example 4.

Yield: 87.1% of theory,
Melting point: 107°–112° C.

| | | | | |
|---|---|---|---|---|
| Calculated: | C 61.99 | H 7.51 | N 5.35 | Cl 7.02 |
| Found: | 62.07 | 7.37 | 5.28 | 7.31 |

EXAMPLE 241

2-[(N-(3-(3,4-Methylenedioxy-phenoxy)-propyl)-hexahydroazepin-3-yl)-methyl]-5,6-dimethoxy-1-oxo-1,3-dihydro-isoindolehydrochloride Prepared from 2-[(N-(3-(3,4-methylenedioxy-phenoxy)-propyl)hexahydro-azepin-3-yl)-methyl]-5,6-dimethoxy-phthalimide and zinc/glacial acetic acid analogously to Example 4.

Yield: 59% of theory,
Melting point: 104°–107° C.

| | | | | |
|---|---|---|---|---|
| Calculated: | C 60.38 | H 6.94 | N 5.20 | Cl 7.31 |
| Found: | 60.40 | 7.15 | 4.95 | 7.25 |

EXAMPLE 242

2-[(N-(3-(3,4-Methylenedioxy-phenoxy)-propyl)-hexahydroazepin-3-yl)-methyl]-5,6-dimethoxy-1-oxo-1,3-dihydro-isoindolehydrochloride Prepared from 2-[(N-(3-(3,4-methylenedioxy-phenoxy)-propyl)hexahydro-azepin-3-yl)-methyl]-5,6-dimethoxy-phthalimide and zinc/glacial acetic acid analogously to Example 4.
Yield: 79.4% of theory,
Melting point: 112°–116° C.

| | | | | | | | |
|---|---|---|---|---|---|---|---|
| Calculated: | C | 62.23 | H | 7.15 | N | 5.37 | Cl 7.05 |
| Found: | | 62.16 | | 7.25 | | 4.96 | 7.03 |

EXAMPLE 243

3-[(N-(3-(Pyrid-3-yl)-propyl)-hexahydro-azepin-3-yl)methyl]-7,8-dimethoxy-2-oxo-1,3-dihydro-2H-3-benzazepinedihydrochloride-dihydrate Prepared from 7,8-dimethoxy-2-oxo-1,3-dihydro-2H-3-benzazepine and N-[3-(pyrid-3-yl)-propyl]-3-chloromethyl-hexahydro-azepine in dimethylsulphoxide with potassium tert.butoxide analogously to example 2.
Yield: 86% of theory,
Melting point: 106°–108° C.

| | | | | | | | |
|---|---|---|---|---|---|---|---|
| Calculated: | C | 58.05 | H | 7.40 | N | 7.52 | Cl 12.69 |
| Found: | | 57.94 | | 7.55 | | 7.75 | 12.42 |

EXAMPLE 244

3-[(N-(3-(Pyrid-3-yl)-propyl)-hexahydro-azepin-3-yl)methyl]-7,8-dimethoxy-2-oxo-1,3,4,5-tetrahydro-2H-3-benzazepinedihydrochloride-dihydrate Prepared from 3-[(N-(3-(pyrid-3-yl)-propyl)-hexahydro-azepin-3-yl)-methyl]-7,8-dimethoxy-2-oxo-1,3-dihydro-2H-3-benzazepine and 5 bar hydrogen in the presence of 10% palladium on charcoal in dimethylformamide at 80° C. analogously to Example 5.
Yield: 43% of theory,
Melting point: 119°–121° C.

| | | | | | | | |
|---|---|---|---|---|---|---|---|
| Calculated: | C | 57.85 | H | 7.73 | N | 7.49 | Cl 12.65 |
| Found: | | 57.74 | | 7.79 | | 7.23 | 12.50 |

EXAMPLE 245

3-[(N-(3-(Pyrid-3-yl)-propyl)-hexahydro-azepin-3-yl)methyl]-7,8-dimethoxy-1,3,4,5-tetrahydro-2H-3-benzazepinetrihydrochloride-monohydrate Prepared from 3-[(N-(3-(pyrid-3-yl)-propyl)-hexahydro-azepin-3-yl)-methyl]-7,8-dimethoxy-2-oxo-1,3,4,5-tetrahydro-2H-3-benzazepine and lithium aluminium hydride in tetrahydrofuran and diethylether analogously to Example 3.
Yield: 82% of theory,
Melting point: 139°–141° C.

| | | | | | | | |
|---|---|---|---|---|---|---|---|
| Calculated: | C | 57.39 | H | 7.85 | N | 7.43 | Cl 18.82 |
| Found: | | 57.42 | | 8.15 | | 7.56 | 19.04 |

EXAMPLE 246

2-[(N-(1-(Pyrid-3-yl)-methyl)-pyrrolidin-3-yl)-methyl]-6,7-methylenedioxy-1-oxo-1,2,3,4-tetrahydro-isoquinolinedihydrochloride-dihydrate Prepared from 6,7-methylenedioxy-1-oxo-1,2,3,4-tetrahydroisoquinoline and 3-chloromethyl-N-[(pyrid-3-yl)-methyl]pyrrolidine and dimethylsulphoxide with potassium tert.butoxide analogously to Example 2.
Yield: 46% of theory,
Melting point: 91°–93° C.

| | | | | | | | |
|---|---|---|---|---|---|---|---|
| Calculated: | C | 53.17 | H | 6.16 | N | 8.85 | Cl 14.95 |
| Found: | | 53.31 | | 5.93 | | 8.71 | 15.01 |

EXAMPLE 247

2-[(N-(1-(Pyrid-3-yl)-methyl)-pyrrolidin-3-yl)-methyl]-6,7-methylenedioxy-1,2,3,4-tetrahydro-isoquinoline-trihydrochloride-1.5 x hydrate Prepared from 2-[(N-(1-(pyrid-3-yl)-methyl)-pyrrolidin-3-yl)methyl]-6,7-methylenedioxy-1-oxo-1,2,3,4-tetrahydro-isoquinoline and lithium aluminium hydride in tetrahydrofuran and diethylether analogously to Example 3.
Yield: 67% of theory,
Melting point: 178°–181° C.

| | | | | | | | |
|---|---|---|---|---|---|---|---|
| Calculated: | C | 51.70 | H | 6.41 | N | 8.61 | Cl 21.80 |
| Found: | | 51.63 | | 6.62 | | 8.45 | 21.07 |

EXAMPLE 248

3-[(N-(2-(6-Methyl-pyrid-2-yl)-ethyl)-hexahydro-azepin-3-yl)-methyl]-7,8-dimethoxy-2-oxo-1,3-dihydro-2H-3-benzazepinedihydrochloride-dihydrate Prepared from 7,8-dimethoxy-2-oxo-1,3-dihydro-2H-3-benzazepine and N-[2-(6-methyl-pyrid-2-yl)-ethyl]-3-chloromethyl-hexahydroazepine in dimethylsulphoxide with potassium tert.butoxide analogously to Example 2.
Yield: 63% of theory,
Melting point: 134°–136° C.

| | | | | | | | |
|---|---|---|---|---|---|---|---|
| Calculated: | C | 58.05 | H | 7.40 | N | 7.52 | Cl 12.69 |
| Found: | | 58.15 | | 7.60 | | 7.45 | 12.45 |

EXAMPLE 249

3-[(N-(2-(6-Methyl-pyrid-2-yl)-ethyl)-pyrrolidin-3-yl)methyl]-7,8-dimethoxy-2-oxo-1,3-dihydro-2H-3-benzazepinedihydrochloride x 1.5 hydrate Prepared from 7,8-dimethoxy-2-oxo-1,3-dihydro-2H-3-benzazepine and 3-chloromethyl-N-[2-(6-methyl-pyrid-2-yl)-ethyl]-pyrrolidine in dimethylsulphoxide with potassium tert.butoxide analogously to Example 2.
Yield: 61% of theory,
Melting point: 78°–80° C.

| | | | | | | | |
|---|---|---|---|---|---|---|---|
| Calculated: | C | 57.58 | H | 6.96 | N | 8.06 | Cl 13.60 |
| Found: | | 57.40 | | 7.18 | | 8.24 | 13.39 |

EXAMPLE 250

3-[(N-(2-(6-Methyl-pyrid-2-yl)-ethyl)-hexahydro-azepin-3-yl)-methyl]-7,8-dimethoxy-2-oxo-1,3,4,5-tetrahydro-2H-3-benzazepine-dihydrochloride x 2.5 hydrate Prepared from 3-[(N-(2-(6-methyl-pyrid-2-yl)-ethyl)-hexahydro-azepin-3-yl)-methyl]-7,8-dimethoxy-2-oxo-1,3-dihydro-2H-3-benzazepine and 5 bar hydrogen in the presence of palladium/charcoal and dimethyl-formamide analogously to Example 5.
Yield: 34% of theory,
Melting point: 112°–114° C.

| Calculated: | C 56.93 | H 7.78 | N 7.38 | Cl 12.45 |
|---|---|---|---|---|
| Found: | 56.83 | 8.04 | 7.43 | 12.26 |

EXAMPLE 251

3-[(N-(2-(6-Methyl-pyrid-2-yl)-ethyl)-hexahydro-azepin-3-yl)-methyl]-7,8-dimethoxy-1,3,4,5-tetrahydro-2H-3-benzazepinetrihydrochloride-dihydrate Prepared from 3-[(N-(2-(6-methyl-pyrid-2-yl)-ethyl)-hexahydroazepin-3-yl)-methyl]-7,8-dimethoxy-2-oxo-1,3,4,5-tetrahydro-2H-3-benzazepine and lithium aluminium hydride in tetrahydrofuran and diethylether analogously to Example 3.
Yield: 74% of theory,
Melting point: 148°–150° C.

| Calculated: | C 55.61 | H 7.95 | N 7.20 | Cl 18.24 |
|---|---|---|---|---|
| Found: | 55.72 | 8.10 | 7.03 | 18.00 |

EXAMPLE 252

3-[(N-(2-(6-Methyl-pyrid-2-yl)-ethyl)-pyrrolidin-3-yl)methyl]-7,8-dimethoxy-2-oxo-1,3,4,5-tetrahydro-2H-3-benzazepinedihydrochloride-dihydrate Prepared from 3-[(N-(2-(6-methyl-pyrid-2-yl)-ethyl)-pyrrolidin-3-yl)-methyl]-7,8-dimethoxy-2-oxo-1,3-dihydro-2H-3-benzazepine and palladium/charcoal in dimethylformamide at 50° C. and 6 bar hydrogen pressure analogously to Example 5.
Yield: 28% of theory,
Melting point: 87°–90° C.

| Calculated: | C 56.38 | H 7.38 | N 7.89 | Cl 13.31 |
|---|---|---|---|---|
| Found: | 56.33 | 7.53 | 8.09 | 13.43 |

EXAMPLE 253

3-[(N-(2-(6-Methyl-pyrid-2-yl)-ethyl)-pyrrolidin-3-yl)methyl]-7,8-dimethoxy-1,3,4,5-tetrahydro-2H-3-benzazepinetrihydrochloride-dihydrate Prepared from 7,8-dimethoxy-1,3,4,5-tetrahydro-2H-3-benzazepine and N-[2-(6-methyl-pyrid-2-yl)-ethyl]-3-(benzenesulphonyloxymethyl)-pyrrolidine in dimethylformamide and triethylamine analogously to Example 2.
Yield: 42% of theory,
Melting point: 225°–227° C.

| Calculated: | C 54.10 | H 7.62 | N 7.57 | Cl 19.16 |
|---|---|---|---|---|
| Found: | 54.18 | 7.55 | 7.51 | 19.30 |

EXAMPLE 254

2-[(N-(3-(Indol-3-yl)-propyl)-piperidin-3-yl)-methyl]-5,6-dimethoxy-1-oxo-1,3-dihydro-isoindole x 1.5 benzenesulphonatetrihydrate Prepared from 2-[(piperidin-3-yl)-methyl]-5,6-dimethoxy-1-oxo-1,3-dihydro-isoindole and 3-(3-benzenesulphonyloxy-propyl)-indole in dimethylformamide and triethylamine analogously to Example 1.
Yield: 45% of theory,
Melting point: 87°–89° C.

| Calculated: | C 58.51 | H 6.54 | N 5.68 |
|---|---|---|---|
| Found: | 58.66 | 6.43 | 5.34 |

EXAMPLE 255

2-[(N-(3-(Indol-3-yl)-propyl)-piperidin-3-yl)-methyl]-6,7-dimethyl-1-oxo-1,2,3,4-tetrahydro-isoquinoline-benzenesulphonatedihydrate Prepared from 2-[(piperidin-3-yl)-methyl]-5,6-dimethyl-1-oxo-1,2,3,4-tetrahydro-isoquinoline and 3-(3-benzenesulphonyloxypropyl)-indole in dimethylformamide and triethylamine analogously to Example 1.
Yield: 94% of theory,
Melting point: 117°–119° C.

| Calculated: | C 65.46 | H 7.27 | N 6.73 |
|---|---|---|---|
| Found: | 65.51 | 6.91 | 6.72 |

EXAMPLE 256

3-[(N-(3-(Indol-3-yl)-propyl)-pyrrolidin-3-yl)-methyl]-7,8-dimethoxy-2-oxo-1,3,4,5-tetrahydro-2H-3-benzazepinehydrochloride-monohydrate Prepared from 3-[(N-(3-(indol-3-yl)-propyl)-pyrrolidin-3-yl)methyl]-7,8-dimethoxy-2-oxo-1,3-dihydro-2H-3-benzazepine and 5 bar hydrogen in the presence of palladium/charcoal in dimethylformamide at 80° C. analogously to Example 5.
Yield: 58% of theory,
Melting point: 128°–130° C.

| Calculated: | C 65.16 | H 7.42 | N 8.14 | Cl 6.87 |
|---|---|---|---|---|
| Found: | 65.12 | 7.55 | 8.11 | 7.06 |

EXAMPLE 257

3-[(N-(3-(Indol-3-yl)-propyl)-hexahydro-azepin-3-yl)methyl]-7,8-dimethoxy-2-oxo-1,3,4,5-tetrahydro-2H-3-benzazepinemonohydrate Prepared from 3-[(hexahydro-azepin-3-yl)-methyl]-7,8-dimethoxy-2-oxo-1,3,4,5-tetrahydro-2H-3-benzazepine and 3-(3-benzenesulphonyloxy-propyl)-indole in dimethylformamide and triethylamine analogously to Example 1.
Yield: 49% of theory,
Melting point: 56°–58° C.

| Calculated: | C 70.98 | H 8.14 | N 8.27 |
|---|---|---|---|
| Found: | 71.08 | 8.10 | 8.16 |

EXAMPLE 258

3-[(N-(3-(Indol-3-yl)-propyl)-hexahydro-azepin-3-yl)methyl]-7,8-methylenedioxy-1,3,4,5-tetrahydro-2H-3-benzazepinedihydrochloride-monohydrate Prepared from 3-[(N-(3-(indol-3-yl)-propyl)-hexahydro-azepin-3-yl)-methyl]-7,8-methylenedioxy-2-oxo-1,3,4,5-tetrahydro-2H-3-benzazepine and lithium aluminium hydride in diethylether and tetrahydrofuran analogously to Example 3.
Yield: 56% of theory,
Melting point: 155°–158° C.

| Calculated: | C 62.26 | H 7.50 | N 7.63 | Cl 12.88 |
|---|---|---|---|---|
| Found: | 62.31 | 7.82 | 7.40 | 12.89 |

EXAMPLE 259

3-[(N-(3-(Indol-3-yl)-propyl)-pyrrolidin-3-yl)-methyl]-7,8-dimethoxy-1,3,4,5-tetrahydro-2H-3-benzazepine-dihydrochloridemonohydrate Prepared from 3-[(N-(3-(indol-3-yl)-propyl)-pyrrolidin-3-yl)methyl]-7,8-dimethoxy-2-oxo-1,3,4,5-tetrahydro-2H-3-benzazepine and lithium aluminium hydride in diethylether and tetrahydrofuran analogously to Example 3.
Yield: 60% of theory,
Melting point: 125°–128° C.

| Calculated: | C 62.44 | H 7.67 | N 7.80 | Cl 13.16 |
|---|---|---|---|---|
| Found: | 62.35 | 7.87 | 7.59 | 13.67 |

EXAMPLE 260

2-[(N-(3-(Indol-3-yl)-propyl)-piperidin-3-yl)-methyl]-6,7-dimethyl-1,2,3,4-tetrahydro-isoquinoline-dihydrochloridemonohydrate Prepared from 2-[(N-(3-(indol-3-yl)-propyl)-piperidin-3-yl)methyl]-6,7-dimethyl-1-oxo-1,2,3,4-tetrahydro-isoquinoline and lithium aluminium hydride in diethylether and tetrahydrofuran analogously to Example 3.
Yield: 90% of theory,
Melting point: 198°–201° C.

| Calculated: | C 66.38 | H 8.16 | N 8.29 | Cl 14.00 |
|---|---|---|---|---|
| Found: | 66.29 | 8.21 | 8.46 | 13.82 |

EXAMPLE 261

3-[(N-(3-(Indol-3-yl)-propyl)-hexahydro-azepin-3-yl)methyl]-7,8-methylenedioxy-2-oxo-1,3,4,5-tetrahydro-2H-3-benzazepine-monohydrate Prepared from 3-[(hexahydro-azepin-3-yl)-methyl]-7,8-methylenedioxy-2-oxo-1,3,4,5-tetrahydro-2H-3-benzazepin and 3-(3-benzenesulphonyloxy-propyl)-indole analogously to Example 1.
Yield: 61.5% of theory,
Melting point: 62°–64° C.

| Calculated: | C 70.84 | H 7.59 | N 8.55 |
|---|---|---|---|
| Found: | 70.73 | 7.59 | 8.42 |

EXAMPLE 262

2-[(N-(3-(Indol-3-yl)-propyl)-pyrrolidin-3-yl)-methyl]-6,7-dimethyl-1,2,3,4-tetrahydro-isoquinoline-dihydrochloridesemihydrate Prepared from 2-[(N-(3-(indol-3-yl)-propyl)-pyrrolidin-3-yl)methyl]-6,7-dimethyl-1-oxo-1,2,3,4-tetrahydro-isoquinoline and lithium aluminium hydride in ether analogously to Example 3.
Yield: 86% of theory,
Melting point: 143°–145° C.

| Calculated: | C 67.06 | H 7.92 | N 8.69 | Cl 14.66 |
|---|---|---|---|---|
| Found: | 66.92 | 8.07 | 8.48 | 14.87 |

EXAMPLE 263

2-[(N-(3-(Indol-3-yl)-propyl)-pyrrolidin-3-yl)-methyl]-6,7-dimethyl-1-oxo-1,2,3,4-tetrahydro-isoquinoline-hydrochloride x 1.5 hydrate Prepared from 2-[(pyrrolidin-3-yl)-methyl]-6,7-dimethyl-1-oxo-1,2,3,4-tetrahydro-isoquinoline and 3-(3-benzenesulphonyloxypropyl)-indole analogously to Example 1.
Yield: 67% of theory,
Melting point: 117°–120° C.

| Calculated: | C 67.69 | H 7.78 | N 8.77 | Cl 7.40 |
|---|---|---|---|---|
| Found: | 67.62 | 7.80 | 8.72 | 7.93 |

EXAMPLE 264

3-[(N-(3-(Indol-3-yl)-propyl)-pyrrolidin-3-yl)-methyl]-7,8-methylenedioxy-1,3,4,5-tetrahydro-2H-3-benzazepinedihydrochloride 1.5 x hydrate Prepared from 7,8-methylenedioxy-1,3,4,5-tetrahydro-2H-3-benzazepine and 3-(benzenesulphonyloxymethyl)-N-[3-(indol-3-yl)propyl]-pyrrolidine analogously to Example 2.
Yield: 75% of theory,
Melting point: 191°–193° C.

| Calculated: | C 61.01 | H 7.21 | N 7.90 | Cl 13.34 |
|---|---|---|---|---|
| Found: | 60.90 | 7.27 | 7.85 | 13.70 |

EXAMPLE 265

3-[(N-(3-(Indol-3-yl)-propyl)-hexahydro-azepin-3-yl)methyl]-7,8-dimethoxy-1,3,4,5-tetrahydro-2H-3-benzazepinedihydrochloride-monohydrate Prepared from 3-[(N-(3-(indol-3-yl)-propyl)-hexahydro-azepin-3-yl)-methyl]-7,8-dimethoxy-2-oxo-1,3,4,5-tetrahydro-2H-3-benzazepine and lithium aluminium hydride in tetrahydrofuran and diethylether analogously to Example 3.
Yield: 53% of theory,
Melting point: 158°–160° C.

| | | | | |
|---|---|---|---|---|
| Calculated: | C 63.58 | H 8.00 | N 7.41 | Cl 12.51 |
| Found: | 63.41 | 8.18 | 7.36 | 12.23 |

EXAMPLE 266

3-[(N-(3-(Indol-3-yl)-propyl)-pyrrolidin-3-yl)-methyl]-7,8-dimethyl-1,3,4,5-tetrahydro-2H-3-benzazepine-dihydrochloridemonohydrate Prepared from 3-[(N-(3-(indol-3-yl)-propyl)-pyrrolidin-3-yl)methyl]-7,8-dimethyl-2-oxo-1,3,4,5-tetrahydro-2H-3-benzazepine and lithium aluminium hydride in tetrahydrofuran/ether analogously to Example 3.
Yield: 65% of theory,
Melting point: 168°-170° C.

| | | | | |
|---|---|---|---|---|
| Calculated: | C 66.39 | H 8.16 | N 8.29 | Cl 13.99 |
| Found: | 66.29 | 8.44 | 8.08 | 14.08 |

EXAMPLE 267

2-[(N-(3-(Indol-3-yl)-propyl)-pyrrolidin-3-yl)-methyl]-5,6-dimethoxy-phthalimide-semihydrate Prepared from 2-[(pyrrolidin-3-yl)-methyl]-5,6-dimethoxyphthalimide and 3-(3-benzenesulphonyloxypropyl)-indole analogously to Example 1.
Yield: 39% of theory,
Melting point: 144°-146° C.

| | | | | |
|---|---|---|---|---|
| Calculated | C 68.40 | H 6.62 | N 9.20 | |
| Found: | 68.50 | 6.71 | 9.10 | |

EXAMPLE 268

2-[(N-(3-(Indol-3-yl)-propyl)-pyrrolidin-3-yl)-methyl]-5,6-dimethoxy-1,3-dihydro-isoindole-dihydrochloride-monohydrate Prepared from 2-[(N-(3-(indol-3-yl)-propyl)-pyrrolidin-3-yl)methyl]-5,6-dimethoxy-phthalimide and lithium aluminium hydride in tetrahydrofuran analogously to Example 3.
Yield: 87% of theory,
Melting point: 262°-264° C.

| | | | | |
|---|---|---|---|---|
| Calculated: | C 61.17 | H 7.30 | N 8.23 | Cl 13.89 |
| Found: | 61.34 | 7.26 | 7.92 | 13.90 |

EXAMPLE I

Tablets containing 7.5 mg of 3-[(N-(2-(naphth-2-yl)-ethyl)piperidin-3-yl)-methyl]-7,8-dimethoxy-2-oxo-1,3,4,5-tetrahydro2H-3-benzazepine-hydrochloride Composition:
1 tablet contains:

| | |
|---|---|
| Active substance | 7.5 mg |
| Corn starch | 59.5 mg |
| Lactose | 48.0 mg |
| Polyvinylpyrrolidone | 4.0 mg |
| Magnesium stearate | 1.0 mg |
| | 120.0 mg |

Method of Preparation

The active substance, corn starch, lactose and polyvinylpyrrolidone are mixed together and moistened with water. The moist mixture is pushed through a screen with a mesh size of 1.5 mm and dried at about 45° C. The dry granulate is passed through a 1.0 mm mesh screen and mixed with magnesium stearate. The final mixture is compressed in a tablet press with dies 7 mm in diameter provided with a dividing notch to form tablets. Weight of tablet: 120 mg.

EXAMPLE II

Coated tablets containing 5 mg of 3-[(N-(2-(naphth-2-yl)ethyl)-piperidin-3-yl)-methyl]-7,8-dimethoxy-2-oxo-1,3,4,5-tetrahydro-2H-3-benzazepine-hydrochloride

| 1 tablet core contains: | |
|---|---|
| Active substance | 5.0 mg |
| Corn starch | 41.5 mg |
| Lactose | 30.0 mg |
| Polyvinylpyrrolidone | 3.0 mg |
| Magnesium stearate | 0.5 mg |
| | 80.0 mg |

Method of Preparation

The active substance, corn starch, lactose and polyvinylpyrrolidone are throughly mixed and moistened with water. The moist mass is forced through a 1 mm screen, dried at about 45° C. and then the granulate is passed through the same screen. After magnesium stearate has been added, convex tablet cores with a diameter of 6 mm are compressed in a tablet making machine. The tablet cores thus produced are coated in known manner with a coating consisting essentially of sugar and talc. The finished coated tablets are polished with wax. Weight of coated tablet: 130 mg.

EXAMPLE III

Ampoules containing 5 mg of 3-[(N-(2-(naphth-2-yl)piperidin-3-yl)-methyl]-7,8-dimethoxy-2-oxo-1,3,4,5-tetrahydro-2H-3-benzazepin-2-one-hydrochloride

| 1 ampoule contains: | |
|---|---|
| Active substance | 5.0 mg |
| Sorbitol | 50.0 mg |
| Water for injections    ad | 2.0 mg |

Method of Preparation

In a suitable mixing vessel the active substance is dissolved in water for injections and the solution is made isotonic with sorbitol. After being filtered through a diaphragm filter the solution is transferred under a current of $N_2$ into purified and sterilized ampoules and auto-claved for 20 minutes in a jet of steam.

EXAMPLE IV

Suppositories containing 10 mg of 3-[(N-(2-(naphth-2-yl)ethyl)-piperidin-3-yl)-methyl]-7,8-dimethoxy-2-oxo-1,3,4,5-tetrahydro-2H-3-benzazepine-hydrochloride

| 1 suppository contains: | |
|---|---|
| Active substance | 0.010 g |
| Hard fat (e.g. Witepsol H 19 and W 45) | 1.690 g |
| | 1.700 g |

Method of Preparation

The hard fat is melted. At 38° C. the ground active substance is homogeneously dispersed in the melt. It is cooled to 35° C. and poured into slightly chilled suppository moulds.

EXAMPLE V

Drops solution containing 10 mg of 3-[(N-(2-(naphth-2-yl)ethyl)-piperidin-3-yl)-methyl]-7,8-dimethoxy-2-oxo-1,3,4,5-tetrahydro-2H-3-benzazepine-hydrochloride

| 100 ml of solution contain: | |
|---|---|
| Active substance | 0.2 g |
| Hydroxyethylcellulose | 0.15 g |
| Tartaric acid | 0.1 g |
| Sorbitol solution with 70% dry matter | 30.0 g |
| Glycerol | 10.0 g |
| Benzoic acid | 0.15 g |
| Dist. water ad | 100 ml |

Method of Preparation

The distilled water is heated to 70° C. The hydroxyethylcellulose, benzoic acid and tartaric acid are dissolved therein with stirring. The mixture is cooled to ambient temperature and the glycerol and sorbitol solution are added with stirring. At ambient temperature the active substance is added and stirred until completely dissolved. The syrup is then evacuated of any air with stirring.

What is claimed is:

1. A compound for the formula I

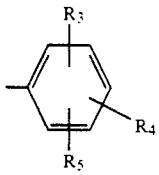

wherein, $R_1$ is hydrogen, halogen, trifluoromethyl, nitro, amino, alkylamino, dialkylamino, alkyl, hydroxy, alkoxy or phenylalkoxy, wherein each alkyl moiety contains 1 to 3 carbon atoms;

$R_2$ is hydrogen, halogen, hydroxy, alkoxy, phenylalkoxy or alkyl, wherein each alkyl moiety may contain 1 to 3 carbon atoms; or, $R_1$ and $R_2$ together form an alkylenedioxy group of 1 or 2 carbon atoms;

E is a straight chain alkylene group of 1 to 3 carbon atoms optionally substituted by an alkyl group of 1 to 3 carbon atoms; and, A, B, G, m, n, and R are as set forth in options (i) and (ii) which appear below:

Option (i)

A is a $-CH_2-CH_2-$, $-CH=CH-$, $-CH_2-CO-$ or $-NH-CO-$ group; and,

B is a $-\underline{C}H_2-CH_2-$, $-\underline{C}H_2CO-$ or $-\underline{C}H_2CS-$ group; or, A is a $-CO-CO-$ or $-\underline{C}HOH-CO-$ group; and, B is a $-CH_2-CH_2-$ group;

in which the atoms indicated by underlining are attached to the phenyl nucleus;

G is a straight-chain alkylene group of 1 to 5 carbon atoms which is optionally substituted by an alkyl group of 1 to 3 carbon atoms, or G is the group $-G'-G''-$, wherein G' is attached to the nitrogen atom and is a straight-chain group of 2 to 4 carbon atoms which is optionally substituted by an alkyl group of 1 to 3 carbon atoms and G'' is attached to the group R and is an oxa, thia, imino, methylimino, sulphinyl or sulfonyl group;

m is 1, 2, 3, 4 or 5;

n is 0, 1 or 2, with the proviso that n+m must equal 3, 4 or 5; and,

R is a group of the formula

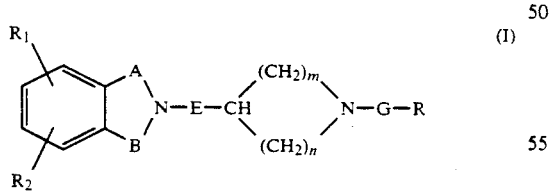

in which $R_3$ is hydrogen, halogen, alkyl or alkoxy of 1 to 3 carbon atoms, hydroxy, nitro, cyano or trifluoromethyl;

$R_4$ is hydrogen, alkoxy, alkylsulfonyloxy of 1 to 3 carbon atoms, amino, alkylamino or dialkylamino of 1 to 3 carbon atoms, or alkanoylamino of 2 or 3 carbon atoms; or, $R_3$ and $R_4$ together form an alkylenedioxy group of 1 or 2 carbon atoms; and, $R_5$ is hydrogen, halogen, hydroxy, or alkyl or alkoxy of 1 to 3 carbon atoms;

Option (ii)

A is a $-CH_2-$, $-CH_2-CH_2-$ or $-CH=CH-$ group;

B is a $-CH_2-$, $-CH_2-CH_2-$, $-CO-$ or $-\underline{C}H_2CO-$ group in which the atom indicated by underlining is attached to the phenyl nucleus;

G is a straight-chain alkylene group of 1 to 6 carbon atoms which is optionally substituted by an alkyl group of 1 to 3 carbon atoms, or G is the group $-G'-G''-$, wherein G' is attached to the nitrogen atom and is a straight-chain alkylene group of 2 to 5 carbon atoms which is optionally substituted by an alkyl group of 1 to 3 carbon atoms and G'' is attached to the group R and is an oxa, thia, sulphinyl or sulfonyl group, or an imino group which is optionally substituted by alkyl of 1 to 3 carbon atoms;

143 m is 1, 2, 3, 4, 5 or 6;
n is 0, 1, 2 or 3, with the proviso that m+n must equal 3, 4, 5 or 6; and,
R is a ring carbon- or ring nitrogen-attached heterocyclic ring system selected from the group consisting of pyrrol-2-yl, pyrrol-3-yl, fur-2-yl, fur-3-yl, benzofur-2-yl, benzofur-3-yl, thien-2-yl, thien-3-yl, 4,5,6,7-tetrahydro-benzothien-2-yl, 4,5,6,7-tetrahydro-benzothien-3-yl, benzothien-2-yl, benzothien-3-yl, benzothien-4-yl, benzothien-5-yl, benzothien-6-yl, benzothien-7-by, pyrazol-1-yl, pyrazol-3-yl, imidazol-1-yl, imidazol-2-yl, imidazol-4-yl, imidazol-4(5)-yl, imidazopyrid-3-yl, oxazol-4-yl, oxazol-5-yl, isoxazol-3-yl, isoxazol-4-yl, isoxazol-5-yl, thiazol-5-yl, benzooxazol-2-yl, benzoisoxazol-3-yl, benzothiazol-2-yl, benzoisothiazol-3-yl, benzopyrazol-1-yl, benzopyrazol-3-yl, pyrid-2-yl, pyrid-3-yl, pyrid-4-yl, pyrid-3-yl-N-oxide, quinol-2-yl, quinol-4-yl, isoquinol-1-yl, isoquinol-4-yl, isoquinol-4-yl-N-oxide, indol-2-yl, and, indol-3-yl, wherein the carbon structure of the cyclic group optionally is mono- or disubstituted by substituents selected from halogen atoms, alkyl, hydroxy, alkoxy, phenylalkoxy, phenyl, dimethoxyphenyl, nitro, amino, acetylamino, carbamoylamino, N-alkylcarbamoylamino, hydroxymethyl, mercapto, alkylmercapto, alkylsuphinyl, alkylsulphonyl, alkylsulphonyloxy, alkylsulphonylamino, alkoxycarbonylmethoxy, carboxymethoxy and alkoxymethyl groups, or optionally is substituted by a methylenedioxy or ethylenedioxy group, wherein any imino group in the said heteroaromatic ring optionally is substituted by an alkyl, phenylalkyl or phenyl group, wherein in the event the said cyclic ring contains an indolyl group it additionally optionally is substituted by a methylamino, dimethylamino, methoxy, acetoxy, trifluoromethyl, trichloromethyl, carboxy, methoxycarbonyl, ethoxycarbonyl, cyano, cyclohexyl, trimethoxyphenyl, trifluorophenyl, trichlorophenyl, tribromophenyl or dihaloaminophenyl group or by a benzyl, benzyloxy or benzylamino group optionally mono-, di- or trisubstituted in the phenyl ring of the benzyl nucleus by methoxy or methyl groups, or a naphthyl group optionally substituted by an alkylenedioxy group containing 1 or 2 carbon atoms or optionally mono- or disubstituted by substituents selected from halogen atoms, alkyl, hydroxy, alkoxy, alkylsulphonyloxy, nitro, amino and alkanoylamino groups, or a benzyloxy or 4,5,6,7-tetrahydrobenzothienyl group, or, if B represents a —CH$_2$— or —CO— group, R may also represent a phenyl group optionally substituted by an alkylenedioxy group containing 1 to 2 carbon atoms or by a halogen atom or by an alkyl, hydroxy, alkoxy, phenylalkoxy, nitro, amino, alkanoylamino, alkylsulphonylamino, bis(alkylsuphonyl)amino, alkylsuphonyloxy, trifluoromethyl, trifluoromethoxy or trifluoromethylsulphonyloxy, or disubstituted by substituents selected from halogen atoms, alkyl and alkoxy groups, a trialkoxyphenyl group, a tetraalkylphenyl group or a dihaloaminophenyl group;
wherein, unless otherwise stated, the alkyl, alkoxy and alkanoyl moieties mentioned in the definition of the group R each contain 1 to 2 carbon atoms;

144 or a pharmaceutically acceptable acid addition salt thereof.

2. In accordance with claim 1, a compound of the formula (I)(i)

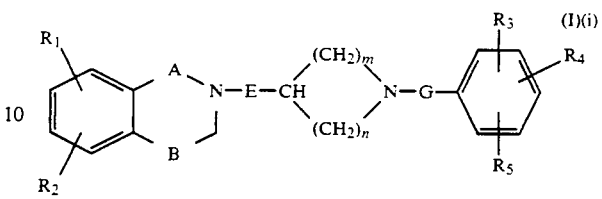

wherein
R$_1$ is hydrogen, halogen, trifluoromethyl, nitro, amino, alkylamino, dialkylamino, alkyl, hydroxy, alkoxy or phenylalkoxy, wherein each alkyl moiety contains 1 to 3 carbon atoms;
R$_2$ is hydrogen, halogen, hydroxy, alkoxy, phenylalkoxy or alkyl, wherein each alkyl moiety may contain 1 to 3 carbon atoms; or,
R$_1$ and R$_2$ together form an alkylenedioxy group of 1 or 2 carbon atoms;
A is a —CH$_2$—CH$_2$—, —CH=CH—, —CH$_2$—CO— or —NH—CO— group; and,
B is a methylene, carbonyl or thiocarbonyl group; or,
A is a —CO—CO— or —CHOH—CO— group; and,
B is a methylene group;
in which the atoms indicated by underlining are attached to the phenyl nucleus;
E is a straight chain alkylene group of 1 to 3 carbon atoms, optionally substituted by an alkyl group of 1 to 3 carbon atoms;
G is a straight-chain alkylene group of 1 to 5 carbon atoms which is optionally substituted by an alkyl group of 1 to 3 carbon atoms, or
G is the group —G'—G"—, wherein G' is attached to the nitrogen atom and is a straight-chain alkylene group of 2 to 4 carbon atoms which is optionally substitutued by an alkyl group of 1 to 3 carbon atoms and G" is attached to the group R and is an oxa, thia, imino, methylimino, sulphinyl or sulfonyl group;
m is 1, 2, 3, 4 or 5;
n is 0, 1 or 2, with the proviso that n+m must equal 3, 4 or 5;
R$_3$ is hydrogen, halogen, alkyl or alkoxy of 1 to 3 carbon atoms, hydroxy, nitro, cyano or trifluoromethyl;
R$_4$ is hydrogen, alkoxy, alkylsulfonyloxy of 1 to 3 carbon atoms, amino, alkylamino or dialkylamino of 1 to 3 carbon atoms, or alkanoylamino of 2 or 3 carbon atoms; or,
R$_3$ and R$_4$ together form an alkylenedioxy group of 1 or 2 carbon atoms; and,
R$_5$ is hydrogen, halogen, hydroxy, or alkyl or alkoxy of 1 to 3 carbon atoms;
or a pharmaceutically acceptable acid addition salt thereof.

3. A compound of formula (I)(i), in accordance with claim 2, wherein,
A, B, m, and n are defined as in claim 2;
E is a methylene or ethylene group;
G is an n-alkylene group of 1 to 4 carbon atoms, or G is the group —G'—G" wherein G' is attached to the nitrogen atom and is ethylene or n-propylene and G" is attached to the phenyl ring and is an oxa, thia, imino, methylimino, sulfinyl or sulphonyl group;

$R_1$ is an hydrogen, fluorine, chlorine, or bromine atom, or a hydroxy, methoxy, triflouromethyl, methylamino or dimethylamino group;

$R_2$ is a hydrogen, chlorine or bromine atom or a methoxy group; or, $R_1$ and $R_2$ together form a methylenedioxy group;

$R_3$ is a hydrogen, fluorine, chlorine or bromine atom or a methyl, hydroxy, methoxy or nitro group;

$R_4$ is a hydrogen atom or a methoxy, methanesulphonyloxy, amino or acetylamino group; or, $R_3$ and $R_4$ together form a methylenedioxy group; and, $R_5$ is a hydrogen, chlorine or bromine atom or a methoxy group, or a pharmaceutically acceptable acid addition salt thereof.

4. A compound of formula (I)(i), in accordance with claim 2, wherein, m and n are defined as in claim 2;

A is a —CH$_2$—CH$_2$— or —CH=CH— group and B is a methylene or carbonyl group; or, A is a —CO—CO— group and B is a methylene group;

E is a methylene or ethylene group;

G is a straight chain alkylene group of 2 to 4 carbon atoms, or G is the group —G'—G"—, wherein G' is attached to the nitrogen atom and is ethylene or n-propylene and G" is attached to the phenyl ring and is an oxa group;

$R_1$ is a hydrogen atom or a methoxy group;

$R_2$ is a hydrogen atom or a methoxy group; or, $R_1$ and $R_2$ together form a methylenedioxy group;

$R_3$ is a hydrogen atom or a methyl, hydroxy or methoxy group;

$R_4$ is a hydrogen atom or a methoxy group; or, $R_3$ and $R_4$ together form a methylenedioxy group; and, $R_5$ is a hydrogen atom;

or a pharmaceutically acceptable acid addition salt thereof.

5. 3-[(N-(2-(3,4-Dimethoxy-phenyl)-ethyl)-piperidin-3-yl)-methyl]-7,8-dimethoxy-1,3,4,5-tetrahydro-2H-3-benzazepin-2-one, or a pharmaceutically acceptable acid addition salt thereof.

6. 3-[(N-(2-(3,4-Dimethoxy-phenyl)-ethyl)-piperidin-2-yl)-ethyl-2]-7,8-dimethoxy-1,3,4,5-tetrahydro-2H-3-benzazepin-2-one, or a pharmaceutically acceptable acid addition salt thereof.

7. A compound of formula I, in accordance with claim 1, wherein, $R_1$ is hydrogen, halogen, trifluoromethyl, nitro, amino, alkylamino, dialkylamino, alkyl, hydroxy, alkoxy or phenylalkoxy, wherein each alkyl moiety contains 1 to 3 carbon atoms;

$R_2$ is hydrogen, halogen, hydroxy, alkoxy, phenylalkoxy or alkyl, wherein each alkyl moiety may contain 1 to 3 carbon atoms; or, $R_1$ and $R_2$ together form an alkylenedioxy group of 1 to 2 carbon atoms;

E is a straight chain alkylene group of 1 to 3 carbon atoms optionally substituted by an alkyl group of 1 to 3 carbon atoms; A is a —CH$_2$—, —CH$_2$—CH$_2$— or —CH=CH— group;

B is a —CH$_2$—, —CH$_2$—CH$_2$—, —CO— or —$\underline{C}$H$_2$CO— group in which the atom indicated by underlining is attached to the phenyl nucleus;

G is a straight-chain alkylene group of 1 to 6 carbon atoms which is optionally substituted by an alkyl group of 1 to 3 carbon atoms, or G is the group —G'—G", wherein G' is attached to the nitrogen atom and is a straight-chain alkylene group of 2 to 5 carbon atoms which is optionally substituted by an alkyl group of 1 to 3 carbon atoms and G" is attached to the group R and is an oxa, thia, sulphinyl or sulfonyl group, or an imino group which is optionally substituted by alkyl of 1 to 3 carbon atoms;

m is 1, 2, 3, 4, 5 or 6;

n is 0, 1, 2, or 3, with the proviso that m+n must equal 3, 4, 5 or 6; and,

R is a ring carbon- or ring nitrogen-attached heterocyclic ring system selected from the group consisting of pyrrol-2-yl, pyrrol-3-yl, fur-2-yl, fur-3-yl, benzofur-2-yl, benzofur-3-yl, thien-2-yl, thien-3-yl, 4,5,6,7-tetrahydro-benzothien-2-yl, 4,5,6,7-tetrahydro-benzothien-3-yl, benzothien-2-yl, benzothien-3-yl, benzothien-4-yl, benzothien-5-yl, benzothien-6-yl, benzothien-7-yl, pyrazol-1-yl, pyrazol-3-yl, imidazol-1-yl, imidazol-2-yl, imidazol-4-yl, imidazol-4(5)-yl, imidazopyrid-3-yl, oxazol-4-yl, oxazol-5-yl, isoxazol-3-yl, isoxazol-4-yl, isoxazol-5-yl, thiazol-5-yl, benzooxazol-2-yl, benzoisoxazol-3-yl, benzothiazol-2-yl, benzoisothiazol-3-yl, benzopyrazol-1-yl, benzopyrazol-3-yl, pyrid-2-yl, pyrid-3-yl, pyrid-4-yl, pyrid-3-yl-N-oxide, quinol-2-yl, quinol-4-yl, isoquinol-1-yl, isoquinol-4-yl, isoquinol-4-yl-N-oxide, indol-2-yl, and, indol-3-yl, wherein the carbon structure of the cyclic group optionally is mono- or disubstituted by substituents selected from halogen atoms, alkyl, hydroxy, alkoxy, phenylalkoxy, phenyl, dimethoxyphenyl, nitro, amino, acetylamino, carbamoylamino, N-alkylcarbamoylamino, hydroxymethyl, mercapto, alkylmercapto, alkylsuphinyl, alkylsulphonyl, alkylsulphonyloxy, alkylsulphonylamino, alkoxycarbonylmethoxy, carboxymethoxy and alkoxymethyl groups, or optionally is substituted by a methylenedioxy or ethylenedioxy group, wherein any imino group in the said heteroaromatic ring optionally is substituted by an alkyl, phenylalkyl or phenyl group, wherein in the event the said cyclic ring contains an indolyl group it additionally optionally is substituted by a methylamino, dimethylamino, methoxy, acetoxy, trifluoromethyl, trichloromethyl, carboxy, methoxycarbonyl, ethoxycarbonyl, cyano, cyclohexyl, trimethoxyphenyl, trifluorophenyl, trichlorophenyl, tribromophenyl or dihaloaminophenyl group or by a benzyl, benzyloxy or benzylamino group optionally mono-, di- or trisubstituted in the phenyl ring of the benzyl nucleus by methoxy or methyl groups, or a naphthyl group optionally substituted by an alkylenedioxy group containing 1 or 2 carbon atoms or optionally mono- or disubstituted by substituents selected from halogen atoms, alkyl, hydroxy, alkoxy, alkylsulphonyloxy, nitro, amino and alkanoylamino groups, or a benzyloxy or 4,5,6,7-tetrahydrobenzothienyl group, or, if B represents a —CH$_2$— or —CO— group, R may also represent a phenyl group optionally substituted by an alkylenedioxy group containing 1 to 2 carbon atoms or by a halogen atom or by an alkyl, hydroxy, alkoxy, phenylalkoxy, nitro, amino, alkanoylamino, alkylsulphonylamino, bis(alkylsuphonyl)amino, alkylsuphonyloxy, trifluoromethyl, trifluoromethoxy or trifluoromethylsulphonyloxy, or disubstituted by substituents selected from halogen atoms, alkyl and alkoxy groups, a trialkoxyphenyl group, a tetraalkylphenyl group or a dihaloaminophenyl group;

wherein, unless otherwise stated, the alkyl, alkoxy and alkanoyl moieties mentioned in the definition of the group R each contain 1 to 3 carbon atoms; or an N-oxide or a pharmaceutically acceptable acid addition salt thereof.

8. A compound of formula I, as claimed in claim 7, wherein,

A, B, m and n are defined as in claim 7;

E is a straight-chained alkylene group of 1 to 3 carbon atoms;

G is a straight-chain alkylene group of 1 to 6 carbon atoms; or

G is the group —G'—G", wherein G' is attached to the nitrogen atom and is a straight-chain alkylene group of 2 to 5 carbon atoms and G" is attached to the group R and is an oxa, methylimino or ethylimino group;

$R_1$ is a methyl or methoxy group;

$R_2$ is a methyl or methoxy group; or, $R_1$ and $R_2$ together form a methylenedioxy group; and, R is an optionally methyl-substituted furyl, thienyl, pyridyl, benzofuryl or benzothienyl group, a benzothienyl group substituted by a halogen atom or by a methoxy or methanesulphonyloxy group, an indolyl or N-methyl-indolyl group optionally substituted by a hydroxy, methoxy or benzyloxy group, a dimethyl-thienyl or dimethoxy-isoquinolyl group, a naphthyl group optionally mono- or disubstituted by methyl or methoxy groups, whilst the substituents may be identical or different, or, if B represents a —CH$_2$— or —CO— group, a phenyl group optionally substituted by a methylenedioxy group, a phenyl group mono- or disubstituted by a chlorine or bromine atom or methyl or methoxy groups, whilst the substituents may be identical or different, a phenyl group substituted by a hydroxy, benzyloxy, methanesulphonyloxy, trifluoro-methanesulphonyloxy, trifluoromethyl, trifluoromethoxy, nitro, amino, acetamido, methanesulphonylamino or bis(methanesulphonyl)amino group, or a trimethoxy-phenyl, tetramethylphenyl or dihaloaminophenyl group;

or an N-oxide and or a pharmaceutically acceptable acid addition salt thereof.

9. In accordance with claim 7, a compound of the formula Ia

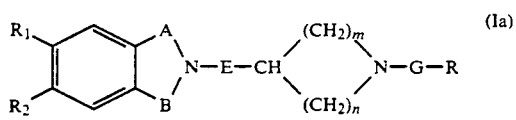

wherein

R, $R_1$, $R_2$, A, B, E, G, m and n are defined as in claim 7, or an N-oxide or a pharmaceutically acceptable acid addition salt thereof.

10. A compound of formula Ia, as claimed in claim 9, wherein

A represents a —CH$_2$CH$_2$— group,

B represents a —CH$_2$—, —CH$_2$—CH$_2$—, —CO— or —CH$_2$CO— group, wherein the carbon atom designated by underlining is linked to the phenyl nucleus, E represents a methylene or ethylene group, G is a straight-chain alkylene group of 2 to 4 carbon atoms; or G is the group —G'—G", wherein G' is attached to the nitrogen atom and is a straight-chain alkylene group of 3 to 4 carbon atoms and G" is attached to the group R and is an oxa group;

$R_1$ represents a methoxy group;

$R_2$ represents a methoxy group; or, $R_1$ and $R_2$ together represent a methylenedioxy group;

m is the number 2, 3 or 4;

n is the number 1; and,

R is a naphth-2-yl, 6-methoxy-naphth-2-yl, 5-methyl-6-methoxy-naphth-2-yl, thien-2-yl, benzofur-2-yl or benzothien-3-yl group or, if B represents a —CH$_2$— or —CO— group, a 4-methoxyphenyl or 3,4-dimethoxyphenyl group;

or a pharmaceutically acceptable acid addition salt thereof.

11. A compound in accordance with claim 9, selected from the group consisting of:

a) 3-[(N-(2-(naphth-2-yl)-ethyl)-piperid-3-yl)methyl]-7,8-dimethoxy-2-oxo-1,3,4,5-tetrahydro-2H-3-benzazepine, b) 3-[(N-(2-(5-methyl-6-methoxy-naphth-2-yl)-ethyl)-piperid-3-yl)-methyl]-7,8-dimethoxy-2-oxo-1,3,4,5-tetrahydro-2H-3-benzazepine, c) 3-[2-(N-(2-(6-methoxy-naphth-2-yl)-ethyl)-piperid-2-yl)-ethyl]-7,8-dimethoxy-2-oxo-1,3,4,5-tetrahydro-2H-3-benzazepine, d) 2-[(N-(2-(6-methoxy-naphth-2-yl)-ethyl)-hexahydroazepin-3-yl)-methyl]-6,7-methylenedioxy-1-oxo-1,2,3,4-tetrahydro-isoquinoline, e) 2-[(N-(2-(naphth-2-yl)-ethyl)-hexahydro-azepin-3-yl)-methyl]-6,7-methylenedioxy-1-oxo-1,2,3,4-tetrahydro-isoquinoline, f) 2-[(N-(2-(3,4-dimethoxy-phenyl)-ethyl)-piperid-3-yl)-methyl]-6,7-dimethyl-1,2,3,4-tetrahydroisoquinoline, g) 2-[(N-(2-(3,4-dimethoxy-phenyl)-ethyl)-piperid-3-yl)-methyl]-6,7-dimethyl-1-oxo-1,2,3,4-tetrahydroisoquinoline, h) 2-[(N-(3-(4-methoxy-phenoxy)-propyl)-piperid-3-yl)-methyl]-6,7-dimethyl-1-oxo-1,2,3,4-tetrahydroisoquinoline, i) 3-[(N-(4-(thien-2-yl)-butyl)-piperid-3-yl)-methyl]-7,8-dimethoxy-2-oxo-1,3,4,5-tetrahydro-2H-3-benzazepine, k) 3-[(N-(2-(benzofur-2-yl)-ethyl)-piperid-3-yl)-methyl]-7,8-dimethoxy-2-oxo-1,3,4,5-tetrahydro-2H-3-benzazepine, l) 3-[(N-(2-(benzothien-3-yl)-ethyl)-piperid-3-yl)-methyl]-7,8-dimethoxy-2-oxo-1,3,4,5-tetrahydro-2H-3-benzazepine, m) 2-[(N-(3-(6-methoxy-naphth-2-yl-oxy)-propyl)pyrrolid-3-yl)-methyl]-6,7-dimethoxy-1-oxo-1,2,3,4-tetrahydro-isoquinoline, n) 2-[(N-(2-(6-methoxy-naphth-2-yl)-ethyl)-hexahydroazepin-3-yl)-methyl]-6,7-methylenedioxy-1-oxo-1,2,3,4-tetrahydro-isoquinoline, o) 3-[(N-(2-(4-methoxy-phenyl)-ethyl)-hexahydroazepin-3-yl)-methyl]-7,8-dimethoxy-2-oxo-1,3,4,5-tetrahydro-2H-3-benzazepine, and p) 3-[(N-(2-(3,4-dimethoxy-phenyl)-ethyl)-hexahydroazepin-3-yl)-methyl]-7,8-methylenedioxy-2-oxo-1,3,4,5-tetrahydro-2H-3-benzazepine, and pharmaceutically acceptable acid addition salts thereof.

12. A compound in accordance with claim 9, selected from the group consisting of:

a) 3-[(N-(2-(naphth-2-yl)-ethyl)-piperid-3-yl)methyl]-7,8-dimethoxy-2-oxo-1,3,4,5-tetrahydro-2H-3-benzazepine, b) 2-[(N-(3-(4-methoxy-phenoxy)-propyl)-piperid-3-yl)-methyl]-6,7-dimethyl-1-oxo-1,2,3,4-tetrahydroisoquinoline, c) 3-[(N-(4-(thien-2-yl)-butyl)-piperid-3-yl)-methyl]-7,8-dimethoxy-2-oxo-1,3,4,5-tetrahydro-2H-3-benzazepine, d) 2-[(N-(3-(6-methoxy-naphthyl-2-oxy)-propyl)pyrrolid-3-yl)-methyl]-6,7-dimethoxy-1-oxo-1,2,3,4-tetrahydro-isoquinoline, e) 2-[(N-(2-(6-methoxy-naphth-2-yl)-ethyl)-hexahydroazepin-3-yl)-methyl]-6,7-methylenedioxy-1-oxo-1,2,3,4-tetrahydro-isoquinoline, f) 3-[(N-(2-(4-methoxy-phenyl)-ethyl)-hexahydroazepin-3-yl)-methyl]-7,8-dimethoxy-2-oxo-1,3,4,5-tetrahydro-2H-3-benzazepine, and g) 3-[(N-(2-(3,4-dimethoxy-phenyl)-ethyl)-hexahydroazepin-3-yl)-methyl]-7,8-methylenedioxy-2-oxo-1,3,4,5-tetrahydro-2H-3-benzazepine, and pharmaceutically acceptable acid addition salts thereof.

13. 3-[(N-(2-(Naphth-2-yl)-ethyl)-piperid-3-yl)methyl]-7,8-dimethoxy-2-oxo-1,3,4,5-tetrahydro-2H-3-benzazepine, or a pharmaceutically acceptable acid addition salt thereof.

14. A pharmaceutical composition, suitable for the treatment of sinus tachycardia, comprising a heart rate lowering amount of a compound of formula I or (I)(i), as claimed in claims 1, 2, 3, 4, 5, 6, 7, 8, 9, 10, 11, 12 or 13, or a pharmaceutically acceptable acid addition salt thereof, together with one or more inert carriers or diluents.

15. A method for treating sinus tachycardia which comprises administering to a host in need of such treatment a heart rate lowering amount of a compound of formula I or (I)(i), as claimed in claims 1, 2, 3, 4, 5, 6, 7, 8, 9, 10, 11, 12 or 13, or a pharmaceutically acceptable acid addition salt thereof.

* * * * *